US008277476B2

(12) United States Patent
Taylor et al.

(10) Patent No.: US 8,277,476 B2
(45) Date of Patent: *Oct. 2, 2012

(54) SURGICAL INSTRUMENTS AND PROCEDURES FOR STABILIZING THE BEATING HEART DURING CORONARY ARTERY BYPASS GRAFT

(75) Inventors: Charles S. Taylor, San Francisco, CA (US); William N. Aldrich, Redwood City, CA (US); Thomas L. Baughman, Cupertino, CA (US); Federico J. Benetti, Rosario (AR); Brian J. Bennett, Menlo Park, CA (US); Michael J. Billig, Cupertino, CA (US); Thomas J. Fogarty, Portola Valley, CA (US); John J. Frantzen, Copperopolis, CA (US); Richard S. Ginn, San Jose, CA (US); Robert C. Glines, Cameron Park, CA (US); Harry L. Green, Santa Cruz, CA (US); Dwight P. Morejohn, Davis, CA (US); Brent Regan, Davis, CA (US); Eugene E. Reis, San Jose, CA (US); Amr Salahieh, Campbell, CA (US); Ivan Sepetka, Los Altos, CA (US); Benjamin Sherman, Milpitas, CA (US); Christian Skieller, Redwood City, CA (US); Valavanur A. Subramanian, New York, NY (US); Gary B. Weller, Los Gatos, CA (US); William F. Witt, Palo Alto, CA (US)

(73) Assignee: Maquet Cardiovascular LLC, San Jose, CA (US)

( * ) Notice: Subject to any disclaimer, the term of this patent is extended or adjusted under 35 U.S.C. 154(b) by 341 days.

This patent is subject to a terminal disclaimer.

(21) Appl. No.: 10/684,557

(22) Filed: Oct. 14, 2003

(65) Prior Publication Data

US 2004/0230099 A1 Nov. 18, 2004

Related U.S. Application Data

(63) Continuation of application No. 09/975,392, filed on Oct. 10, 2001, now Pat. No. 6,743,169, which is a continuation of application No. 08/789,751, filed on Jan. 27, 1997, now Pat. No. 6,346,077, which is a continuation-in-part of application No. 08/603,758, filed on Feb. 20, 1996, now Pat. No. 5,894,843.

(51) Int. Cl.
*A61M 29/00* (2006.01)
(52) U.S. Cl. ...................................... 606/191
(58) Field of Classification Search .................. 600/204, 600/206, 210, 235, 201, 226–229, 231–233, 600/37; 606/191
See application file for complete search history.

(56) References Cited

U.S. PATENT DOCUMENTS

| | | | |
|---|---|---|---|
| 452,131 A | 5/1891 | Haughawout | |
| 810,675 A | 1/1906 | Richter | |
| 1,706,500 A | 3/1929 | Smith | |
| 2,296,793 A | 9/1942 | Kirschbaum | |
| 2,590,527 A | 3/1952 | Fluck | |
| 2,693,795 A | 11/1954 | Grieshaber | |
| 2,863,444 A | 12/1958 | Winsten | |
| 3,392,722 A | 7/1968 | Jorgensen | |
| 3,683,926 A | 8/1972 | Suzuki | |
| 3,720,433 A | 3/1973 | Rosfelder | |
| 3,783,873 A | 1/1974 | Jacobs | |
| 3,858,926 A | 1/1975 | Ottenhues | |
| 3,882,855 A | 5/1975 | Schulte et al. | |
| 3,913,573 A * | 10/1975 | Gutnick | 128/833 |
| 3,916,909 A | 11/1975 | Kletschka et al. | |
| 3,983,863 A | 10/1976 | Janke et al. | |
| 4,047,532 A | 9/1977 | Phillips et al. | |
| 4,048,987 A | 9/1977 | Hurson | |
| 4,049,000 A | 9/1977 | Williams | |
| 4,049,002 A | 9/1977 | Kletschka et al. | |
| 4,052,980 A | 10/1977 | Grams et al. | |
| 4,226,228 A | 10/1980 | Shin et al. | |
| 4,230,119 A | 10/1980 | Blum | |
| 4,306,561 A | 12/1981 | de Medinaceli | |
| 4,350,160 A | 9/1982 | Kolesov et al. | |
| 4,366,819 A | 1/1983 | Kaster | |
| 4,368,736 A | 1/1983 | Kaster | |
| 4,421,107 A | 12/1983 | Estes et al. | |
| 4,428,368 A | 1/1984 | Torii | |

| Patent No. | Date | Inventor(s) |
|---|---|---|
| 4,434,791 A | 3/1984 | Darnell |
| 4,461,284 A | 7/1984 | Fackler |
| 4,492,229 A | 1/1985 | Grunwald |
| 4,617,916 A | 10/1986 | LeVahn et al. |
| 4,627,421 A | 12/1986 | Symbas et al. |
| 4,637,377 A | 1/1987 | Loop |
| 4,646,747 A | 3/1987 | Lundback |
| 4,688,570 A | 8/1987 | Kramer et al. |
| 4,702,230 A | 10/1987 | Pelta |
| 4,718,418 A | 1/1988 | L'Esperance, Jr. |
| 4,726,356 A | 2/1988 | Santilli et al. |
| 4,726,358 A | 2/1988 | Brady |
| 4,736,749 A | 4/1988 | Lundback |
| 4,747,395 A | 5/1988 | Brief |
| 4,754,746 A | 7/1988 | Cox |
| 4,803,984 A | 2/1989 | Narayanan et al. |
| 4,808,163 A | 2/1989 | Laub |
| 4,829,985 A | 5/1989 | Couetil |
| 4,852,552 A | 8/1989 | Chaux |
| 4,854,318 A | 8/1989 | Solem et al. |
| 4,858,552 A | 8/1989 | Glatt et al. |
| 4,863,133 A | 9/1989 | Bonnell |
| 4,865,019 A | 9/1989 | Phillips |
| 4,884,559 A | 12/1989 | Collins |
| 4,925,443 A | 5/1990 | Heilman et al. |
| 4,949,707 A | 8/1990 | LeVahn et al. |
| 4,955,896 A | 9/1990 | Freeman |
| 4,962,758 A | 10/1990 | Lasner et al. |
| 4,971,037 A | 11/1990 | Pelta |
| 4,973,300 A | 11/1990 | Wright |
| 4,989,587 A | 2/1991 | Farley |
| 4,991,578 A | 2/1991 | Cohen |
| 4,993,862 A | 2/1991 | Pelta |
| 5,009,660 A | 4/1991 | Clapham |
| 5,011,469 A | 4/1991 | Buckberg et al. |
| 5,025,779 A | 6/1991 | Bugge |
| 5,036,868 A | 8/1991 | Berggren et al. |
| 5,037,428 A | 8/1991 | Picha et al. |
| 5,052,373 A | 10/1991 | Michelson |
| 5,053,041 A | 10/1991 | Ansari et al. |
| 5,078,716 A * | 1/1992 | Doll ........................ 606/47 |
| 5,080,088 A | 1/1992 | LeVahn |
| 5,098,369 A * | 3/1992 | Heilman et al. .......... 600/16 |
| 5,119,804 A | 6/1992 | Anstadt |
| 5,125,395 A | 6/1992 | Adair |
| 5,131,905 A | 7/1992 | Grooters |
| 5,133,724 A | 7/1992 | Wilson, Jr. et al. |
| 5,152,777 A | 10/1992 | Goldberg et al. |
| 5,159,921 A | 11/1992 | Hoover |
| RE34,150 E | 12/1992 | Santilli et al. |
| 5,167,223 A | 12/1992 | Koros et al. |
| 5,171,254 A | 12/1992 | Sher |
| 5,231,974 A | 8/1993 | Giglio et al. |
| 5,287,861 A | 2/1994 | Wilk |
| 5,293,863 A | 3/1994 | Zhu et al. |
| 5,300,087 A | 4/1994 | Knoepfler |
| 5,318,013 A | 6/1994 | Wilk |
| 5,336,252 A | 8/1994 | Cohen |
| 5,363,882 A | 11/1994 | Chikama |
| 5,382,256 A | 1/1995 | Del Castillo |
| 5,382,756 A | 1/1995 | Dagan |
| 5,383,840 A | 1/1995 | Heilman et al. |
| 5,417,709 A | 5/1995 | Slater |
| 5,425,705 A | 6/1995 | Evard et al. |
| 5,437,651 A | 8/1995 | Todd et al. |
| 5,452,733 A | 9/1995 | Sterman et al. |
| 5,467,763 A | 11/1995 | McMahon et al. |
| 5,498,256 A | 3/1996 | Furnish |
| 5,503,617 A | 4/1996 | Jako |
| 5,509,890 A | 4/1996 | Kazama |
| 5,512,037 A | 4/1996 | Russell et al. |
| 5,514,075 A | 5/1996 | Moll et al. |
| 5,514,076 A * | 5/1996 | Ley ........................ 600/206 |
| 5,520,610 A | 5/1996 | Giglio et al. |
| 5,522,819 A | 6/1996 | Graves et al. |
| 5,529,571 A | 6/1996 | Daniel |
| 5,536,251 A | 7/1996 | Evard et al. |
| 5,547,458 A | 8/1996 | Ortiz et al. |
| 5,569,274 A | 10/1996 | Rapacki et al. |
| 5,571,074 A | 11/1996 | Buckman, Jr. et al. |
| 5,571,215 A | 11/1996 | Sterman et al. |
| 5,573,496 A | 11/1996 | McPherson et al. |
| 5,582,580 A * | 12/1996 | Buckman et al. ........... 601/41 |
| 5,607,421 A | 3/1997 | Jeevanandam et al. |
| 5,607,446 A | 3/1997 | Beehler et al. |
| 5,613,937 A | 3/1997 | Garrison et al. |
| 5,620,458 A * | 4/1997 | Green et al. ............. 606/188 |
| 5,651,378 A | 7/1997 | Matheny et al. |
| 5,667,480 A | 9/1997 | Knight et al. |
| 5,713,951 A | 2/1998 | Garrison et al. |
| 5,727,569 A | 3/1998 | Benetti et al. |
| 5,728,151 A | 3/1998 | Garrison et al. |
| 5,730,757 A | 3/1998 | Benetti et al. |
| 5,735,290 A | 4/1998 | Sterman et al. |
| 5,749,892 A * | 5/1998 | Vierra et al. ............. 600/204 |
| 5,755,660 A | 5/1998 | Tyagi |
| 5,766,151 A | 6/1998 | Valley et al. |
| 5,772,583 A | 6/1998 | Wright et al. |
| 5,782,746 A | 7/1998 | Wright |
| 5,795,291 A | 8/1998 | Koros et al. |
| 5,797,960 A | 8/1998 | Stevens et al. |
| 5,799,661 A * | 9/1998 | Boyd et al. ............... 128/898 |
| 5,807,243 A | 9/1998 | Vierra et al. |
| 5,813,410 A | 9/1998 | Levin |
| 5,836,311 A | 11/1998 | Borst et al. |
| 5,846,187 A | 12/1998 | Wells et al. |
| 5,846,193 A | 12/1998 | Wright |
| 5,846,194 A | 12/1998 | Wasson et al. |
| 5,865,730 A | 2/1999 | Fox et al. |
| 5,868,770 A | 2/1999 | Rygaard |
| 5,875,782 A | 3/1999 | Ferrari et al. |
| 5,876,332 A | 3/1999 | Looney |
| 5,879,291 A | 3/1999 | Kolata et al. |
| 5,882,299 A | 3/1999 | Rastegar et al. |
| 5,885,271 A | 3/1999 | Hamilton et al. |
| 5,888,247 A | 3/1999 | Benetti |
| 5,891,017 A | 4/1999 | Swindle et al. |
| 5,894,843 A | 4/1999 | Benetti et al. |
| 5,904,711 A * | 5/1999 | Flom et al. ............... 607/129 |
| 5,906,607 A | 5/1999 | Taylor et al. |
| 5,908,382 A | 6/1999 | Koros et al. |
| 5,913,876 A | 6/1999 | Taylor et al. |
| 5,927,284 A | 7/1999 | Borst et al. |
| 5,944,658 A | 8/1999 | Koros et al. |
| 5,944,736 A | 8/1999 | Taylor et al. |
| 5,947,125 A | 9/1999 | Benetti |
| 5,947,896 A | 9/1999 | Sherts et al. |
| 5,957,835 A | 9/1999 | Anderson et al. |
| 5,967,972 A | 10/1999 | Santilli et al. |
| 5,967,973 A | 10/1999 | Sherts et al. |
| 5,976,080 A | 11/1999 | Farascioni |
| 5,976,171 A | 11/1999 | Taylor |
| 5,984,865 A | 11/1999 | Farley et al. |
| 5,984,867 A | 11/1999 | Deckman et al. |
| 6,007,486 A | 12/1999 | Hunt et al. |
| 6,007,523 A | 12/1999 | Mangosong |
| 6,010,531 A | 1/2000 | Donlon et al. |
| 6,013,027 A | 1/2000 | Khan et al. |
| 6,015,378 A | 1/2000 | Borst et al. |
| 6,017,304 A | 1/2000 | Vierra et al. |
| 6,019,722 A | 2/2000 | Spence et al. |
| 6,027,476 A | 2/2000 | Sterman et al. |
| 6,029,671 A | 2/2000 | Stevens et al. |
| 6,030,340 A | 2/2000 | Maffei et al. |
| 421,803 A | 3/2000 | Koros et al. |
| 6,032,672 A | 3/2000 | Taylor |
| 6,033,362 A | 3/2000 | Cohn |
| 6,036,641 A | 3/2000 | Taylor et al. |
| 6,050,266 A | 4/2000 | Benetti et al. |
| 6,063,021 A | 5/2000 | Hossain et al. |
| 6,071,295 A | 6/2000 | Takahashi |
| 6,099,468 A | 8/2000 | Santilli et al. |
| 6,102,853 A | 8/2000 | Scirica et al. |
| 6,102,854 A | 8/2000 | Carfier et al. |
| 6,113,534 A * | 9/2000 | Koros et al. ............. 600/213 |
| 6,139,492 A | 10/2000 | Vierra et al. |
| 6,149,583 A | 11/2000 | Vierra et al. |
| 6,183,486 B1 | 2/2001 | Snow et al. |

| | | |
|---|---|---|
| 6,190,311 B1 | 2/2001 | Glines et al. |
| 6,193,652 B1 | 2/2001 | Berky et al. |
| 6,200,263 B1 | 3/2001 | Person |
| 6,210,323 B1 | 4/2001 | Gilhuly et al. |
| 6,213,940 B1 | 4/2001 | Sherts et al. |
| 6,213,941 B1 | 4/2001 | Benetti et al. |
| 6,231,506 B1 | 5/2001 | Hu et al. |
| 6,283,912 B1 | 9/2001 | Hu et al. |
| 6,290,644 B1 | 9/2001 | Green, II et al. |
| 6,315,717 B1 | 11/2001 | Benetti et al. |
| 6,331,158 B1 | 12/2001 | Hu et al. |
| 6,346,077 B1 | 2/2002 | Taylor et al. |
| 6,350,229 B1 | 2/2002 | Borst et al. |
| 6,371,906 B1 | 4/2002 | Borst et al. |
| 6,394,951 B1 | 5/2002 | Taylor et al. |
| 6,464,630 B1 | 10/2002 | Borst et al. |
| 6,478,029 B1 | 11/2002 | Boyd et al. |
| 6,482,151 B1 | 11/2002 | Vierra et al. |
| 6,494,211 B1 | 12/2002 | Boyd et al. |
| 6,537,212 B2 | 3/2003 | Sherts et al. |
| 6,733,445 B2 | 5/2004 | Sherts et al. |
| 6,743,169 B1 | 6/2004 | Taylor et al. |
| 7,056,287 B2 | 6/2006 | Taylor et al. |

FOREIGN PATENT DOCUMENTS

| | | |
|---|---|---|
| DE | 90 04513 | 6/1990 |
| EP | 0 293 760 A2 | 12/1988 |
| EP | 0 293 760 A3 | 12/1988 |
| EP | 0 293 760 B1 | 12/1988 |
| EP | 0 630 629 | 5/1994 |
| EP | 668 058 A1 | 8/1995 |
| EP | 0 993 806 A2 | 4/2000 |
| FR | 473451 | 1/1915 |
| GB | 168216 | 9/1921 |
| GB | 2 233 561 A | 1/1991 |
| GB | 2 267 827 A | 12/1993 |
| WO | WO 87/04081 | 7/1987 |
| WO | WO 94/14383 | 7/1994 |
| WO | WO 94/18881 | 9/1994 |
| WO | WO 95/01757 | 1/1995 |
| WO | WO 95/15715 | 6/1995 |
| WO | WO 95/17127 | 6/1995 |
| WO | WO 96/00033 | 1/1996 |
| WO | WO 97/10753 | 3/1997 |
| WO | WO 97/26828 | 7/1997 |
| WO | WO 97/32514 A2 | 9/1997 |
| WO | WO 97/32514 A3 | 9/1997 |
| WO | WO 97/40752 | 11/1997 |
| WO | WO 98/27869 | 7/1998 |
| WO | WO 98/48703 | 11/1998 |
| WO | WO 98/49947 | 11/1998 |
| WO | WO 99/08585 | 2/1999 |
| WO | WO 99/09892 | 3/1999 |
| WO | WO 99/16367 | 4/1999 |
| WO | WO 00/06041 | 2/2000 |
| WO | WO 00/10466 | 3/2000 |
| WO | WO 00/16367 | 3/2000 |
| WO | WO 00/42920 | 7/2000 |
| WO | WO 00/42921 | 7/2000 |
| WO | WO 00/42935 | 7/2000 |
| WO | WO 00/42936 | 7/2000 |
| WO | WO 00/42937 | 7/2000 |

OTHER PUBLICATIONS

U.S. Appl. No. 09/345,859 Looney et al. filed Jul. 1, 1999.
U.S. Appl. No. 09/438,670 Parsons, et al. filed Nov. 12, 1999.
U.S. Appl. No. 09/489,274 Brown et al. filed Jan. 21, 2000.
U.S. Appl. No. 60/117,333 Looney et al. (provisional) filed Jan. 24, 1999.
Akins, et al., "Preservation of Interventricular Septal Function in Patients Having Coronary Artery Bypass Graft Without Cardiopulmonary Bypass," American Heart Journal, vol. 107, No. 2, Feb. 1984, pp. 304-309.
Ancalmo, N. and J. L. Ochsner: "A Modified Sternal Retractor," Ann. Thorac, Surg. 21 (1976) 174.
Angelini, G.D., M.D. et al., "Fiber-Optic Retractor for Harvesting the Internal Mammary Artery," Ann. Thorac. Surg. (1990; 50:314-5).

Angelini, G.D., M.D., "Simple, Inexpensive Method of Heart Retraction During Coronary Artery Bypass Surgery," Ann. Thora. Surg 46:46-247, Aug. 1988.
Anstadt, M.D., et al., Direct Mechanical Ventricular Actuation for Cardiac Arrest in Humans,@ Chest, vol. 100, No. 1, Jul. 1991.
Antinori, C. et al., "A Method of Retraction During Reoperative Coronary Operations Using the Favaloro Retractor," The Society of Thoracic Surgeons: 1989.
Archer, DO, et al., "Coronary Artery Revascularization Without Cardiopulmonary Bypass," Texas Heart Institute Journal, vol. 11, No. 1, Mar. 1984, pp. 52-57.
Arom, K.V., et al., "Mini-Sternotomy for Coronary Artery Bypass Grafting," The Annals of Thoracic Surgery 1996; 61:1271-2.
Arom, K.V., et al., "Mini-Sternotomy for Coronary Artery Bypass Grafting," The Annals of Thoracic Surgery 1996; 62:1884-85.
Ballantyne, M.D., et al., "Delayed Recovery of Severely "Stunned" Myocardium With the Support of a Left Ventricular Assist Device After Coronary Artery Bypass Graft Surgery," Journal of the American College of Cardiology, vol. 10, No. 3, Sep. 1987, pp. 710-712.
Bedellino, M.M., et al., "The Cardiac Rag—Simple Exposure of the Heart," Texas Heart Institute Journal, vol. 15, No. 2, 1988, 134-35.
Beg, R.A., et al., "Internal Mammary Retractor," Ann Thorac, Surg., vol. 39, No. 1, pp. 286-287, Jan. 1985.
Benetti, et al., "Direct Coronary Surgery with Saphenous Vein Bypass Without Either Cardiopulmonary Bypass or Cardiac Arrest," The Journal of Cardiovascular Surgery, vol. 26, No. 3, May-Jun. 1985, pp. 217-222.
Benetti, et al., "Direct Myocardial Revascularization Without Extracorporeal Circulation," Chest, vol. 100, No. 2 Aug. 1991, pp. 312-316.
Benetti, J., et al., "A Single Coronary Artery Bypass Grafting—A Comparison Between Minimally Invasive Off Pump Techniques and Conventional Procedures," European Journal of Cardio-Thoracic Surgery, 14 (Supp. I) (1998) S7-S12.
Borst, et al., "Coronary Artery Bypass Grafting Without Cardiopulmonary Bypass and Without Interruption of Native Coronary Flow Using a Novel Anastomosis Site Restraining Device ("Octopus")," J Am Coll Cardiol, May 1996, vol. 27, No. 6, pp. 1356-1364.
Borst, et al., "Regional Cardiac Wall Immunobilization for Open Chest and Closed Chest Coronary Artery Bypass Grafting on the Beating Heart: The 'Octopus' Method," Circulation, Oct. 15, 1995, vol. 92, No. 8, Supplement 1, 1-177.
British Heart Journal, "Coronary Surgery Without Cardiopulmonary Bypass," pp. 203-205, 1995.
Buffolo, et al., "Direct Myocardial Revascularization Without Cardiopulmonary Bypass," Thoac. Cardiovasc. Surgeon, 33 (1985) pp. 26-29.
Bugge, M., "A New Internal Mammary Artery Retractor," Thorac. Cardiovasc Surgeon 38, pp. 316-317 (1990).
Calafiore, A. M., et al., "Minimally Invasive Coronary Artery Bypass Grafting," The Annals of Thoracic Surgery, 62:1545-8, 1996.
Campalani et al., "A New Self-Retaining Internal mammary Artery Retractor." J. Cardiovas. Surg., vol. 28. (1987).
Cartier, R, MD., "Triple Coronary Artery Revascularization on the Stabilized Beating Heart: Initial Experience," Montreal Heart Institute, CJS, vol. 41, No. 4, pp. 283-288, Aug. 1998.
Chaux, A. and C. Blanche, "A New Concept in Sternal Retraction: Applications for Internal Mammary Artery Dissection and Valve Replacement Surgery," Ann. Thorac. Surg. 42, pp. 473-474, Oct. 1986.
Cooley, D. A., "Limited Access Myocardial Revascularization," Texas Heart Institute Journal, pp. 81-84, vol. 23, No. 2, 1996.
Correspondence and Brief Communications, Archives of Surgery—vol. 115, 1136-37, Sep. 1980.
Cremer, J, MD, "Off-Bypass Coronary Bypass Grafting Via Minithoracotomy Using Mechanical Epicardial Stabilization," The Annals of Thoracic Surgery, 63:S79-83, 1997.
Delacroix-Chevalier Surgical Instruments, IMA Saving Packages Brochure.
DelRossi, A J and Lemole, GM, "A New Retractor to Aid in Coronary Artery Surgery," The Annals of Thoracic Surgery, vol. 36, No. 1, 101-102, Jul. 1983.

Fanning, MD., "Reoperative Coronary Artery Bypass Grafting Without Cardiopulmonary Bypass," The Annals of Thoracic Surgery, vol. 55, No. 2, Feb. 1993, pp. 486-489.

Favaloro, M.D., et al, "Direct Myocardial Revascularization by Saphenous Vein Graft," The Annals of Thoracic Surgery, vol. 10, No. 2, Aug. 1970.

Fonger, et al., "Enhanced Preservation of Acutely Ischemic Myocardium with Transeptal Left Ventricular Assist," The Annals of Thoracic Surgery, vol. 57, No. 3, Mar. 1994, pp. 570-575.

Gacioch, et al., "Cardiogenic Shock Complicating Acute Myocardial Infarction: The Use of Coronary Angioplasty and the Integration of the New Support Device into Patient Management," Journal of the American College of Cardiology, vol. 19, No. 3, Mar. 1, 1992.

Green, GE., "Technique of Internal Mammary-Coronary Artery Anastomosis," The Journal of Cardiovascular Surgery, 78:455-79, 1979.

Groopman, J., "Heart Surgery, Unplugged; Making the Coronary Bypass Safer, Cheaper, and Easier," The New Yorker, Jan. 11, 1999, pp. 43-46, 50-51.

Guzman, F. M.D., "Transient Radial Nerve Injury Related to the Use of a Self Retraining Retractor for Internal Mammary Artery Dissection," J. Cardiovasc. Surg. 30, 1989, pp. 1015-1016.

Hasan, RI, et al., "Technique of Dissecting the Internal Mammary After Using the Moussalli Bar," European Journal of Cardiothoracic Surgery, 4:571-572, 1990.

Itoh, Toshiaki, M.D., et al., "New Modification of a Mammary Artery Retractor," Ann. Thorac. Surg. 9, 1994; 57:1670-1.

Izzat, FRCS, et al., "Cardiac Stabilizer for Minimally Invasive Direct Coronary Artery Bypass," Elsevier Science Inc., 1997 by the Society of Thoracic Surgeons.

Japanese Article "Heart Retractor".

Japanese Journal of Thoracic Surgery, vol. 42, No. 2, 1989.

Kazama, S. et al., "Fabric Heart Retractor for Coronary Artery Bypass Operations," The Annals of Thoracic Surgery, 55:1582-3, 1993.

Kolessov, M.D., "Mammary Artery-Coronary Artery Anastomosis as Method of Treatment for Angina Pectoris," Thoracic and Cardiovascular Surgery, vol. 54, No. 4, Oct. 1967, pp. 535-544.

Konishi, T. MD, et al., "Hybrid-Type Stabilizer for Off-Pump Direct Coronary Artery Bypass Grafting," Annals of Thoracic Surgery 66:961-2, 1998.

Kresh, et al., "Heart-Mechanical Assist Device Interaction," Trans. Am. Soc. Artif. Intern. Organs, vol. XXXII, 1986, pp. 437-443.

Lavergne, et al., "Transcatheter Radio Frequency Ablation of a Trial Tissue Using a Suction Catheter," PACE, vol. 12, Jan. 1989, Part II, pp. 177-186.

Lonn, M.D., et al. "Coronary Artery Operation Supported by the Hemopump: An Experimental Study on Pigs," The Annals of Thoracic Surgery, vol. 58, No. 1, Jul. 1994, pp. 516-523.

Matsuura, A. MD, et al., "A New Device for Exposing the Circumflex Coronary Artery" The Annals of Thoracic Surgery, 59:1249-50, 1995, pp. 1249-1250.

McGee, et al. "Extended Clinical Support with an Implantable Left Ventricular Assist Device," Trans. Am Soc. Artif. Intern. Organs, vol. XXXV, 1989, pp. 614-616.

McKeown, P.P. et al., "A Modified Sternal Retractor for Exposure of the Internal Mammary Artery," Ann. Thorac. Surg. 32 (1981) 619.

Ochsner, JL, et al., "Surgical Management of Diseased Intracavitary Coronary Arteries," The Annals of Thoracic Surgery, vol. 38, No. 4, July, pp. 356-362, Oct. 1984.

Parsonnet, V. MD, et al., "Graduated probes for Coronary Bypass Surgery," The Journal of Thoracic and Cardiovascular Surgery, vol. 68, No. 3, 424-426 (Sep. 1974).

Parsonnet, V. MD, et al., "Self-Retaining Epicardial Retractor for Aortocoronary Bypass Surgery," The Journal of Thoracic and Cardiovascular Surgery, 629-630 1979.

Perrault, L. et al., "Snaring of the Target Vessel in Less Invasive Bypass Operations Does Not Cause Endothelial Dysfunction," The Society of Thoracic Surgeons, pp. 751-755, 1997.

Pfister, et al., "Coronary Artery Bypass Without Cardiopulmonary Bypass," The Annals of Thoracic Surgery, vol. 54, No. 6, Dec. 1992, pp. 1085-1092.

Phillips, Steven J., M.D. et al., "A Versatile Retractor for Use in Harvesting the Internal Mammary Artery and Performing Standard Cardiac Operations," J. Thorac. Cardiovasc. Surg. (1989; 97:633-5).

Pilling Surgical Instruments, A Rusch International Company Brochure.

Pittman, John, M.D., et al., "Improved Visualization of the Internal Mammary Artery with a New Retractor System," Ann. Thorac. Surg., 1989; 48:869-70.

Riahi, et al., "A Simple Technique and Device to Provide a Bloodless Operative Field in Coronary Artery Surgery Without Cross-Clamping the Aorta," The Journal of Thoracic and Cardiovascular Surgery, vol. 66, No. 6., Dec. 1973, pp. 974-978.

Richenbacher, M.D., et al., "Current Status of Cardiac Surgery: A 40-Year Review," Journal of American College of Cardiology, vol. 14, No. 3, pp. 535-544.

Robicsek, F., "Aortic Spoon-Jaw Clamp for Aorta-Saphenous Vein Anastomosis," Journal of Cardiac Surgery, 10:583-585, 1995.

Robinson, et al., "A Minimally Invasive Surgical Method for Coronary Revascularization—Preliminary Experience in Five Patients," Circulation, Oct. 15, 1995, vol. 92, No. 8, 1-176.

Rousou, J. et al., "Cardiac Retractor for Coronary Bypass Operations," The Society of Thoracic Surgeons, pp. 52:877-78, 1991.

Roux, D. MD. et al., "New Helper Instrument in Cardiac Surgery," The Annals of Thoracic Surgery, 48: 595-6, 1989.

Roux, D., M.D. et al., "Internal Mammary Artery Dissection: A Three Dimensional Sternal Retractor," J. Cardiovasc. Surg., 1989; 30:996-7.

Ruzevich et al. "Long-Term Follow-up of Survivors of Postcardiotomy Circulatory Support," Trans. Am. Soc. Artif. Intern. Organs, vol. XXXIV, 1988, pp. 116-124.

Scholz, et al. "Transfemoral Placement of the Left Ventricular Assist Device "Hemopump" During Mechanical Resuscitation," Thoracic and Cardiovascular Surgeon, vol. 38 (1990) pp. 69-72.

Stevens, et al., "Closed Chest Coronary Artery Bypass With Cardioplegic Arrest in the Dog," $67^{th}$ Scientific Session, 238, I-251.

Trapp and R. Bisarya, "To Use or Not to Use the Pump Oxygenator in Coronary Bypass Operations," The Annals of Thoracic Surgery, vol. 19, No. 1, Jan. 1975, pp. 108-109.

Trapp, et al., "Placement of Coronary Artery Bypass Graft without Pump Oxygenator," Journal of the Society of Thoracic Surgeons and The Southern Thoracic Surgeons Assn. vol. 19, No. 1, Jan. 1975.

USSC Cardiovascular Thora-Lift J, United States Surgical Corporation, Norwalk, Connecticut, Product Brochure.

Vigano, M., "Tecnica Operatoria," Minerva Cardioangiologica, vol. 23-N. 6-7 (1975).

Vincent, J.G., "A Compact Single Post Internal Mammary Artery Dissection Retractor," Eur. J. Cardio-Thor. Surg. 3 (1989) 276-277.

Westaby, S. et al., "Less Invasive Coronary Surgery: Consensus From the Oxford Meeting," The Annals of Thoracic Surgery, 62:924-31, 1996.

Zumbro, et al., AA Prospective Evaluation of the Pulsatile Assist Device,@ The Annals of Thoracic Surgery, vol. 28, No. 2, Aug. 1979, pp. 269-273.

* cited by examiner

*Primary Examiner* — Sunil K Singh

(74) *Attorney, Agent, or Firm* — Law Office of Alan W. Cannon

(57) ABSTRACT

The invention is methods and devices which a surgeon may use to stabilize the beating heart during a surgical procedure on the heart. Pursuant to the invention, a stabilizing device is introduced through an opening in the chest and brought into contact with the beating heart. By contacting the heart with the device and by exerting a stabilizing force on the device, the motion of the heart caused by the contraction of the heart muscles is effectively eliminated such that the heart is stabilized and the site of the surgery moves only minimally if at all. Typically, in separate steps, the surgeon contacts the heart with the stabilizing means, assesses the degree of movement of the anastomosis site, and exerts a force on the stabilizing means such that the contraction of the beating heart causes orgy minimal excess motion at the surgery site. By fixing the position of the stabilizing means in a configuration where the motion of the beating heart is effectively eliminated, the surgeon is able to stabilize the beating heart for the duration of the procedure. The stabilizing means may be attached to a rigid support or may be attached to a semi-rigid support which is rendered motionless mechanically, chemically, or by human intervention. In certain preferred embodiments, the stabilizing means is affixed to a semi-rigid support which is caused to become rigid, by any of a variety of techniques, such that the position of the stabilizing means becomes fixed by the support, and the heart remains substantially motionless for the duration of the procedure.

21 Claims, 83 Drawing Sheets

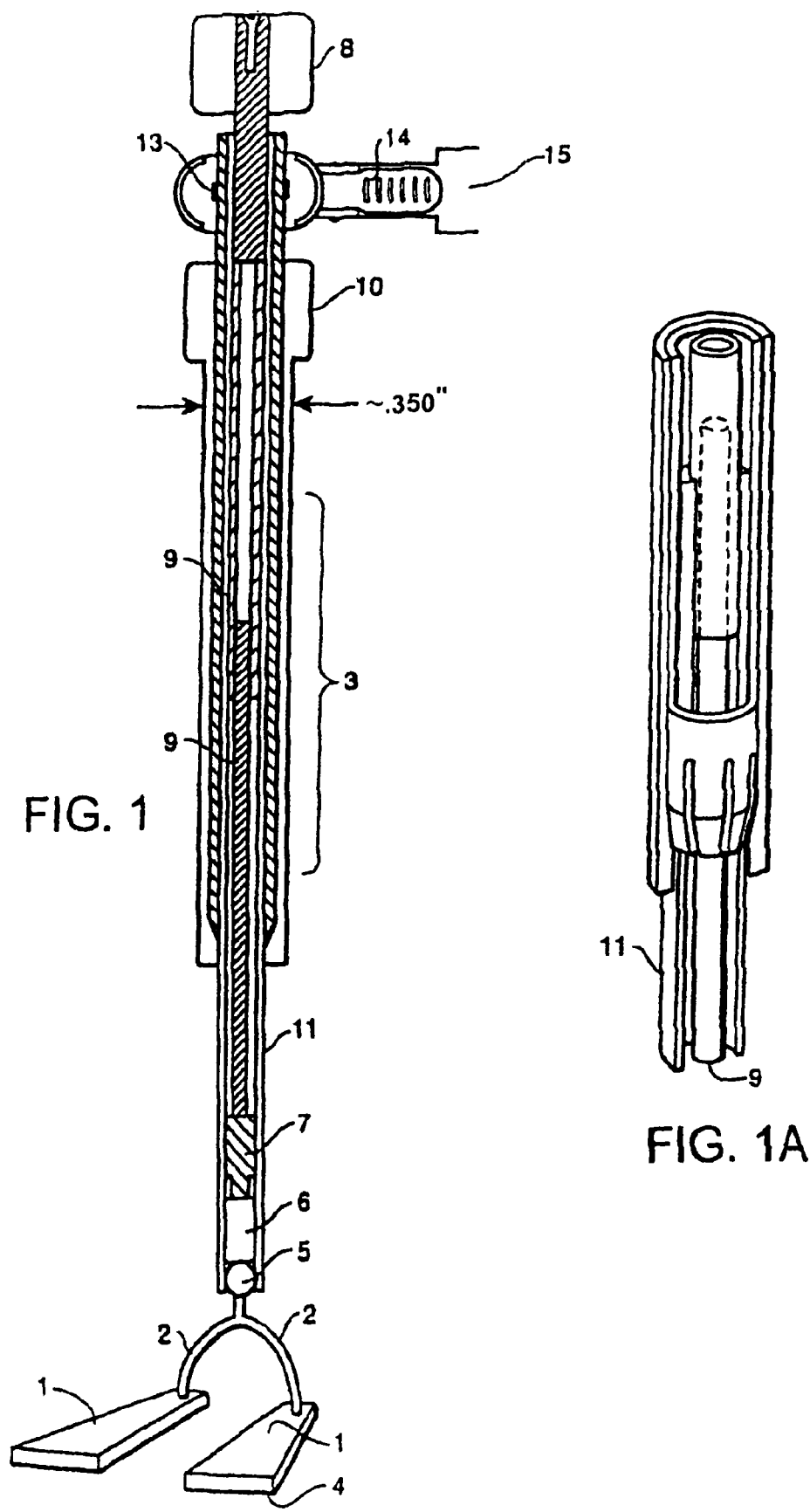

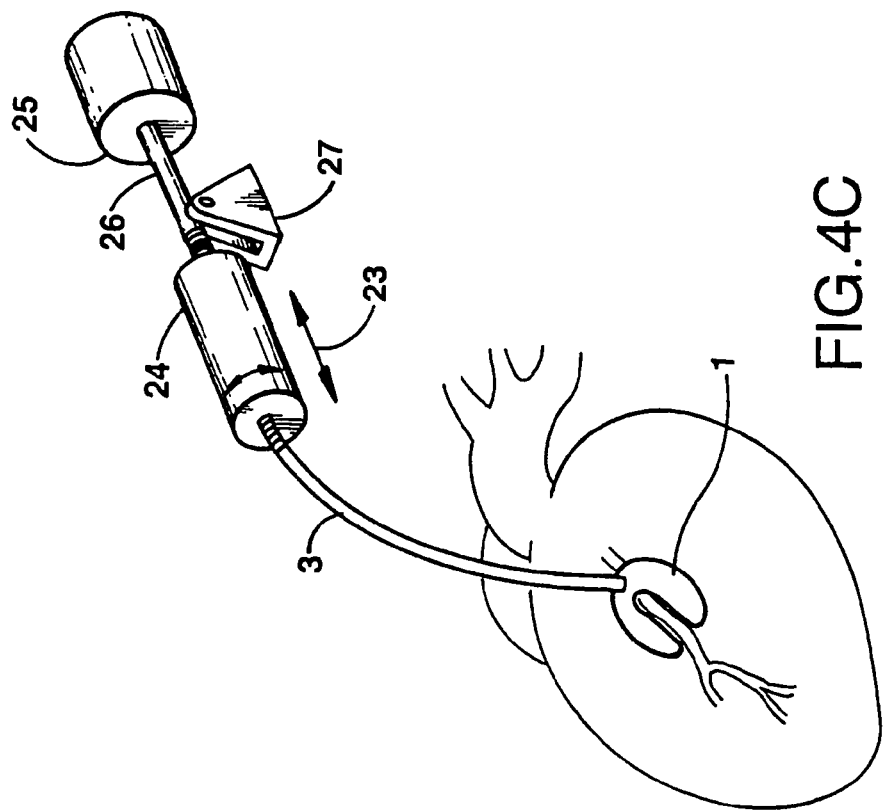
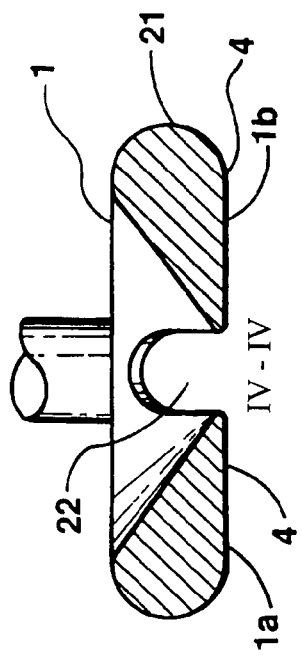
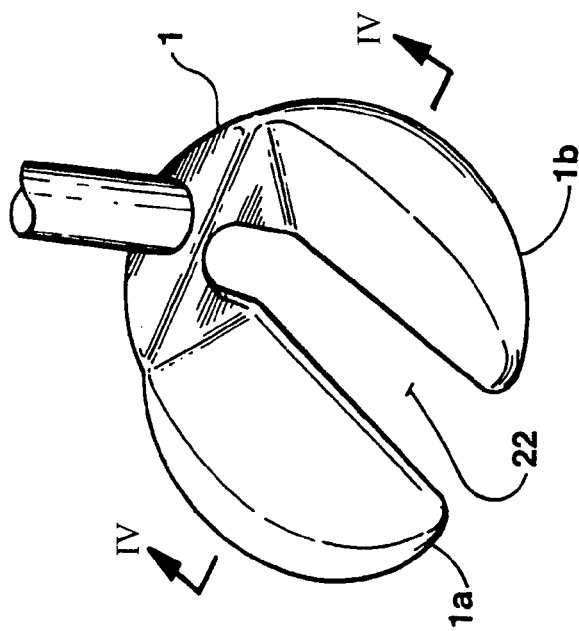
FIG.4C
FIG.4B
FIG.4A

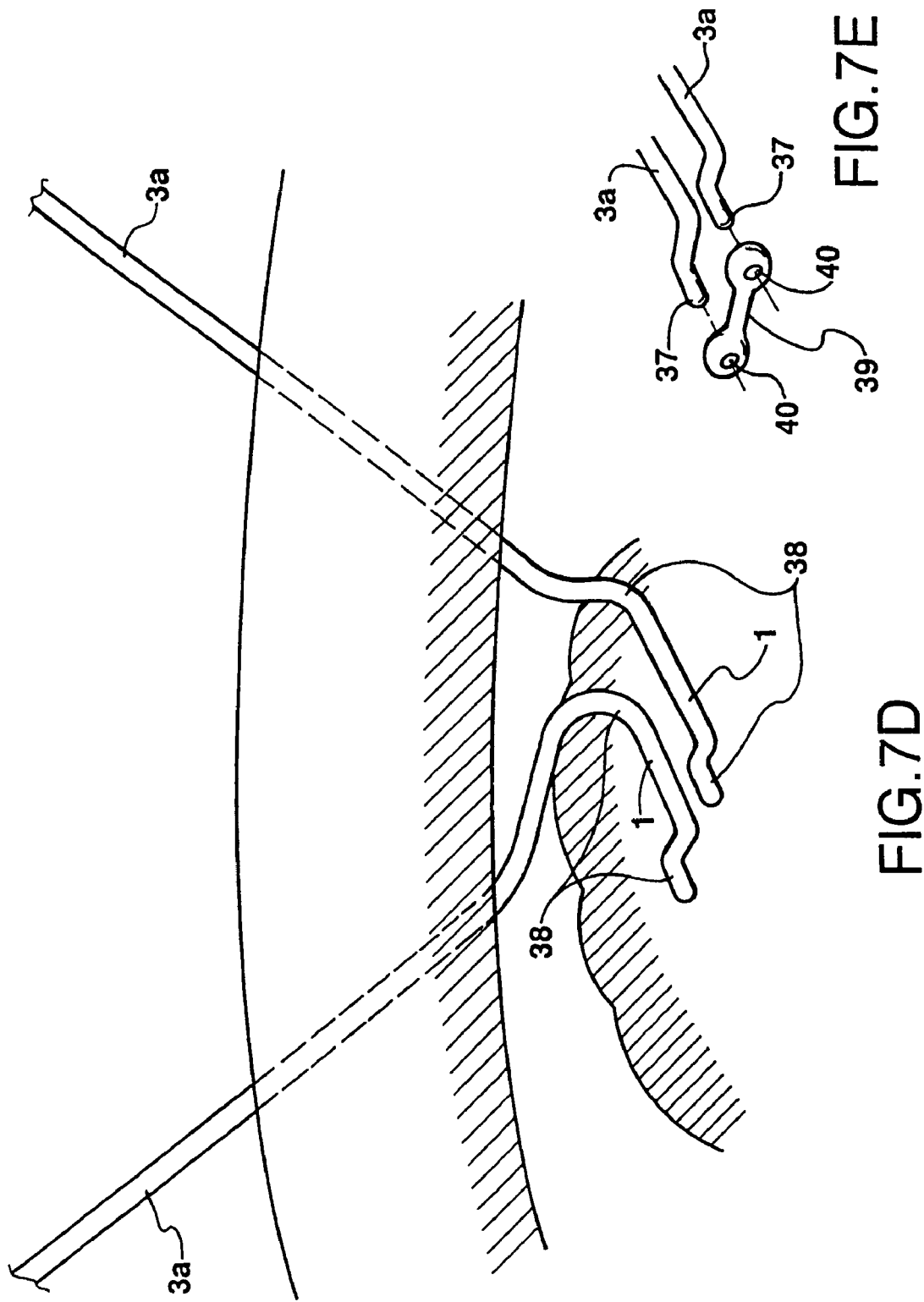

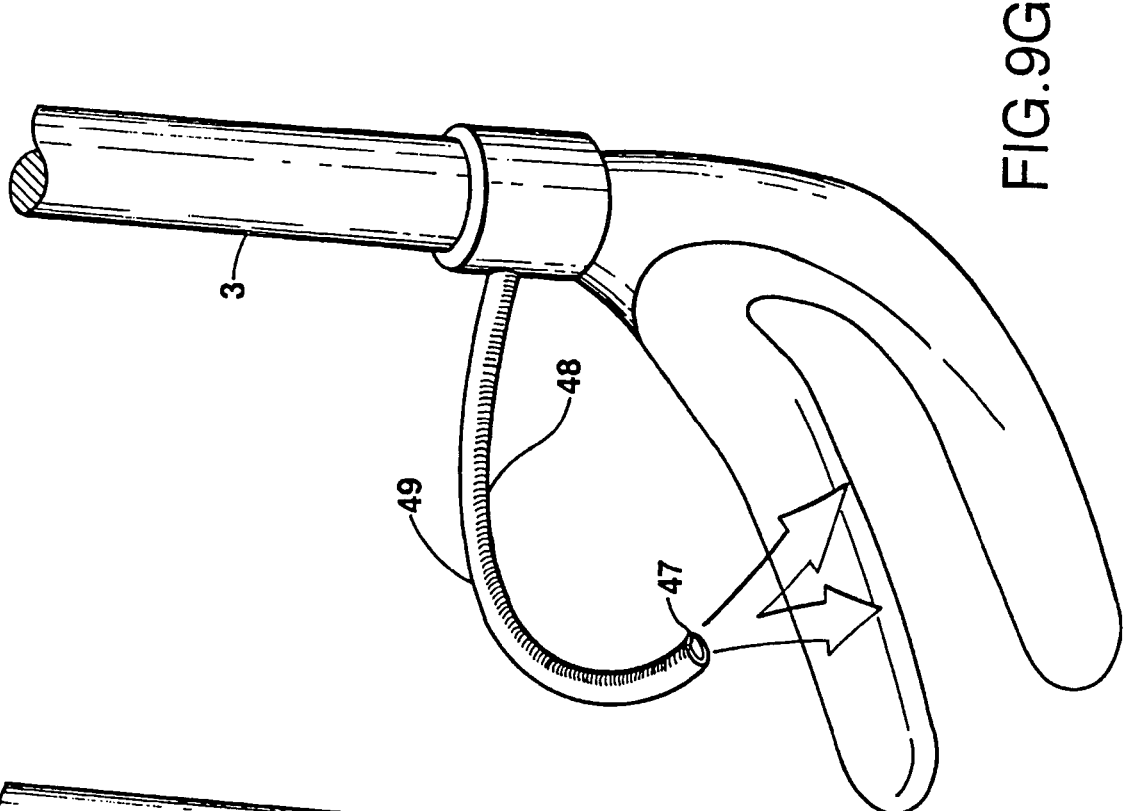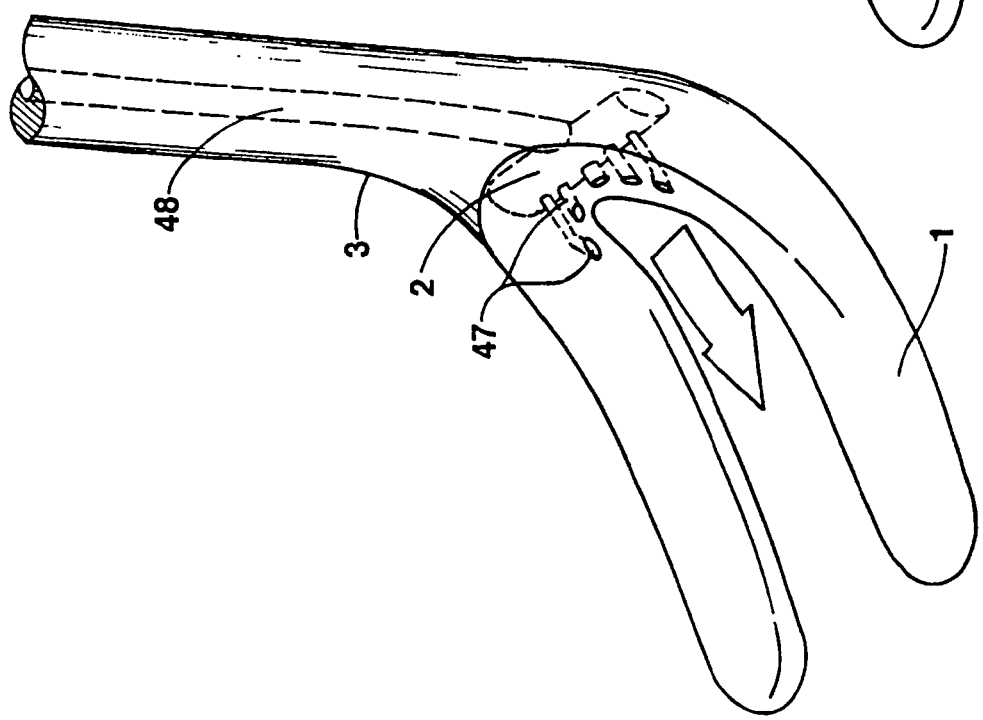

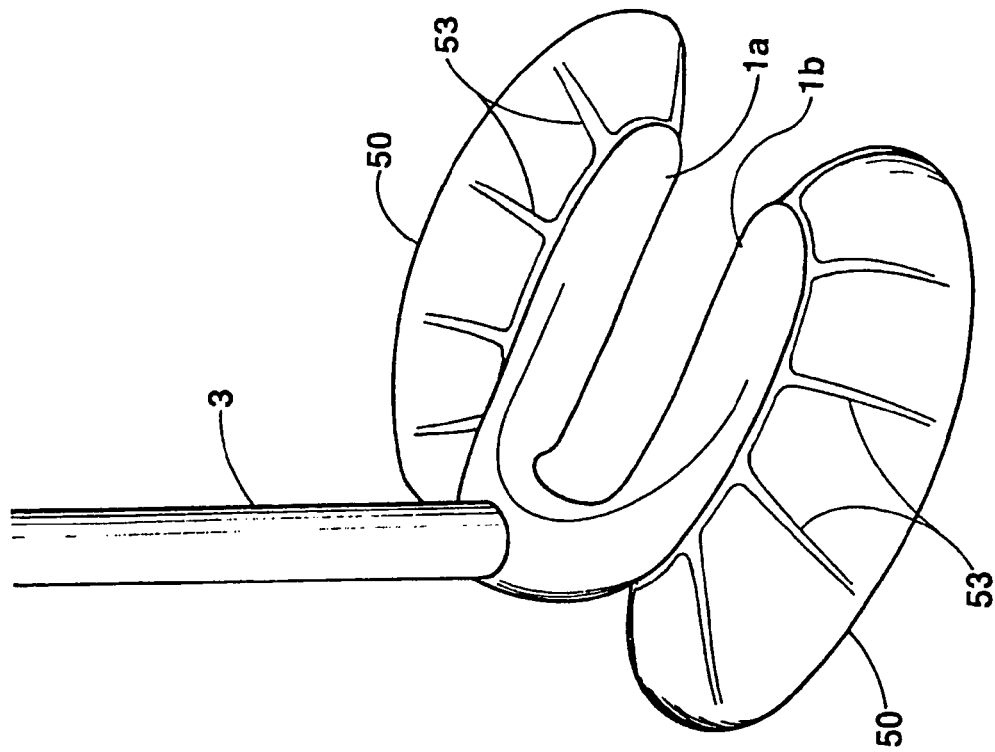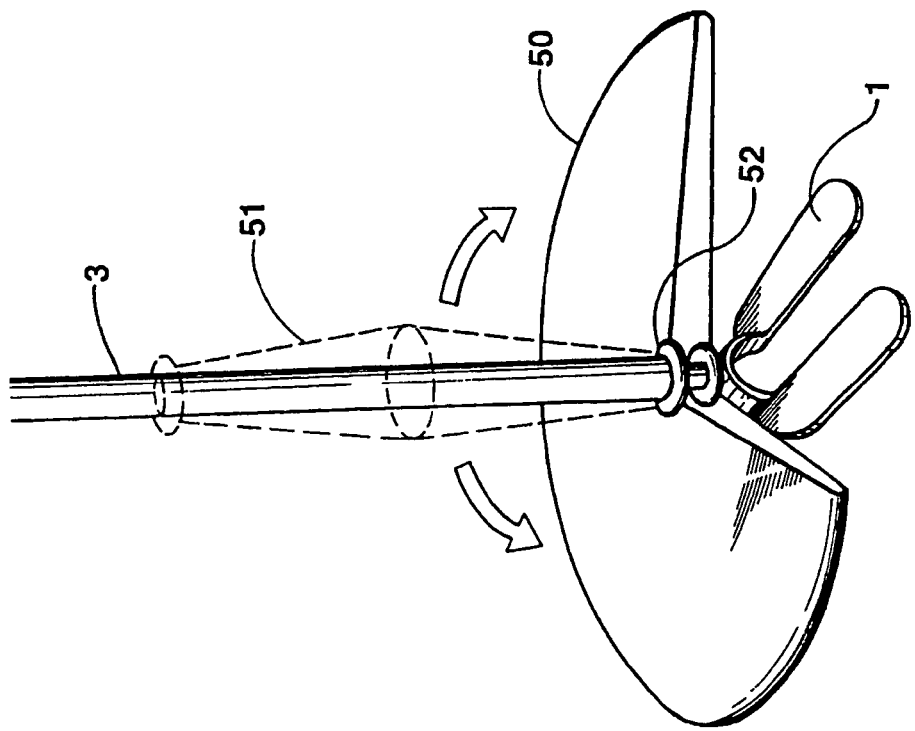

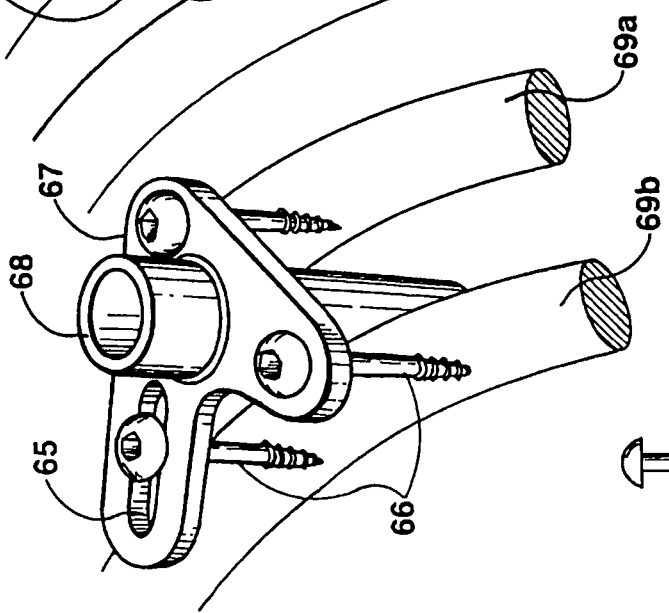
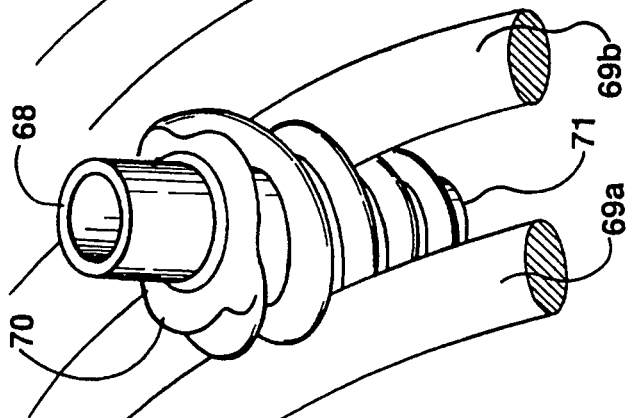
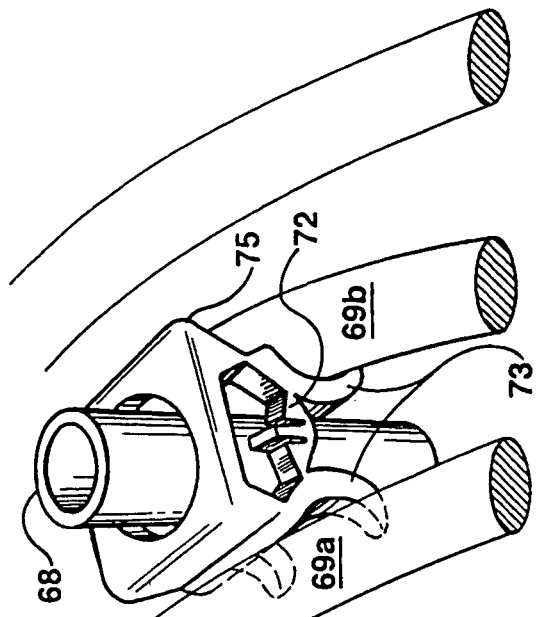
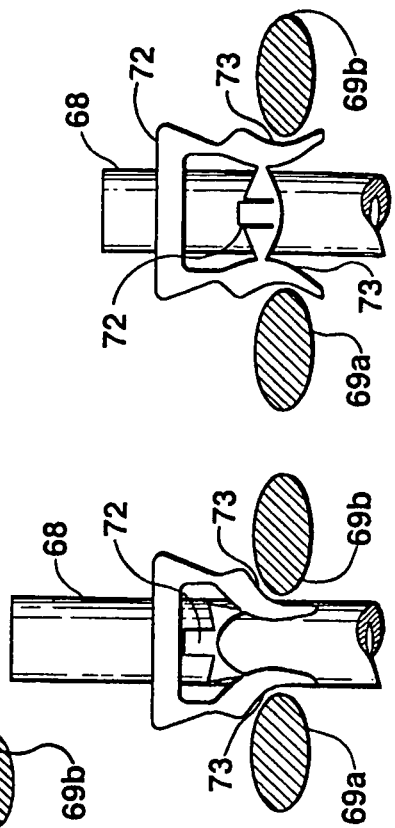

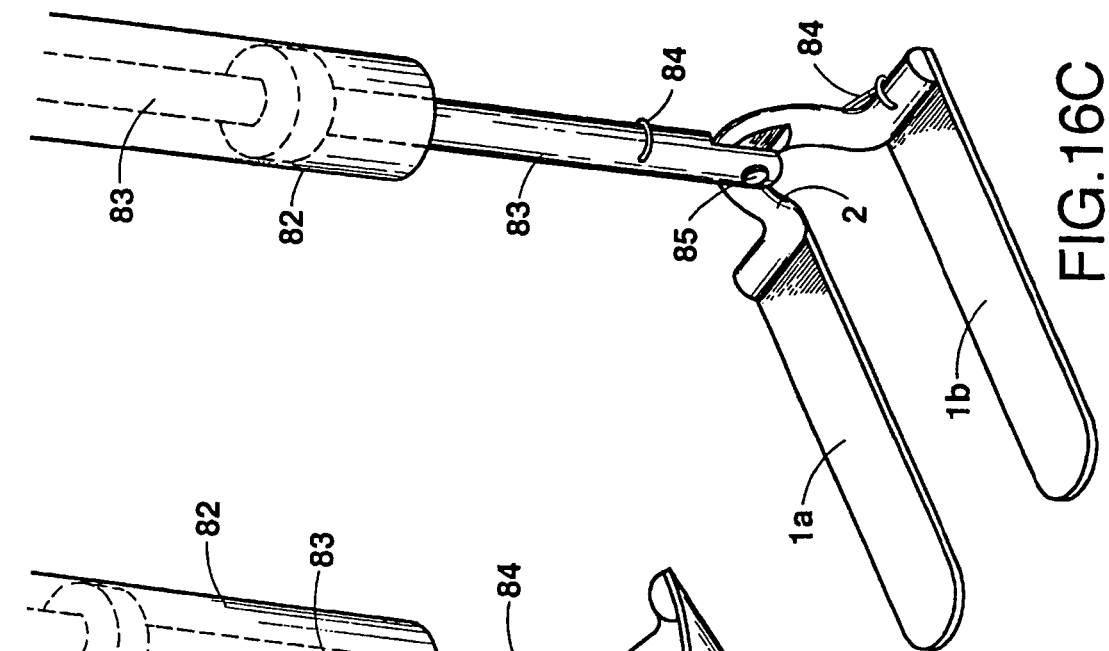
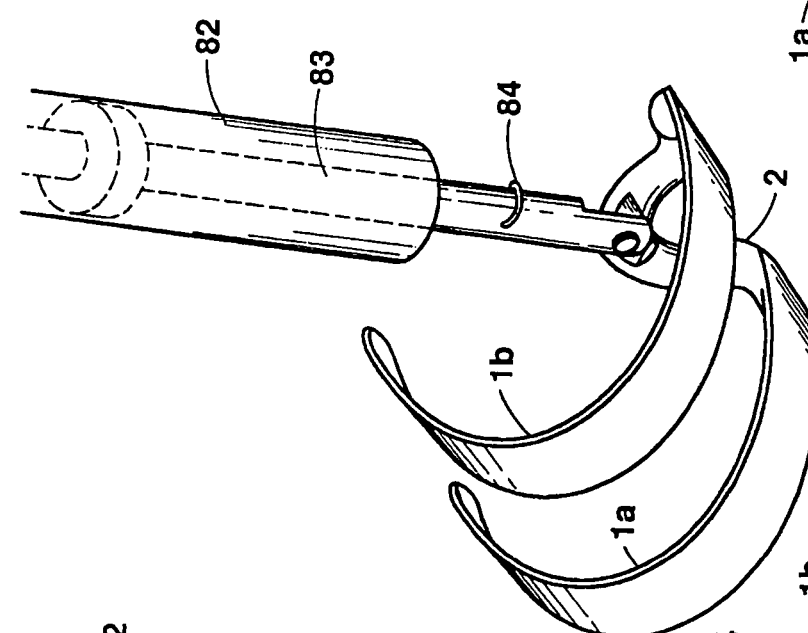
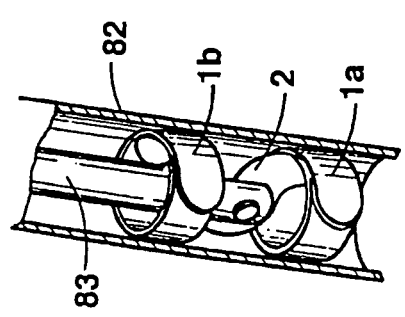
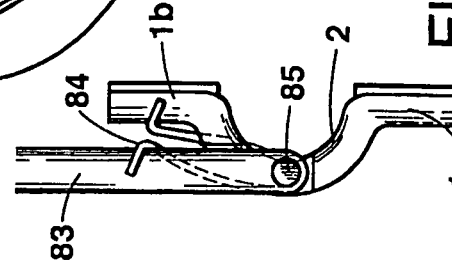
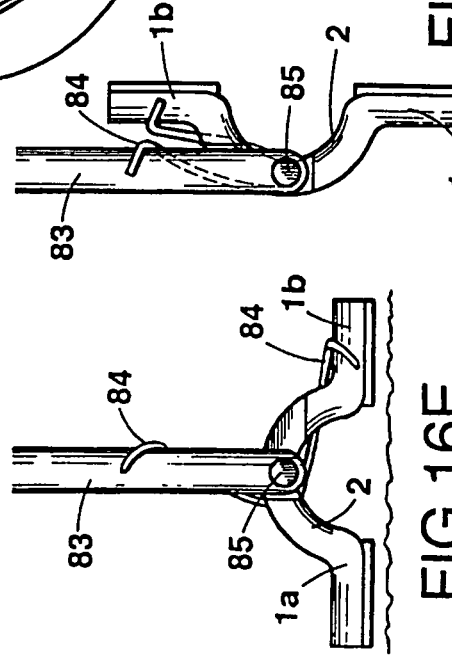

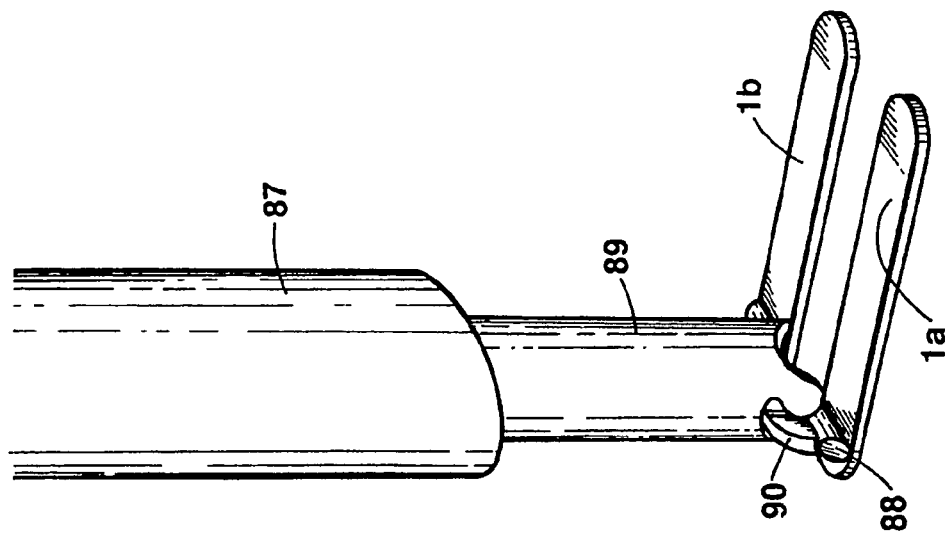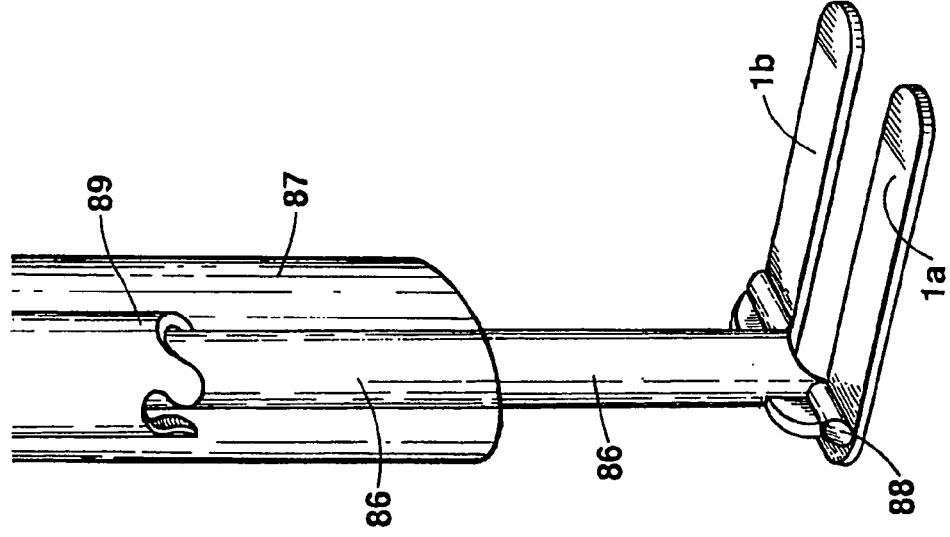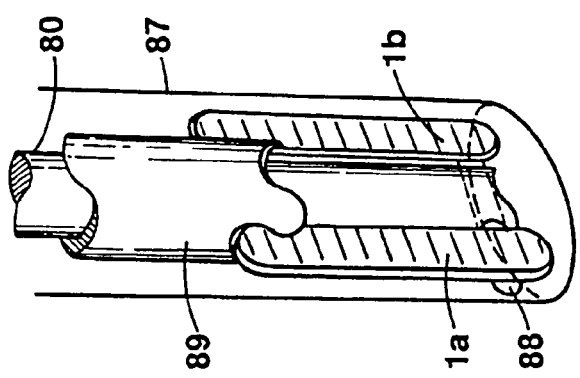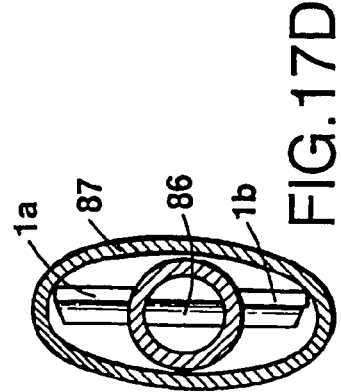

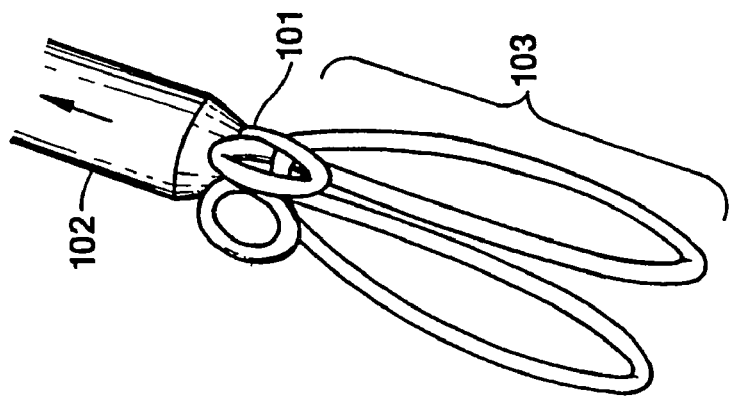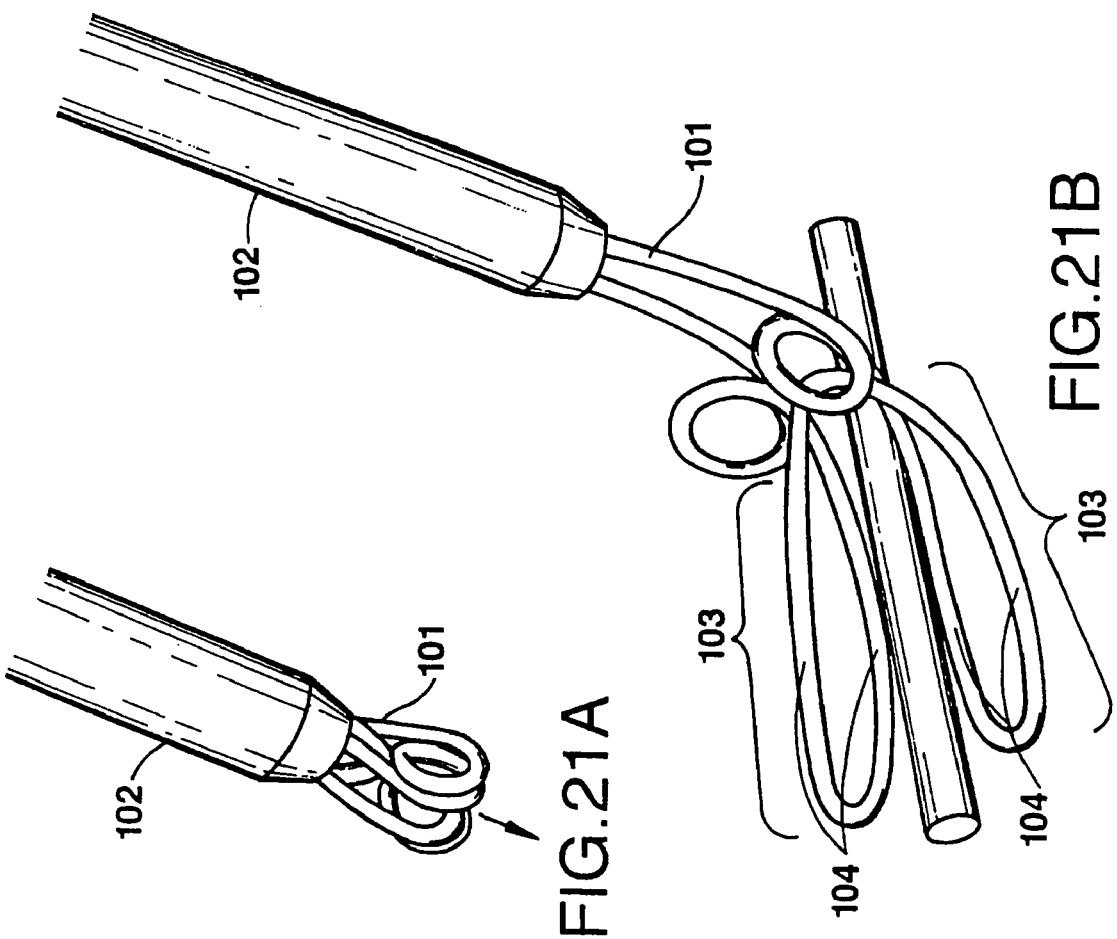

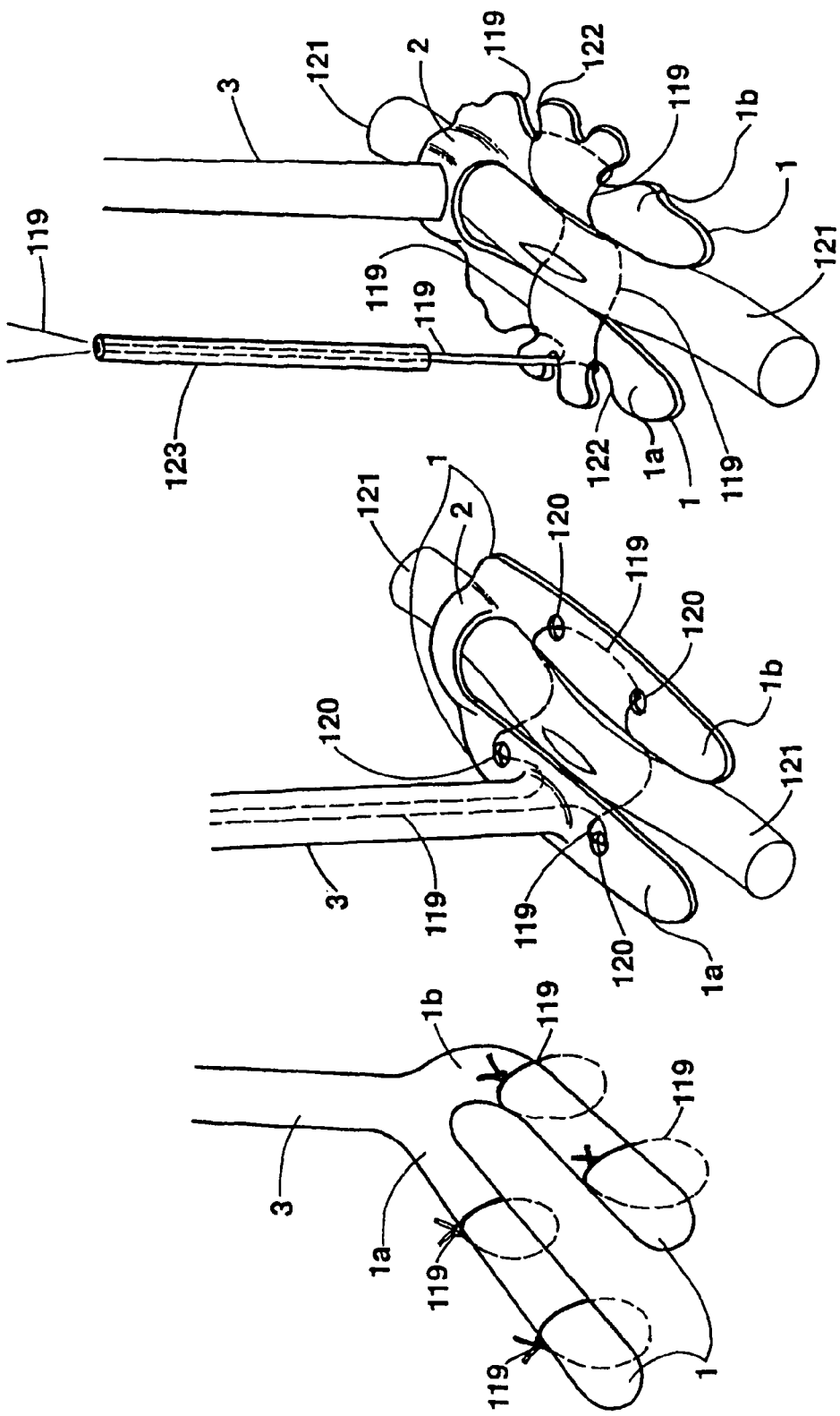

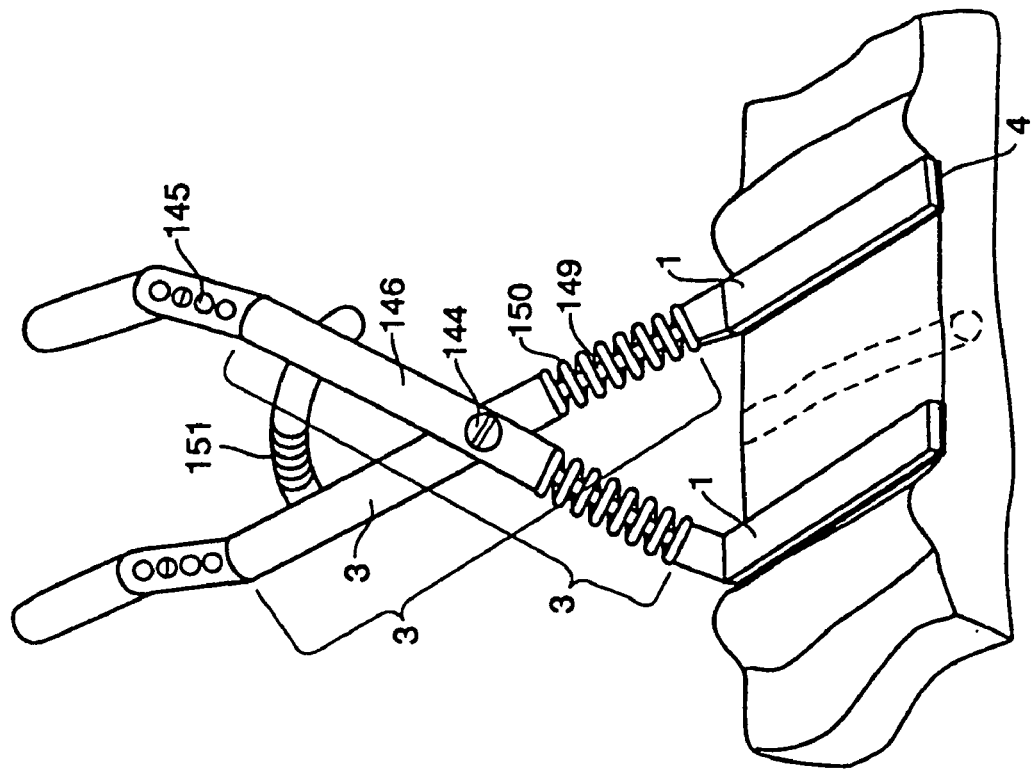
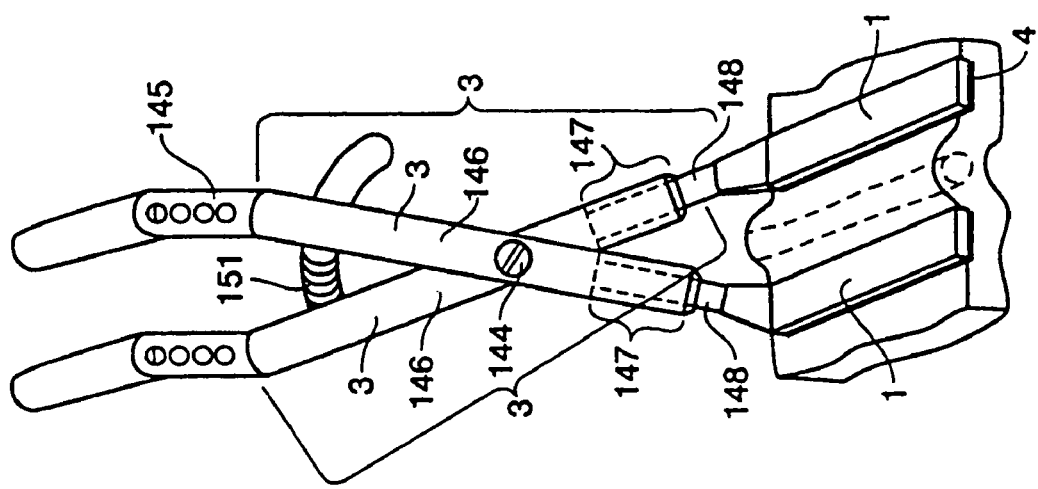
FIG. 31B
FIG. 31A

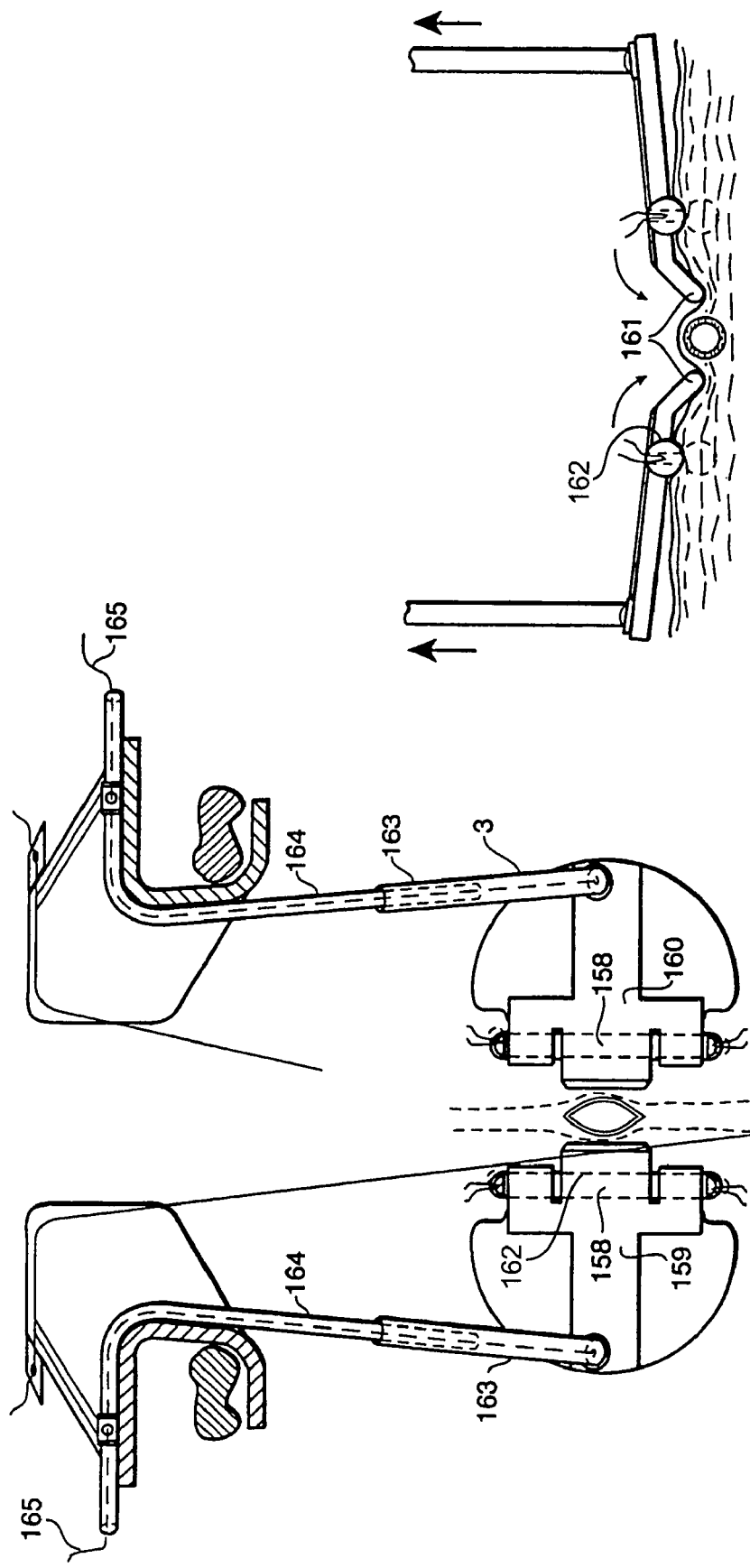

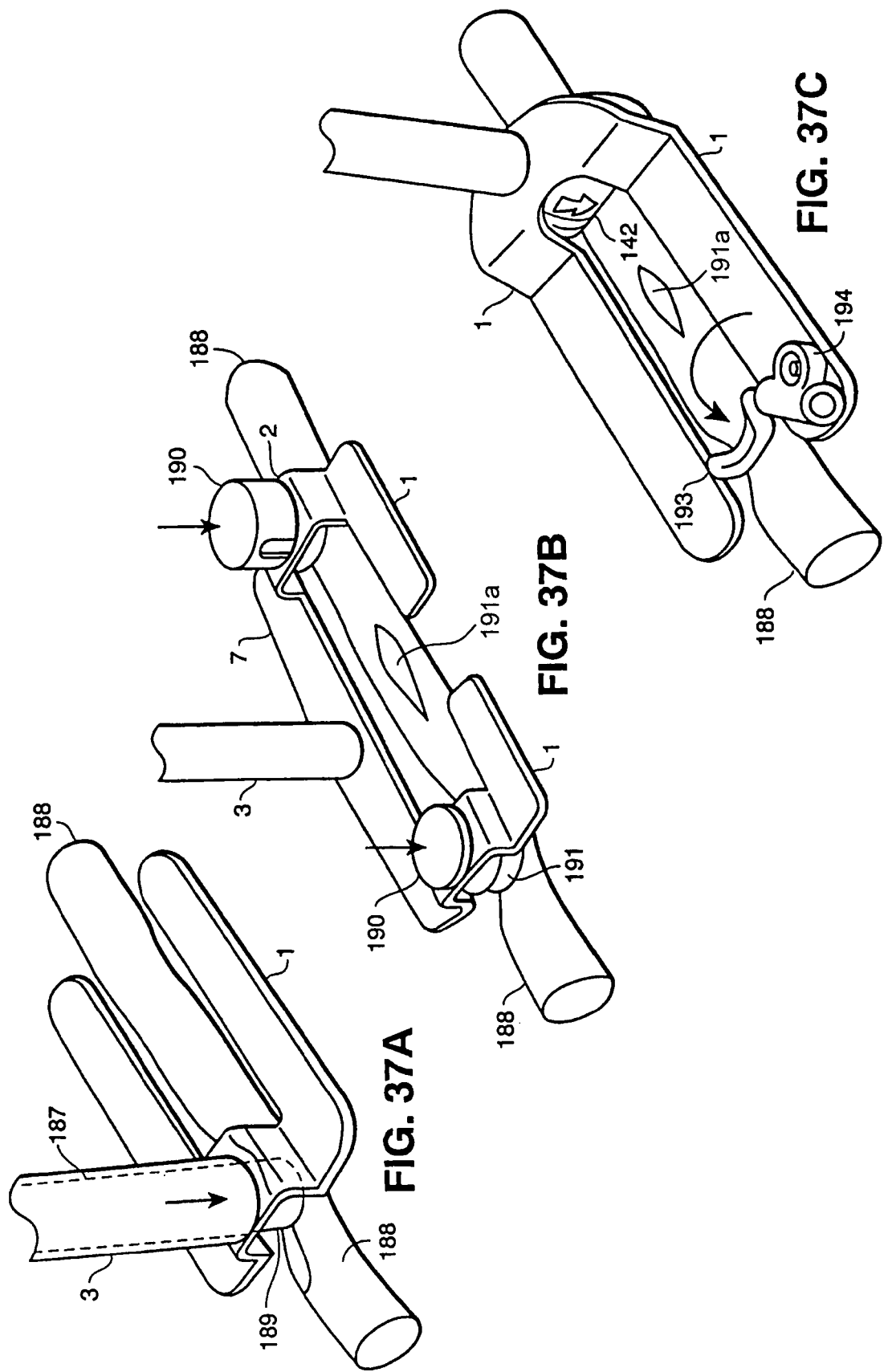

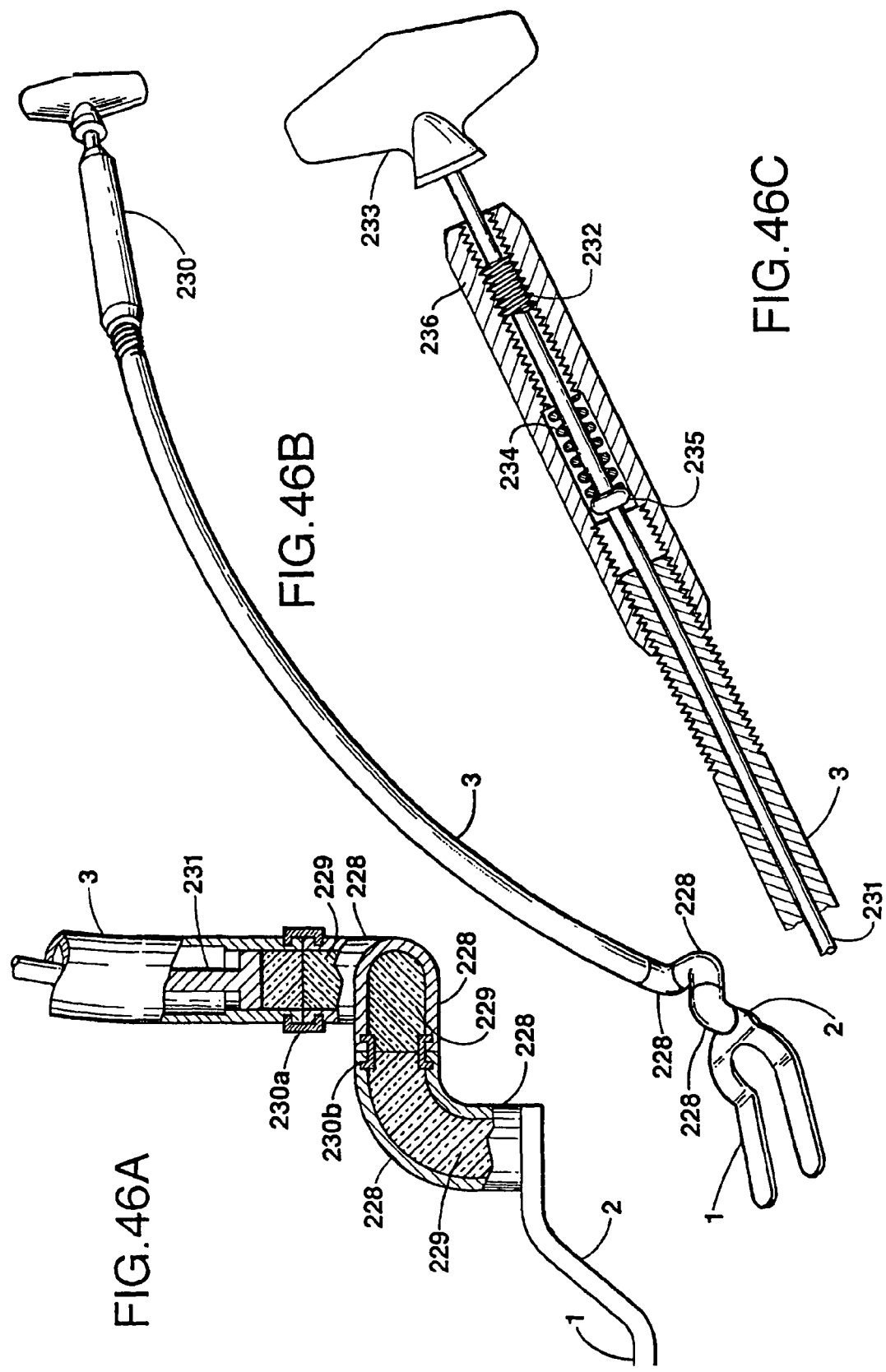

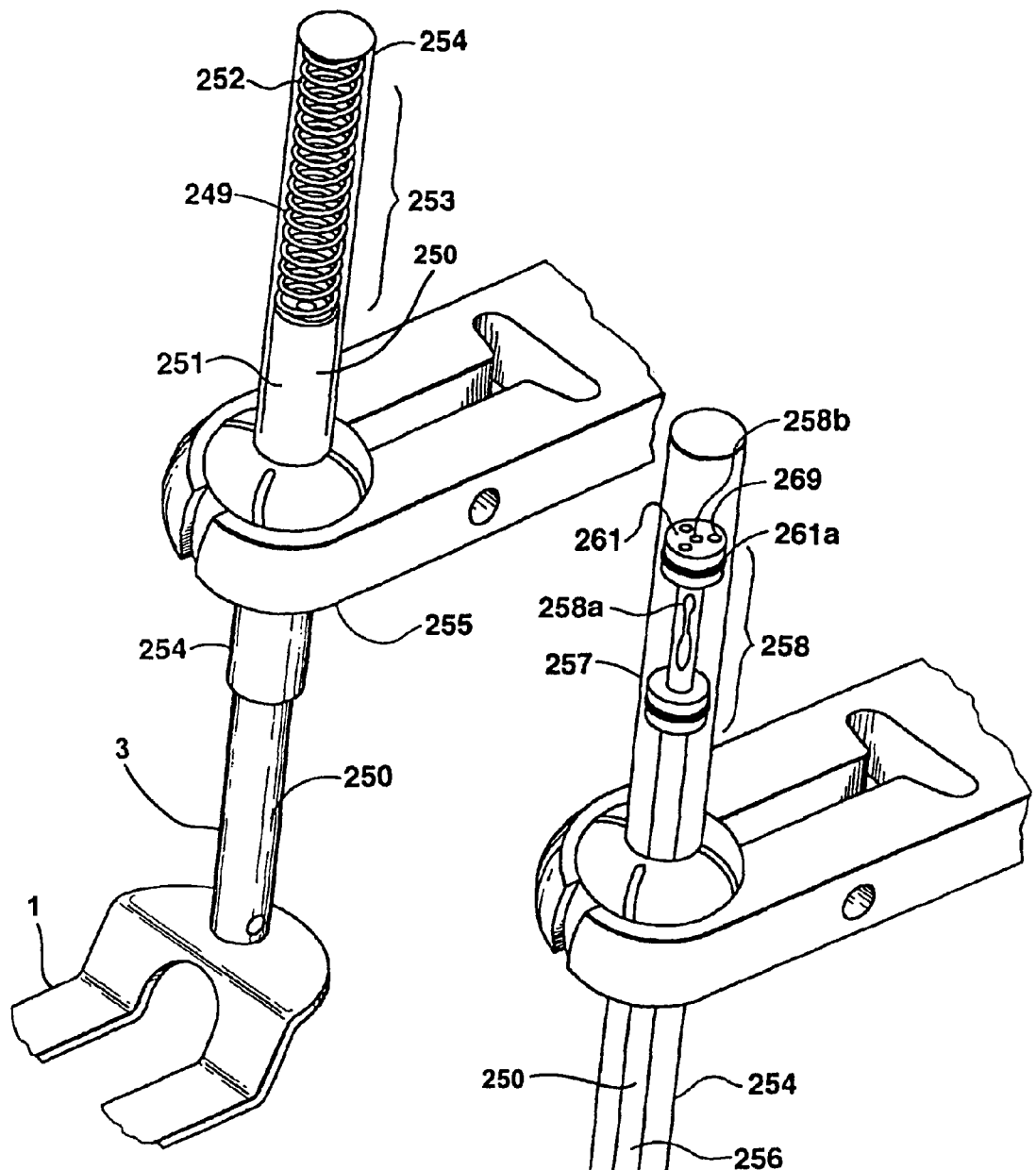
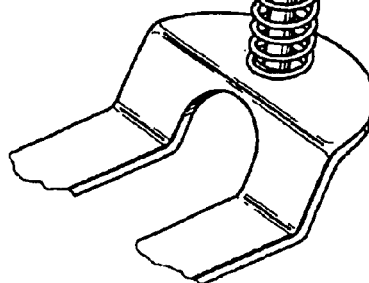

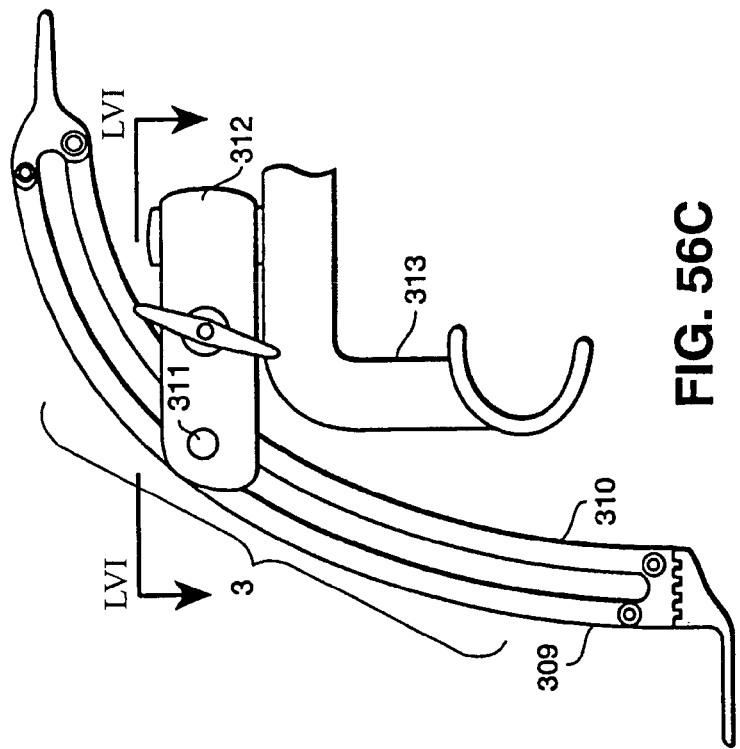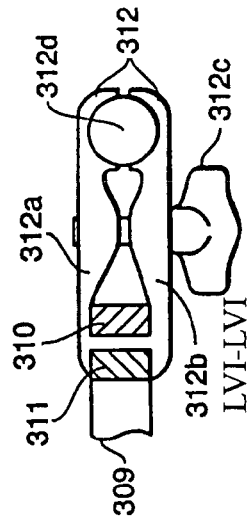
FIG. 56C
FIG. 56D
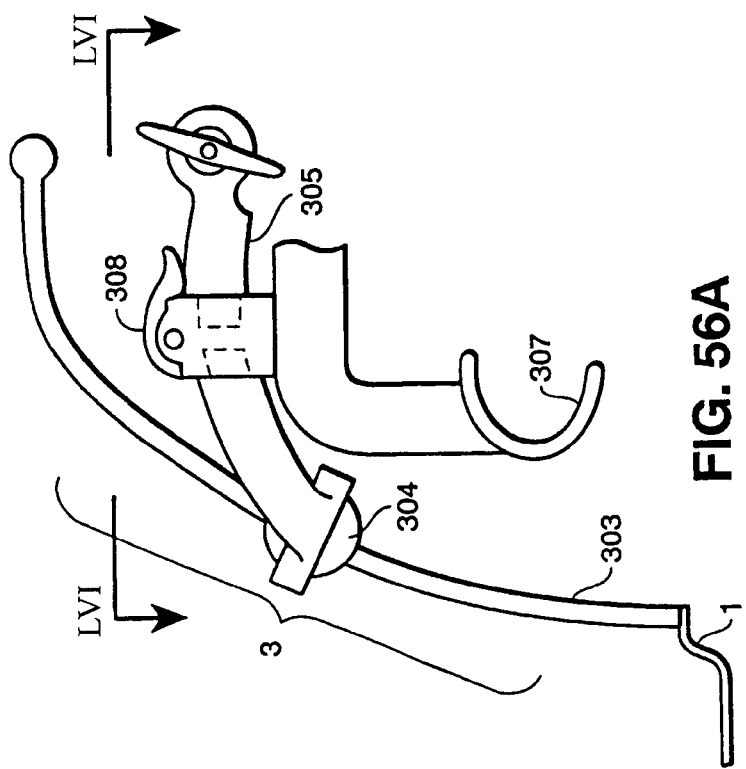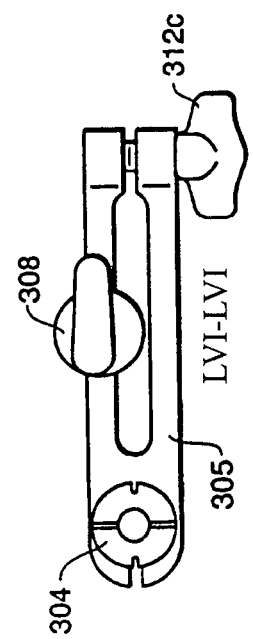
FIG. 56A
FIG. 56B

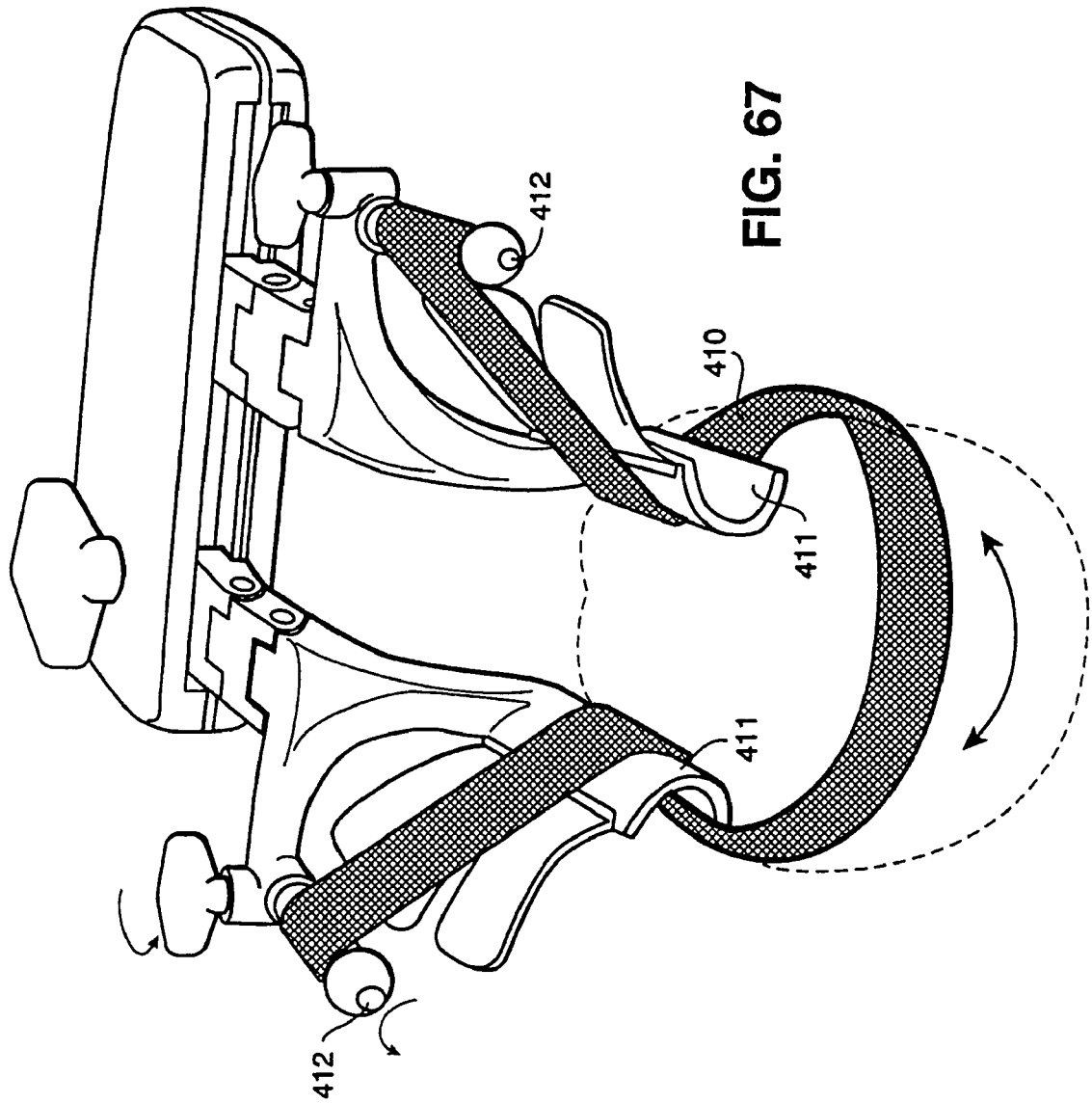

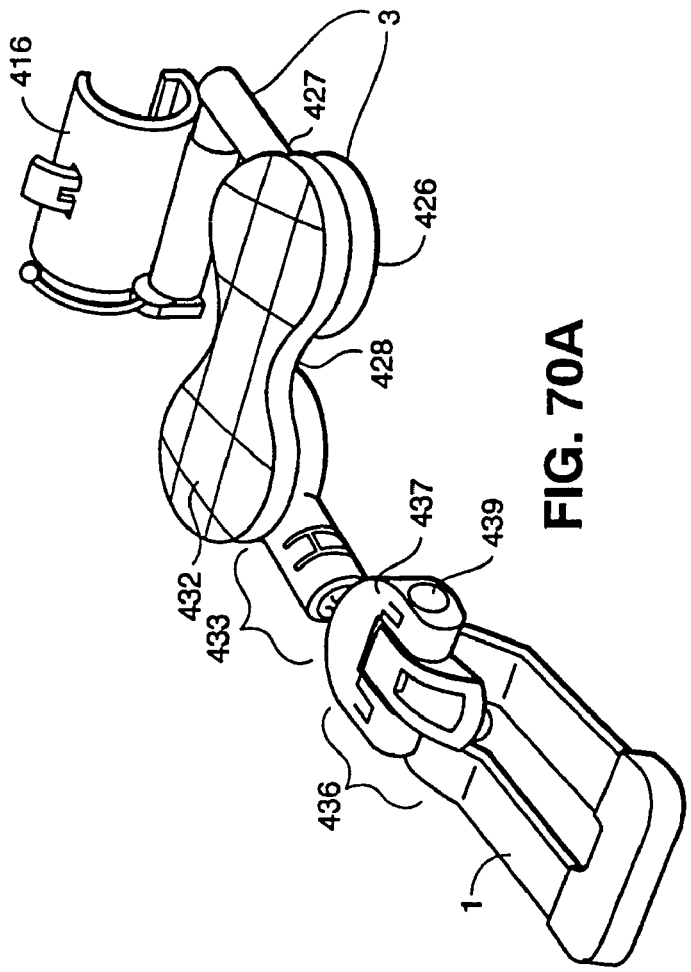
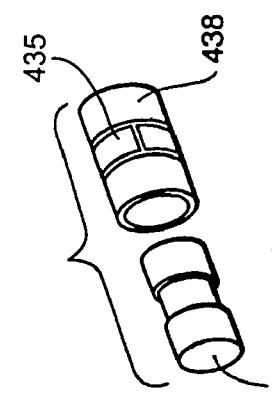
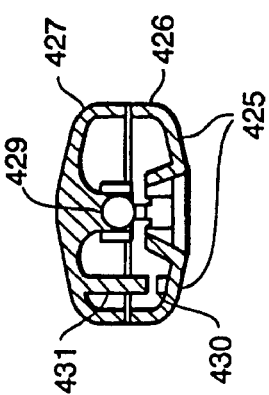
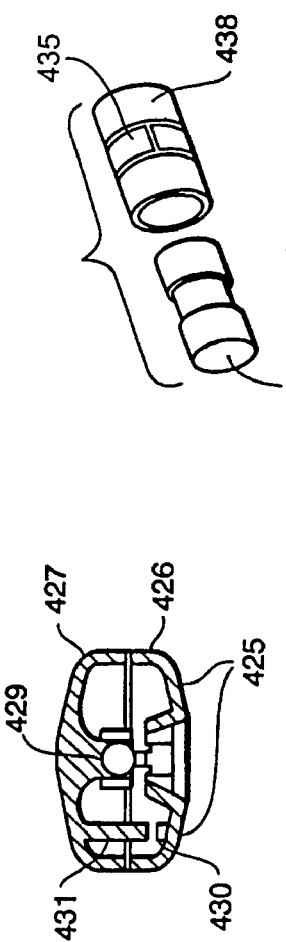
FIG. 70A
FIG. 70B
FIG. 70C
FIG. 70D

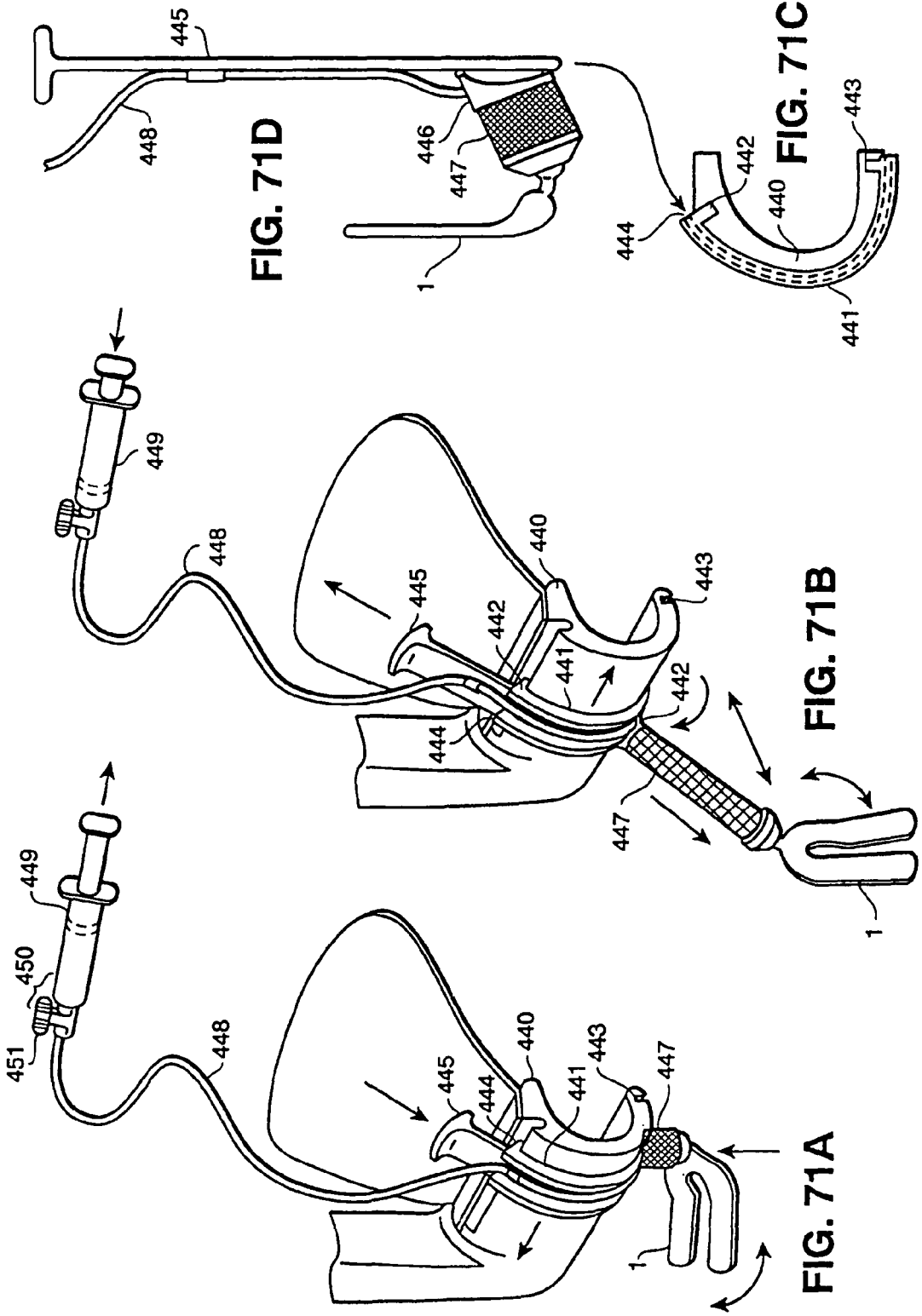

SURGICAL INSTRUMENTS AND PROCEDURES FOR STABILIZING THE BEATING HEART DURING CORONARY ARTERY BYPASS GRAFT

The present application is a continuation of U.S. application Ser. No. 09/975,392 filed Oct. 10, 2001, pending, which is a continuation of U.S. application Ser. No. 08/789,751 filed Jan. 27, 1997, which is now U.S. Pat. No. 6,346,077, which is a continuation-in-part of U.S. application Ser. No. 08/603,758 filed on Feb. 20, 1996 which is now U.S. Pat. No. 5,894,843. U.S. application Ser. Nos. 08/975,392 and U.S. Pat. Nos. 6,346,077 and 5,894,843 are hereby incorporated herein, in their entireties, by reference thereto.

Diseases of the cardiovascular system affect millions of people each year and are a leading cause of death throughout the world. The costs to society from such diseases is enormous both in terms of the lives lost and in terms of the cost of treating patients through traditional surgical techniques. A particularly prevalent form of cardiovascular disease is a reduction in the blood supply leading to the heart caused by atherosclerosis or other condition that creates a restriction in blood flow at a critical point in the cardiovascular system that supplies blood to the heart. In many cases, such a blockage or restriction in the blood flow leading to the heart is treated by a surgical procedure known as a Coronary Artery Bypass Graft (CABG) procedure, which is more commonly known as a "heart bypass" operation. In the CABG procedure, the surgeon "bypasses" the obstruction to restore normal blood flow to the heart by attaching an available source vessel to an obstructed target coronary artery or by removing a portion of a vein or artery from another part of the body, to use as a graft, and by installing the graft at points between a source vessel and a target artery to restore normal blood flow.

Although the CABG procedure has become relatively common, the procedure itself is lengthy and traumatic and can damage the heart, the cardiovascular system, the central nervous system, and the blood supply itself. In a conventional CABG procedure, the surgeon must make a long incision down the center of the chest, cut through the entire length of the sternum, perform several other procedures necessary to attach the patient to a heart-lung bypass machine, cut off the blood flow to the heart, and then stop the heart from beating in order to complete the bypass. The most lengthy and traumatic surgical procedures are necessary, in part, to connect the patient to a cardiopulmonary bypass (CPB) machine to continue the circulation of oxygenated blood to the rest of the body while the bypass is completed.

Although several efforts have been made to make the CABG procedure less invasive and less traumatic, most techniques still require cardiopulmonary bypass (CPB) and cardioplegia (stopping the heart). The safety and efficacy of the CABG procedure could be improved if the surgeon could avoid the need to stop the heart from beating during the procedure, thereby eliminating cardiopulmonary bypass and the lengthy and traumatic surgical procedures necessary to connect the patient to a cardiopulmonary bypass machine to sustain the patient's life during the procedure. In recent years, a small number of surgeons have begun performing CABG procedures using surgical techniques especially developed so that the CABG procedure could be performed while the heart is still beating. In such procedures, there is no need for any form of cardiopulmonary bypass, no need to perform the extensive surgical procedures necessary to connect the patient to a cardiopulmonary bypass machine, and no need to stop the heart. As a result, the surgery is much less invasive and the entire procedure can typically be achieved through a small number, typically one or two, comparatively small incisions in the chest.

Despite the advantages, the beating-heart CABG procedure is not widely practiced, in part, because of the difficulty in performing the necessary surgical procedures using conventional surgical instruments. If specially designed instruments were available so that the CABG procedure could be performed on the beating heart, the beating-heart CABG procedure would be more widely practiced and the treatment of cardiovascular disease in a significant patient population would be improved.

As noted above, the CABG procedure requires that a fluid connection for restoring the flow of blood be established between two points to "bypass" a diseased or obstructed area to restore blood flow to the heart. This procedure is known as an "anastomosis." Typically, a source vessel, such as a source artery with an unobstructed blood flow, i.e., the left internal mammary artery (LIMA), or a bypass-graft having one end sewn to an unobstructed blood source such as the aorta, is sewn to a target occluded coronary artery, such as the left anterior descending (LAD) artery or other vessel, that provides blood flow to the muscles of the heart. Because the beating-heart CABG procedure is performed while the heart muscle is continuing to contract and pump blood, the anastomosis procedure is difficult to perform because the heart continues to move while the surgeon is sewing the anastomosis.

The specific part of the surgical procedure that creates the anastomosis in the beating-heart CABG procedure requires placing a series of sutures through extremely small vessels on the surface of the heart and requires completing the anastomosis while the heart muscle continues to beat to pump blood during the procedure. Moreover, the sutures must be carefully placed so that the source vessel or graft is firmly attached when the anastomosis is complete and does not leak when blood flow through the vessel is established. It is also important that the anastomosis procedure be performed rapidly because the blood flow through the target coronary artery may be temporarily interrupted or reduced to avoid excessive blood loss. Also, the working space and visual access are limited because the surgeon may be working through a small incision in the chest or may be viewing the procedure on a video monitor if the site of the surgery is viewed via a surgical scope.

In one current practice, the surgeon places sutures through the heart tissue and, by exerting opposing tension on the sutures, stretches the tissue surrounding the site of the anastomosis to partially reduce the motion of the heart while the anastomosis is completed. This approach is far from ideal. Alternatively, a suction device may be attached to the surface of the heart to fix the motion of the outer layer of surface tissue. In such cases, a suction device typically has several ports incorporated into an instrument that may be attached to the heart to apply a negative pressure to the surface tissue. The negative pressure essentially attaches the surface tissue to the apparatus thereby fixing the position of a portion of the surface of the heart Such devices are described in co-pending United States patent application no. 603,328.

While the negative pressure approach may be effective in fixing a portion of the surface tissue of the heart, the negative pressure applied to cardiac tissue can result in temporary hematomas at the site where the suction ports attach to the tissue. Also, the exterior cardiac tissue is fixed in a configuration defined by the shape of the instrument and the orientation of the suction ports. While the heart continues to beat, the heart muscles are contracting to pump blood, which results in the muscles exerting a force directed away from the exterior tissue fixed by suction.

The beating-heart CABG procedure could be greatly improved if the heart could be stabilized during the procedure such that the motion of the heart, particularly at the site of the anastomosis, is minimized even though the heart continues to beat to supply blood to the body. If effective means for stabilizing the beating heart were available, the beating-heart CABG procedure could be performed more easily, more rapidly, more safely, and with less trauma to the patient.

SUMMARY OF INVENTION

The advantages provided to a surgeon by the instruments and techniques of the invention allow the beating heart CABG procedure to be performed more rapidly, with less trauma to the patient, and enable a surgeon to perform a CABG procedure without CPB or cardioplegia. This invention provides an alternative approach to a suction apparatus by providing devices and methods for stabilizing the motion of the heart using mechanical instruments specially designed to apply a stabilizing force to the heart to minimize the motion of the beating heart during a surgical procedure. The invention enables a surgeon to readily and rapidly perform a beating-heart CABG procedure thus avoiding the need for cardioplegia or cardiopulmonary bypass. In particular, the methods and devices described herein enable the surgeon to stabilize the heart such that an anastomosis can be more readily accomplished by enabling the surgeon to attach a source vessel or bypass graft to a target coronary artery whose motion is minimized for the duration of the surgical procedure.

Pursuant to the invention, a stabilizing device is introduced through a suitable opening in the chest that provides access to the beating heart. By contacting the heart with the means for stabilizing the beating heart of this invention, and by exerting a stabilizing force on the heart, the motion of the heart caused by the contraction of the heart muscles is effectively eliminated such that movement of the target artery at the site of the anastomosis is minimized. The remainder of the heart may be allowed to contract normally or may have additional devices in place to support the heart or to restrain its motion. Additionally, several of the devices of the invention may be used to position the beating heart to provide an improved surgical field, to maintain the heart in a preferred configuration for surgery, or to rotate the heart to present distinct features of the heart to the surgeon's visible and accessible surgical field.

An important advantage of this invention is derived from the discovery that a new and effective technique can be described herein and performed in surgery using the devices of the invention to provide an advantageous technique for stabilizing or positioning the beating heart during a surgical procedure. The procedure for stabilizing the beating heart generally requires exerting a stabilizing force on the beating heart using devices constructed as described herein Typically, in separate steps, the surgeon contacts the heart with at least one component of the means for stabilizing the beating heart of this invention, assesses the degree of movement of the heart, particularly at the site of the surgery, and positions the component of the stabilizing means proximate to the site of the surgery such as a target coronary artery of an anastomosis. With the functional portion of a stabilizing means in place, the surgeon applies a stabilizing force to the beating heart such that the portion of the instrument in contact with the surface of the heart displaces the surface of the heart a sufficient distance that the contraction of the heart does not cause substantial motion, either vertical or horizontal, at the surgery site. The stabilizing force is applied directly or indirectly using at least one component of the stabilizing means of the invention and is comprised of exerting a mechanical force onto the beating heart, generally at a specific location such as a target coronary artery and generally exerting force that is at least partially applied in a direction perpendicular to the surface of the beating heart. Thus, an important aspect of this invention is the discovery that the beating heart may be effectively stabilized for the purpose of a surgical procedure by using a specially designed instrument as described herein to exert a mechanical stabilizing force on the exterior of the heart, particularly where the force is exerted proximate to the site of the surgery. The stabilizing force may consist of a force that resists the motion supplied by the beating heart, or additional forces applied to the heart, or the stabilizing force.

By fixing the position of the stabilizing means in a configuration where the motion of the beating heart is effectively eliminated, the surgeon maintains the stabilizing force on the beating heart for the duration of the procedure. To fix the position of the means for stabilizing the beating heart, the stabilizing means may be attached to a retractor used to separate the ribs or to another fixed support. The stabilizing means may also be attached to a comformable, flexible, or semi-rigid arm or shaft means which is rendered substantially rigid mechanically, chemically, or by human intervention. In certain preferred embodiments, the stabilizing means has an adjustable shaft means which may be oriented in several directions and has a fixture adapted to be attached to a retractor. In a preferred technique of the invention, the surgeon first performs a thoracotomy and retracts the ribs using a retractor, which may then be locked in an open position providing access to the beating heart. The surgeon then contacts the surface of the heart with a component of the stabilizing means, which has been provided with an adjustable shaft, at a point proximate to the target coronary artery, and exerts a stabilizing force on the means for stabilizing the beating heart. By manipulating the adjustable shaft, the site of the surgery will become substantially motionless. This force may be advantageously applied, and the absolute amount of force minimized with the additional feature of an adhesive or high-friction surface on the component of the stabilizing means that contacts the beating heart. At this point, the adjustable shaft means is fixed in position, for example by being stably attached to the retractor, thereby rendering the target coronary artery substantially motionless for the duration of the procedure.

DESCRIPTION OF THE FIGURES

FIG. 1 is a means for stabilizing the beating heart having a pair of substantially planar contact members which are oriented to engage the heart proximate to the site at which a bypass will be sewn. FIG. 1 also shows the contact members attached to a shaft means which ma be adjustable in several directions and which may be attached to a retractor or other fixed support structure. FIG. 1A is a detail of the shaft means and the structure of the adjustable positioning mechanisms.

FIGS. 4A through 4C are an embodiment of the invention having weighted contact members that engage the beating heart, and which may be part of a system to achieve stabilization of the heart by applying a stabilizing force via a balanced mass having an adjustable weight and counterweight configuration. FIG. 4A shows the weighted contact member in cross section. FIG. 4B is the contact members having an opening disposed therebetween for positioning of a vessel. FIG. 4C shows the contact member coupled to a shaft that is affixed to a fulcrum having an adjustable weight and a counter-weight.

FIGS. 7D and 7E are an embodiment of the invention wherein the contact members are formed from the distal portion of a shaft means for minimally invasive applications. FIG. 7E shows an interconnecting member for joining the distal portions of the shaft means.

FIGS. 9A through 9G are embodiments of the invention where a positive or negative pressure is provided proximate to the contact members.

FIGS. 10A through 10C are embodiments of the invention where a surgical drape is operably associated with the contact members to provide an isolated visual field.

FIGS. 13A through 13E are a cannula assembly preferred for providing minimally invasive access for the stabilizing means of the invention. FIG. 13A has screws for attaching the cannula assembly to the chest wall. FIG. 13B has a threaded portion about the periphery of the cannula. FIGS. 13C through 13E are a locking mechanism designed to engage adjacent ribs.

FIGS. 16A through 16E are an embodiment of the invention design for minimally invasive insertion and removal of flexible contact members whereby the contact members are maintained in a retracted state within a hollow portion of a shaft and are deployed upon extension of a central shaft.

FIGS. 17A through 17D are an additional embodiment providing minimally invasive insertion and removal of the contact members of the invention whereby individual contact members are rotated into position by a hinge at the distal end of a shaft.

FIGS. 21A through 21C are an embodiment having contact members formed from a unitary wire which is looped such that when extended from a body of the device, the contact members are deployed, and may be removed in a minimally invasive fashion by withdrawing a portion of the wire into the body of the device.

FIGS. 26A through 26C are contact members having sutures associated therewith for manipulation of a target artery.

FIGS. 31A and 31B are embodiments of the stabilizing means having a single shaft means associated with each contact member and where the shaft means are interconnected and can be moved independently about a pivot such that the contact members spread the surface tissue of the heart proximate to the target coronary artery to increase exposure of the target artery at the site of the anastomosis.

FIGS. 33A and 33B are means for stabilizing the beating heart comprising a system which incorporates the retractor which spreads the ribs to provide surgical access to the heart. The stabilizing means is comprised of a pair of stabilizing plates which may be used together with a lever device to improve exposure of the target coronary artery.

FIGS. 37A through 37C are contact members having structures associated therewith for occluding the target coronary artery.

FIGS. 46A through 46C are an embodiment of the invention where a series of adjustable links have a elastomeric hydraulic median disposed therein and where application of force causes the elastomeric hydraulic median to become rigid and fixes the position of the adjustable links.

FIGS. 50A and 50B are embodiments of the shaft means having spring-loaded or air-damping mechanisms to restrict the vertical motion of the shaft relative to a stable support.

FIGS. 56A through 56D are a shaft means of the invention having mechanisms for adjustable positioning of the shaft relative to a stable support.

FIG. 67 is a stabilizing means formed from a movable sheath member that is attached at either end to cranks mounted on the arms of a retractor.

FIG. 70A through 70D are an embodiment of the invention having a conformable arm comprised of a plurality of friction joints that are engaged when the motion of the beating heart presses against the contact member.

FIGS. 71A through 71D are an embodiment of the invention having a contractible shaft attached to a flexible slide. The flexible slide is designed to be inserted into a seed-shaped clip which may be attached to a retractor blade. The contractible shaft is extended to engage the beating heart by application of hydraulic pressure, for example, by a syringe that is preferably supplied with a one-way releasable valve.

DETAILED DESCRIPTION OF THE INVENTION

Figure 1B:
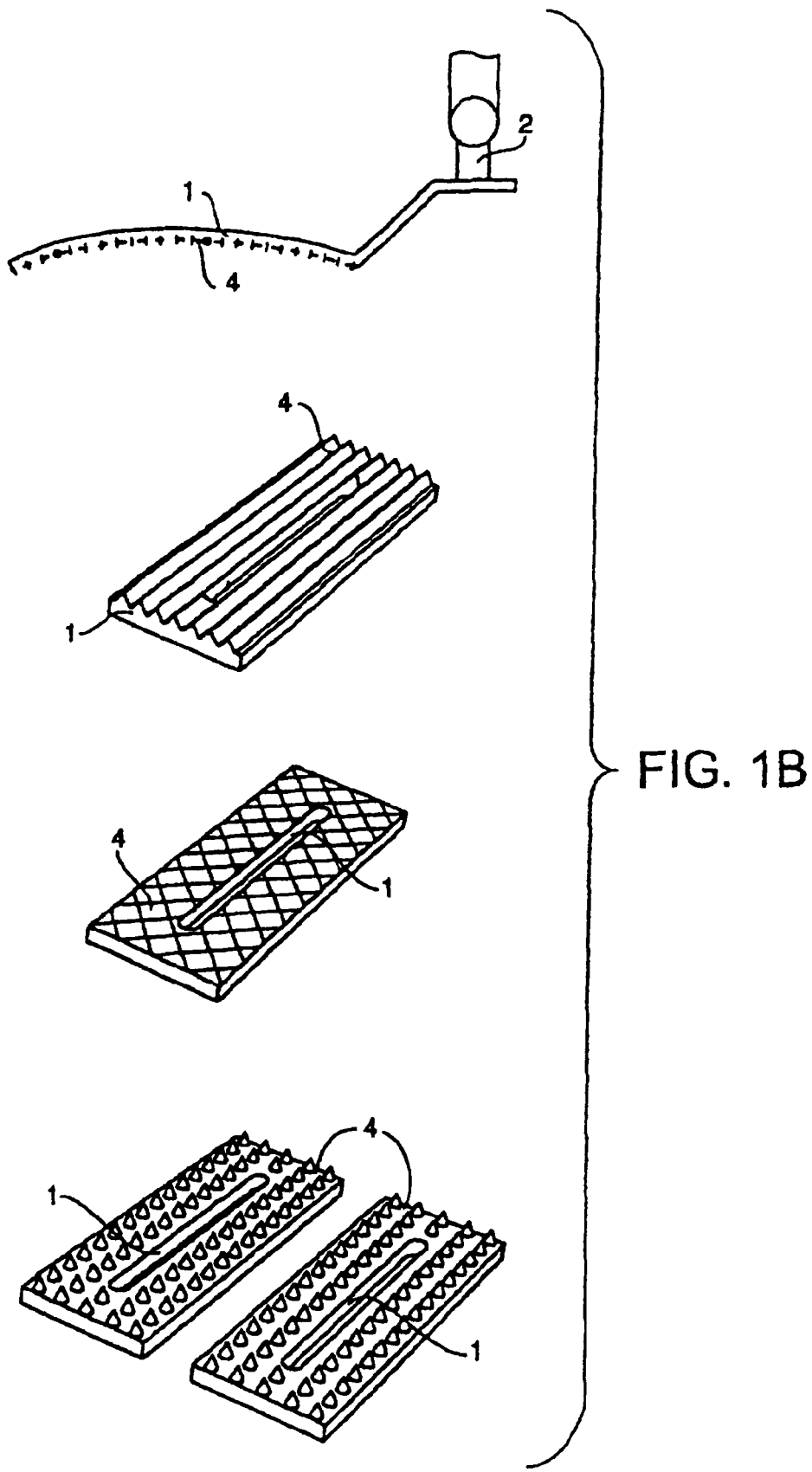
FIG. 1B through 1G are various configurations of a contact member having a friction means which is preferably affixed to the bottom surface of the contact member.
Figure 1D:
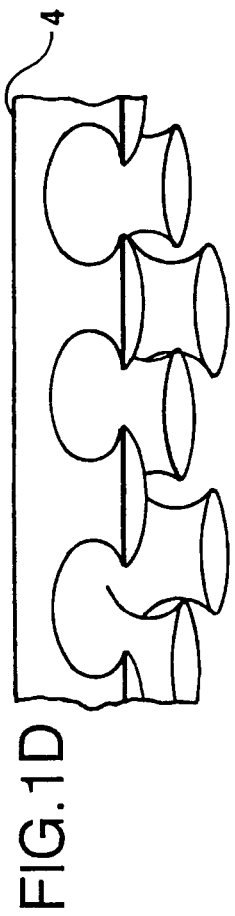
Figure 1E:
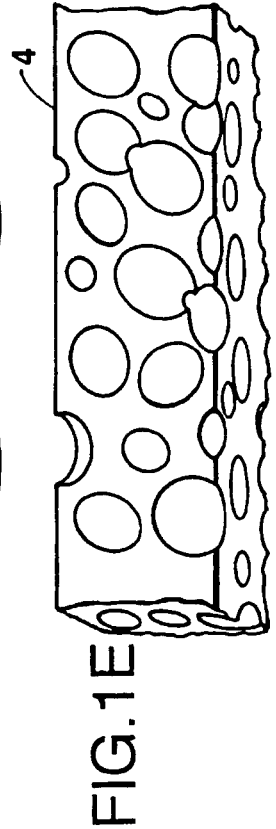
Figure 1F:
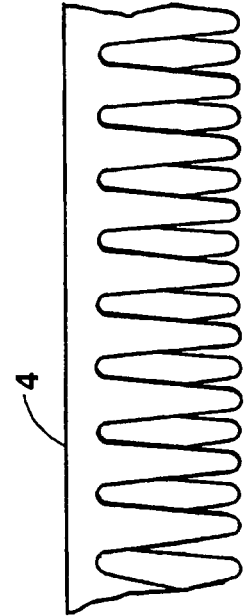
Figure 1G:
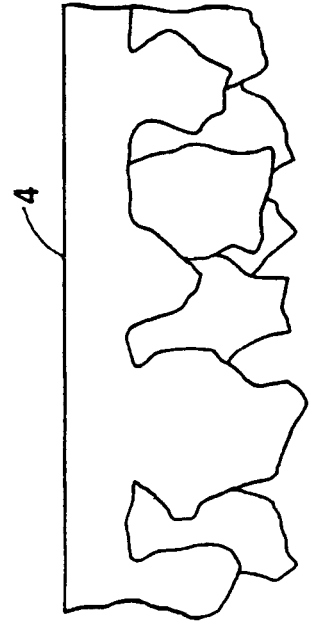
Figure 1C:
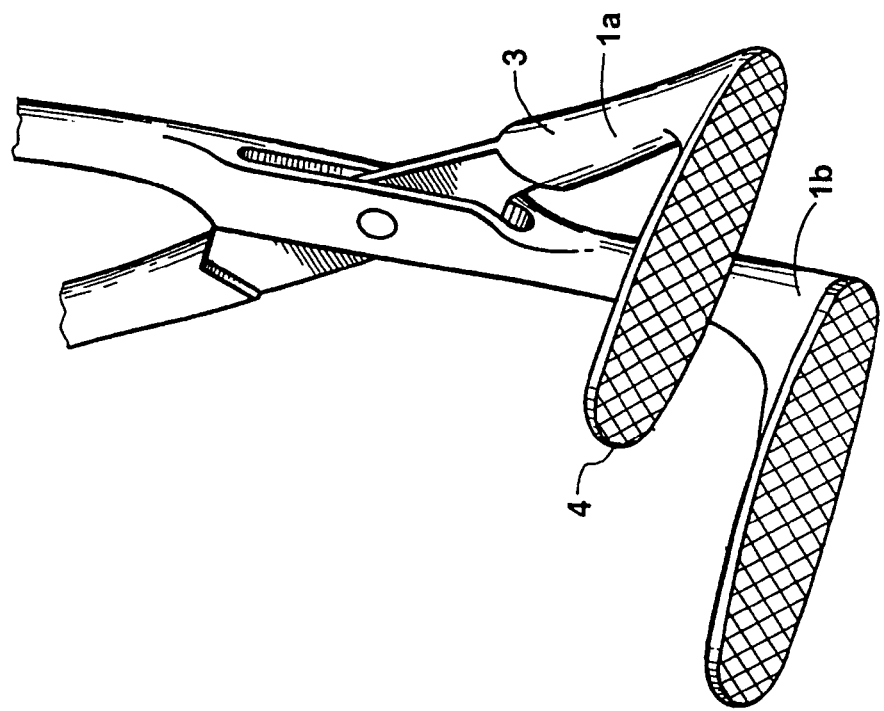

This invention is surgical instruments for stabilizing the beating heart and methods for their use. The means for stabilizing the beating heart are comprised of several alternative structures at least one component of which engages the surface of the heart to stabilize the beating heart during coronary surgery. The instruments provide the capability to exert and maintain a stabilizing force on the heart by contacting the heart with a component of the stabilizing means and by functionally fixing the position of the stabilizing means throughout the duration of a surgical procedure.

The instruments and methods of the invention are preferably used for stabilization of the beating heart during a minimally invasive coronary artery bypass graft (CABG) operation which has been specially developed to facilitate completion of an anastomosis, to a target coronary artery for example by the placement of a bypass graft or the connection of a source artery, without requiring cardiac arrest such as cardioplegia or fibrillation and without cardiopulmonary bypass (CPB). Although the means for stabilizing the beating heart can be applied in different surgical contexts, the devices described herein are most advantageously employed in a CABG procedure wherein only one or two minimally invasive incisions are placed in the chest. The complete structure of the stabilizing means of the invention may be provided by any of several structural embodiments which stabilize the beating heart while the minimally invasive surgical procedure is performed. Discrete components of the stabilizing means may also advantageously function in a multiple component system containing a retractor, an occluder, a surgical blower or suction device, an apparatus for holding the source artery, such as a LIMA holder, or other like discrete or integrated surgical devices or instruments that enable a surgeon to more efficiently complete the anastomosis. While the devices disclosed herein each use mechanical means to stabilize the beating heart, certain embodiments are designed to operate on the entire heart while others have a more localized effect and may be applied to the area immediately proximate to a structure such as the target artery of the anastomosis. In each instance, the beating heart is effectively stabilized at the area where a surgical procedure is to be performed.

Surgical access to the beating heart may be achieved by several conventional surgical procedures which have been developed for traditional cardiac bypass surgery and the surgical may thereby obtain the advantages provided by this invention in any procedure where the bypass is achieved on the beating heart without regard to the surgical method of access to the heart. Preferably, the surgeon takes additional measures to restrict the movement of the entire heart within the chest cavity and may utilize certain embodiments disclosed herein to position or orient the beating heart. For example, an adjustable strap which may have inflatable cushions attached to the straps, or having laces may be inserted beneath or surrounding the heart. When access to the beating heart is achieved by a sternotomy, at least part of the length of the sternum is divided to expose the surface of the heart. Additionally, when the pericardium is available, the pericardium may be incised and used to position the beating heart. When available, the surgeon can use the pericardium to raise and rotate the beating heart within the chest cavity and maintain the position by suturing the pericardium to the periphery of the incision.

In a preferred embodiment, minimally invasive access to the beating heart is achieved by a thoracotomy, which is usually created in the left side of the chest by a smaller incision between the ribs, followed by insertion of a retractor between the ribs, spreading of the ribs, and securing the retractor in an open position to provide access to the source vessel and the target coronary artery. The use of the pericardium to position the beating heart as described above is particularly advantageous when the less invasive thoracotomy is used to provide access to the heart. In this procedure, an incision is created in the pericardium, which is then sutured to the periphery of the thoracotomy. In this configuration, the pericardium acts as a restraining sack to keep the beating heart in a desired orientation to achieve the anastomosis.

Once access to the heart is achieved, and the heart is positioned if necessary, the means for stabilizing the beating heart is introduced through the opening created by the thoracotomy and at least one component of the stabilizing device of the invention is brought into contact with the beating heart. The surgeon then applies a stabilizing force to the beating heart via the stabilizing means which may then be fixed in place by attachment to a fixed support. When the rib retractor or platform is fixed in an open position to expose the heart, the retractor platform may also provide the stable support structure to which the stabilizing means is affixed. When the position of the stabilizing means is fixed by attachment to a stable support or to the retractor platform, the stabilizing force is maintained for the duration of the procedure.

Although the particular source vessel and target artery of the anastomosis are determined clinically, a common minimally invasive bypass procedure on the beating heart includes an anastomosis which forms a connection between the left internal mammary artery (LIMA) as the source artery, and the left anterior descending artery (LAD) as the target artery. The LIMA to LAD anastomosis is used as an example herein but it is readily appreciated that the techniques and instruments described herein may be applied to other procedures depending on the clinical diagnosis and a patient's anatomy. To complete the anastomosis, the surgeon must dissect a portion of the LIMA by separating it from the internal chest cavity. Once dissection of the LIMA is achieved, the surgeon may attach the dissected LIMA to the target coronary artery, i.e., the LAD. In this example, the stabilizing means of this invention would be used to stabilize the beating heart during at least the portion of the procedure during which the surgeon completes the anastomosis of the LIMA to the LAD.

The structure of the portion of the stabilizing means which contacts the heart may include one or more contact members which exert a stabilizing force on the heart proximate to the site of the anastomosis. A pair of contact members may be plates or rectangular members which are placed on either side of the target coronary artery at the site of the anastomosis and which may have friction means or tissue spreading or compressing apparatus associated therewith. The contact members may also be provided by a platform which may be substantially planar or which may be contoured to fit conformingly on the surface of the heart. The stabilizing means may also include a shaft means having several alternative embodiments to facilitate adjusting the position and orientation of the instrument. For example, the shaft means may have an adjustable length and the axis of the shaft means may have at least one ball joint disposed within its length such that the orientation of the shaft means relative to another structure such as the contact members or stable support may be continuously varied. As is apparent from the description of the several embodiments, each of the individual embodiments described and illustrated herein has discrete components and features which may be readily separated from or combined with the features of any of the other several embodiments without departing from the scope or spirit of the invention.

Referring to FIG. 1, a means for stabilizing the beating heart is comprised of one or more, and preferably two, contact members 1, which are attached to a rigid, or semi-rigid connecting shaft 2 which is in turn connected to shaft means 3. The contact members 1 may be substantially planar, may be slightly curved to conform to the shape of the heart, or may be a non-conforming curve to establish contact between only a portion of the contract member 1 and the beating heart. The contact members 1 may have any of several alternate shapes including cylindrical members, members formed into a U-shape, or may comprise a pair of substantially parallel members spaced apart in a parallel configuration such that a target artery can be positioned between the contact members. The shape of the contact members may be varied depending on the clinical assessment by the surgeon, the design of the other features of the stabilizing means, or the design of other instruments used to complete the anastomosis. In some embodiments, as described herein, the contact members 1 may have apertures, openings or attachments to facilitate connection with sutures or other devices to achieve the requisite stabilization, occlusion of the target vessel, or exposure of the target vessel. In a preferred embodiment, a pair of substantially planar rectangular contact members 1 are attached at one end to a continuous connecting shaft 2 and are oriented in a substantially parallel fashion such that a target cardiac artery is positioned therebetween and passes along the greater length of the contact members 1 when the stabilizing means engages the heart. See FIGS. 72 through 74. The connecting shaft 2 may be a continuous shaft for interconnection of the contact members 1 without touching the artery or may include an additional member which may be operated to contact the target artery positioned between the contact members 1, see FIGS. 36 through 38, to occlude the passage of blood through the target artery. The contact members 1, connecting shaft 2, and shaft means 3 may be composed of any non-toxic material such as a biocompatible plastic or stainless steel, having sufficient tensile strength to withstand a stabilizing force exerted on the heart via manipulation or fixation of the shaft means 3 to cause the contact members 1 to exert a stabilizing force on the beating heart. Also, while the contact members 1 may each be connected to the connecting shaft 2 at one end, with the connecting shaft 2 operably attached to the shaft means 3, each of the individual contact member embodiments described and illustrated herein has discrete features which may be readily separated from or combined with the features of any of the other several embodiments, such as differing designs of the shaft means, or other components of the invention by one of ordinary skill in the art.

The shaft means 3 may be a simple rigid post or may be comprised of a multi-component system designed to be adjustable in length and orientation at least one point along its length. Thus, the length of the shaft means 3 and the orientation of the contact members 1 at the distal (lower) end of the shaft means 3 can be altered by the surgeon. Preferably, the length and orientation at the shaft means 3 relative to the contact members 1 can be adjusted by controls located at the proximal (upper) end of shaft means 3. (As used herein, the term "distal" refers to a portion of a device most proximal to the heart while the term proximal refers to the opposite portion which may extend outside of the incision and which is most often readily manipulated by the surgeon). This design provides the advantage that the surgeon can introduce the stabilizing means to the beating heart by placing the contact members 1 on the surface of the heart, followed by the combination of exerting a stabilizing force and locking the contact members 1 in place relative to the shaft means 3. Furthermore, the surgeon may then lock the shaft means 3 into a fixed position by attachment to a stable support such as the retractor, thereby maintaining the stabilizing force for the duration of the procedure. In one embodiment, the shaft means 3 has a housing 11 whose overall length is adjustable by a telescoping release operated by an annular thumbscrew 8 which tightens about the housing 11. The position and orientation of the contact members 1 relative to the shaft means 3 is adjustable by virtue of a locking ball joint 5 which is interposed between the connecting shaft 2 and which is located at the distal end of shaft means 3. The locking ball joint 5 allows the position of the shaft means 3 to be positioned with three degrees of freedom relative to the contact members 1.

Referring again to FIG. 1, a locking ball joint 5 is provided by including a block 6 within the shaft means 3 which conformingly contacts the ball joint 5 and fixes the position of the ball joint 5. Block 6 is compressed against ball joint 5 when a threaded push block 7, connected to a long telescoping keyed shaft and socket combination 9, and is actuated by means such as a thumbscrew 8 at the upper end of the shaft means 3. In operation, a rotation of the top thumbscrew 8 loosens the lower ball joint 5 to allow continuous positioning of the shaft means 3 relative to the contact members 1, and a counter-rotation locks the ball joint 5 into place, fixing the position of the contact members 1 relative to shaft means 3.

The upper end of shaft means 3 may also have associated therewith an upper ball joint 13 such that the shaft means 3 can be oriented with four degrees of freedom relative to a fixed support such as a retractor (not shown). The position and orientation of the shaft means 3 may thus be fixed relative to the stable support by a locking latch 14 or other conventional mechanism which prevents movement of the upper ball joint 13. Either the shaft means 3 or the retractor may contain the locking latch 14 surrounding the upper ball joint 13 or any like fixture to firmly attach the shaft means 3 to a stable support, e.g., an anchor portion 15 extending from the retractor (not shown).

Referring to FIGS. 1B through 1G, the contact members 1 preferably have friction means associated with their bottom surface 4 such that the contact members 1 more securely engage the beating heart when a stabilizing force is exerted on the shaft means 3. The friction means are preferably comprised of a textured surface covering the bottom surface 4 of the contact member 1, and may be comprised of several bio-compatible substances such as a textured rubber, textured or ridged aluminum, stainless steel or the like.

The friction means may also be affixed to or comprised of a member disposed between the bottom surface 4 of the contact members 1 and the surface of the beating heart. In these embodiments, the friction means is provided to facilitate stabilization of the beating heart by maintaining close and conforming contact between the contact member 1 and the beating heart and reducing the amount of force necessary to be applied to the exterior of the beating heart in order to achieve stabilization. Referring to FIGS. 1B and 1D through 1G, any number of different configurations and may have a textured surface in a diamond plate, granular, nail-bed, anti-skid, open foam, or other friction-providing configuration. The geometric configuration of the surface, having one side affixed to the contact member 1, may be flat, triangular, rectangular, square, or circular. Alternatively, surfaces providing a functional adhesive may be obtained using hydrogel, fibrogen, collagen, hydroxy epitate, or other biocompatible material and may be chemically etched, mechanically scored, or electrically activated.

Figure 2:
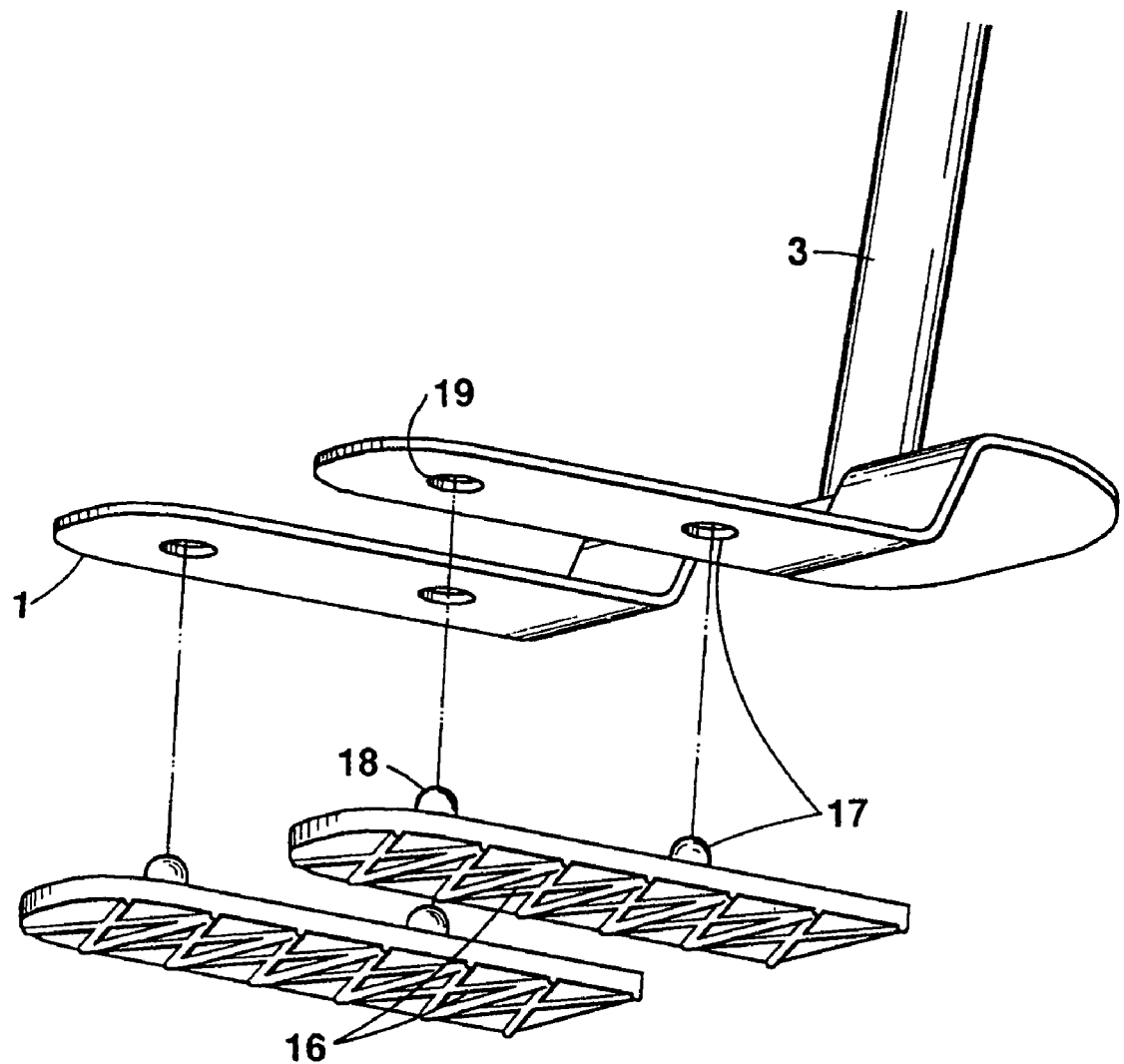
FIG. 2 is an example of a snap-on member affixed to the bottom surface of a contact member for ease of manufacture and disposability advantages.

Referring to FIG. 2, one practical method for providing the friction means is a separate member affixed to the bottom surface 4 of a contact member 1 comprising a snap-in member 16 having means 17 for removably attaching the snap-in member 16 to the bottom surface 4 of the contact member 1. This removable attachment feature may be readily provided by a post 18 affixed to each snap-in member 16 and which fits engagingly in a port 19 formed in the body of the contact member 1, or by other like configuration. This embodiment offers several advantages in disposability and ease of manufacture, particularly where it is desirable to provide an adhesive or friction-providing member separately to the bottom surface 4 of the contact member 1, and especially where the friction or adhesive member is formed of a different material than the body of the contact member 1. The bottom surface 4 of the snap-in member 16 may have any of the configurations described previously (See FIGS. 1B and 1D through 1G).

Figure 3:
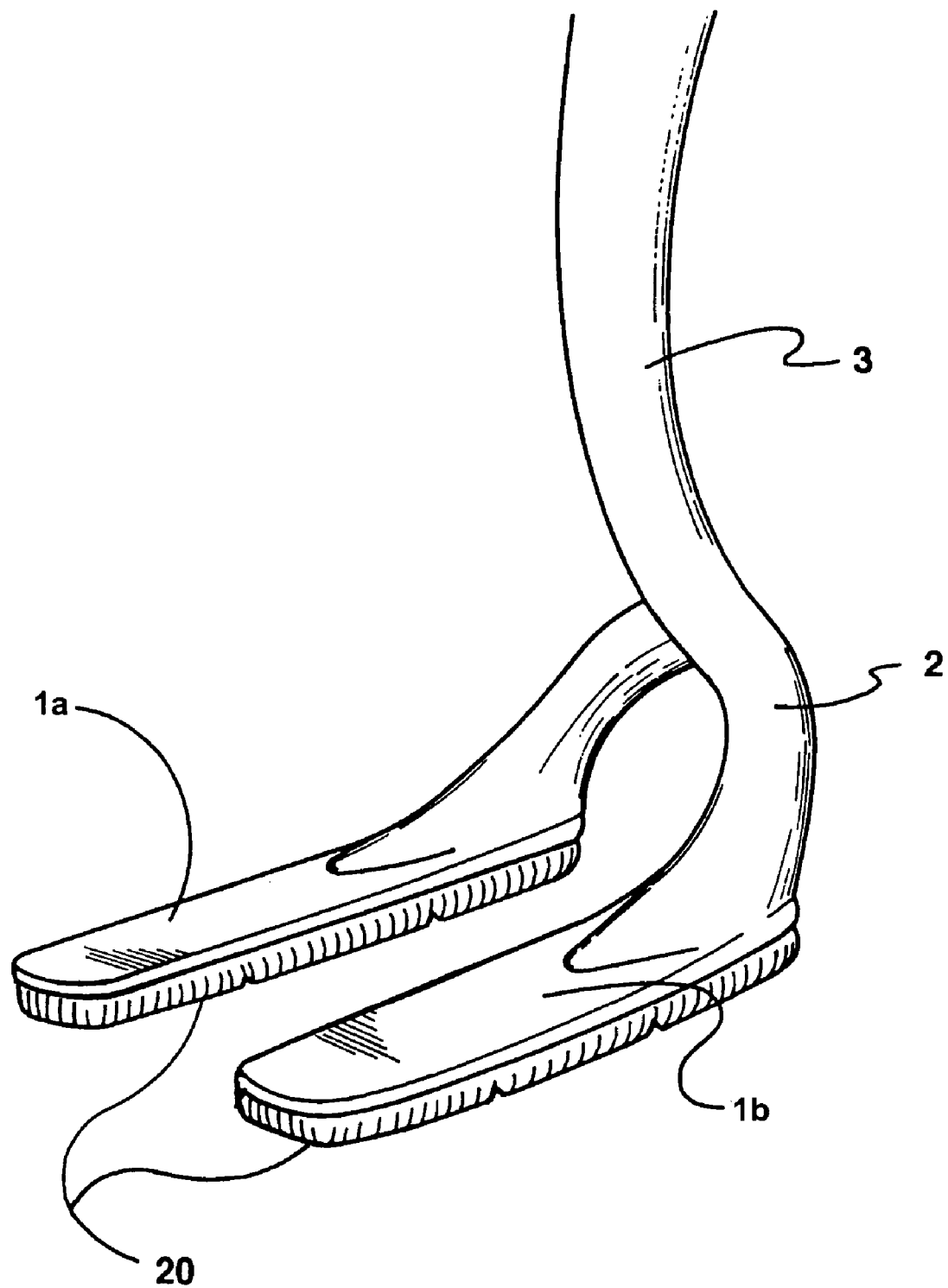
FIG. 3 is an example of a stabilizing means of the invention having an inflatable or fluid-filled cushioning member disposed between the bottom surface of the contact member and the surface of the beating heart.

Given the delicacy of the epicardial cardiac tissue, and the desire to avoid the possibility for damaging the heart as it beats throughout the beating heart bypass procedure, and to avoid the possibility that the stabilizing means might slip, the contact members 1 of the invention may be provided with a friction-providing and/or cushioning material at the lower or bottom surface 4 of the contact member 1 to cushion the point where the contact member(s) 1 engage the beating heart. For example, FIG. 3 shows an exemplary material 20 comprising a textured soft rubber or fluid-filled member affixed to the bottom or lower surface 4 of the contact members 1 to prevent damage to the heart tissue, and to minimize slippage.

As noted above, a fundamental element of the intention is the contact members which engage the surface of the beating heart, in some embodiments proximal to the site of the anastomosis, to directly apply the stabilizing force to the beating heart. The actual shape, size, configuration, and relative orientation of the contact members may vary without departing from the spirit of the invention. For example, referring to FIGS. 4A and 4B, the contact members 1 that engage the surface of the beating heart may be provided by a solid structure 21, preferably a dense metal, which provides an added weight to add to the stabilizing effect achieved by contacting the beating heart with the stabilizing means of the invention. This embodiment facilitates motion cancellation and stabilization of the beating heart by adding additional weight directly at the site where the contact member engages the beating heart, which in this embodiment is at the site of the anastomosis. As can be seen in FIG. 4B through line IV-IV of FIG. 4A, in this embodiment, two contact members 1a, 1b engage the beating heart at their lower or bottom surface 4, have a greater thickness at their outer edges, and have an opening 22 positioned therebetween, and which traverses the entire space between the contact members 1a, 1b such that a vessel may be positioned therebetween.

FIG. 4C shows an integrated apparatus which may advantageously apply the contact members 1 to the surface of the beating heart by the action of a balance provided by an adjustable weight 24 and counterweight 25 mounted on opposite ends of a shaft 26 mounted on a fulcrum 27 which is preferably affixed to a stable support such as the operating table or an access platform providing retraction during the surgery. By manipulating the adjustable weight 24, varying degrees of stabilizing force may be applied to the beating heart via shaft means 3 and the contact members 1. This embodiment provides a continuously variable quantity of stabilizing force directed downward by the positioning of the weights 24, 25 and the rotation of the shaft 26 about the point of the fulcrum 27. Thus, in use, the surgeon may rest the contact members 1 on the surface of the beating heart with a minimal force applied, and by moving the adjustable weight 24 away from the fulcrum, cause additional force to be applied, via the shaft means 3, and the contact members 1, to the surface of the beating heart.

Figure 5:
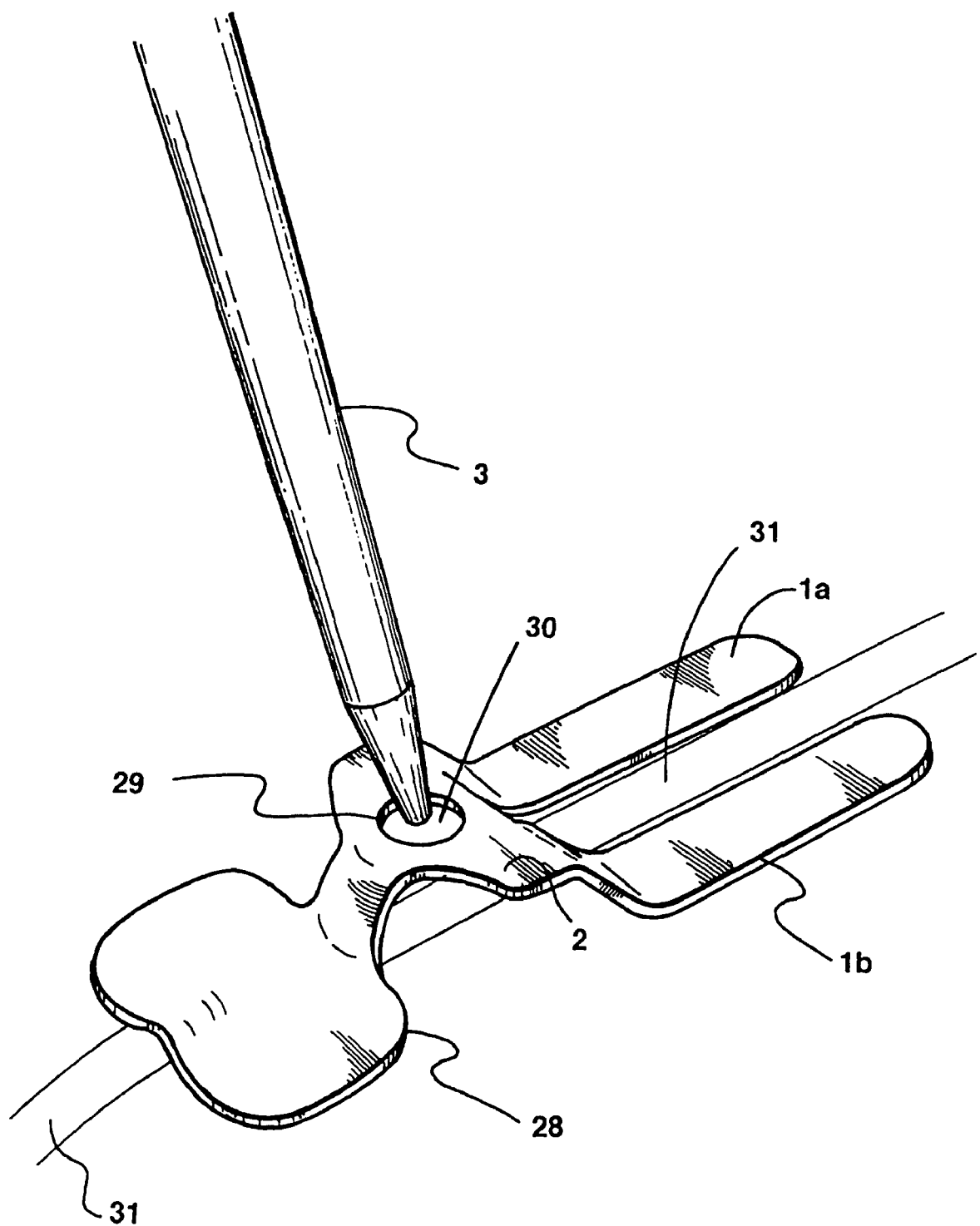
FIG. 5 is an embodiment of the invention having a counter-contact member positioned opposite a pair of contact members and having a shaft positioned at an intermediate point therebetween.

The positioning of the contact members 1 at the surface of the beating heart to provide the requisite degree of stabilization may be achieved by several techniques designed to apply a mechanical force to the contact members that rest in a conformingly fashion at the surface of the beating heart to substantially arrest the movement in an atraumatic manner. The device shown in FIG. 5 has a pair of contact members 1a, 1b disposed in substantially parallel fashion as in the embodiments previously described. However, the device has an additional counter contact member 28 that also engages the surface of the beating heart, but does so at a point slightly removed from the point of engagement of the other contact members 1a, 1b which are preferably located at the site of the anastomosis. Additionally, the shaft means 3 may be attached to and be rotatable about a point 29 located between the contact members 1a, 1b and the counter contact member 28 and preferably at a point on the connecting shaft 2 that is slightly elevated. The shaft means 3 is preferably rotatable, for example by virtue of a ball joint 30, about the point 29 of contact thereby permitting the contact members 1 to self-align and engagingly conform to the surface of the beating heart. Moreover, in this embodiment, when a stabilizing force is applied to the surface of the beating heart, the force directed down the length of the shaft means 3 is not centered over the site of the anastomosis. The counter contact member 28 may also be configured to occlude the target vessel 31. As with the other embodiments disclosed herein, an embodiment of the type of FIG. 5 may be selected by the surgeon depending on the particular clinical indication, the particular physiology of a given patient, and/or the surgical environment dictated by the access method used to gain access to the beating heart, for example, sternotomy, thoracotomy, or puncture incision.

Figure 6A:
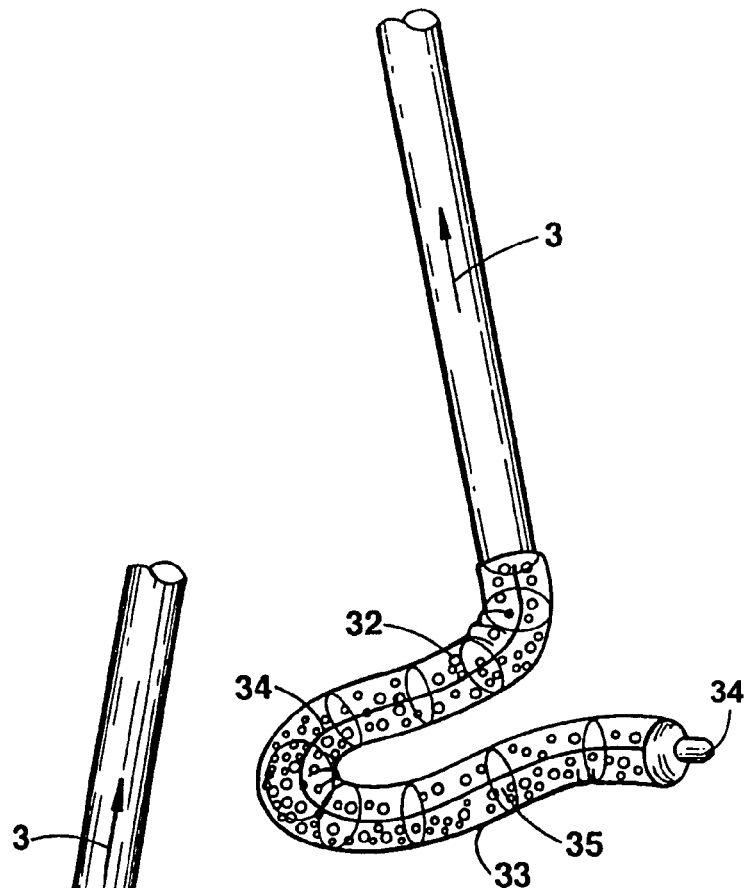
FIGS. 6A and 6B are embodiments of the invention having contact members which have a conformable shape, and where a flexible or semi-rigid member may be passed through the body of the contact member.
Figure 6B:
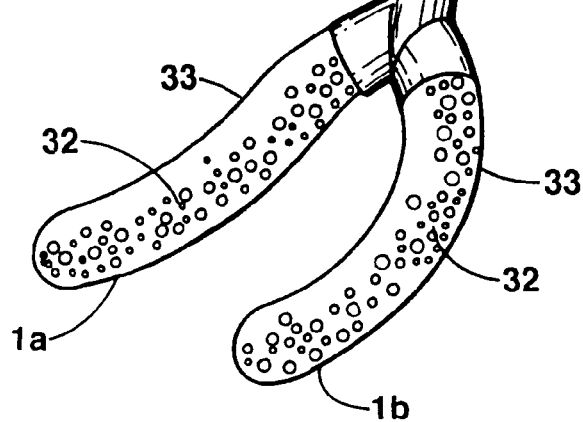

Thus, different surgical methods of access, different target vessels, and the anatomical differences between individual patients, may dictate the use of alternate embodiments of the invention, typically at the discretion of the surgeon. For this reason, contact members which are continuously adjustable, may be particularly preferred for some clinical indications. For example, FIGS. 6A and 6B show an embodiment of the invention having a plurality of particles or beads 32 disposed within a substantially flexible tubular structure or structures 33, and which may have a vacuum lumen (not shown) located therein, to provide a contact means 1 whose shape and position is adjustable. Preferably, the flexible tube structure 33 has a malleable member 34 such as a wire disposed along the length thereof to provide a structural memory function and additional tensile strength. In the embodiment of FIG. 6A, the flexible tube 33 is a single unitary structure which can be bent, typically in a U-shape configuration, to engage the surface of the heart and may have plurality of discs 35 disposed along the malleable member 34. Also, as illustrated by FIG. 6B, the stabilizing means may be provided by a plurality of contact members 1a, 1b as otherwise described herein. As with the single unitary structure of FIG. 6A, the plurality of the flexible contact members 1a, 1b may be provided with a plurality of beads or particles 32 disposed therein and may additionally have the ability to be inflated selectively, or selectively deflated, to adjust or fix the position of the contact members 1. When suction is applied via the suction lumen, the particles 32 are compressed by atmospheric pressure causing the tubular structure 33 to become rigid, thereby fixing the information of the contact members 1.

Figure 7A:
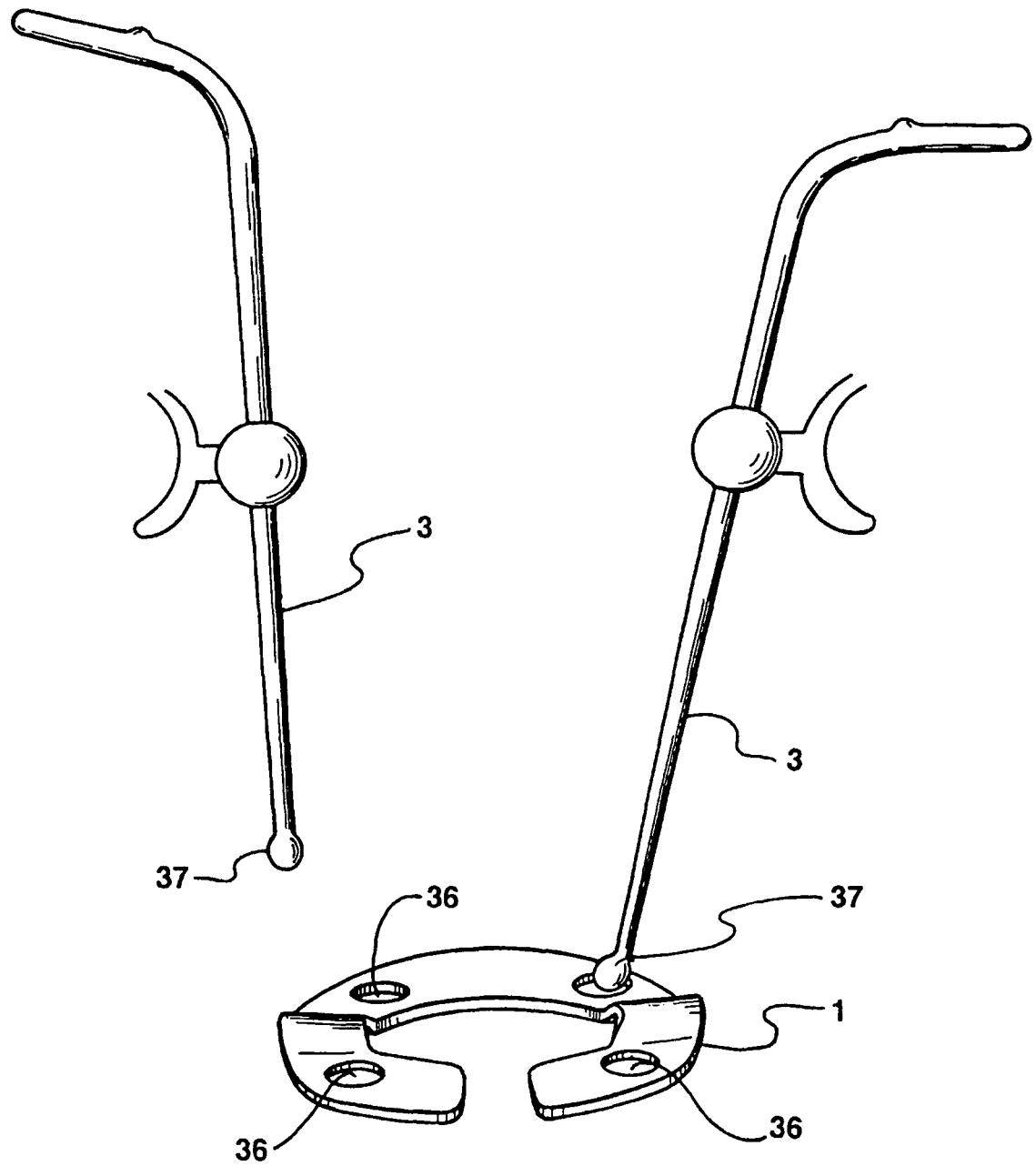
FIG. 7A is an embodiment of the contact member wherein the contact member has ports for releasable attachment of the distal end of a shaft means.
Figure 7B:
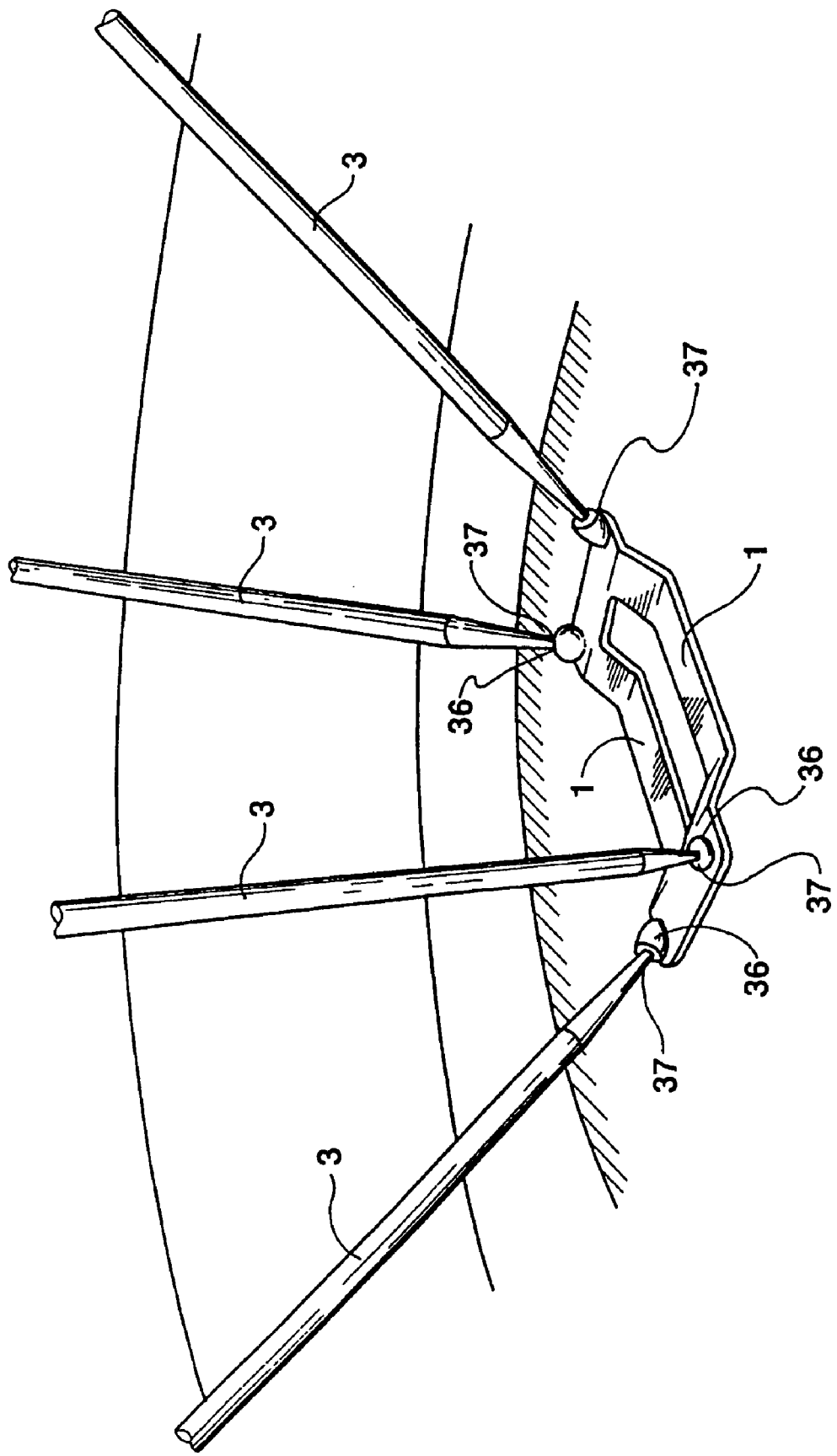
FIG. 7B is an embodiment wherein a plurality of ports are disposed about the periphery of a contact member for releasable attachment to the distal end of a shaft means.

As with the embodiments described above, adjustable placement of the contact members may be particularly useful in a minimally invasive procedure. Contact members that releasably contact or are releasably attached to a shaft may be deployed by separate insertion of the contact member, and a shaft or shafts which may be independently introduced, manipulated, and withdrawn to provide a stabilizing device held in place by pressure exerted on the shafts while the anastomosis procedure is performed at which time the contact members and shafts are removed in an atraumatic manner. Referring to FIGS. 7A and 7B, a unitary contact member 1 has a plurality of recessed ports 36 adapted to receive the distal end 37 of a shaft means 3, wherein the distal end 37 is shaped to fit conformingly within the recessed port 36 and wherein the shaft means 3 may be removably attached to the contact member 1. As seen in FIG. 7B, this embodiment provides the advantage that the shaft means 3 may be introduced through a plurality of very small incisions such that several shaft means 3 may removably engage the contact member 1 at the several points about the periphery of the contact member 1 where the recessed ports 36 are formed in the contact member 1 and receive the distal end 37 of a plurality of shaft means 3.

Figure 7C:
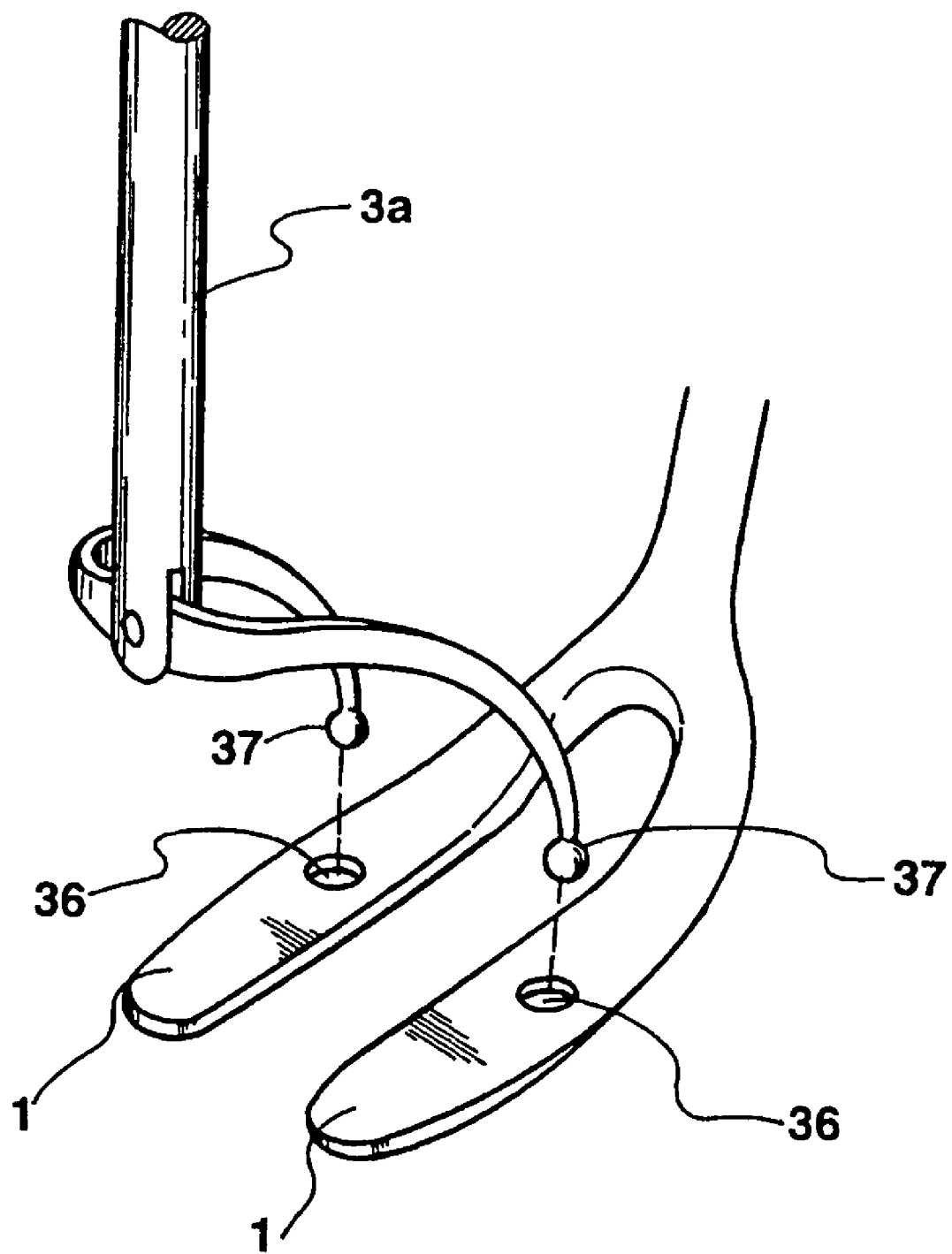
FIG. 7C is an embodiment of the invention wherein a separate shaft is provided having distal portions adapted to fit within ports on a contact member.

FIG. 7C illustrates a separate removable shaft means 3a that may be utilized with any of the embodiments of the contact members 1 previously described. In FIG. 7C, the separate shaft means 3a is separately introduced and has a pair of distal ends 37 that engage equivalently oriented and spaced ports 36 found in the contact member 1 to provide an additional positioning and stabilizing capability by manipulating the separate shaft means 3a when the distal ends 37 engage the ports 36.

FIG. 7D is a simplified use of separate shaft means 3a having an integral contact member 1 formed from the distal portion 38 of the separate shaft means 3a. In this embodiment, the separate shaft means 3a are separately introduced into the surgical field through minimally invasive puncture incisions and are separately positioned to bring the distal portion 38 of each of the separate shaft 3a to contact the surface of the heart. Referring to FIG. 7E, the separate shafts 3a may be joined at the most distal tip by a discrete interconnecting member 39 having openings 40 configured to receive the most distal tip 37 of both of the separate shaft means 3a.

Figure 8:
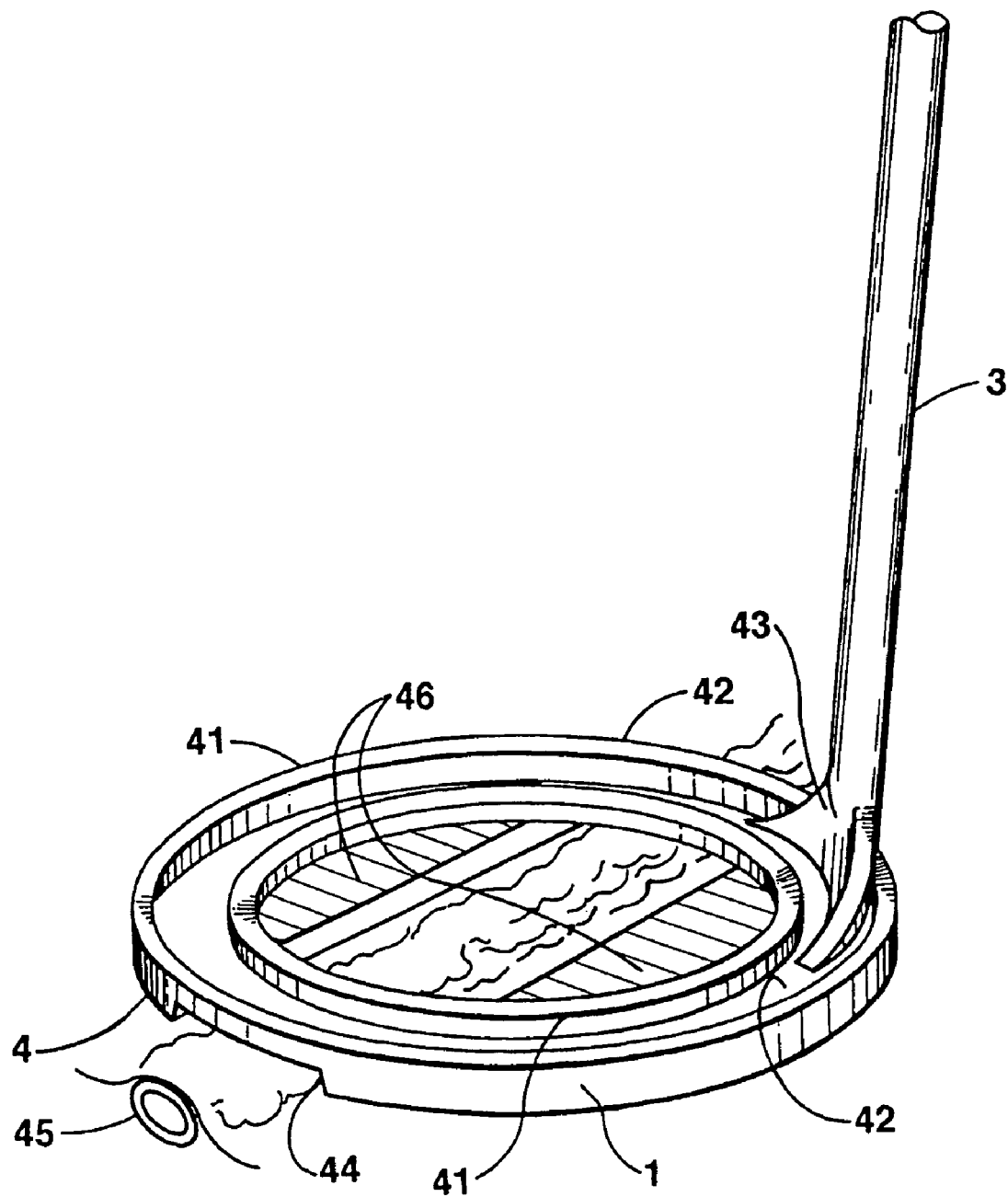
FIG. 8 is an embodiment of the invention having a substantially annular contact member which is affixed to a shaft which is rotatable about the annular contact member and which may be locked into position at a given point about the periphery of the contact member.

FIG. 8 is an additional embodiment of the contact members 1 of the invention generally comprised of an annular structure 41 which is rotatable relative to the shaft means 3 which is attached at a point about the periphery of the contact member 1. In this embodiment, a portion of the bottom surface 4 of the annular portion 41 contacts the beating heart at a site proximate to the target site for the anastomosis. The annular portion 41 of the contact member 1 may be provided with a lockable fixture 42 which engages the distal end of the shaft 43, where the shaft means 3 contacts the annular structure 41, to lock the shaft in place. Alternatively, the shaft means 3 may rotate freely about the periphery of the annular portion 41 of the contact member 1. Preferably, a portion of the annular contact member 41 has a passage 44 formed through the bottom surface 4 of the annular contact member 41 where the target vessel 45 passes beneath the annular contact member 41. Additionally, the annular contact member 41 may have substantially planar surfaces 46 which are generally co-planar with the bottom surface 4 of the annular contact member 41 and have a rectangular opening therein for access to the target vessel 45. Planar surfaces 46 may assist in providing stabilization at the tissue proximate to the anastomosis, and which also assist in positioning the target vessel 45 relative to the annular contact member 41.

The contact members of the invention may also be provided with other related apparatus or fixtures that are commonly used in traditional surgical procedures. Such structures or fixtures may be operably associated with the body of the shaft means 3, the interconnecting shaft 2, or the contact members 1.

Figure 9C:
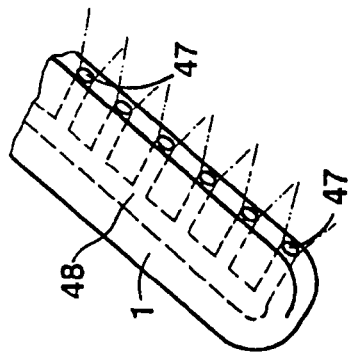
Figure 9B:
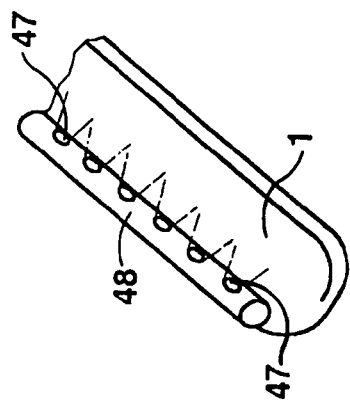
Figure 9E:
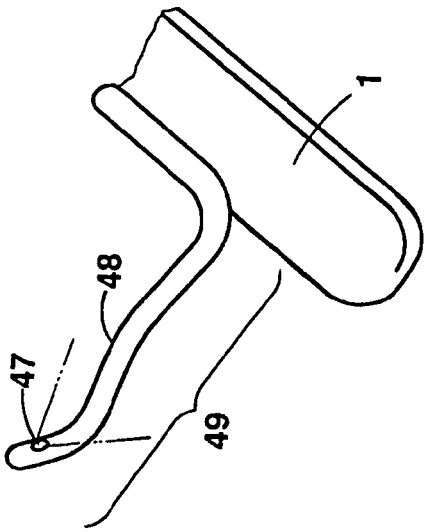
Figure 9D:
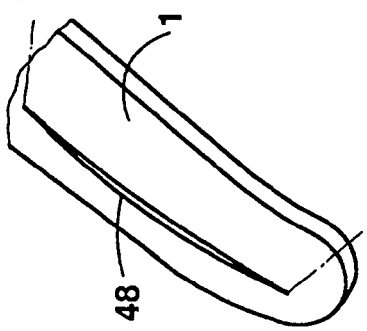
Figure 9A:
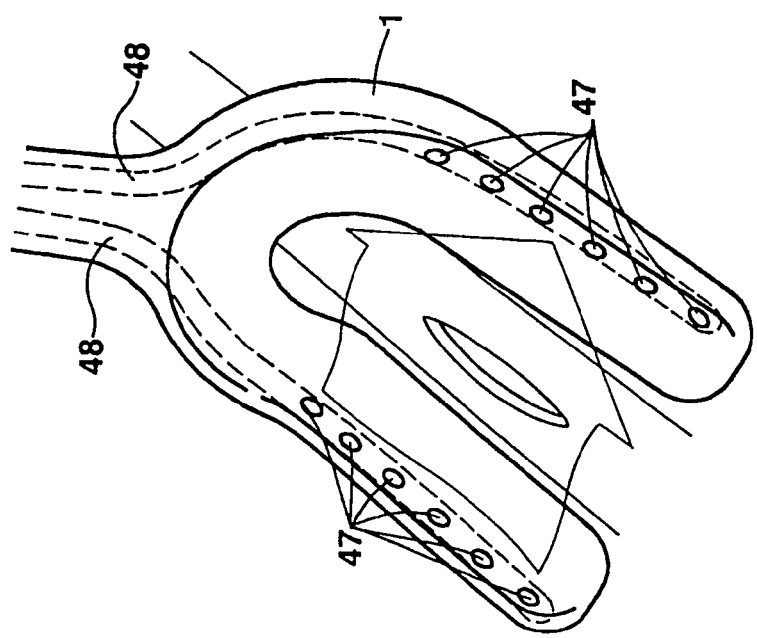
Figure 9H:
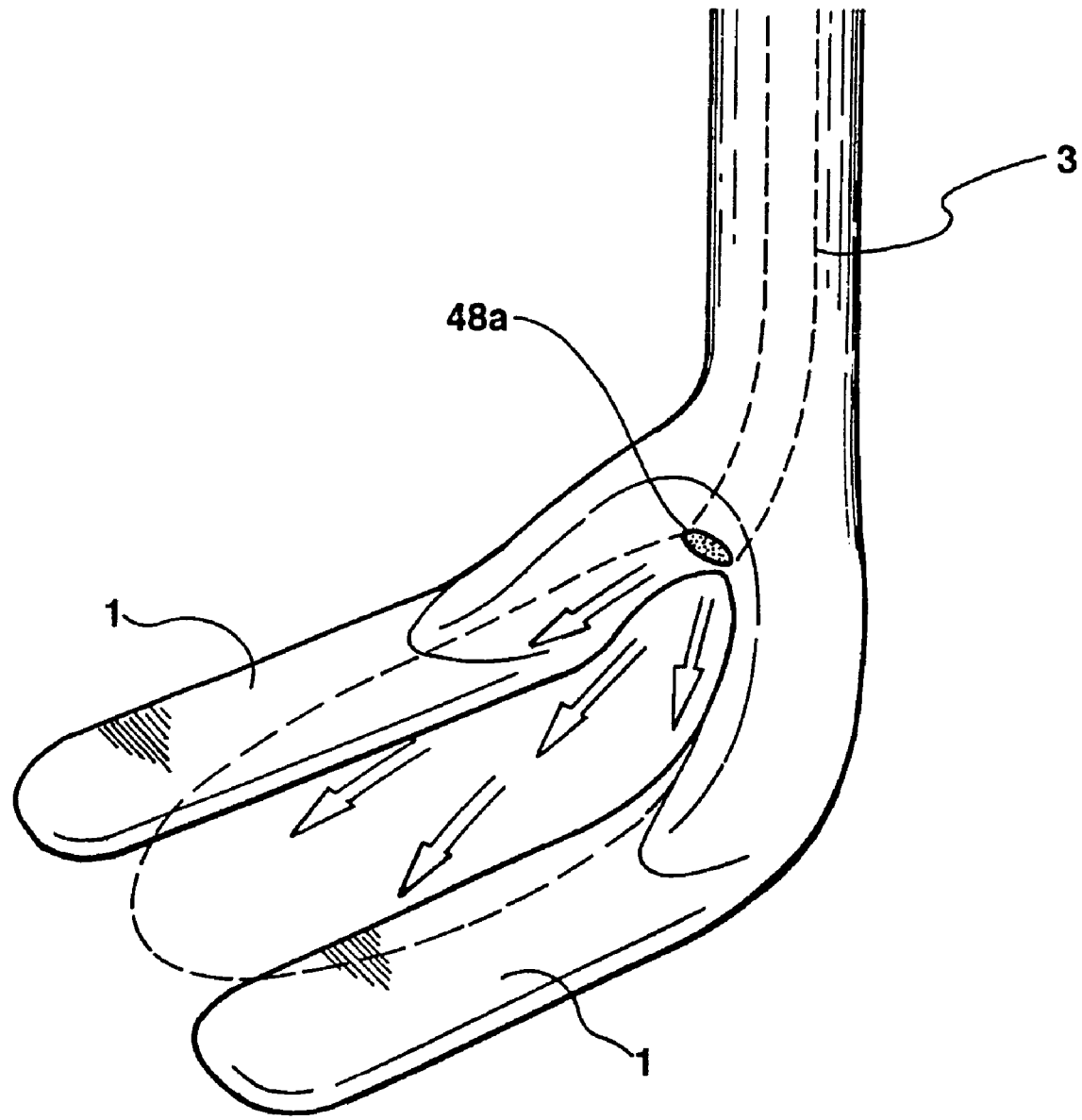
FIG. 9H is an embodiment of the invention where a light source is provided to illuminate the area that the beating heart contacted by the contact members.

Referring to FIGS. 9A through 9E, a suction (negative) pressure or a blower (positive) pressure is useful to maintain a clear and dry anastomosis site. The positive or negative pressure may be provided to the contact member by a plurality of ports 47 formed in the body of the contact member. Each port is in pneumatic communication with a lumen 48 that is in turn connected to a suction or positive pressure source. Thus, by exerting either a positive or negative pressure on lumen 48, the suction or positive pressure is applied to the site of the anastomosis via ports 47. In FIG. 9A, the ports 47 are disposed in the top surface of the contact members 1 and have aligned openings in the direction of the anastomosis site.

As shown in FIG. 9B, the plurality of ports 47 may be provided in a discreet lumen 48 which is affixed to, and runs longitudinally along, the length of the contact member 1. In this configuration, the plurality of ports 47 are preferably disposed in a linear configuration along one surface of lumen 48 to provide negative suction pressure or a positive flow of pressure about the surface of the contact member 1.

Referring to FIG. 9C, as mentioned above, the plurality of ports 47 and the lumen 48 may be provided in a manifold-like fashion wherein the openings of the plurality of ports 47 are formed in the body of the contact member 1, as is the lumen 48 which is in communication with each port 47. As an alternate to the plurality of ports 47, a single slot may be formed from the lumen 48, such that the slot runs along the greater length of the contact member 1 as shown in FIG. 9D.

Referring to FIG. 9E, in a variation on the embodiment of FIG. 9B, the lumen 48 may be provided as a malleable tube which is separable from the contact member 1 along at least a malleable portion 49 of said lumen 48. In this configuration, by manipulating the malleable tube portion 49 of lumen 48, port(s) 47 may be selectively positioned at any point proximate to the contact member 1.

Referring to FIG. 9F, a manifold similar to that shown in FIG. 9C, may be provided within the body of the contact member 1 in a configuration wherein the ports 47 are more closely associated with the interconnecting shaft 2 or the shaft means 3. As in the embodiment of FIG. 9C, the ports 47 are in communication with a lumen 48 that runs the length of the shaft means 3 terminating in the plurality of ports 47. As shown in FIG. 9F, the plurality of ports 47 may apply the positive or negative pressure from the portion of the interconnecting shaft 2 that joins the individual contact members 1.

Referring now to FIG. 9G, as in FIG. 9E, a lumen 48 having a malleable portion 49 may be provided for selective positioning of a positive or negative pressure which may be applied at any point proximate to the stabilizing means of the invention by manipulating the position of the malleable portion 49 of the lumen 48 to selectively position port 47.

In a similar structural configuration to FIGS. 9A through 9G, FIG. 9H supplies an incandescent or fiber optic light source 48a proximate to the contact members 1 by placing the light source within the shaft means 3 to have an opening or lens to provide light at the site of the stabilization.

Figure 10C:
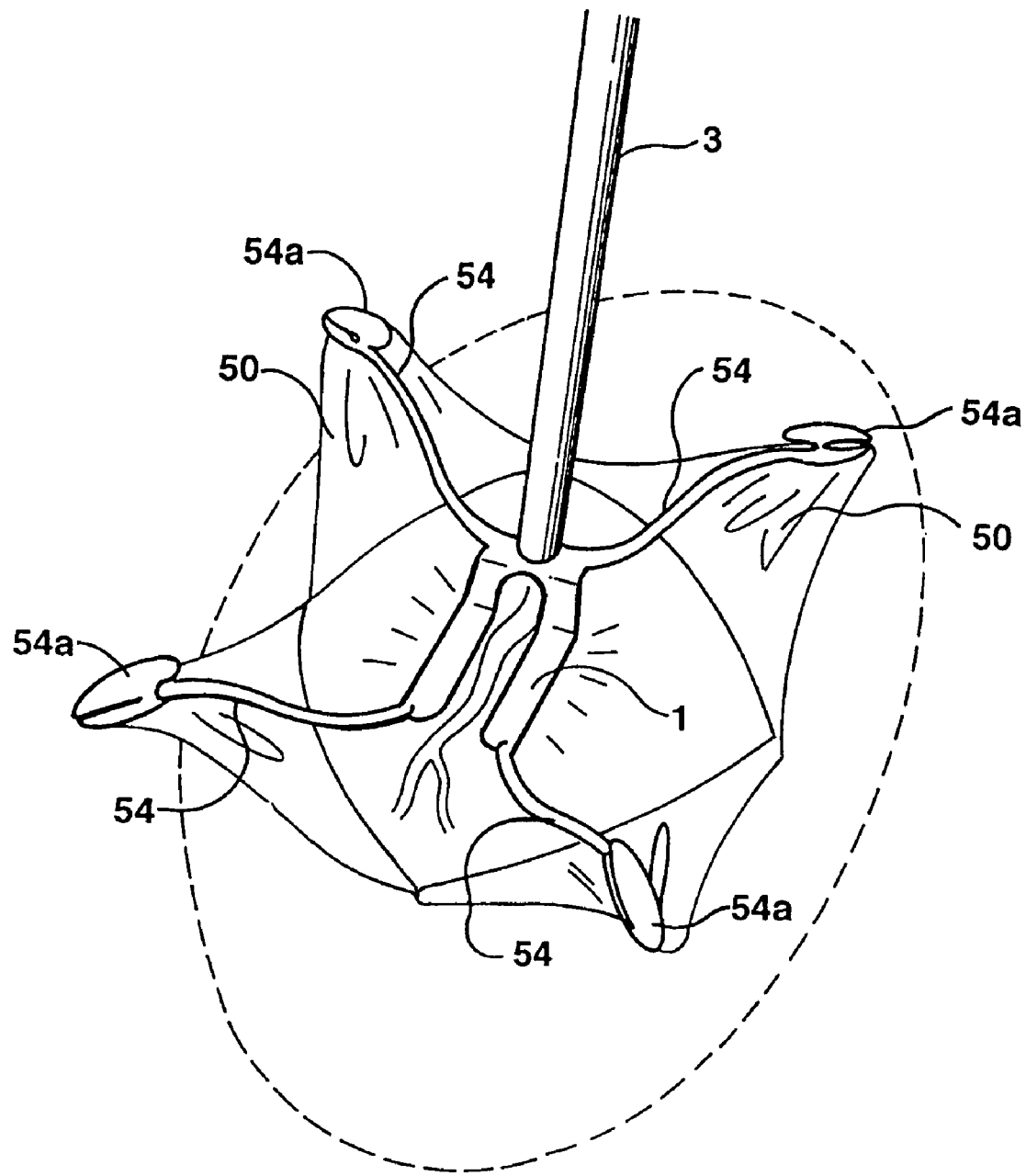

An additional conventional surgical apparatus which may be advantageously applied to the stabilizing means of the present invention is a selectively positionable surgical drape that assists in providing a dry and sterile field, and which assists the surgeon during the procedure by visually isolating the site of the anastomosis. FIG. 10A shows a retractable and extendable drape 50 surrounding shaft means 3. In the retracted configuration 51, shown in phantom in FIG. 10A, the retractable drape is closely conformed to the shaft means 3 to be unobtrusive. The drape 50 may be affixed to the shaft means 3 by a washer element 52 that is directed downward to deploy the drape 50. When the washer element 52 reaches the maximum downward position, the retractable drape 50 is doubled over to form a portion of a circular covering surrounding the surgical site and generally opposite the area where the contact members 1 abut the surface of the beating heart. An additional embodiment, shown in FIG. 10B, has a surgical drape 50 affixed to the outer portion of each contact member 1a, 1b. While this configuration is not retractable, surgical drapes 50 as shown in FIG. 10B may be provided with structural support members 53 that provide tensile strength and shape to the surgical drape 50 and which may provide supplemental stabilizing force by contacting the beating heart about the periphery of the contact members 1a, 1b. An additional configuration for surgical drapes 50 affixed to contact members 1 is shown in FIG. 10C where a plurality of drape supports protrude radially from several points about the periphery of the contact members 1a, 1b and terminate in drape fastening means 54a at their most distal portion. A portion of the drape 50 is attached to each drape fastening means 54a to spread the drape over the surgical site and may provide coverage extending in all directions outward from the contact members 1.

Figure 11:
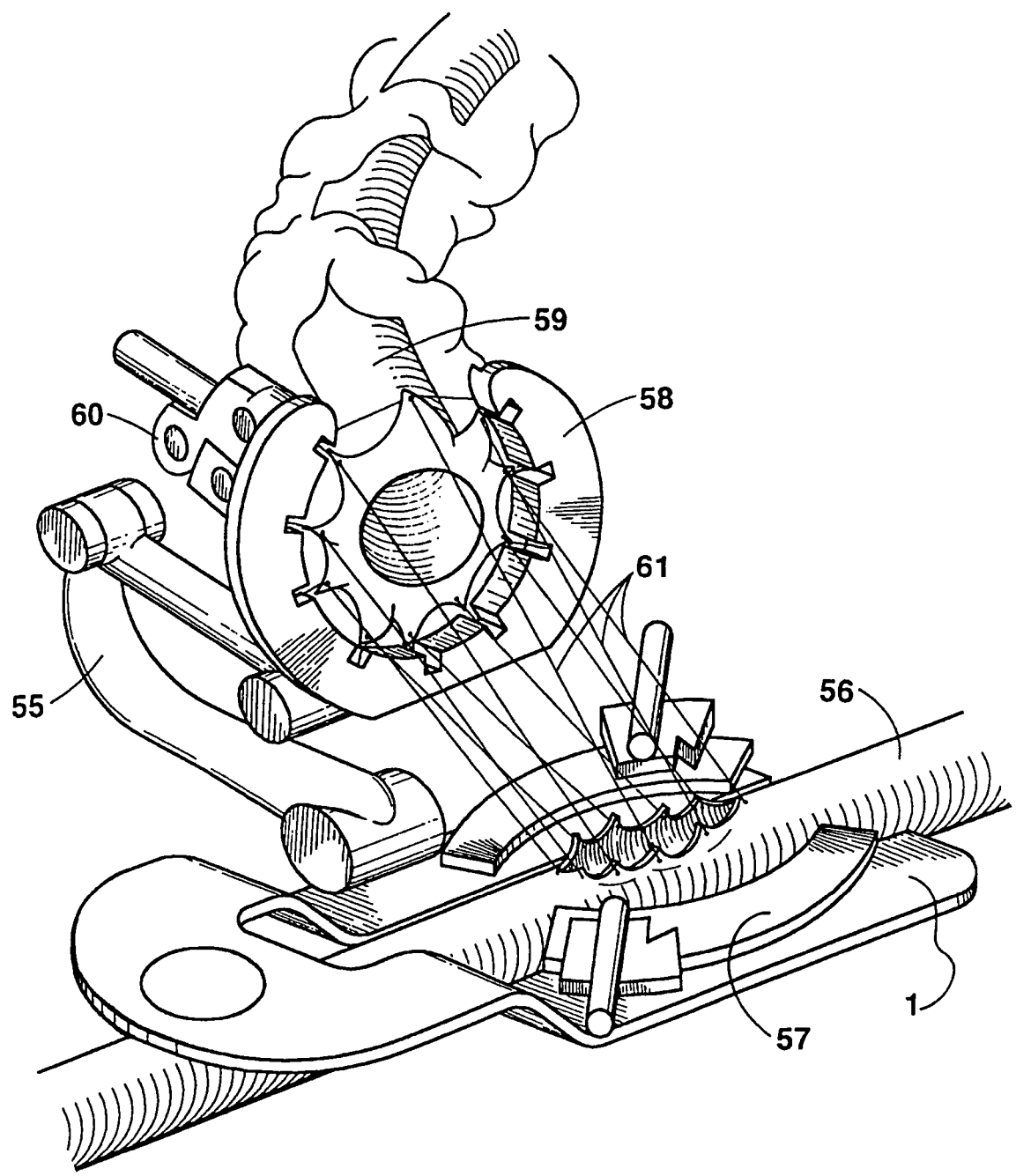
FIG. 11 is the contact members of the invention having an associated apparatus to facilitate completing the anastomosis.

Referring to FIG. 11, a mechanical fixture to facilitate completing the anastomosis may be directly attached to the contact member 1. A separate device to facilitate completing the anastomosis is generally comprised of a hinged or rotatable vessel support member 55 that permits selective positioning of the source vessel, such as the distal end of an internal mammary archery or the distal end of a venous or arterial graft, proximate to the target vessel 56. The vessel support member 55 is oriented on the contact member 1 such that the vessel source brought into direct alignment with an arteriotomy formed in the target vessel 56, which is disposed between the contact members 1. To facilitate the completion of the anastomosis, a vessel receiving member 57 is closely associated with the contact members 1 and generally surrounds the arteriotomy in the target vessel 56. The vessel support member 55 has an anastomosis coupling fixture 58 that is attached to the distal end of the source vessel and is shaped to be brought into engagement with the vessel receiving member 57. The anastomosis coupling fixture 58 is attached to the periphery of the IMA or graft such that when the vessel support member 55 is positioned proximate to the arteriotomy, the vessel receiving member 57 and the anastomosis coupling fixture 58 are brought into alignment such that a fluid communication between the source vessel 59 and the target vessel 56 is established upon completion of the anastomosis. Completion of the anastomoses is facilitated by an automatic suturing securing mechanism 60 or other like apparatus for tightening the sutures to join the two vessels. Preferably, the vessel receiving member 57 and the anastomosis coupling fixture 58 are operably associated with a plurality of sutures 61 which penetrate the periphery of the arteriotomy formed in target vessel 56 and connect the periphery of target vessel 56 to the periphery of the source vessel 59. Thus, while simultaneously actuating the vessel support member 55, the automatic suturing device 60 brings the vessels into close conformity and completes the anastomosis procedure to establish fluid communication between the source vessel 59 and the target vessel 56.

Figure 12:
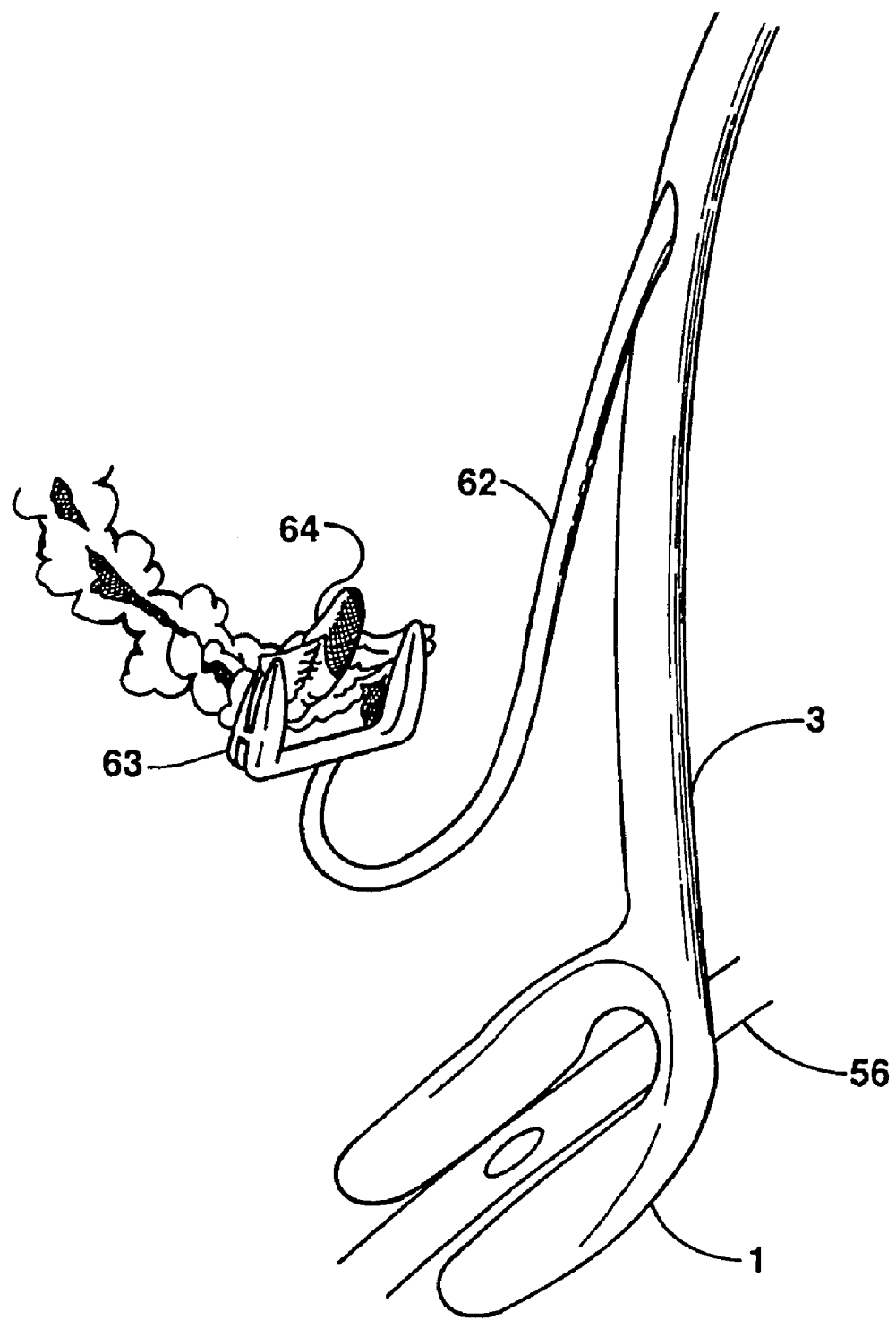
FIG. 12 is an embodiment of the invention where the shaft means has associated therewith a separate vessel holder.

Referring to FIG. 12, a separate member for conveniently holding the source vessel may be provided without a dedicated apparatus for completing the anastomosis. A malleable wire 62 is operably affixed to the shaft means 3 or to the contact member (not shown) and has a source vessel holder 63 such that the source vessel 64 may be prepared and conveniently held at a point away from the target vessel 56 until the surgeon is prepared to complete the anastomosis. Preferably, the source vessel holder means 63 is comprised of a clamp for gripping and maintaining the source vessel 64 in a preferred configuration prior to completing the anastomosis, such as by separating or spreading the tissue attached to the most distal portion of the source vessel 64 to maintain the integrity and patency of the distal end of the source vessel 64.

As mentioned above, it is particularly preferred that the instruments of the invention be used in a minimally invasive bypass graft procedure wherein a minimal thoracotomy provides access to the beating heart. A minimal thoracotomy is a small surgical opening provided between the ribs and is formed, to the extent possible, proximate to the target artery of the beating heart where the anastomosis is to be formed. To provide access to the beating heart via the minimal thoracotomy, the cannula may be disposed between the ribs to provide access to the beating heart. Referring to FIGS. 13A through 13E, alternate configurations for a cannula disposed between adjacent ribs are shown. The embodiment of FIG. 13A has a cannula support bracket 67 having a plurality of holes through which screws 66 may pass to provide means to attach the assembly to the chest such as by placing the screws in adjacent ribs 69a, 69b. The cannula receiving assembly 67 may have one slot 65 formed therein such that one of the screws 66 may slide therein for spreading the adjacent ribs 69a, 69b apart. The cannula receiving assembly 67 provides an opening between adjacent ribs 69a and 69b such that the cannula 68 may be passed therethrough. Referring to FIG. 13B, in an alternate embodiment, the cannula receiving assembly 67 is replaced by a cannula 68 surrounded by a large thread means 70. The distal end 71 of the cannula 68 may be inserted between the ribs and rotated such that the thread means 70 cause cannula 68 to be advanced between the adjoining ribs 69a, 69b, and by virtue of the expanding diameter of the thread means 70, to spread adjoining ribs 69a, 69b apart while positioning the cannula 68 therebetween. In yet a further embodiment, in FIG. 13C, a cannula assembly 75 is provided having a claw mechanism comprised of opposing blades 73 and interlocking member 72. Adjacent ribs 69a, 69b are engaged by opposing blades 73, and, by forcing the cannula 68 downward, the opposing blades 73 rotate outwards until a locking member 72 fixes the position of the opposing blades 73 in a locked and opposing relationship as shown in FIGS. 13D and 13E. Thus, by forcing cannula 68 downward, adjacent ribs 69a and 69b are spread apart by opposing blades 73 and the cannula assembly 75 is fixed in position by locking member 72 such that cannula 68 is positioned to provide access to the beating heart.

Figure 14:
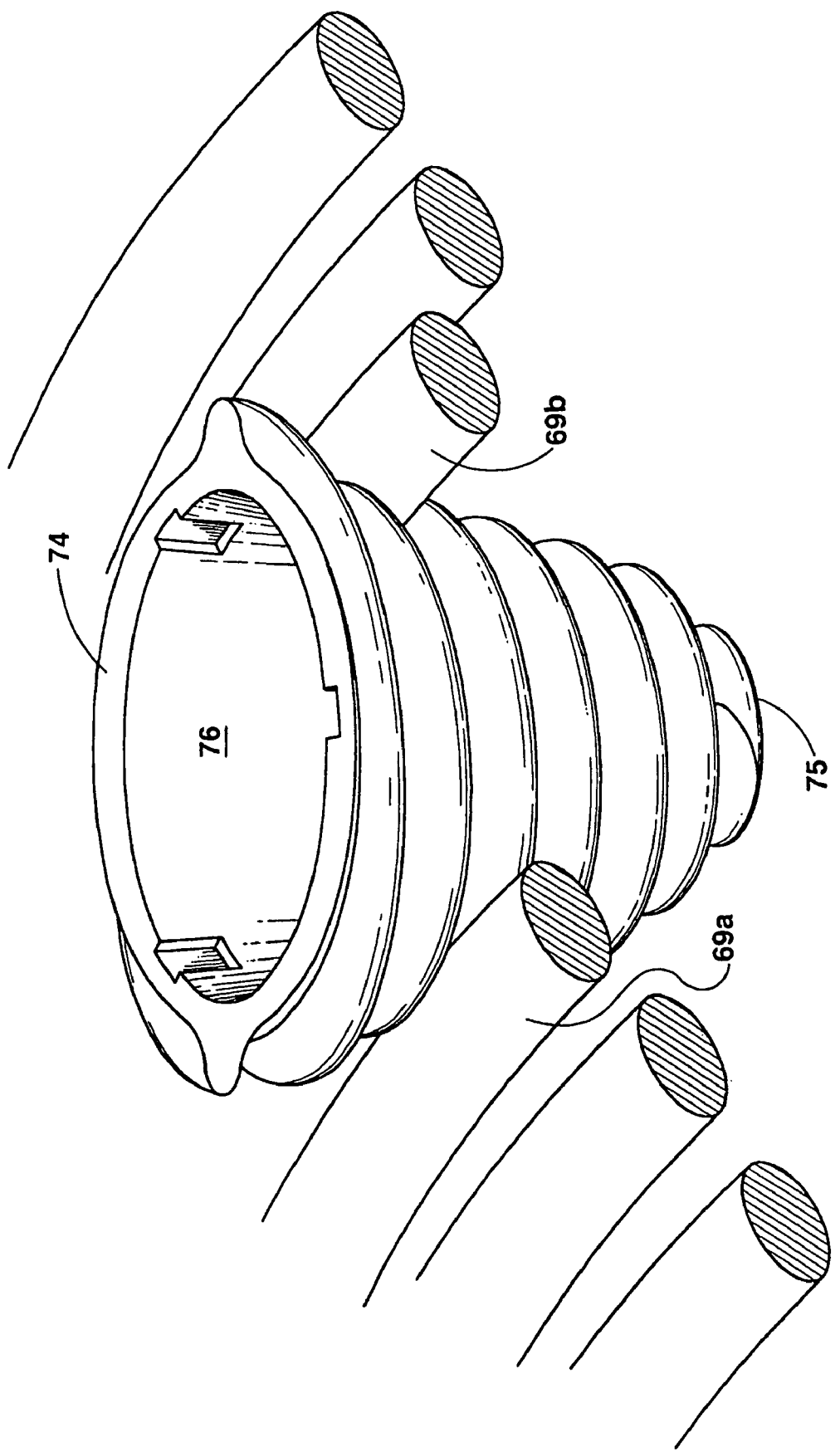
FIG. 14 is a conical cannula having a smaller: distal end to engage the surface of the beating heart and a larger proximal opening for introducing surgical instruments to the beating heart.

A modified large diameter cannula having an extended vertical height, may perform several functions in a minimally invasive CABG procedure. For example, referring to FIG. 14, an enlarged cannula 74 may be provided in the shape of an inverted cone structure having an enlarged proximal opening 76 with an enlarged diameter, and a distal opening 75 having a reduced diameter and where said distal opening 75 abuts the surface of said beating heart. By exerting a downward force on the inverted, enlarged cannula 74, the inverted conical shape of the cannula 74 forcibly spreads adjacent ribs 69a, 69b, and provides a stabilizing force when the distal portion 75 contacts the surface of the beating heart. Surgical access to the stabilized heart is provided through enlarged proximal opening 76.

Figure 15A:
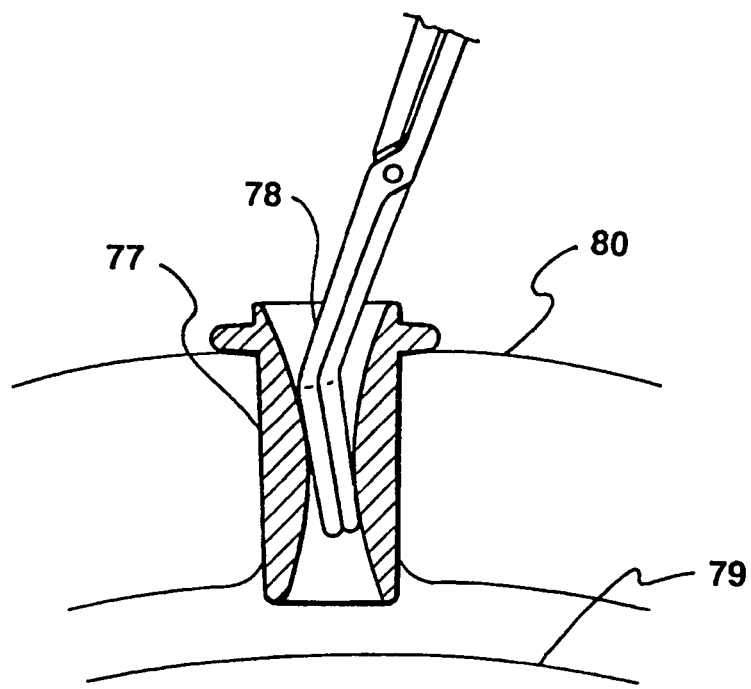
FIGS. 15A and 15B are an embodiment of the invention inserted through the chest wall in a minimally invasive fashion via a cannula to bring the contact members into engagement with the beating heart.
Figure 15B:
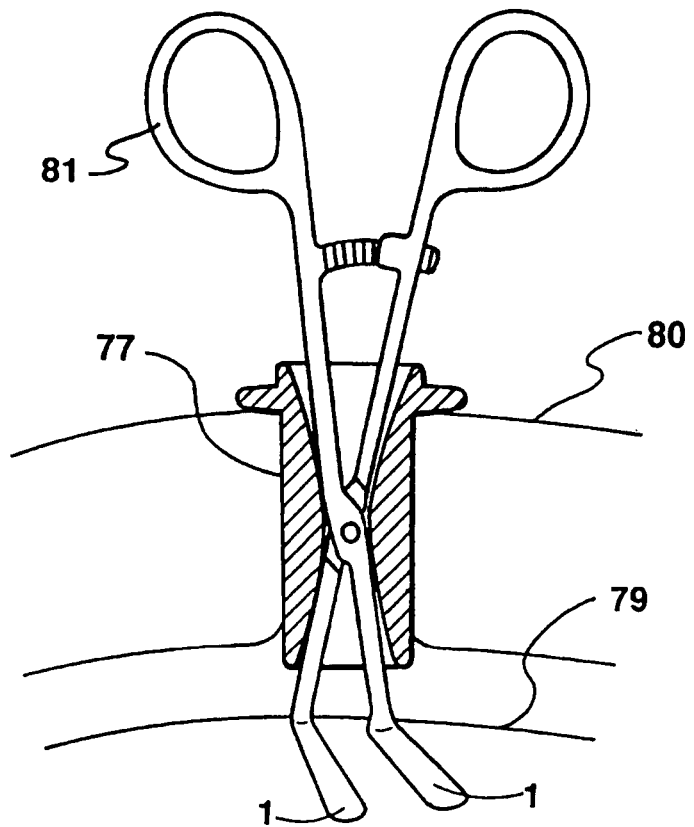

FIGS. 15A and 15B show an embodiment of the invention in use with a conventional cannula. In FIG. 15A, a conventional cannula 77 is inserted through a puncture incision in chest wall 80. The distal end of the stabilizing means 78 (similar to FIGS. 31A and 31B below), is introduced in a contracted configuration through the cannula 77 to bring the distal end thereof in contact with the surface of the beating heart 79. Referring to FIG. 15B, the stabilizing means of the invention are fully inserted through the cannula 77 and manipulated to bring the contact members 1 into contact with the surface of the beating heart 79. By manipulating handles 81 of the stabilizing means, the contact members 1 are spread apart at the surface of the beating heart to provide the stabilizing function during the surgical procedure.

Where a minimally invasive procedure is employed, the means for stabilizing the beating heart of the invention are preferably provided in an embodiment where the contact members 1 that engage the surface of the beating heart are inserted and withdrawn from the surgical field in a position or a configuration having a reduced dimensional profile, i.e., a reduced effective diameter when inserted and removed from the thoracic cavity. For example, these embodiments are particularly useful when the surgery is performed through a plurality of puncture incisions.

In the embodiment of FIGS. 16A through 16E, a pair of rectangular, and substantially planar contact members 1a, 1b are disposed within a generally cylindrical main shaft 82. In the retracted configuration shown in FIG. 16A, each contact member 1a, 1b is rolled into a collapsed, annular configuration to reduce the effective diameter of the device by having the contact members 1a, 1b maintained within the shaft 82 when the device is inserted through an incision. In this configuration, each contact member 1a, 1b is attached to a central shaft 83 by a connecting shaft 2 which has a tensioning wire 84 or spring mounted to the connecting shaft 2 and the central shaft 83 to deploy each contact member 1a, 1b when the central shaft 83 is extended from the substantially cylindrical main shaft 82 in which the contact members 1a, 1b are originally retained. Thus, in use, the contact members 1a, 1b are maintained in the retracted annular configuration of FIG. 16A until deployed within the surgical field as shown in FIGS. 16B through 16E, by extending the central shaft 83 downward causing the contact members 1a, 1b to be deployed below the main shaft 82. The contact members 1a, 1b unfold from their annular configuration and deploy into their substantially planar shape as shown in FIG. 16C. The contact members 1a, 1b rotate into position relative to the central shaft 83 by the tension in wire or spring 84 which is preferably disposed to act upon the connecting shaft 2 to cause contact members 1a, 1b to be fixed in a substantially parallel position to one another and substantially co-planar with the surface of the beating heart as shown in FIGS. 16D and 16E.

Thus, FIG. 16A shows the contact members 1a, 1b in their collapsed or retracted position. FIG. 16B shows the contact members in the process of being deployed as the central shaft 83 is extended from the bottom of the main shaft 82. FIGS. 16D and 16E show the tensioning wire 84 for repositioning the contact members 1a, 1b in the desired position for use in surgery. FIG. 16C shows the central shaft 83 fully extended from the bottom of the body of the main shaft 82 causing the deployment of the contact members 1a, 1b into the desired configuration for stabilizing the beating heart.

Preferably, the connecting shaft 2 joining the individual contact members 1a, 1b is hinged 85, such that upon completion of the anastomosis, the contact members 1a, 1b may be withdrawn by pulling the central shaft 83 upward relative to the main shaft 82 and into the body of the device, thereby causing the contact members 1a, 1b to be removable in a low-profile configuration.

Referring to FIGS. 17A through 17D, a similar strategy as is shown in FIGS. 16A through 16E is used whereby a pair of contact members 1a, 1b are deployed by a main shaft 86 within a hollow portion of the body 87 of the device. In the embodiment shown in FIGS. 17A through 17D, a pair of non-flexible contact members 1a, 1b may be provided to stabilize the beating heart in a minimally invasive environment by containing the contact members 1a, 1b in a body or housing 87 which is inserted through the minimally invasive incision. In this embodiment, the contact members 1a, 1b are mounted to a central shaft 86 by virtue of a pin or hinge 88 which affixes the end of the contact members 1a, 1b to the central shaft 86 such that the contact members 1a, 1b may be deployed by rotating around the pin or hinge 88 when the shaft 86 is extended downward from the body 87 of the device. The opposite portion of the contact members 1a, 1b (most distal from the hinge) may fit within a guide fixture 89 concentrically associated with the central shaft 86 that retains the contact members 1a, 1b in the desired configuration prior to deployment. In use, the central shaft 86 telescopes from an opening in the distal end of the body or housing 87 of the device by a distance at least as great as the overall length of the contact members 1a, 1b, at which point the contact members 1a, 1b may be deployed and locked into position, for example, in an orientation substantially perpendicular to the shaft as shown in FIGS. 17A and 17C. Once fixed in position by locking mechanism 90 as shown in FIG. 17C, the central shaft 86 may be rotated using the guide fixture 89 which is positioned downward to engage the contact members 1a, 1b. Thus, the guide fixture 89 engages the contact members 1a, 1b, the pin 88, or the locking mechanism 90, and by applying mechanical force, the position of the contact members 1a, 1b may be adjusted. Upon removal, the central shaft 86 is withdrawn into the body 87 of the device. Alternatively, the housing 87 may disengage the locking mechanism 90 from the guide fixture 89 releasing the position of the contact members 1a, 1b thereby allowing the contact members 1a, 1b to be returned to their original or other configuration that allows the contact members 1a, 1b to be drawn into the body of the device 87 to facilitate minimally invasive removal thereof.

Figure 18A:
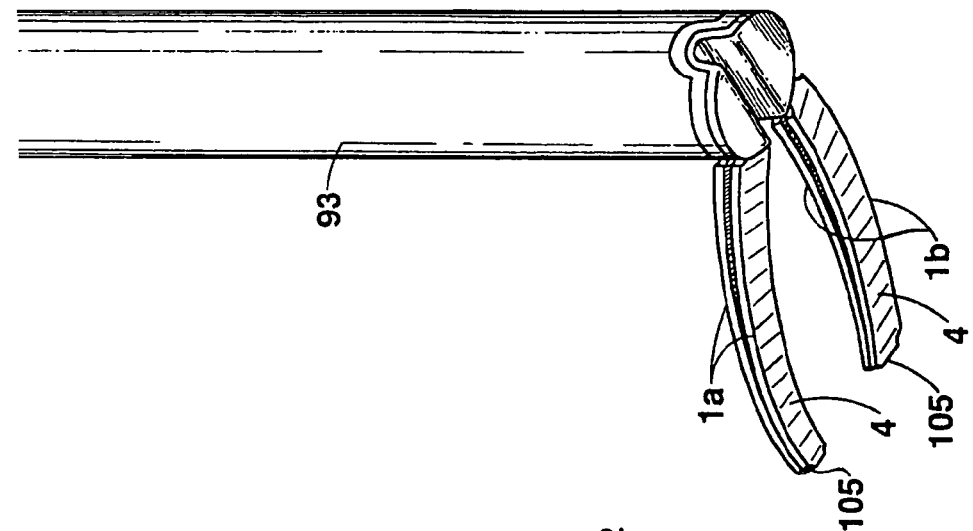
FIGS. 18A through 18D are contact members which are attached to a guide that is positioned about a shaft such that downward movement of the guide causes the contact members to be deployed.
Figure 18B:
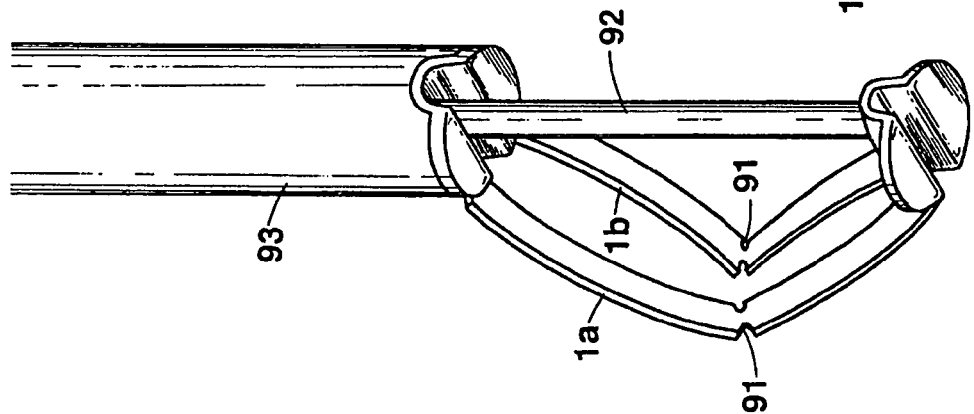
Figure 18C:
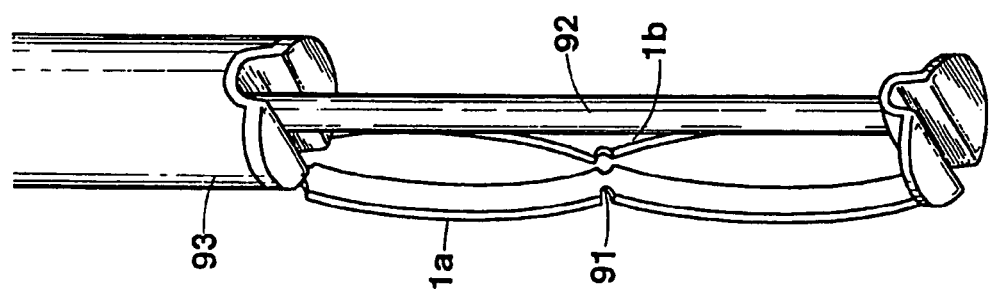
Figure 18D:
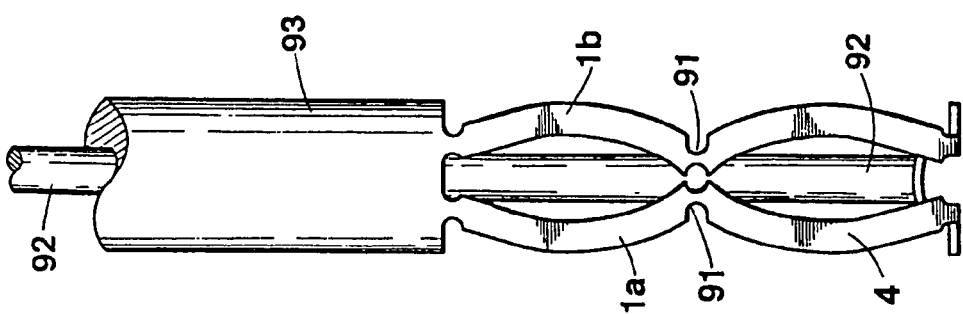

FIGS. 18A through 18D are an analagous embodiment having contact members 1a, 1b retained in the undeployed configuration suitable for insertion through a minimally invasion incision. As shown in FIGS. 18A and 18B, the contact members 1a, 1b may be maintained in a retracted position such that the length of the contact members 1a, 1b is substantially parallel to the central shaft 92. The proximal end of each contact member 1a, 1b is affixed to the guide fixture 93 while the distal end (below the hinge at central portion 91) has the bottom surface 4 formed therein and is affixed to the distal end of the central shaft 92. Referring to FIG. 18C, the contact members 1a, 1b are deployed by the downward motion of the guide fixture 93, such that the contact members 1a, 1b fold about the central portion 91. When the guide fixture 93 is fully extended downward, the contact members 1a, 1b are formed of a pair of two-part structures wherein the lower structure contains the bottom surface 4.

Figure 19A:
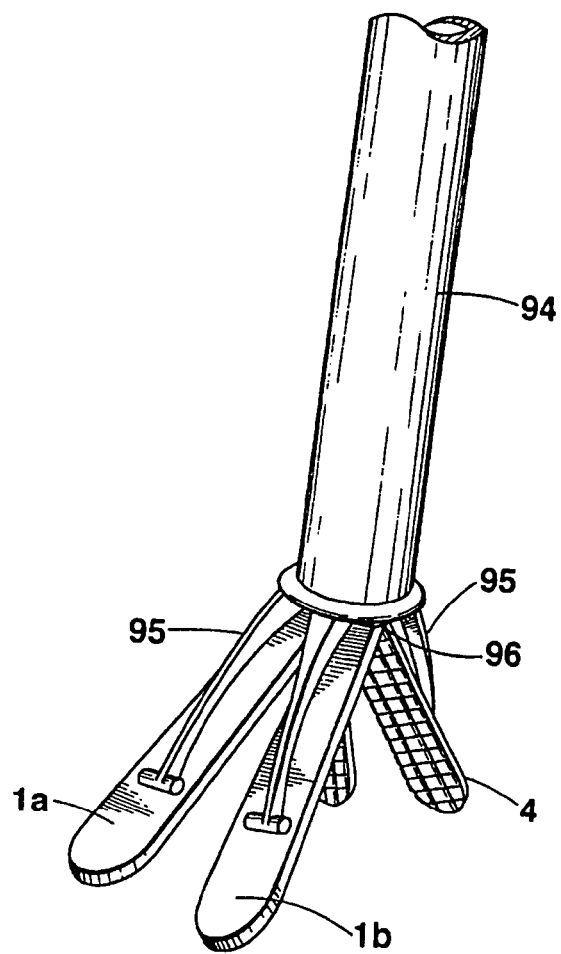
FIGS. 19A and 19B are contact members of the invention attached to a shaft means by a plurality of struts that extend the contact members into position.
Figure 19B:
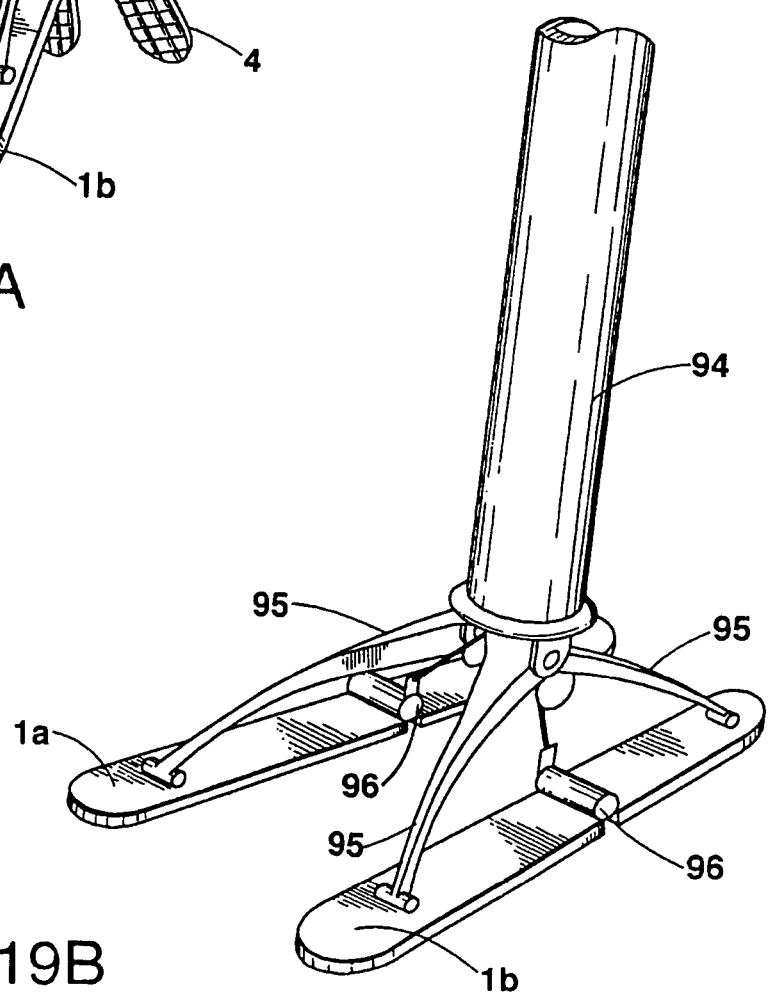

FIGS. 19A and 19B are an additional embodiment having foldable contact members 1a, 1b wherein a central shaft 94 is affixed to a plurality of hinged struts 95 that are connected to opposite ends of contact members 1a, 1b about a hinged central portion 96. When the central shaft 94 is extended downward, the hinged struts 95 deploy outward. As shown in FIG. 19A, the individual contact members 1a, 1b fold at the central hinged portion 96 to reduce the overall dimensional profile of the device for minimally invasive insertion or removal. When fully deployed (FIG. 19B), the contact members 1a, 1b are extendable to a substantially planar configuration as with other embodiments disclosed herein.

Figures 20A, 20B, 20C:
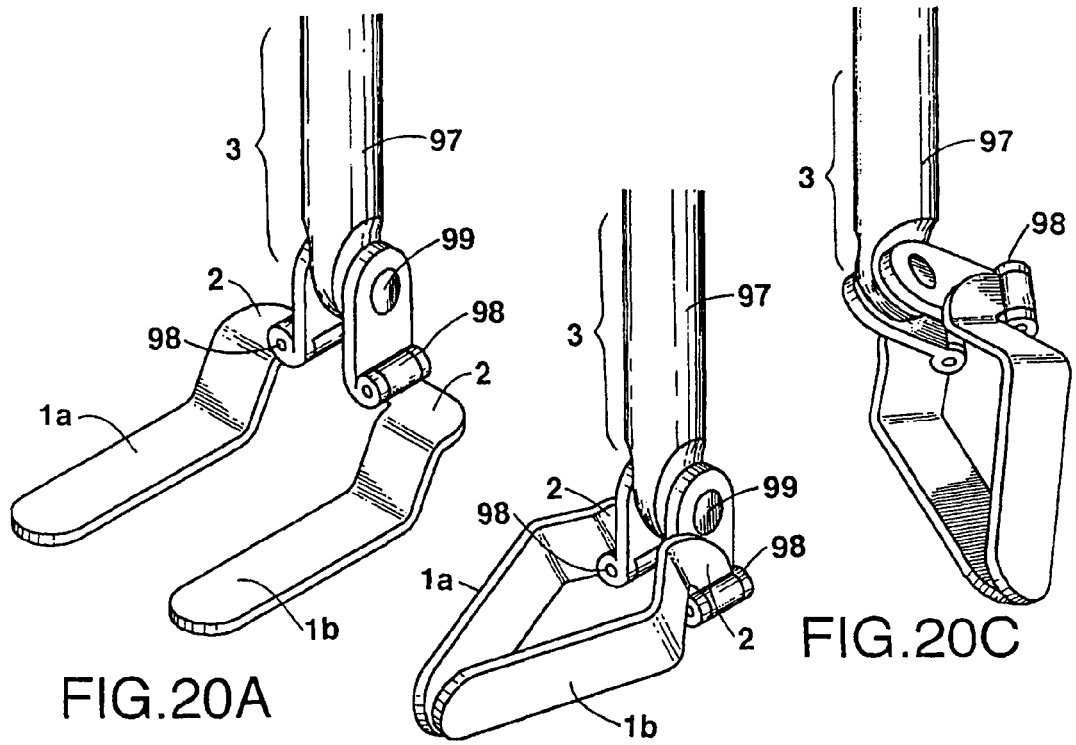
FIGS. 20A through 20E are contact members of the invention that are rotatable about the distal portion of a shaft means by a plurality of hinges.
Figures 20D, 20E:
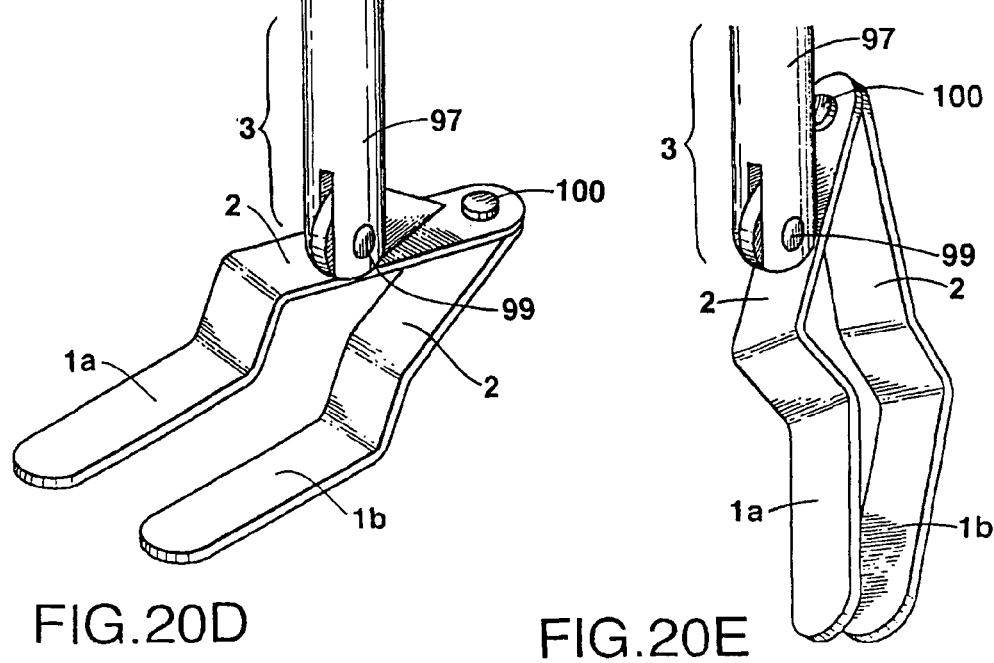

FIGS. 20A through 20E show the central shaft 97 and contact members 1a, 1b with alternate configurations for positioning the contact members for minimally invasive insertion and removal. Referring to FIG. 20A, first hinges 98 are provided in the connecting shaft 2 such that the contact members 1a, 1b can be rotated approximately 90° out of their co-planar configuration. A second hinge 99 is provided between the shaft means 3 and the connecting shaft 2 to tilt the distal end of the contact members 1a, 1b downwards as shown in FIG. 20C. The embodiments of FIGS. 20D and 20E are modified such that two interconnecting shafts 2a, 2b maintain the contact members 1a, 1b in slightly separate, yet parallel, vertical positions. A single hinge 100 with a vertical axis of rotation allows the contact members to be brought into close conformity before being tilted downward.

FIGS. 21A through 21C show a deployable stabilizer of the invention having contact members comprised of a single continuous wire 101 that is deployable from within a housing or body 102 which is ideally inserted through a minimally invasive incision. As shown in FIG. 21A, the single continuous wire 101 may be coiled and contained within the housing 102 such that the dimensional profile of the stabilizer is minimized for insertion. The wire 101 which forms the contact member(s) of this embodiment is preferably round and smooth, and may be formed of a material such as Nitinol that is collapsible, and deployable into a predetermined shape. As can be seen in FIG. 21B, following insertion, the wire 101 is extended from the body 102 of the device to form at least one loop 103 wherein at least one side 104 of the loop 103 contacts the surface of the heart. Preferably, at least two loops 103 extend from the body 102 of the device and are formed from a single wire 101. In this configuration, maximum stabilization is achieved if substantial portions of the sides 104 of both loops 103 contact the beating heart proximate to the target vessel. As in the previous embodiments, the insertion and removal of the stabilizing device through a very small incision is least traumatic when the dimensional profile, or effective diameter, of the contact members in a retracted configuration is not substantially greater than the dimensional profile or diameter of the body 102 of the device. Thus, as can be seen in FIG. 21C, the contact members of the embodiment of FIGS. 21A through 21C are drawn upward by exerting force on the wire 101, the contact members comprised of loops 103 are drawn into a configuration which is in alignment with the body 102 of the device such that their removal may be achieved through a puncture incision with minimal additional trauma to the patient.

Figure 22A:
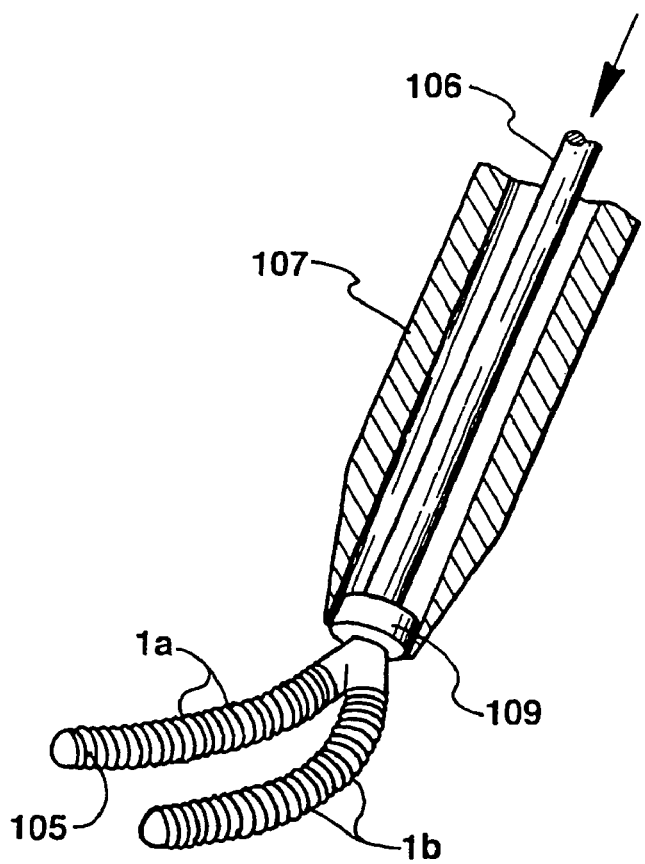
FIGS. 22A through 22C are an embodiment of the invention wherein the contact members are formed from a helical coil which may be withdrawn into the hollow portion of a shaft for minimally invasive insertion and removal.
Figure 22B:
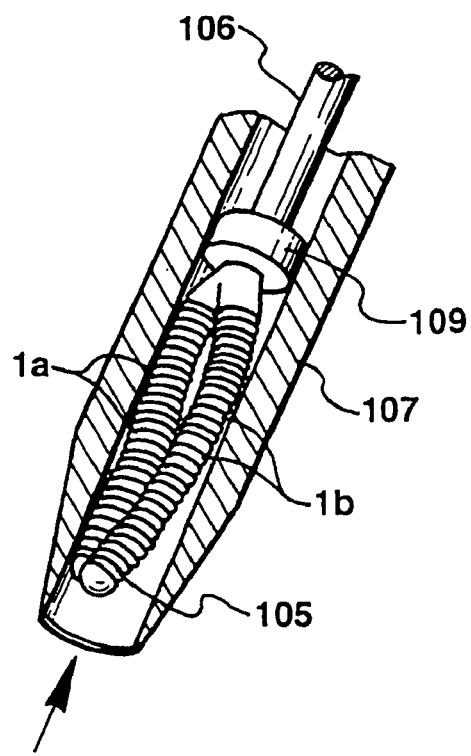
Figure 22C:
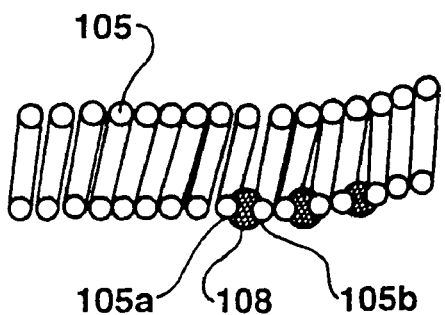

In addition to a single continuous wire 101, the contact members may be formed of a helical wire coil 105 as shown in FIGS. 22A through 22C. As in the embodiments described previously, the contact members 1a, 1b are deployed by extending a tubular central shaft 106 through a body or housing 107 of the device to deploy the contact members 1a, 1b. The downward motion of the central shaft 106 is terminated by the contact between a stop 109 and the distal end of the body 107. The contact members 1a, 1b are withdrawn into the body 107 of the device upon completion of the surgical procedure by pulling the central shaft 106 vertically through the body 107 of the device. A predetermined curve in the helical coil 105 may be provided by spacing members 108 placed between adjacent individual loops 105a and 105b of the helical coil 105. The central locking wires or cables may be tensioned upon deployment to increase the rigidity of the structure.

Figure 23A:
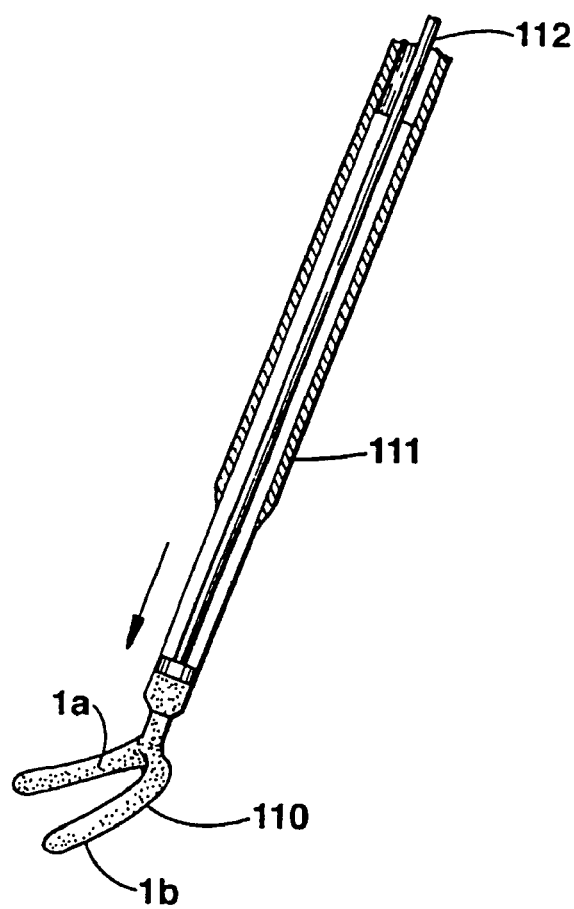
FIGS. 23A and 23B are inflatable contact members that may be deflated for insertion or removal by being drawn into the body of a shaft.
Figure 23B:
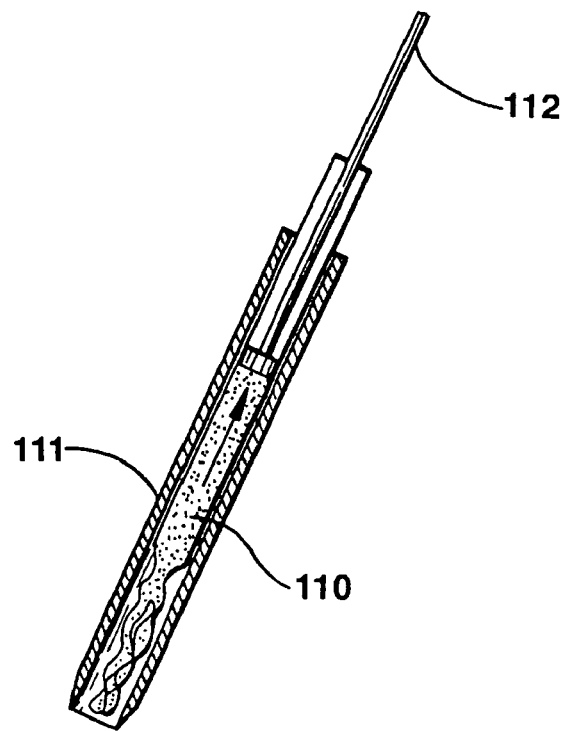

An additional configuration for minimally invasive insertion and removal is shown in FIGS. 23A and 23B wherein the contact members 1a, 1b are formed of an inflatable balloon 110 that is pre-shaped to provide any desired configuration of the contact members 1a, 1b. FIG. 23A shows a pre-formed inflatable balloon 110 in an inflated state and extended from the housing 111. Inflation is achieved by a central lumen 112 disposed within the central shaft 111. FIG. 23B shows the inflatable balloon 111 in an uninflated state for insertion or for removal.

Figure 24A:
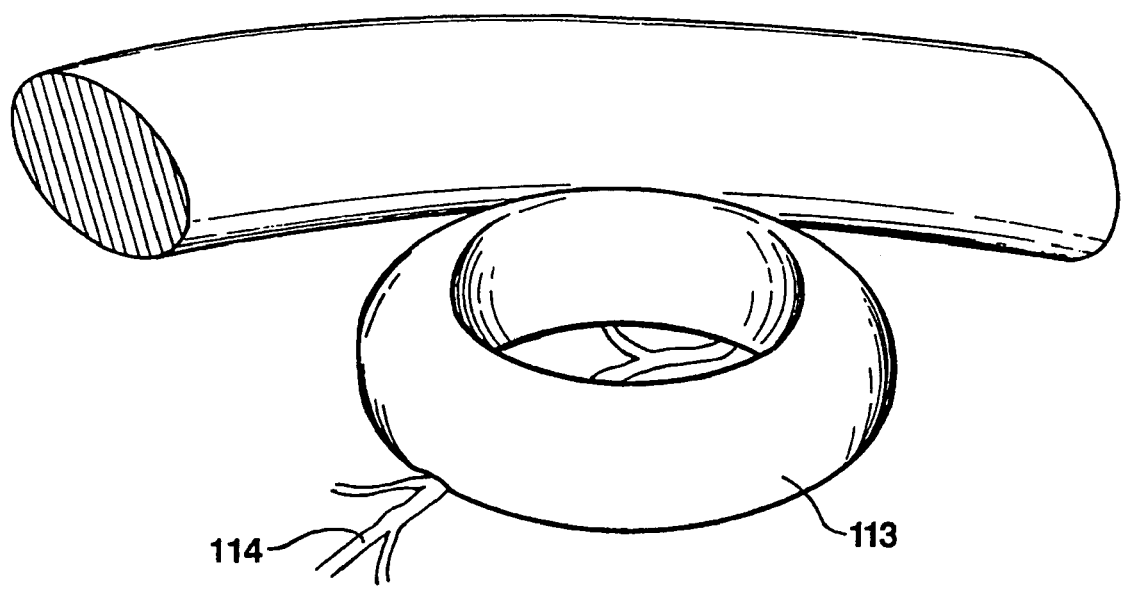
FIGS. 24A and 24B are a contact member of the invention formed from an inflatable annular cuff.
Figure 24B:
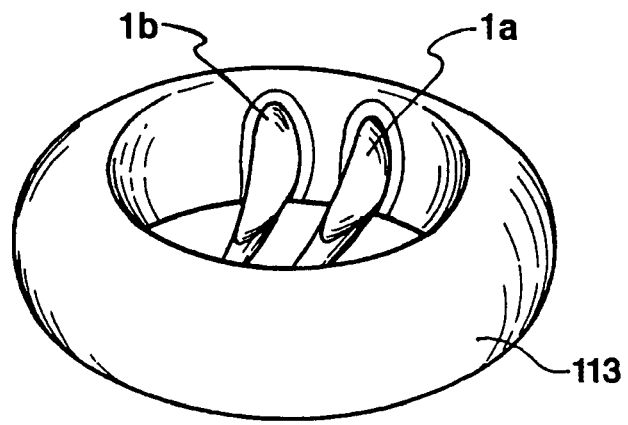

Referring to FIGS. 24A and 24B, an inflatable contact member may also be provided by a cuff 113 which is positioned such that the circumference of the cuff 113 contacts the beating heart about its periphery. Preferably, the target vessel 114 is positioned to bisect an annular cuff 113 to provide maximum stabilization. Additionally, referring to FIG. 24B, separate contact members 1a, 1b, as previously described herein, may be integrally formed with the cuff 113 by mounting the contact members 1a, 1b in the wall of the cuff 113 to extend into the interior thereof.

Figure 25A:
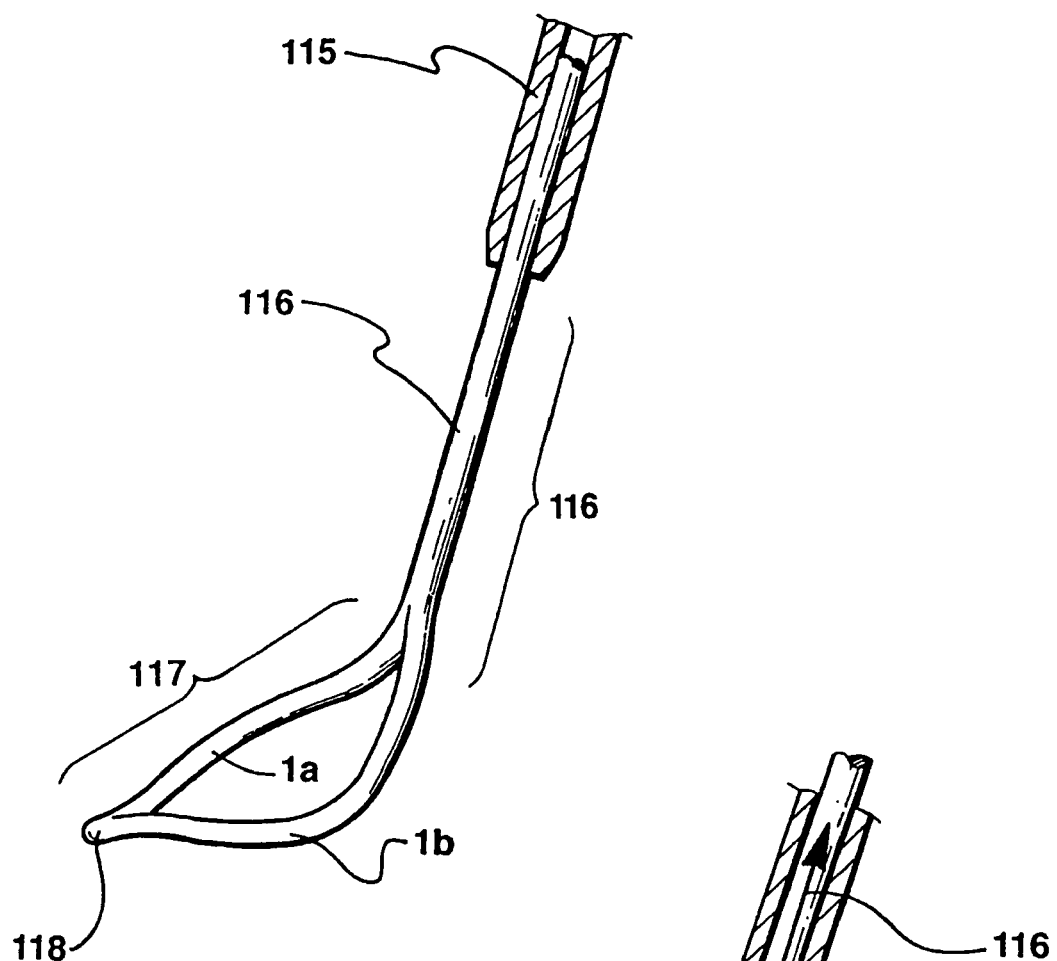
FIGS. 25A and 25B are contact members formed from the divided portion of the distal end of a shaft.
Figure 25B:
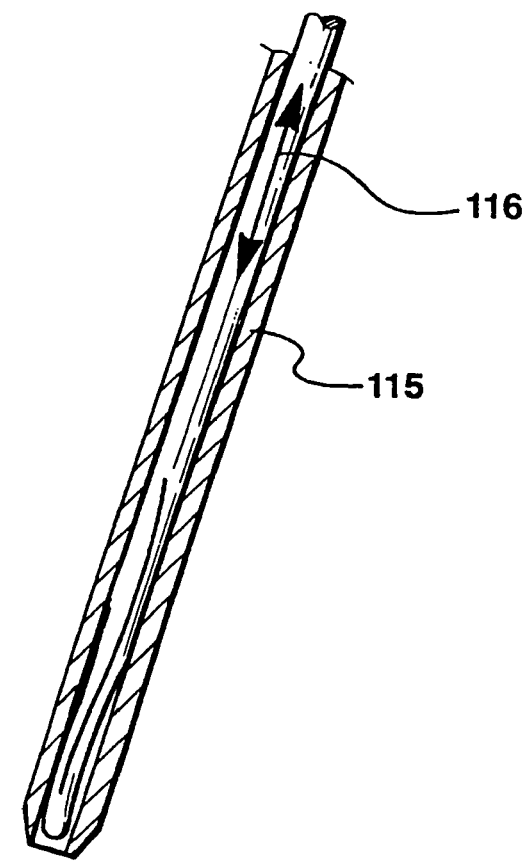

FIGS. 25A and 25B illustrate an embodiment of the invention which provides minimal trauma to the patient during insertion and removal of the stabilizing means by containing a simple stabilizer in an instrument having a housing 115 with an extremely limited cross-section such that the instrument can be inserted through an extremely small incision. In this embodiment, the entire stabilizing means is contained within the hollow housing 115 and is comprised of a pair of contact members 1a, 1b which are joined at the most distal end thereof. As can be seen in FIG. 25B, the contact members 1a, 1b are formed from a unitary shaft 116 having a divided portion 117 at the distal end such that upon deployment from the housing 115 of the device, the divided portion 117 splits into two contact members 1a, 1b joined at their most distal tip 118 and which may be brought into contact with the beating heart along the divided portion 117 of the unitary shaft 116.

In addition to the friction means or cushioning members described above in FIGS. 1B through 1G and FIG. 3, sutures may be used to attach or position epicardial tissue relative to a contact member 1 to enhance the stabilization function of the invention and to position epicardial tissue or the target vessel of the anastomosis. FIG. 26A, 26B, and 26C are embodiments where means for fixing the position of epicardial tissue is comprised of sutures 119 used in combination with the contact members 1a, 1b to stabilize and position tissue surrounding the site of an anastomosis and the target cardiac artery. In FIG. 26A, a series of sutures 119 is placed through the epicardial tissue (not shown) and looped around the contact members 1a, 1b to effectively position several points on the surface of the beating heart in fixed relationship to the contact members 1a, 1b. In FIG. 26B, the contact members 1a, 1b and optionally the shaft means 3 associated therewith have passages 120 formed therein through which a suture line 119 may be passed. In the particular example of FIG. 26B, a single suture 119 is passed through the body of the shaft 3, exits from within the first contact member 1a through a passage 120 formed therein, passes underneath the target vessel 121, emerges from an opposite side of the target vessel 121, and enters a passage 120 in the opposite contact member 1b joined to the first contact member 1a by the connecting shaft 2. The suture 119 exits the opposite contact member 1b again passes beneath the target vessel 121, reenters the first contact member 1a at a separate passage 120, and passes through the body of the first contact member 1a and into the shaft means 3. In this configuration, the suture lines may be manipulated by the surgeon from a remote location, such as external to the incision in the chest, to remotely position the vessel by drawing tension on the suture line 119. FIG. 26C shows a similar arrangement for the suture line 119 as in FIG. 26B, however in FIG. 26C, apertures 122 in the body of the contact member 1 are used to select the direction of the suture 119 rather than having passages 120 which traverse the body of the contact member 1. Also, in this or the other embodiments, a separate sliding shaft 123 may be provided that gathers and is traversed by the sutures 119. The step of drawing tension on the suture line 119 is facilitated by advancing the sliding shaft 123 to abut the contact member 1 and exerting a small downward force on the sliding shaft 123 while exerting an upward force to draw tension on the suture line(s) 119. By maintaining downward force on the sliding shaft 123, the target vessel 121 is raised while the potential for displacing the contact member 1 is minimized because the upward force exerted on the suture lines 119 is countered by the downward force exerted on the sliding shaft 123.

Figure 27A:
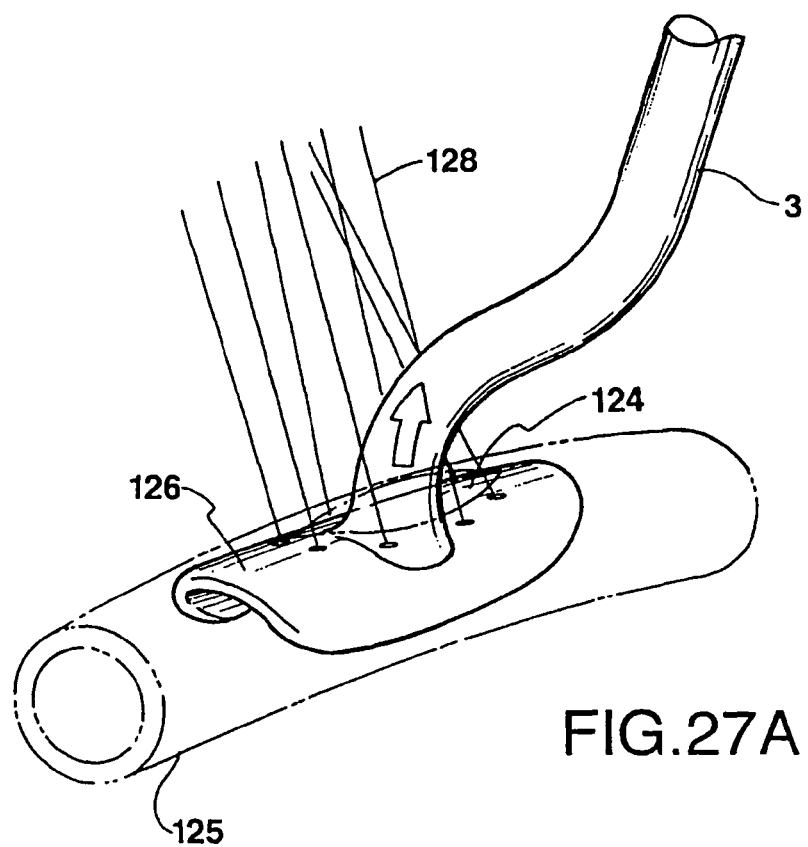
FIGS. 27A and 27B are an intravessel stabilizer adapted to fit within the target coronary artery.
Figure 27B:
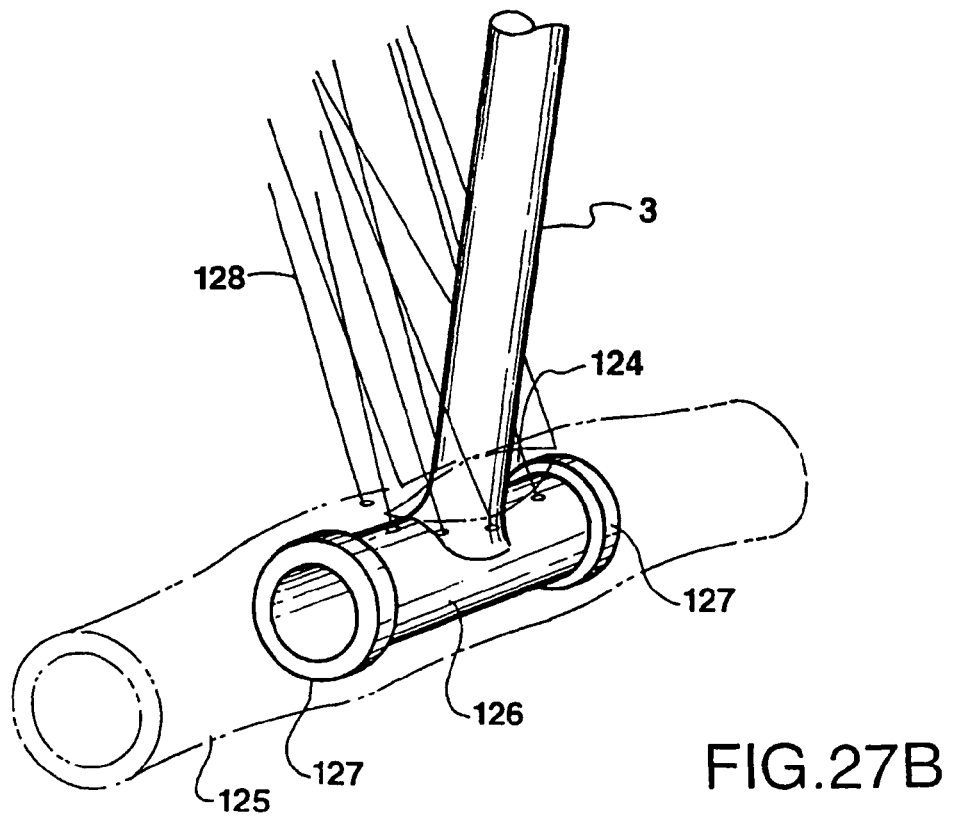

Referring to FIGS. 27A and 27B, a modification of the contact member 1 of the invention may be provided by a structure formed at the distal end of the shaft means 3 and which is inserted directly into the arteriotomy 124 formed in the target vessel. This intravessel stabilizer 126 has a body designed to fit conformingly about the interior of the target vessel, and may be in communication (including fluid communication) with a hollow portion of the shaft means 3. The body 126 of the intravessel stabilizing means may be a substantially cylindrical lumen as shown in FIG. 27B and should have an overall length which is greater than the length of the incision creating the arteriotomy 125. Additionally, in the embodiment of FIG. 27B, the intravessel stabilizer 126 may be perpendicular to the shaft means 3 and have cuffs 127 at the distal end of the body 126 to provide conforming engagement with the interior of the target vessel. As shown in both FIGS. 27A and 27B, this embodiment of the stabilizing means of the invention is preferably used in connection with a plurality of sutures 128 that penetrate the edges of the target vessel about the circumference of the arteriotomy 125. By exerting pressure on the shaft means 3 and the plurality of sutures 128, the target vessel is stabilized, and its position may be manipulated, to facilitate completion of the anastomosis.

Figures 28A, 28B:
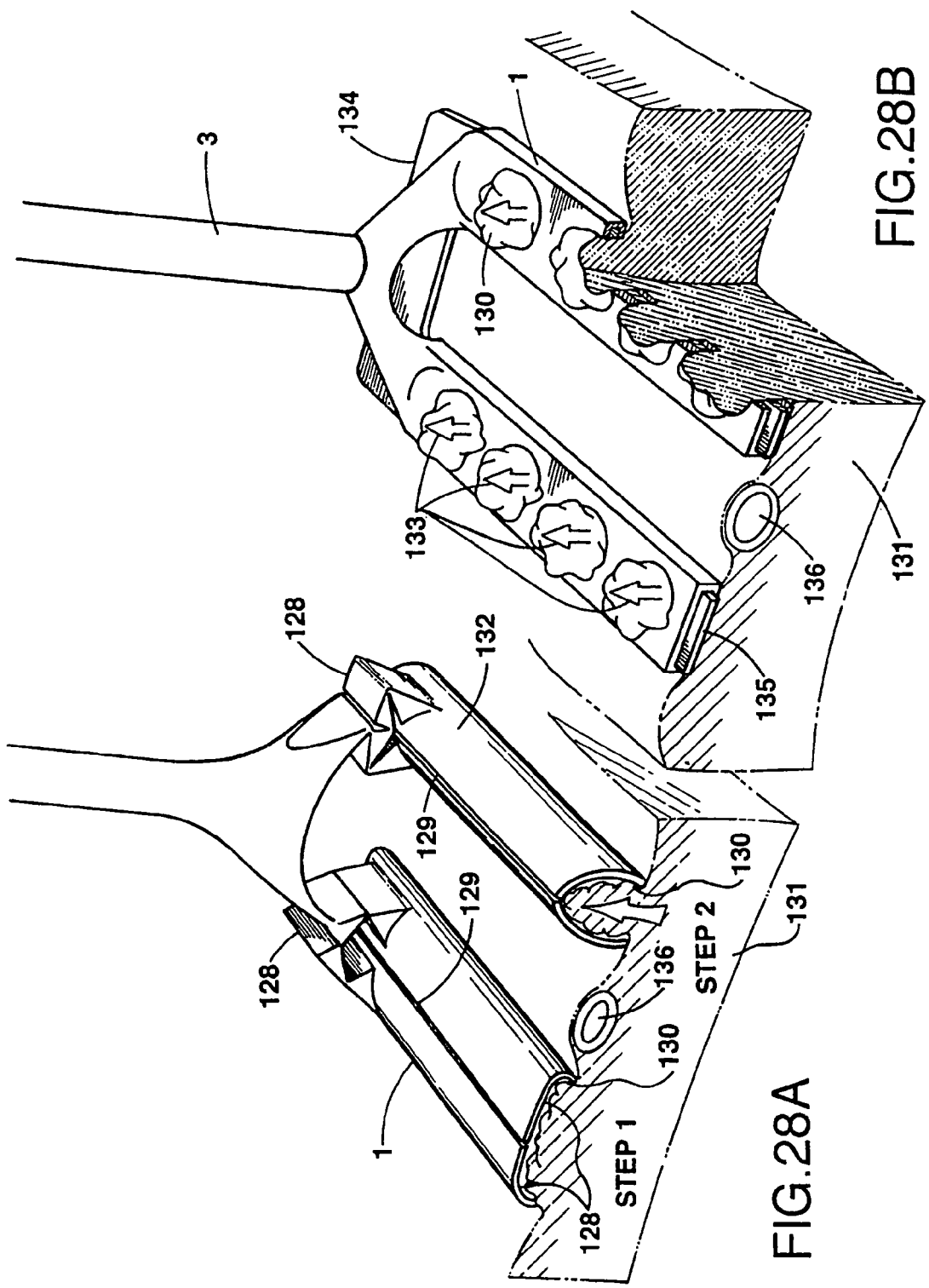
FIGS. 28A and 28B are contact members of the invention having means associated therewith for positioning said epicardial tissue.

In addition to stabilization of the beating heart proximate to the target vessel of the anastomosis, additional fixtures, structures or elements associated with the contact members 1 can be used to retract or fix epicardial tissue proximate to the target vessel and the site of the anastomosis by using a means for gripping epicardial tissue at the surface of the exterior of the heart. The means for gripping may be provided by several different embodiments. For example, FIG. 28A shows a functional clamp 128 formed by a crimping contact member 1 that has a fold 129 disposed longitudinally at the center of the length of the contact member 1. When force is applied to the sides of the contact member 1 opposite the fold 129, the crimping action of the contact member 1 grasps the epicardial tissue 130 at the heart surface 131 and contains it within the folded contact member 132. In another embodiment, as shown in FIG. 28B, a plurality of open passages 133 are provided in a contact member 1 that has a slidable member 134 disposed within a slot 135 formed within the contact member 1. When sufficient force is exerted in a downward direction on shaft 3 to force epicardial tissue 130 through the open passages 133, the slidable member 134 then may be actuated to grip the tissue 130 contained within the open passages 133. By gripping a portion of epicardial tissue 130, the tissue may be spread to more readily expose the target vessel 136 of the anastomosis.

Figure 29A:
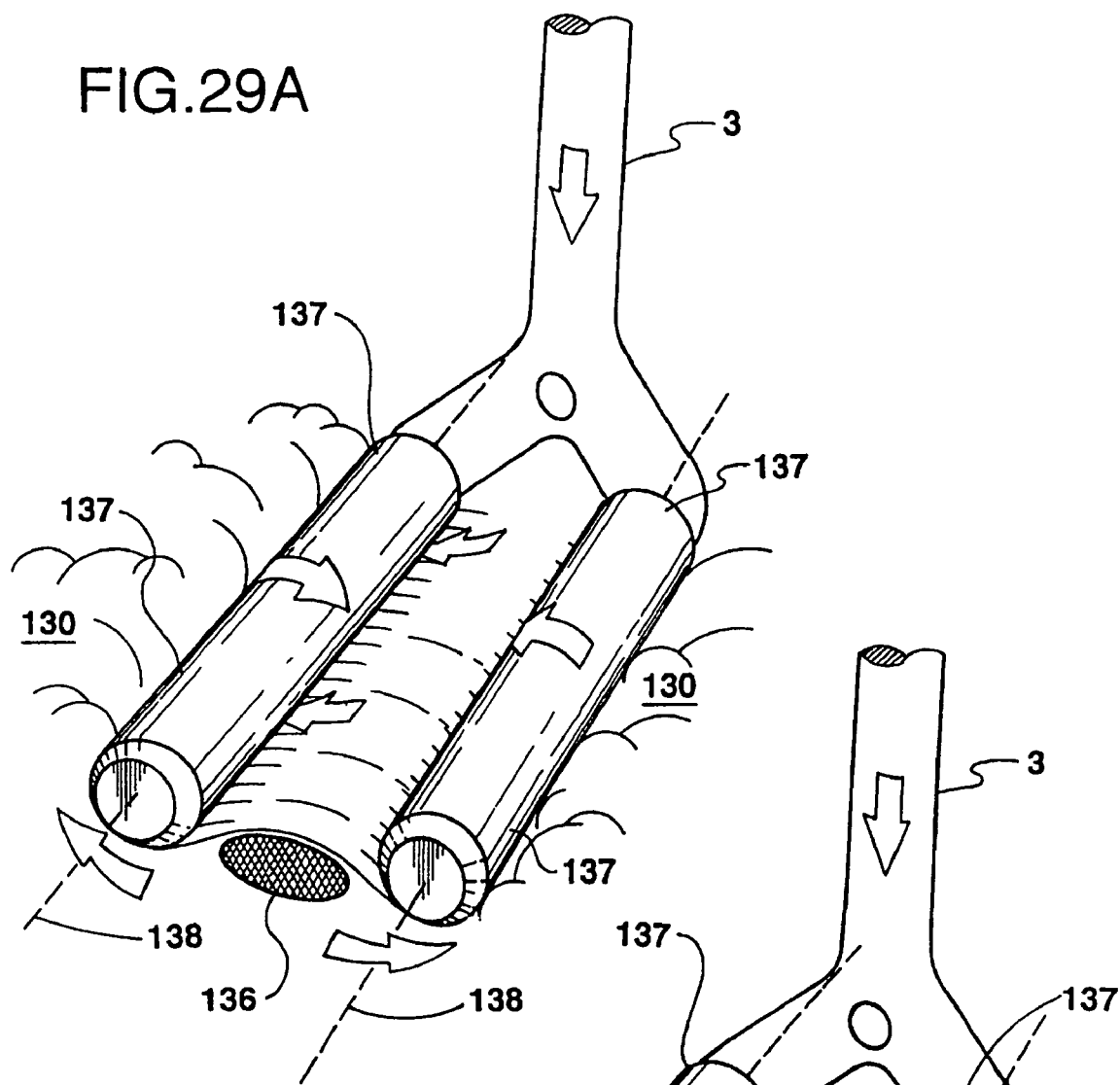
FIGS. 29A and 29B are contact members of the invention having rotatable cylindrical rollers for collecting or spreading epicardial tissue proximate to a target artery.
Figure 29B:
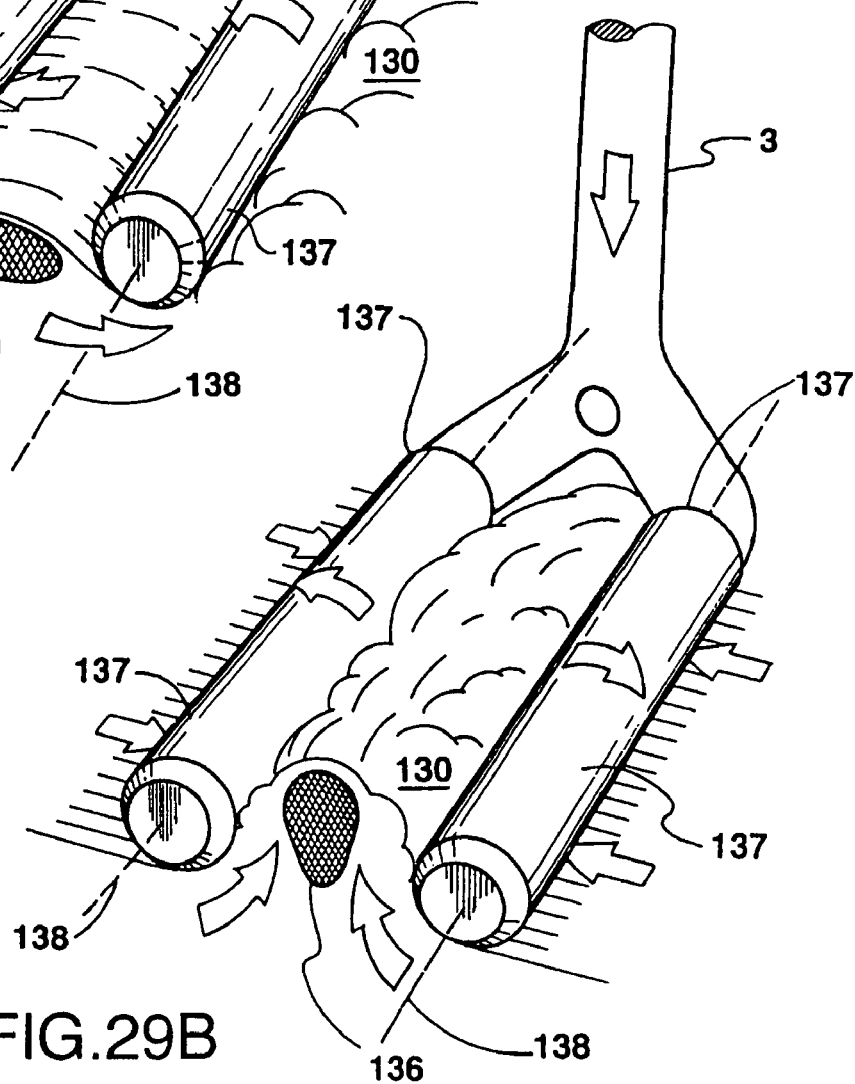

A similar function is provided by a pair of contact members 1 that are formed of circular rollers 137 that lie longitudinally parallel to the direction of the target vessel 136 as shown in FIGS. 29A and 29B. The contact members 1 may be comprised of movable rollers 137, belts, or pivoting surfaces that may be rotated independently about an axis 138 dedicated to each contact member 1 such that the epicardial tissue 130 is gathered or spread, depending on the respective directions of rotation of the rollers 137, as desired at the surface of the heart to expose the target vessel 136. As will be apparent to those skilled in the art, each of these embodiments may be provided with contact members 1 that are independently movable in a parallel, V-shaped, or other adjustable configuration as described and illustrated herein.

Figure 30:
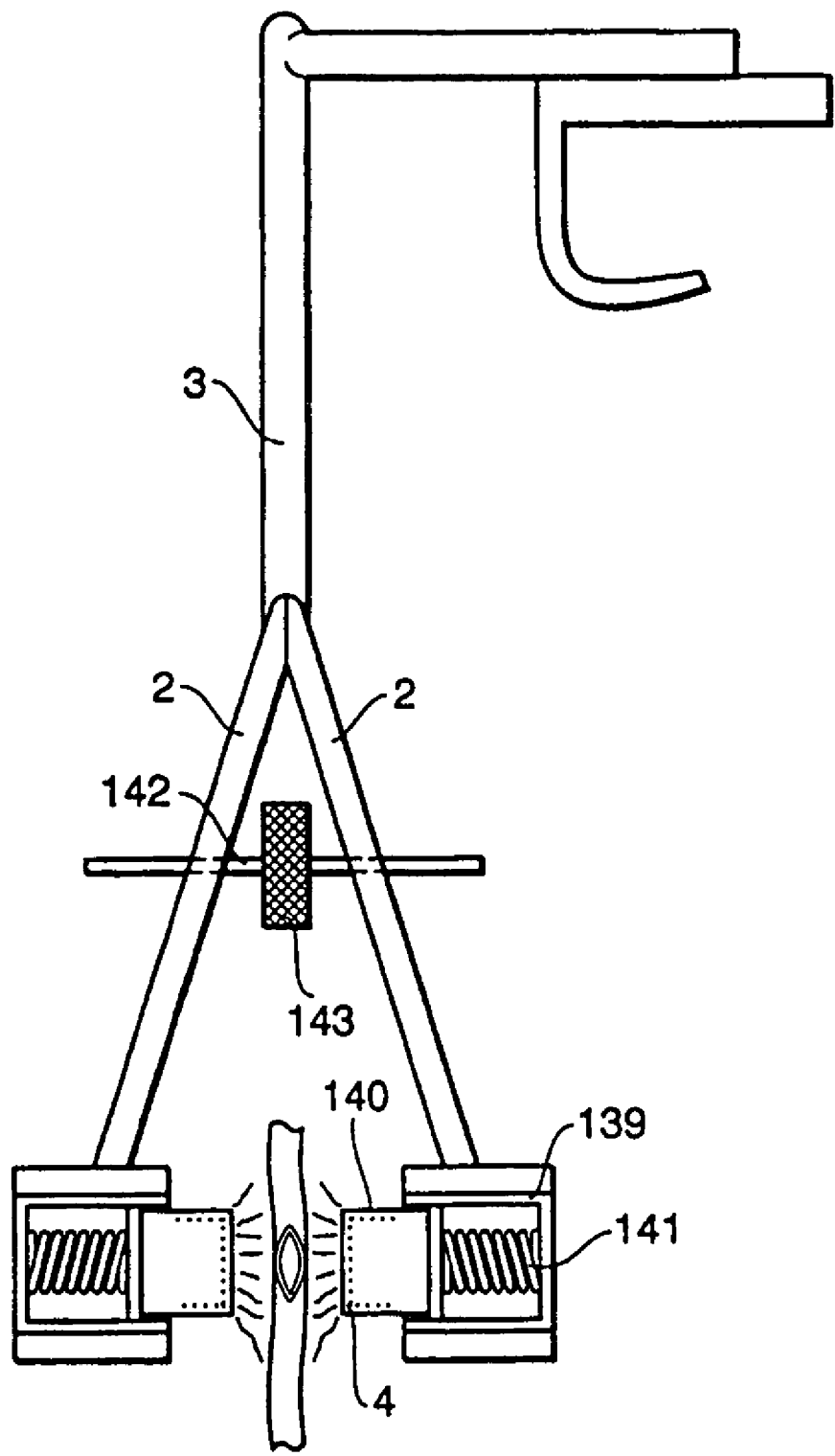
FIG. 30 is a means for stabilizing the beating heart having a pair of contact members which are additionally comprised of a spring-tensioned frame having an extension that engages and spreads the tissue at the site of the surgery to better expose the coronary artery.

Referring to FIG. 30, the contact members 1 may be further comprised of a spring-tensioned frame 139 having a movable frame extension 140 which may have pins or an associated friction means 4 at the bottom surface 4 of the contact members 1a, 1b to engage the tissue proximate to the target artery. The movement of the frame extension 140 is tensioned by a spring means 141 which draws the frame extension 140 toward the contact member 1 after the frame extension 140 has been manually positioned to engage the tissue. The use of this embodiment of the invention is the same as is described for the other embodiments herein, with the frame extension 140 providing the improved exposure of the target artery by retraction of the epicardial tissue. As with the other embodiments, the contact members 1 may be attached at one end by a connecting shaft 2 which is attached to a shaft means 3 as described above. The connecting shafts 2 may also be positioned relative to one another by a conventional threaded post 142 with a positioning thumbscrew 143.

Referring to FIGS. 31A and 31B, the stabilizer means may also be comprised of a single shaft means 3 connected to each contact member 1. In a preferred embodiments the shaft means 3 are interconnected at an intermediate pivot point 144 which permits the contact members 1 to be continuously positioned in parallel fashion relative to one another. The proximal (upper) portion of the individual shaft means 3 may have grips adapted to be grasped by the hand or may have an anchor portion 145 for attachment to a retractor or other fixed support. As with the other embodiments described herein, the length of the shaft means 3 may be adjustable by a conventional telescope configuration. In such a configuration, a first shaft 148 has a partially hollow segment 147 adapted to receive the complimentary portion of the second shaft 148. Either first 146 or second 148 shafts may be connected to the contact members 1 and may each have a conventional interlocking mechanism 151 to fix the relative positions of the shafts. The shaft means 3 may also have a tensioning spring mechanism 150 having an axis 149 which is displaced between a portion of the shaft means 3 affixed to the contact members 1 and the remainder of the shaft means 3. In this configuration, the contact members 1 remain tensioned against the heart proximate to the anastomosis site when the proximal end of the shaft means 3 is affixed to a stable support. This embodiment also preferably has a friction means as described above affixed to the bottom surface 4 of each contact member 1. An additional advantage of this embodiment is derived from the capability to move the contact members 1 apart from one another in a parallel configuration. Thus, the contact members 1 can first be positioned to engage the surface of the heart tissue, followed by the application of a stabilizing force in combination with spreading or joining of the proximal (upper) end of the shaft means 3. Application of a stabilizing force causes the tissue on either side of the target artery to be spread or compressed while the heart is stabilized. Thus, by coincidentally spreading or joining the proximal portion of the shaft means 3, the epicardial tissue engaged by the contact members 1 is stretched or compressed to provide stabilization and improved exposure and positioning of the target coronary artery.

Figure 32C:
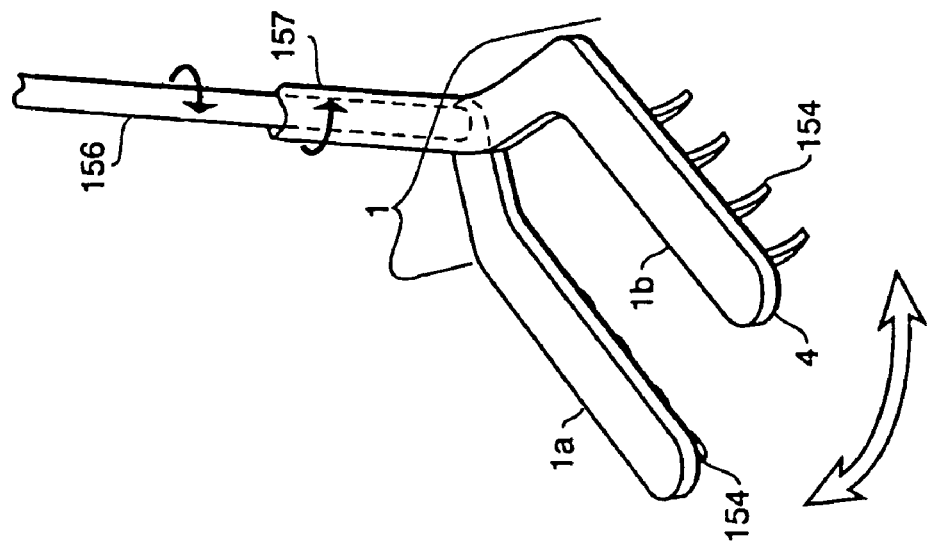
FIGS. 32A through 32C are embodiments of the invention wherein the contact members have additional structures associated therewith for retraction of epicardial tissue, the epicardial retractors may be comprised of pins which extend from the bottom surface of the contact member.
Figure 32B:
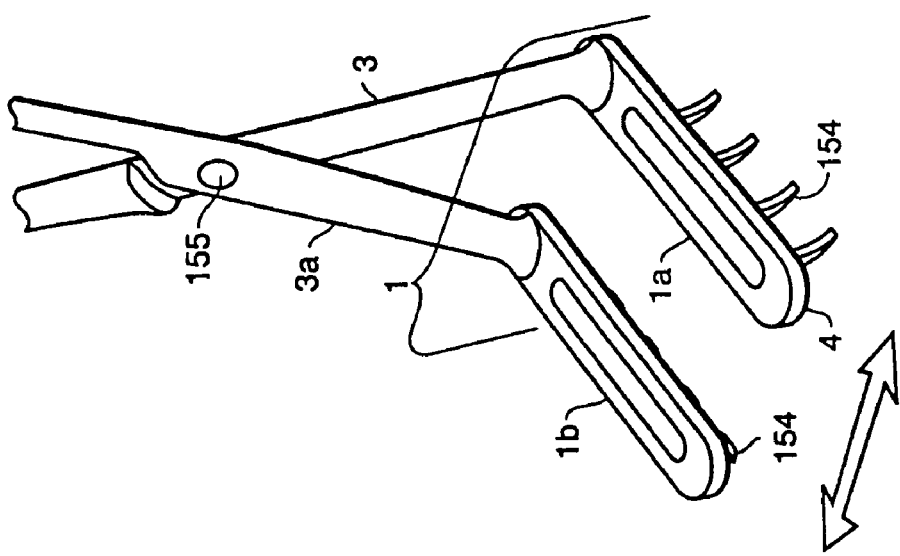
Figure 32A:
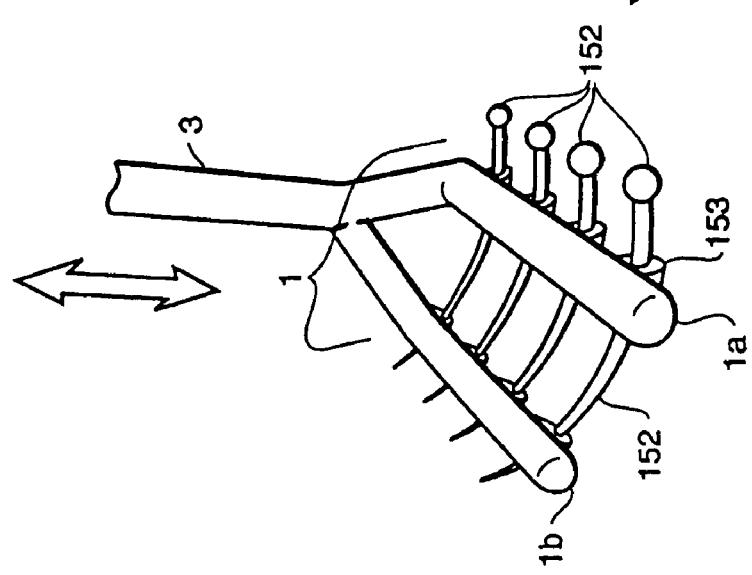

Referring to FIGS. 32A through 32C, the contact members 1 may have associated therewith additional structures which serve to position or retract epicardial tissue, at or around the surface of the heart, particularly tissue in the vicinity of the site of the anastomosis. Often, the surgeon wishes to retract the epicardial tissue near the target vessel to increase exposure of the vessel where the anastomosis is to be performed. Additionally, these associated structures provide an additional amount of stabilization by actually penetrating the tissue at the outer layer of the heart and holding the tissue in close conformity to the contact member.

Referring to FIG. 32A, epicardial tissue retractors are provided by a series of curved pins 152 which generally extend from one contact member 1a to the other 1b by virtue of a guide 153 attached to the bottom of each contact member 1 and which is dedicated to a single pin 152. In this embodiment, a plurality of pins 152 are substantially parallel to one another and may be inserted and positioned to pass beneath the vessel where the anastomosis is to be performed. In this fashion, the surgeon can position the vessel, by virtue of the tissue engaged by the pins 152 and the contact members 1a, 1b in any direction. This embodiment is particularly useful to vertically displace the tissue, i.e., in a direction perpendicular to the shaft means 3.

An additional embodiment is shown in FIG. 32B, whereby a plurality of short pins 154 extend down from the bottom surface 4 of the contact member 1 to enter the epicardial tissue. The short pins 154 may extend in a direction substantially perpendicular to the surface of the tissue and the bottom surface 4 of the contact member 1, or may be angled outward to engage the tissue. The advantages of this embodiment are best utilized with a stabilizing means wherein the individual contact members 1a, 1b may be selectively positioned such that the distance between the individual contact members is varied. Thus, the contact members 1a, 1b can be brought into contact with the surface of the beating heart followed by spreading the contact members 1a, 1b apart from one another to provide retraction and spreading of the epicardial tissue. This is readily achieved in the embodiment of FIG. 32B, wherein a single shaft means is dedicated to each contact member 1a, 1b, respectively and the individual shafts are joined by an intermediate pivot point 155.

A similar embodiment is shown in FIG. 32C, however, in this embodiment, while each contact member 1a, 1b has a dedicated shaft, the shaft 156 dedicated to the first contact member 1a is disposed within a hollow shaft 157 dedicated to the second contact member 1b. In this configuration, each shaft 156, 157 may be individually rotated about the other to provide a V-shaped retraction of the epicardial tissue. In this embodiment, the epicardial retractor pins 154 are preferably similar in structure and orientation to the embodiment of FIG. 32B. The pins in both designs could alternatively be curved or angled inward, and the contrast members 1 moved toward each other, providing a compression of the epicardium to stabilize the tissue and present the anastomosis site to best advantage. This action may also serve to occlude the blood flow in the coronary artery, minimizing blood loss and obstructions of the visual field.

Referring to FIGS. 33A and 33B, the stabilizer means may comprise at least one stabilizer plate which is attached to a stable support by the shaft means 3 and which may be used with a lever member 158 for improving exposure at the target artery while the anastomosis is completed. In this embodiment, the means for stabilizing the beating heart comprises a left and right stabilizing plate 159, 160 which are oriented to exe a downward force on the epicardial tissue at either side of the target artery at the anastomosis site and which may be substantially planar or may be curved to conform to the surface of the heart. One or both of the stabilizing plates 159, 160 may have an edge 161 deflected downward along its length so that the edge 161 depresses the tissue proximate to the artery to increase the exposure of the artery during the completion of the anastomosis. Preferably, the edge 16 of the stabilizing plates 159, 160 has a separate lever member 158 running substantially parallel to the artery and on both sides thereof. The top portion of each lever member 158 contacts the underside of the stabilizing plates 159, 160. In this embodiment, the lever member 158 is substantially cylindrical, traverses the stabilizing plate along its length, and is oriented to be parallel to the edge 161 of the stabilizing plate 159, 160. The lever member 158 is fixed in place, and may be affixed to the heart by a suture. In such a configuration, each of the stabilizing plates 159, 160, which is in contact with the lever member 158 along its length, contacts the heart such that the edge 161 depresses the tissue on both sides of the target coronary to restrict the movement of the beating heart. The stabilizing plates 159, 160 can be attached to one another or can move independently as desired.

Opposite the edge 162, at a point separate from the lever member 158, the stabilizing plates 159, 160 are connected to a shaft means 3 which holds the stabilizing plates 159, 160 in position and which may be manipulated relative to the lever member 158 to cause the edge 161 to engage the heart. The shaft means 3 is preferably affixed to each stabilizing plate 159, 160 at a point opposite the edge 161 and removed from thr point where the lever member 158 contacts the stabilizer plates 159, 160 at a location to maximize leverage when the stabilizer plates 159, 160 are drawn upwards at the point of attachment of the shaft means 3. The shaft means 3 may be constructed as described elsewhere herein and should be of sufficient length to facilitate manipulation of the shaft means 3 by the surgeon. As noted, the shaft means may also be attached to the retractor to fix movement of the stabilizing plates 159, 160 during the procedure.

In a preferred embodiment, the length of the shaft means 3 is adjustable relative to the retractor or other stable support. For example, the shaft means 3 may be telescopic as described above or may be comprised of a hollow post 163 which receives a rigid shaft 164 which is in turn fixed to the retractor. The rigid shaft 164 may also be substantially hollow and may have a suture or other line 165 passed therethrough and which also passes through the length of the hollow post 163. In this configuration, one end of the or line 165 is attached to the stabilizing plates 159, 160 and the other end extends through the hollow post 163 or the rigid shaft 164 to a position where it may be manipulated by the surgeon. The position of the stabilizing plate 159, 160 may thereby be remotely actuated. By drawing tension on the suture or line 165, the stabilizing plate 159, 160 pivots about the lever member 158 and the edge 62 of the stabilizer plates 159, 160 depress the tissue on either side of the target artery.

Figure 34A:
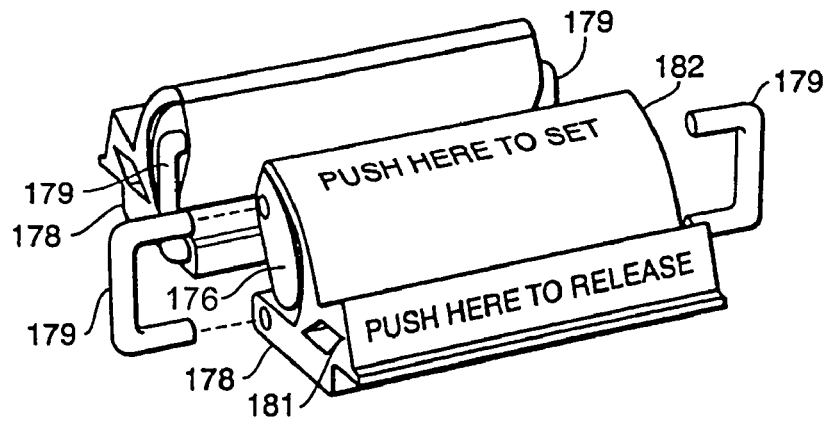
FIGS. 34A through 34D are an embodiment of the invention having a lockable mechanism for depressing epicardial tissue on either side of a target coronary artery.
Figure 34B:
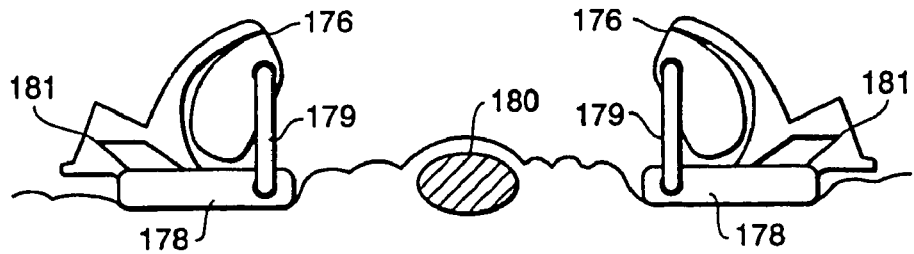
Figure 34C:
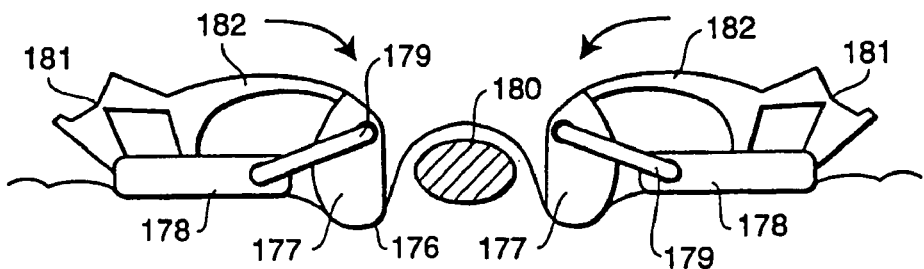
Figure 34D:
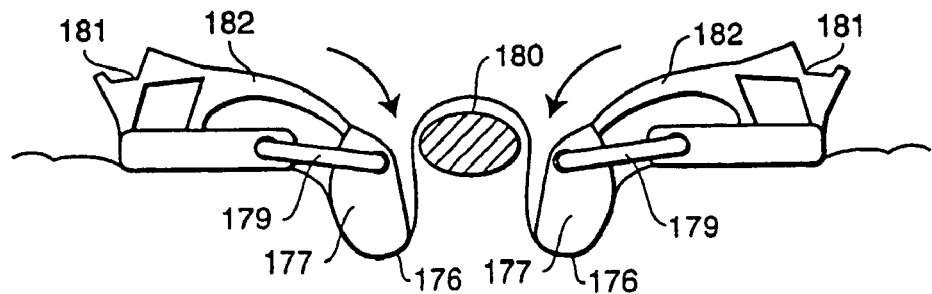

Referring to FIGS. 34A through 34E, a lockable mechanism may be provided to depress tissue on either side of a target vessel by a movable edge 176 formed along the edge of a block 177 which rotates about a support member 178 by means of a hinge pin 179. The support member 178 may be affixed to the upper surface of a contact member as described herein or may itself comprise the contact member. In use, as shown in FIG. 34B, the block 177 is rotated about the support member 178 using hinge pin 179 until the movable edge 176 contacts the surface of the heart parallel to the target vessel 180 (FIG. 34C). The moveable edge 176 and block 177 are fixed in place by depressing locking member 181 to force the block 177 to rotate until an interconnecting member 182 extends the block 177 and edge 17 to fully depress the tissue proximate to the target vessel 180. At this point, and shown in FIG. 34D, the locking member 181 fixes the interconnecting member 182 in an extended position and is locked in place (FIG. 34E). The position of the block 177 may be released by actuating the locking member 181 to release the interconnecting member 182.

Due to the fact that the heart continues to beat during the CABG procedures described herein, features of the invention which provide the capability to manipulate the target vessel, and to control the flow of blood therein, may greatly facilitate an efficient completion of the anastomosis. For example, additional components associated with the contact members 1 may be used to occlude the target vessel during the anastomosis procedure. Any of a variety of fixtures may be provided to operate in association with the contact members of the invention in order to occlude the vessel that is the target of the anastomosis.

Figure 35:
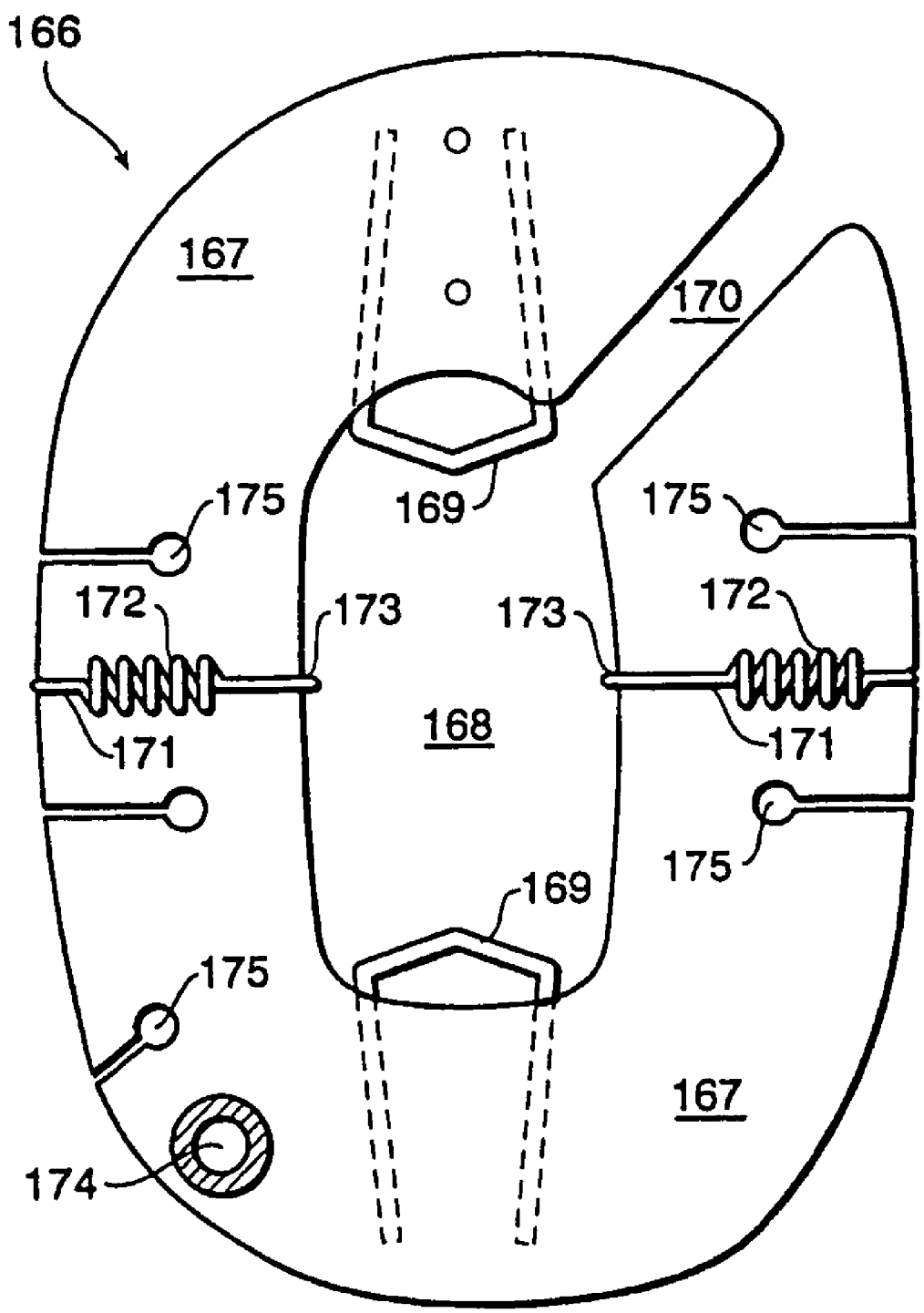
FIG. 35 is a substantially planar stabilizing platform which contacts the heart at a site proximate to and surrounding the coronary vessel. The platform may also have associated therewith at least one occluder which restricts or eliminates blood flow through an artery and an associated device for spreading the tissue proximate to the anastomosis.

Referring to FIG. 35, a stabilizing means 166 is comprised of a contact member which is substantially planar and has a substantially rigid surface 167 having a centrally disposed opening 168 in which the target artery of the anastomosis positioned longitudinally through the opening. At either or both ends of the centrally disposed opening 168, an occluder 169 extends below the surface 167 and engages the target artery to substantially reduce or eliminate the flow of blood through the artery. The occluder 169 is a deformable member having a smooth outer surface for adjustably contacting and depressing the target artery without damaging the tissue. The planar surface 167 of the stabilizing means also has an aperture 170 comprising an opening which traverses the entire planar surface 167 so that the graft can be passed through the aperture 170 when the anastomosis is completed. The planar surface 167 so may also provide a mounting surface for springed tissue retractors 171 comprising a coiled spring 172 attached to the planar surface at one end and having a hook or pin 73 at the opposite end to engage and spread the tissue proximate to the anastomosis site to improve the exposure of the target artery. The planar surface 167 is attached to a post 174 which may be attached to a stable support such as a rib retractor. The planar surface 167 may also have at least one port 175 for receiving a suture line.

Figure 36:
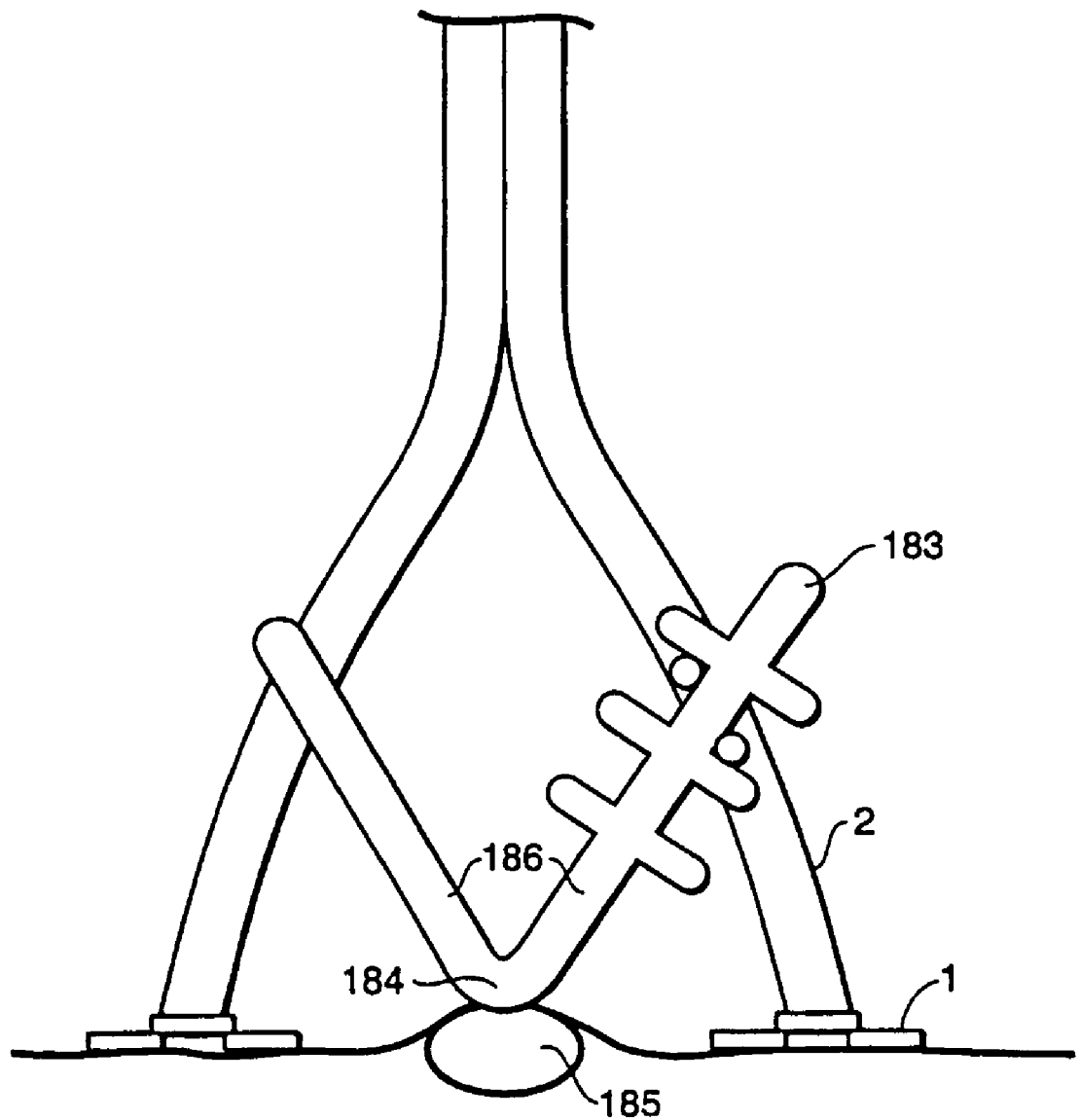
FIG. 36 is an artery occluder comprised of a shaft portion and having a blunt portion to engage a target artery.

Referring to FIG. 36, the stabilizing means may have operably associated therewith an artery occluder 183, which is preferably attached to the contact members 1 or to the connecting shaft 2. The artery occluder 183 may comprise a semi-rigid member which has a blunt portion 184, which may be positioned such that the blunt portion 184 engages the target artery 185 and compresses the target artery 185 to a point causing occlusion of the target artery 185 passing between the contact members 1 such that the blood flow through the artery is substantially reduced or eliminated. Preferably, the occluder 183 has a shaft portion 186 which traverses the connecting shaft 2 such that the blunt portion 184 of the occluder may move from above the level of the target artery 185 to a point below the level of the original vessel sufficient to occlude the blood flow through the vessel.

Referring to FIG. 37A, a concentrically movable shaft 187 is disposed within the shaft means 3 to which the contact members 1 are connected. In this embodiment, the target vessel 188 is positioned directly between and parallel to the longitudinal or greater length of the contact members 1. When so positioned, the concentric shaft 187 within the main shaft means 3 may be pressed downward such that the distal end 189 of the concentric shaft 187 encounters the vessel 188 and compresses the vessel, thereby occluding the vessel 188 to substantially prevent the flow of blood therethrough. This embodiment has the advantage that the amount of occlusion is continuously variable by varying the force applied and the distance by which the concentric shaft 187 is depressed relative to the shaft means 3. FIG. 37B is a similar embodiment of the invention whereby a means for occluding the vessel is affixed directly proximate to the contact members 1. In the example of FIG. 37B, a pushbolt 196 is disposed on the connecting shaft 2 that joins opposing contact members 1 and is generally positioned in a raised portion thereof such that when the pushbolt 1901s not deployed downward, the vessel remains in its native position when oriented between the contact members 1. Occlusion of the vessel 188 is achieved by pressing the pushbolt 190 down until the lower portion 191 engages the vessel 188 when the vessel 188 is disposed between the contact members 1. This embodiment provides the ability to occlude the vessel 188 both proximal and distal to an arteriotomy 191 in the target vessel 188 at the site of the anastomosis. Referring to FIG. 37C, a similar embodiment is provided by a roller 192 or clip mechanism 193 which is affixed to one or both contact members 1, for example by a hinge 194, which is selectively movable, to contact the target vessel 188 at a point either proximal or distal or to the arteriotomy.

Figure 38B:
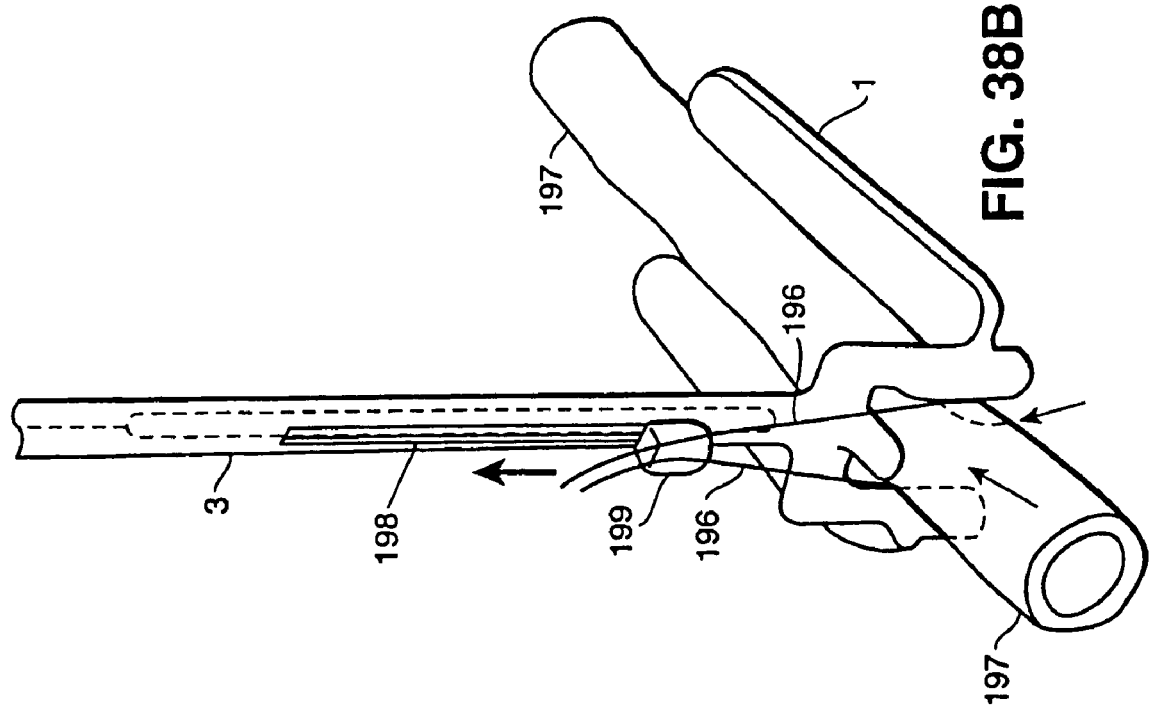
FIGS. 38A and 38B are contact members of the invention having a flange associated therewith for use with sutures that surround the target vessel and may be used in connection with a movable shaft or suture guide to occlude the target vessel.
Figure 38A:
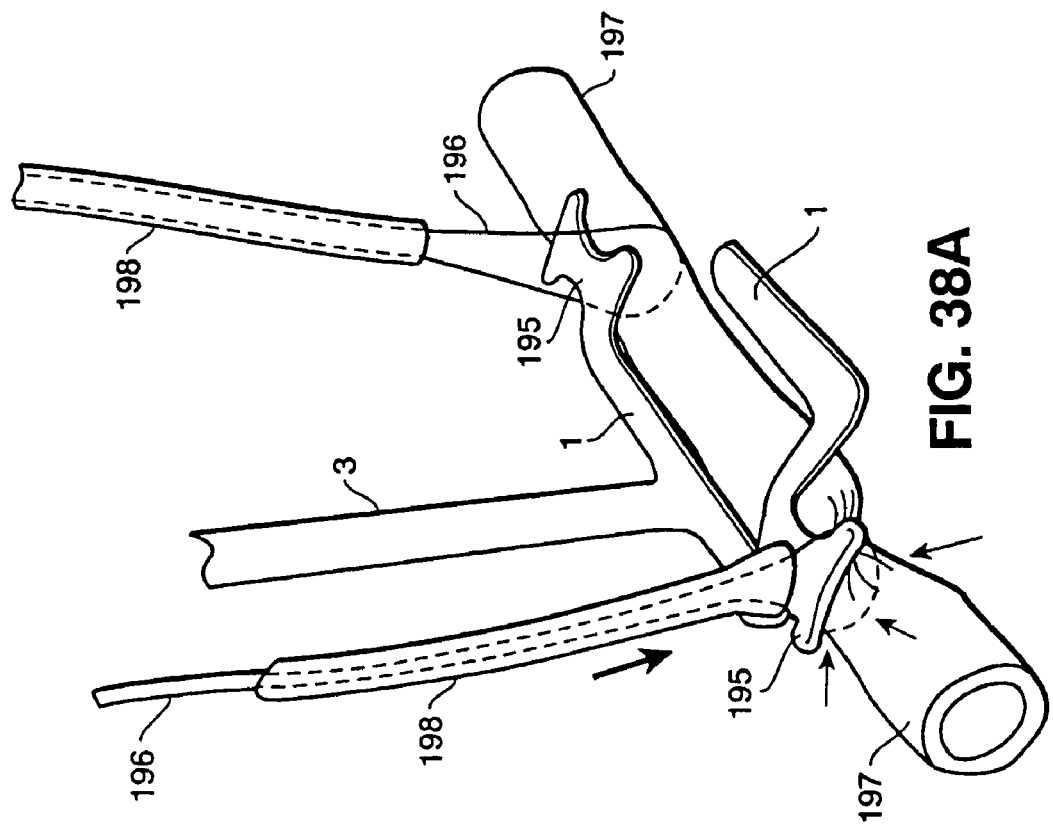

In addition to positioning the target vessel for performing the anastomosis as shown in FIGS. 26A through 26C above, sutures associated with the stabilizer may be used to occlude the vessel to permit the anastomosis to be performed in a bloodless field. Referring to FIGS. 38A and 38B, an embodiment of the invention may have a flange 195 protruding from the contact member 1 to permit silastic vessel loops or sutures 196 to be drawn about the target vessel 197 and the flange 195. To occlude the vessel 197 the suture 196 is passed around the vessel 197 and drawn tight around the flange 195. To facilitate occluding the vessel, a sliding shaft 198 may be used to surround the sutures 197 such that the suture lines 196 traverse the length of the sliding shaft 198 and extend out the bottom to surround the vessel 197. In one embodiment, as shown in FIG. 38B, the shaft 3 of the stabilizing means has a movable rod 198 having suture guides 199 disposed therein or operably associated therewith for adjusting tension on the suture lines. The movable rod 198 may be concentrically disposed within the shaft means 3 such that downward pressure on the shaft means 3 and upward pressure on the sliding shaft 196 draws tension on the sutures 196 to occlude the vessel 197.

Figure 39:
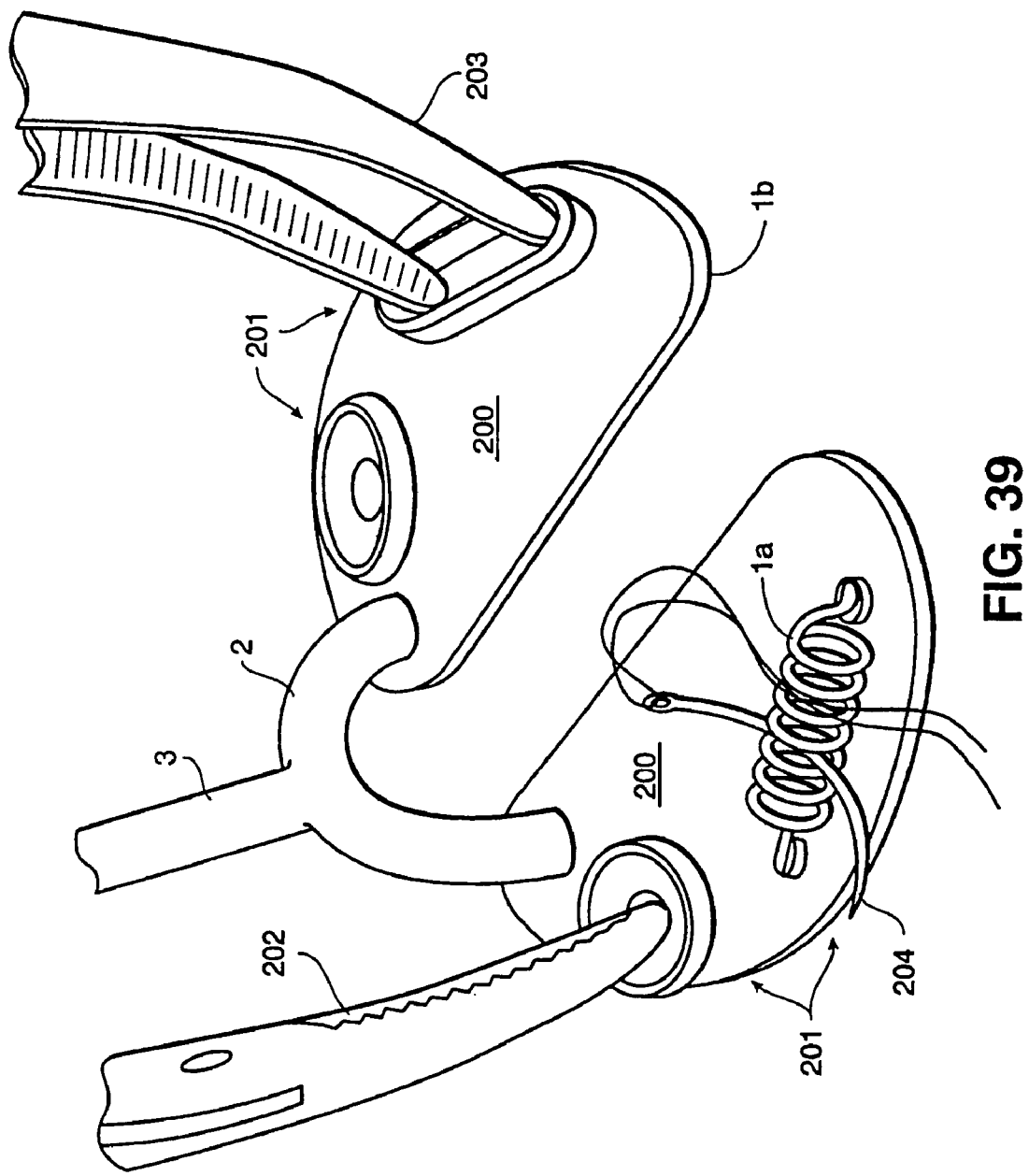
FIG. 39 is an embodiment of the contact member of the invention having one or more fixtures attached, preferably to a planar surface thereof, and adapted to receive a surgical tool or accessory such as scissors, forceps, or surgical needles for the convenience of the surgeon during the anastomosis procedure.

FIG. 39 shows modifications to the upper surface of contact members 1a, 1b of the invention wherein fixtures 201 are adapted to provide a resting place or attachment point for other surgical instruments such as scissors 202, forceps 203, or sutures and suture needles 204 Preferably, the fixtures 201 are magnetic to facilitate retaining metallic surgical instruments in conforming contact with the upper surface of the contact member 1.

Figure 40:
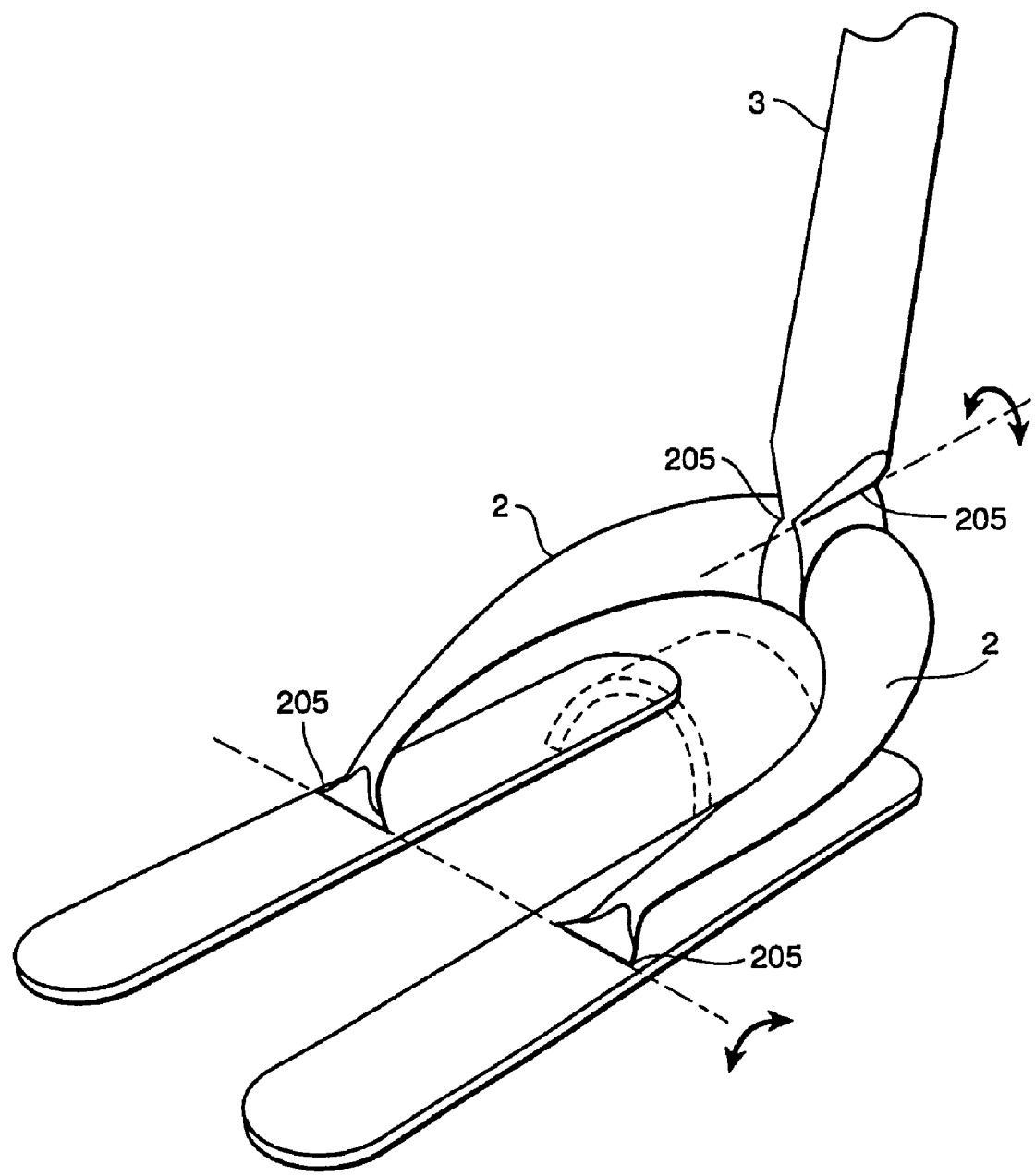
FIG. 40 is an embodiment of the invention having flex joints between the contact members, the interconnecting shaft, or the shaft means to provide continuous positioning of the contact members.

Referring to FIG. 40, the contact members 1 of the invention and/or the shaft means 3 to which the contact members 1 are attached may be provided with one or more flexible joints 205 that permit positioning of either the contact members 1 or the shaft means 3 about an axis. Preferably, the flex joint 205 may be provided at the point where the shaft 3 engages the contact member 1 (not shown), at the point where the connecting shaft 2 engages the shaft means 3, or at the point where the connecting shaft 2 is attached to the contact members 1.

Figure 41:
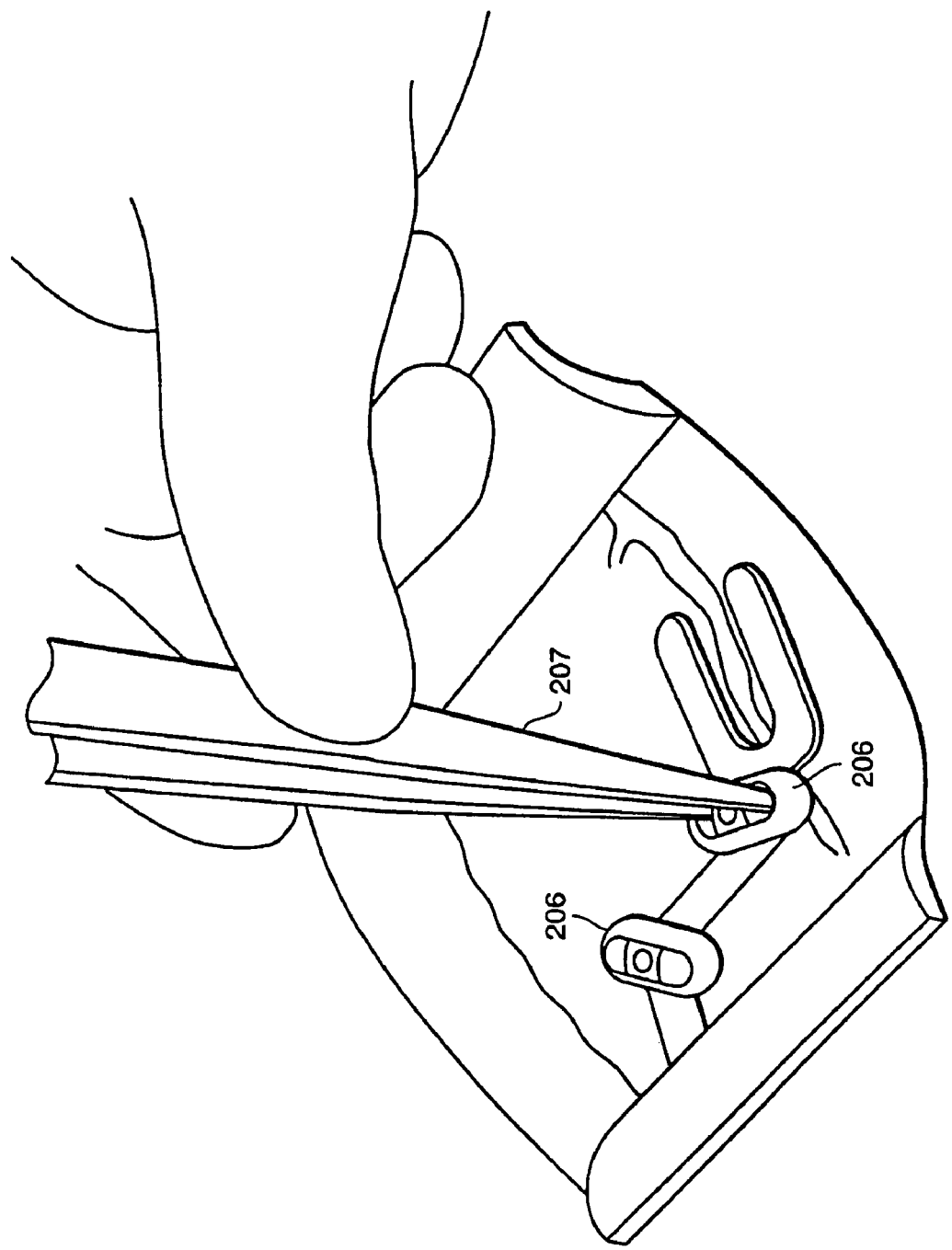
FIG. 41 is an embodiment of the invention having lockable joints associated with the shaft means.

Thus, in the embodiment of FIG. 40, the flexible joint 205 provided at the point where the connecting shaft 2 is attached to each contact member 1 allows the connecting shaft 2 and the shaft means 3 to be tilted about an axis which is perpendicular to the target vessel. The flexible joint 205 provided at the point where the shaft means 3 is attached to the connecting shaft permits the shaft 3 to be tilted from side-to-side relative to the connecting shaft 2. In the embodiment of FIG. 40, or in the embodiments described herein having hinges or flexible joints, the hinges or flex joints may be replaced by conventional lockable joints 206, as shown in FIG. 41, that are selectively locked and unlocked mechanically as with forceps 207.

As can be seen, such occluders are similar to the stabilizing contact members 1 described in several other embodiments herein, and can be expected to provide significant stabilization of the beating heart. These occluders can be used in conjunction with other stabilizing means or independently. They may be placed beside, rather than upon, the coronary artery to provide stabilization without occlusion, if desired. In like fashion, most of the contact members 1 of other embodiments will provide some occlusion of blood flow if placed upon, rather than beside, the target vessel.

As will be described in individual embodiments below, the shaft means 3 may be attached, to or comprised of, a conformable arm which is used to position the contact members against the heart, and then to lock the stabilizing means in place once a stabilizing force has been exerted. The conformable arm is flexible and lockable and may have several configurations including a plurality of links, segments, or universal joints in serial configuration and having a cable fixture passed through the interior of the links which causes the entire conformable arm to become rigid by tightening the cable fixture. Also, the conformable arm may be comprised of a synthetic gel or polymer contained within a conformable cylindrical housing and which becomes rigid upon exposure to light or heat, such as the commercially available Dymax 183-M. Where the shaft means 3 is further comprised of the conformable arm, the conformable arm may be attached directly to the connecting shaft 2 or the contact members 1.

Figure 42:
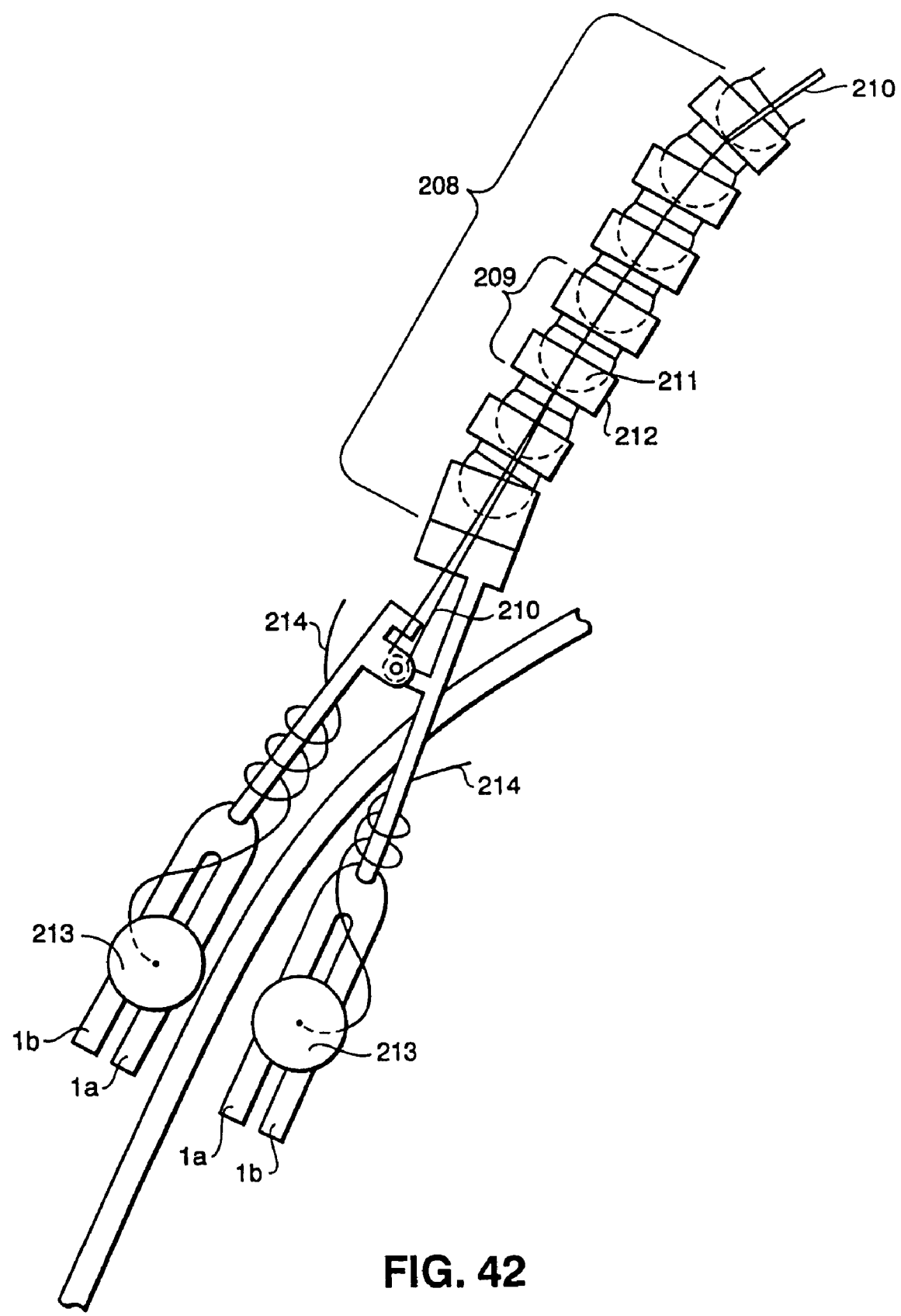
FIG. 42 is a flexible, lockable arm which allows positioning in every direction to place and orient the contact members until the requisite degree of stabilization is achieved at which point the arm having a stabilizing means is fixed in position. The flexible, lockable arm may be attached to a retractor and is caused to become rigid when the entire stabilizing means is properly positioned.

Referring to FIG. 42, this embodiment of the invention is a means for stabilizing the beating heart wherein the shaft means is comprised of a flexible, lockable arm 208 having a plurality of interconnecting links 209 which allow positioning of the flexible arm 208 in every direction until the desired configuration is achieved at which point the flexible arm 208 may be locked into fixed configuration by tightening a cable fixture (not shown) attached to a cable 210 running axially through the interconnecting links 209. Each interconnecting link is comprised of a ball portion 211 and a receiving portion 212 such that the ball portion 211 fits conformingly within the receiving portion 212. The proximate (uppermost) end of the flexible, lockable arm 208 can be attached to a stable support, or to the retractor. In a preferred embodiment, the flexible, lockable arm 208 is a series of interconnecting links 209 having a cable 210 running through the center of each interconnecting link 209 such that when tension is exerted on the cable 210, the flexible, lockable arm 208 is fixed in a rigid position. FIG. 42 also shows an embodiment of the invention wherein the contact members 1 are comprised of a pair of substantially parallel elements 1a, 1b which are positioned to receive a simple snap fixture 213 which is affixed to the surface of the heart. In this embodiment, the snap fixture 213 is positioned between the two parallel elements 1a, 1b of the contact member 1, in order to fix the position of the heart tissue relative to the contact members 1. As in the above embodiment, the contact members 1 are preferably oriented in a substantially parallel fashion with the target artery of the anastomosis passing therebetween. The snap fixtures 213 are affixed to the heart by a suture, wherein the suture line 214 may then also be attached to the contact member 1 via a notch, which may form a one-way locking mechanism to secure the suture line 214, or may be attached to a circular post disposed in the body of the contact member 1 (not shown). The suture line 214 then may be tied through the notch or to the post in the contact member 1, to the contact member 1a, 1b itself, or to the connecting shaft 2 to more tightly secure the heart to the contact member 1. An additional advantage of this embodiment is that the stabilizing means is actually affixed to the cardiac tissue via the suture line 214, such that when the heart is moving laterally or downward the artery being stabilized remains immobile and the surface of the heart may be lifted using the shaft means 3.

Figure 43:
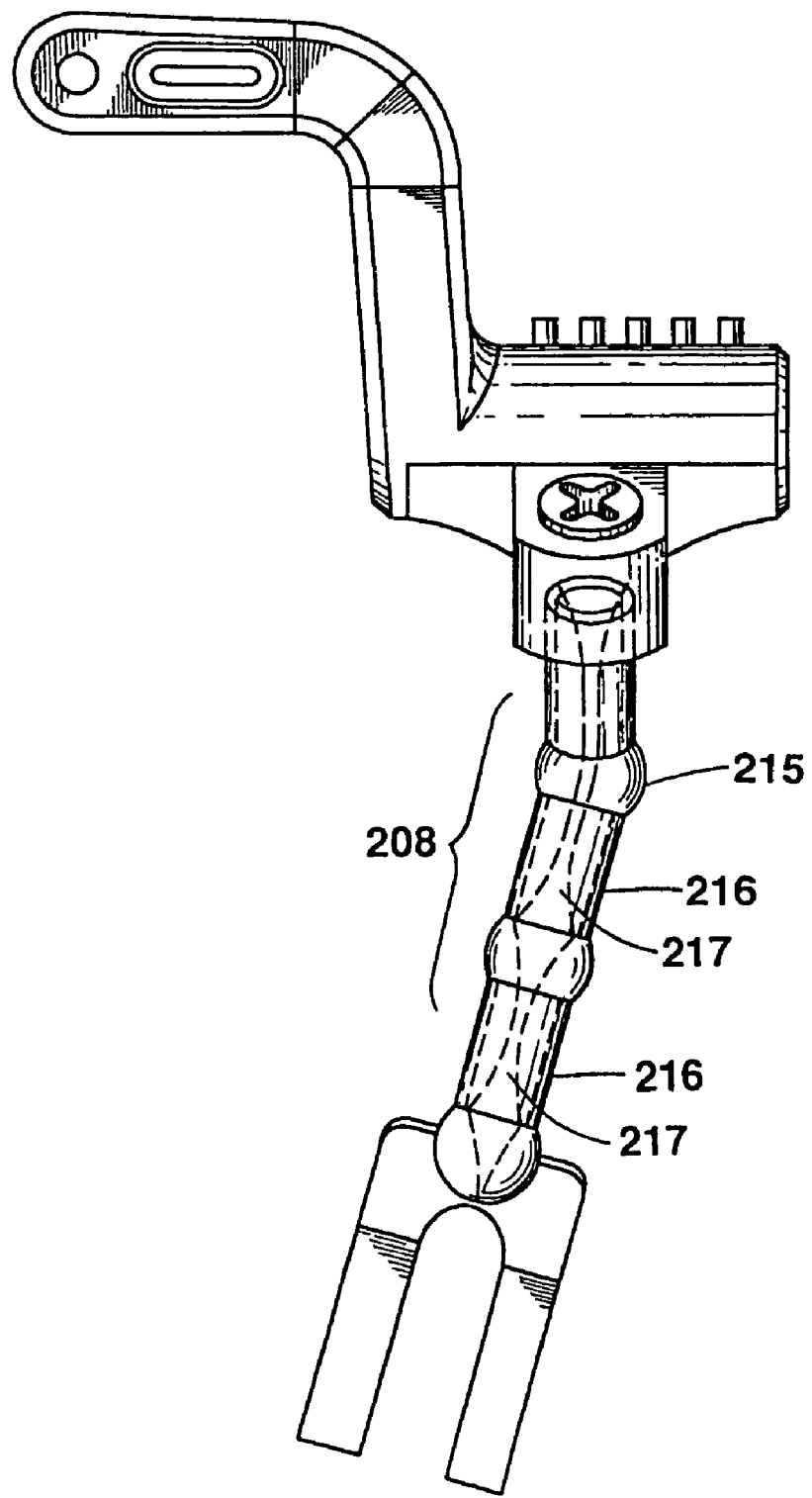
FIG. 43 is a conformable, lockable arm having hollow cylinders and spheres and an inflatable balloon member disposed therein to lock the arm into position.

FIG. 43 shows an alternate embodiment of the flexible lockable arm 208 attached to a retractor and having a series of interconnecting links comprised of sphere joints 215 and cylindrical tubes 216 and which may have a tensioning cable traversing the length of the flexible, lockable arm as in the design of FIG. 42. Additionally, these embodiments may have other tensioning means such as an inflatable internal balloon 217 that expands against the interior of the links rendering the individual links immobile, and thereby locking the entire arm 208 into a fixed position.

Figures 44A, 44B:
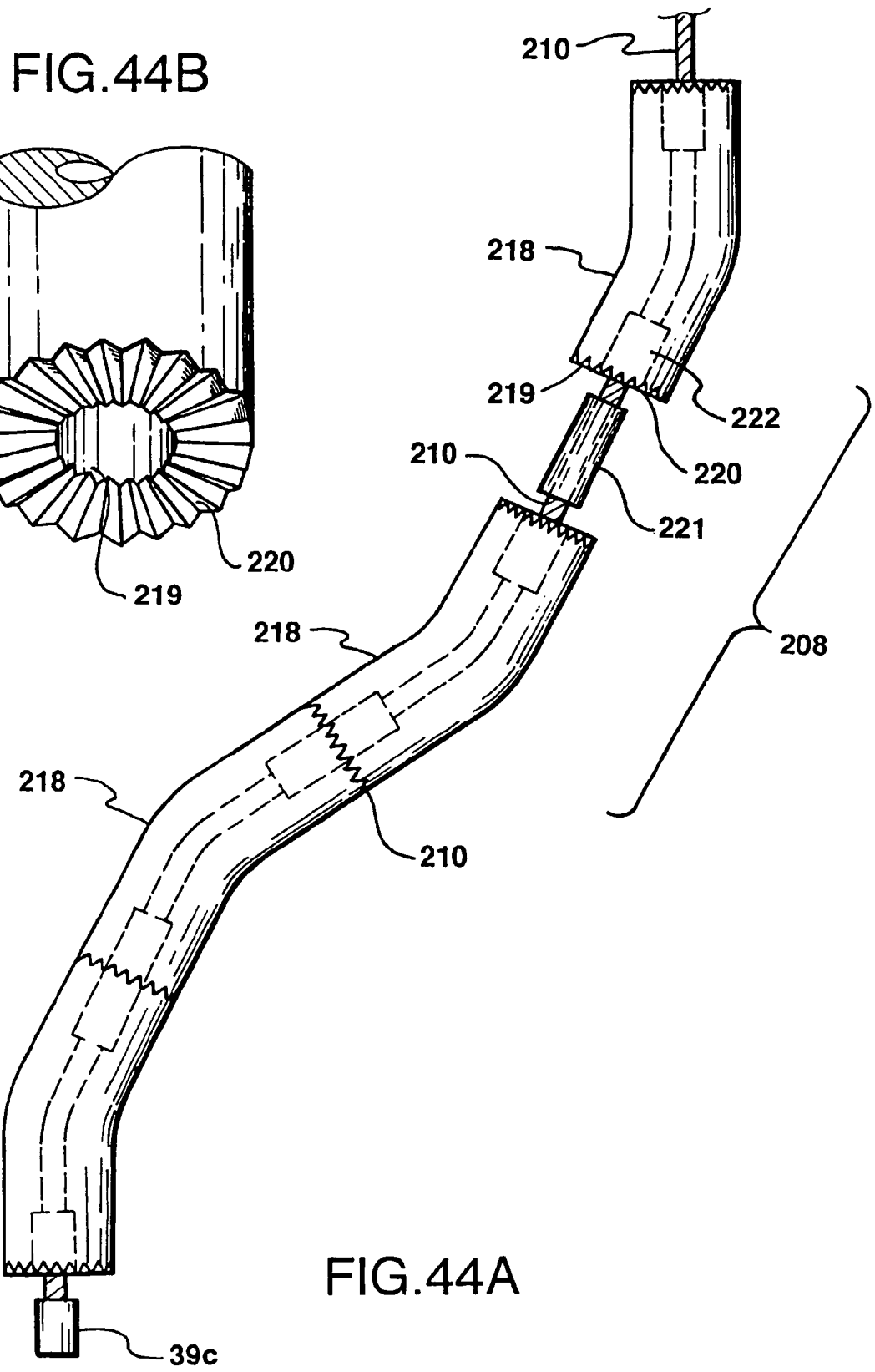
FIGS. 44A and 44B are embodiments of the invention having curved interlocking segments wherein teeth formed at the interconnecting surfaces of each segment prevent rotation of the respective segments.

Additionally, the flexible, lockable arm 208 may be provided by a plurality of curved or bent tubular segments 218 as shown in FIG. 44A that are interconnected by an internal tensioning cable 210 or other tightening means. In the embodiment of FIG. 44A, the curved or bent tubular segments 218 have interfacing surfaces 219 with teeth 220 such that when brought into conforming relationship, the curved tubular segments 218 do not rotate relative to one another due to the interlocking relationship of the teeth 220. See FIG. 44B. As above, the flexible lockable arm 208 is fixed in position by applying tension via a centrally disposed tensioning cable 210 or other tensioning means such as a spring-loaded rod, bolt, or wire. The interconnection between adjoining segments 218 may also be facilitated by brushings 221 that are disposed around the wire 210 and are shaped to fit within a recessed portion 222 of interfacing surface 219.

Figures 45A, 45B:
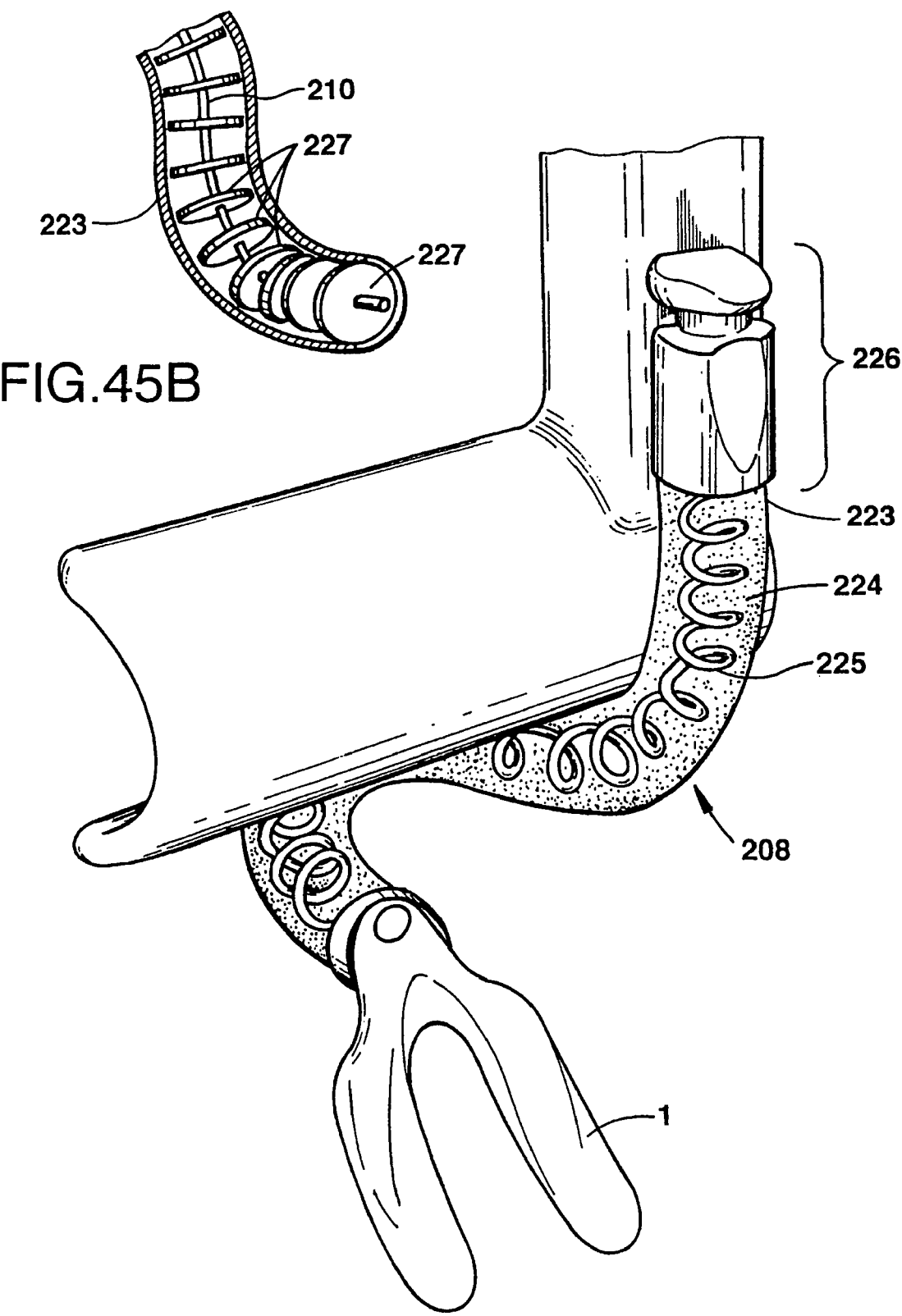
FIGS. 45A and 45B are a flexible shaft having means incorporated therein for fixing the position of the shaft.

Referring to FIG. 45A, a continuously flexible, lockable arm 208 is provided by a hollow flexible shaft 223 having a material 224 disposed within which may become semi-rigid or stiff by a variety of methods. In use, the contact members 1 are positioned at the desired orientation relative to the beating heart, and the material 224 inside the flexible shaft 223 is caused to be rendered stiff or semi-rigid. The material disposed within the flexible shaft 223 may be an epoxy-type glue, a low melting temperature metal with an electric heating wire 225 disposed therein, a fine granular material or known chemicals which become semi-solid upon exposure to light, heat, or chemical means. Where a fine granular material is used, a mechanical compression fixture 226 or vacuum suction may be provided to compress the material 224 to cause the shaft 208 to become rigid.

Referring to FIG. 45B, additionally disposed within the flexible shafts 223 may be a plurality of interconnected discs 227 which are substantially parallel and which engage the inner-surface of the flexible shaft 223. As with the above-described embodiments, the discs 227 may be interconnected by a wire 210 running the length of the shaft. The plurality of discs 227 reduce shear forces across the flexible shaft 223 and may provide separately activated sections that provide for selective stiffening of the flexible shaft along its length. As would be apparent to one of ordinary skill in the art, a flexible lockable shaft may be provided by a hybrid of the various embodiments described herein, such that selective portions of the shaft may be rendered more or less flexible as desired.

Referring to FIG. 46A, an adjustable shaft mean 3 may also be provided by a plurality of adjustable links 228 that are connected to, or comprise, the shaft means 3. Preferably, the adjustable links 228 are positioned at the distal end of shaft means 3 and are connected to the connecting shaft 2, or directly to the contact members 1. Referring to FIG. 46A, a plurality of curved or bent links are provided, preferably at least three such links, which are independently adjustable to provide multiple rotational adjustments. The plurality of adjustable links 228 provides a compact mechanism for positioning the contact members 1 throughout a wide range of motion.

Referring to FIG. 46B, the links are independent rotatable relative to the shaft means 3 and the shaft 2 connecting end contact members 1 and to each other. The assembly formed of the plurality of connected links may be lockable by providing an elastomers liquid or gas shredded elastomer rubber, granulated plastic, or tint rubber metallic ball bearings hydraulic medium within the body of the links 228.

Referring again to FIG. 46A, an elastomeric hydraulic medium 229 is disposed within the adjustable links. The point of interconnection between the adjustable links may have internal or external retaining rings 230a, 230b and a means for compressing the elastomeric hydraulic medium 229 that is operably associated with the interior of the adjustable links 228 such that a force can be exerted on the medium 229 to pressurize the medium to lock each link 228 against the retaining rings 230a, 230b to fix the position of each adjustable link 228 relative to the adjoining link, thereby locking the entire assembly of the shaft means 3 into position.

Referring to FIG. 46C, a means for compressing the elastomeric hydraulic medium may be provided by a pushrod 231 that encounters the medium at its distal end, and which may be actuated by a handle 233 attached to a screw 232 at the proximal end of the shaft means 3. The handle 233 has a spring 234 disposed about a piston to maintain a constant small force upon the medium 229. The compression spring 234 in the proximal end of the shaft 3 provides a minimal preloaded force on the pushrod 231 in the same direction as when the handle engages the pushrod with screw 232. The force provided by spring 234 allows repositioning of the contact members 1 in a non-locked state. Additionally, the handle 233 is threaded into a housing 236 which is in turn threaded onto the shaft 3. Rotating the housing 236 on the threaded shaft 3 provides for an adjustment in the length of the shaft which in turn will adjust the preload force that the above-mentioned spring maintains, as well as, the axial position of the handle 233.

Figure 47:
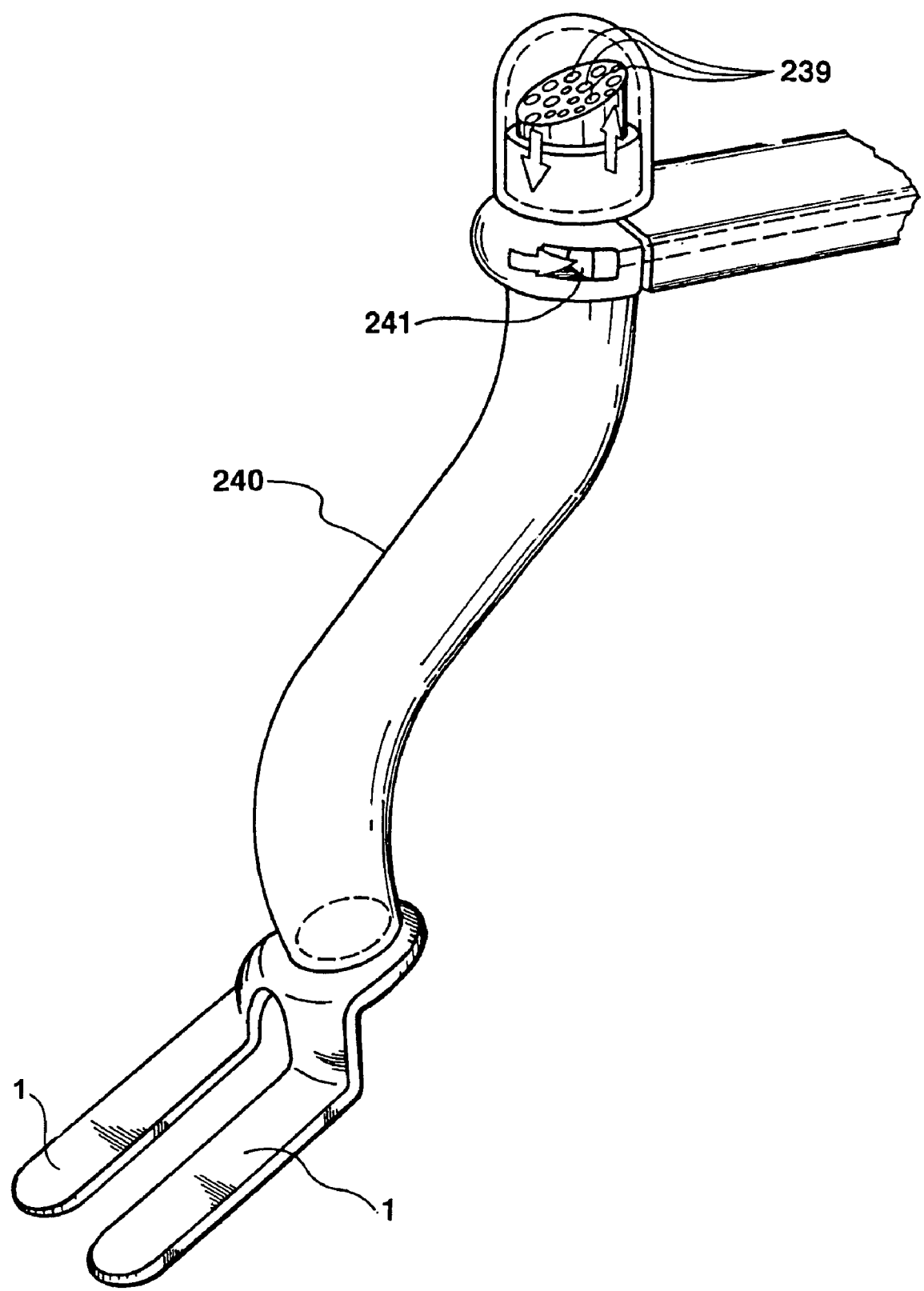
FIG. 47 is an embodiment of the invention having a flexible shaft with a plurality of strands located therein wherein locking the strands in position at a distal portion causes the shaft to become rigid.

A flexible shaft may also be provided by the embodiment of FIG. 47 having a plurality of substantially unstretchable strands 239 contained within a flexible outer shaft 240 that has a locking means comprised of clamp 241 at the proximal end for compressing the strands 239 at the proximal end and thus fixing the position of the flexible shaft. Thus, by actuating the locking means comprised of clamp 241 the strands 239 within the flexible shaft 240 are compressed against one another, preventing an individual strand from sliding relative to one another, thereby fixing the position of the plurality of strands 239 and locking the contact members 1 in place.

Figure 48:
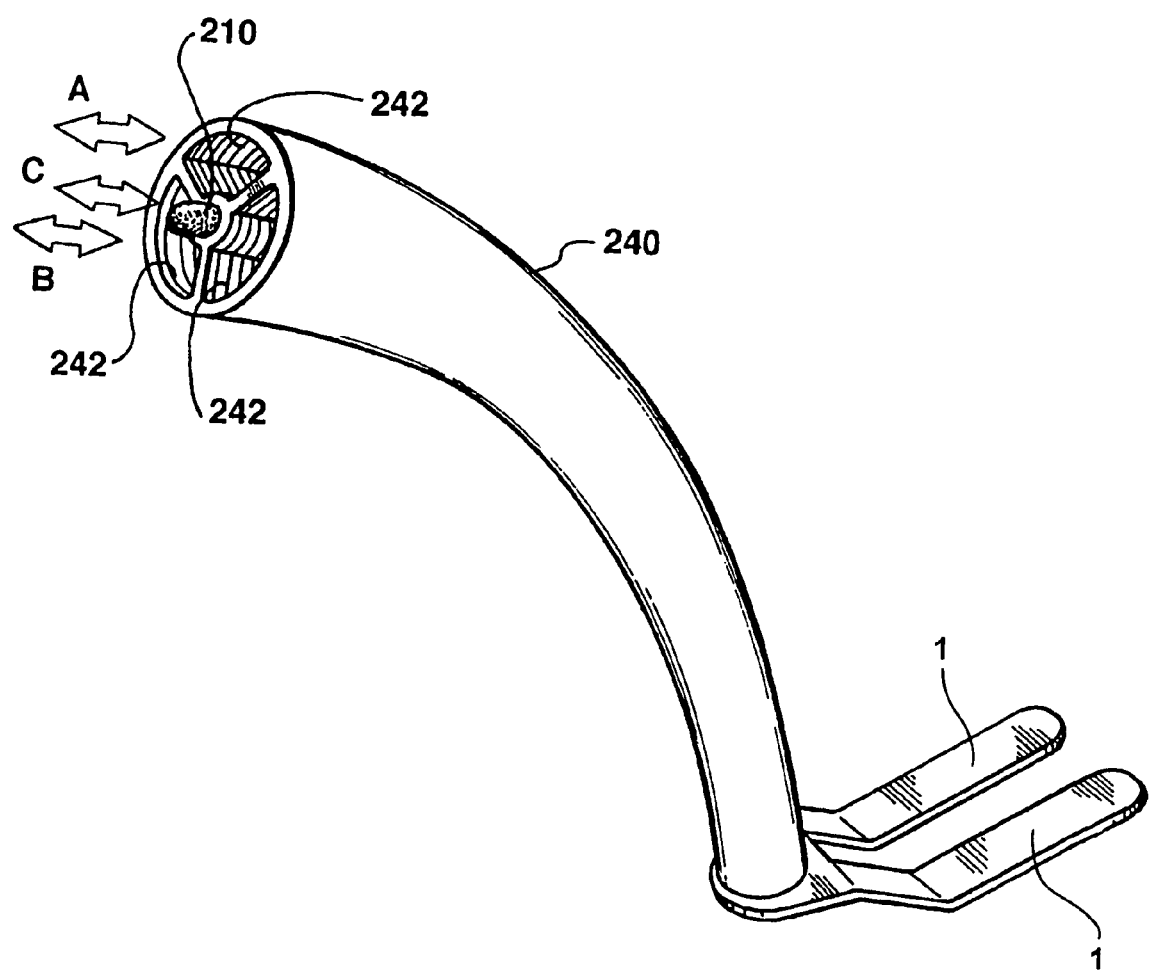
FIG. 48 is a flexible shaft having a plurality of lumens disposed therein such that sealing of the lumens fixes the position of the flexible shaft.

The interior of the flexible shaft 240 may be provide with several flexible substances which may be rendered solid by chemical or mechanical means or may have sealed portions that cause the flexible shaft 240 to become rigid or semi-rigid. For example, FIG. 48 has a flexible shaft 240 with a cable 210 running along its length and plurality of fluid-filled lumens 242 disposed therein. When the lumens 242 are not sealed, the contact members 1 may be continuously positioned and the flexible shaft 240 set in any configuration. When the desired orientation of the contact members 1 is achieved, the lumens 242 are sealed to fix the position of the flexible shaft 240. Additionally, these lumens 242 may be differentially pressurized or evacuated to adjust the position of contact members 1.

Figure 49:
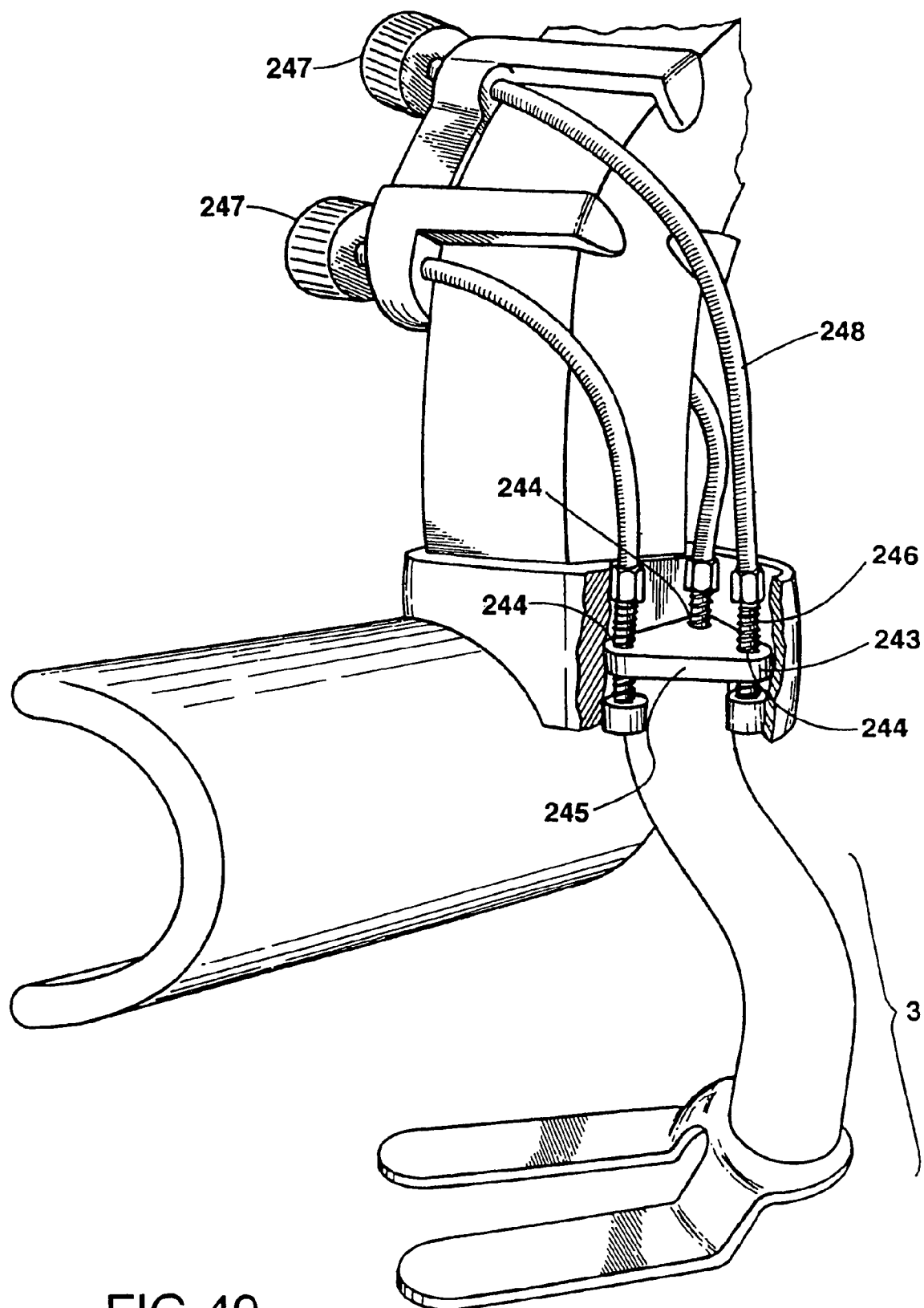
FIG. 49 is a fine adjusting mechanism wherein a plurality of threaded cables are attached to a proximal portion of a shaft means whereby turning the threaded cables causes the proximal portion of the shaft means to be adjusted.

Referring to FIG. 49, a fine adjustment mechanism is provided by a plurality of threaded positioning cables 248 that traverse threaded ports 244 of a proximal portion 243 of the shaft means 3 and about the periphery of an end member 245 of the shaft. The end member 245 of the shaft 3 is positioned at each of the plurality of threaded ports 244 by turning the threaded cables 246. By rotating the cables by knobs 247, the portion of the end member 245 of the shaft is moved either upward or downward relative to its original position.

FIG. 50A shows the interior of a shaft means 3 of the invention having a spring-loaded mechanism 249 in the proximal portion thereof for damping the vertical motion of the proximal end of an inner shaft 251. A spring 252 is mounted within the interior of the proximal portion 253 of an outer shaft 254 such that when the contact members 1 are lowered onto the beating heart, the proximal end 250 of inner shaft 251 gently compresses the spring 252. The outer shaft 254 may be positioned downward until a point of resistance is met at which the beating heart achieves adequate stabilization. At that point, the outer shaft 254 may be fixed in position, i.e., by attaching to the retractor or other stabilized support 255 while the inner shaft 251 may move up and down in a vertical direction. The oscillation of the inner shaft 251 is dampened by the spring 252 mounted in the proximal portion 253 of the outer shaft 254 or may be rendered motionless by lower positioning of the outer shaft 254 relative to the surface of the beating heart.

As shown in FIG. 50A, the spring mechanism 249 may also be mounted at the distal portion of the shaft means 3 and the spring 252 may be external to a central shaft 256. An additional configuration (FIG. 50B) having a damped vertical motion is provided by a fluid-dampening mechanism consisting of a chamber 257 with a seal 260 having a plunger 258 for moving therein wherein said plunger has a piston 261 having an annular seal 261a thereabout, such as a rubber 0-ring seal, that engages the internal portion of the chamber 257 to substantially seal the passage of fluid. Piston 261 has one or more orifices 269 to restrict the flow of fluid therethrough. Additionally, inside plunger 258 is a one-way valve such as a spring-loaded ball 258a within a bypass passage 258b. As an upward vertical force is imparted upon the central shaft 250, the fluid dampening mechanism restricts the ability of the central shaft 250 to move upward, while its downward motion is relatively unrestricted, due to fluid flowing through bypass passage 258b.

Figures 51A, 51B:
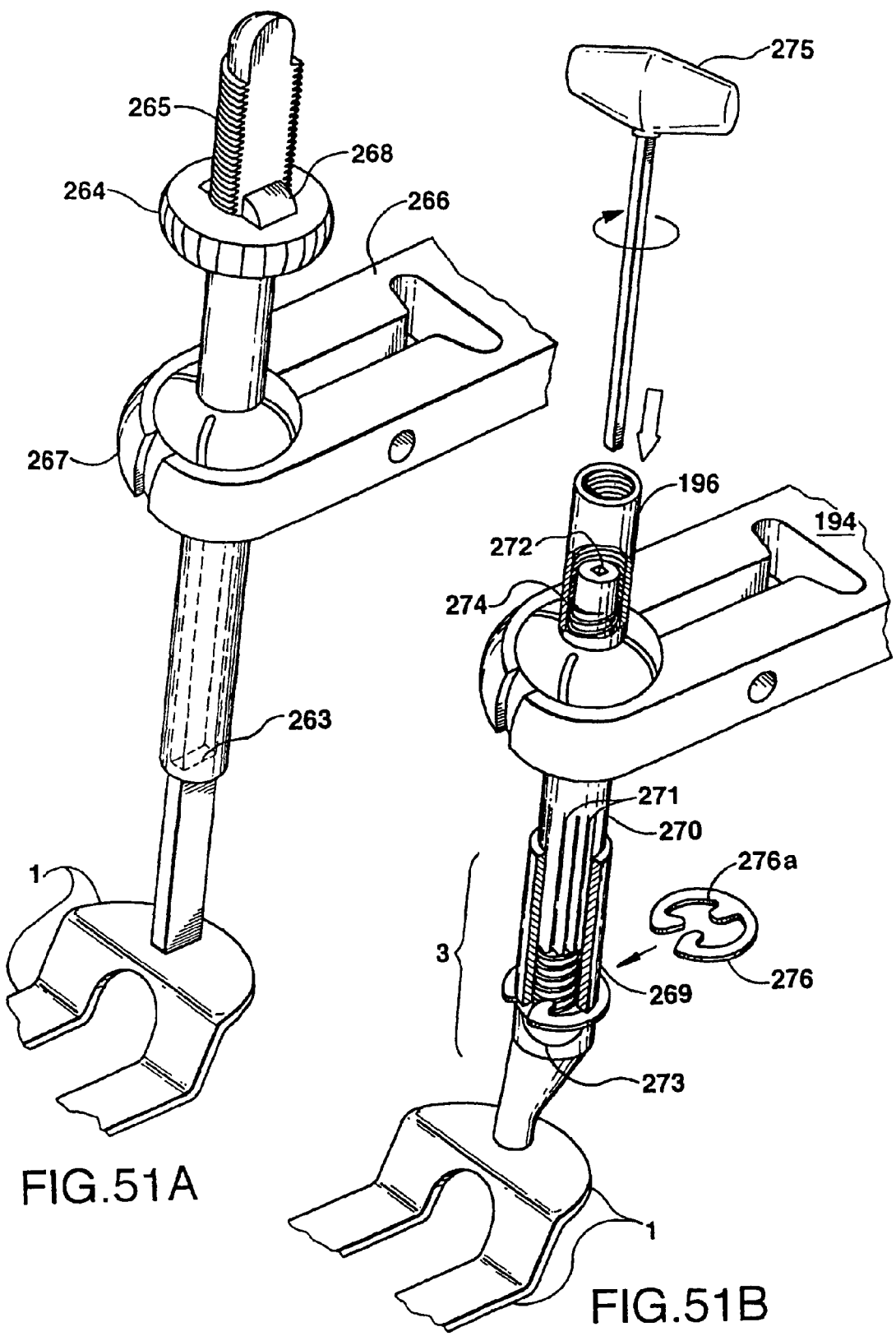
FIG. 51A and 51B are shaft means of the invention provided with fine adjustment mechanisms for vertical positioning of the shaft.

Referring to FIG. 51A, the shaft means 3 depicted therein has an adjustable central shaft 263 with a fine adjust capability provided by a thumbscrew 264 which is rotatable about a threaded portion 265 of the central shaft 263 and which is connected at the most distal end to the contact members 1. Independent rotation of the central shaft 263 is prevented by a stop 268. As in FIG. 1, the shaft of this embodiment may be rotatably attached to a portion of a retractor or stabilized support 266 by passing the shaft through a ball and socket joint 267.

Referring to FIG. 51B, the contact members 1 are attached to a partial portion of the shaft means 3 comprised of an outer sleeve 269 that extend to engage a second shaft 270 having a plurality of splines 271 about the exterior. A first internal shaft 272 is attached to a ball joint 273 operably connected to the contact members 1. The first internal shaft 272 is disposed inside both the outer sleeve 269 and the second shaft 270 and has threads 274 to permit adjustment by a handle 275 (which may be removable). At the end of the threaded internal shaft 272, the ball joint 273 allows the contact members 1 to rotate at the base of the shaft means 3. The second shaft 270 is engaged through the outer sleeve 269 by the splines 271 to keep the ball joint 273 from rotating. A circular clip 275 has inner ridges 276 that pass through the outer sleeve 260 and maintain the ball joint 273 in a fixed position.

Figure 52:
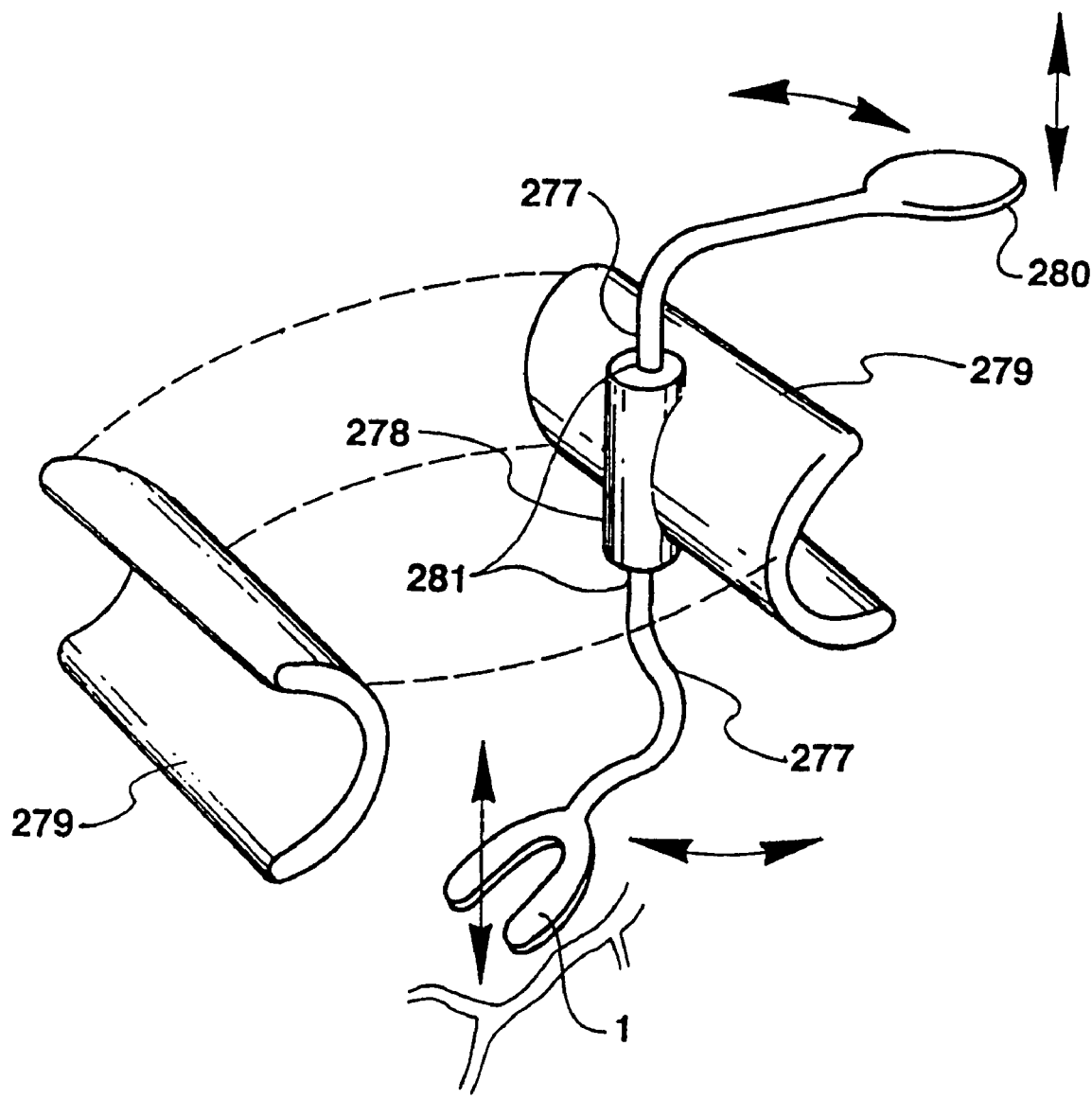
FIG. 52 is a malleable shaft that is mounted on a fixture attached to a retractor blade and having a handle for vertical positioning of the shaft.

Referring to FIG. 52, a method for providing continuous and adjustable positioning of the contact members 1 of the invention may be readily provided by a malleable shaft 277 which is attached to the contact members 1 and which may slide and be molded by hand. In particular, the malleable shaft 277 may slide through a fixture 278 attached to a stable support such as a retractor blade 279 used to open the surgical incision. The vertical positioning of the device may be achieved by a handle 280 which is manipulated from outside of the incision and causes a vertical portion 281 of the malleable shaft 277 to slide through the fixture 278.

Figure 53:
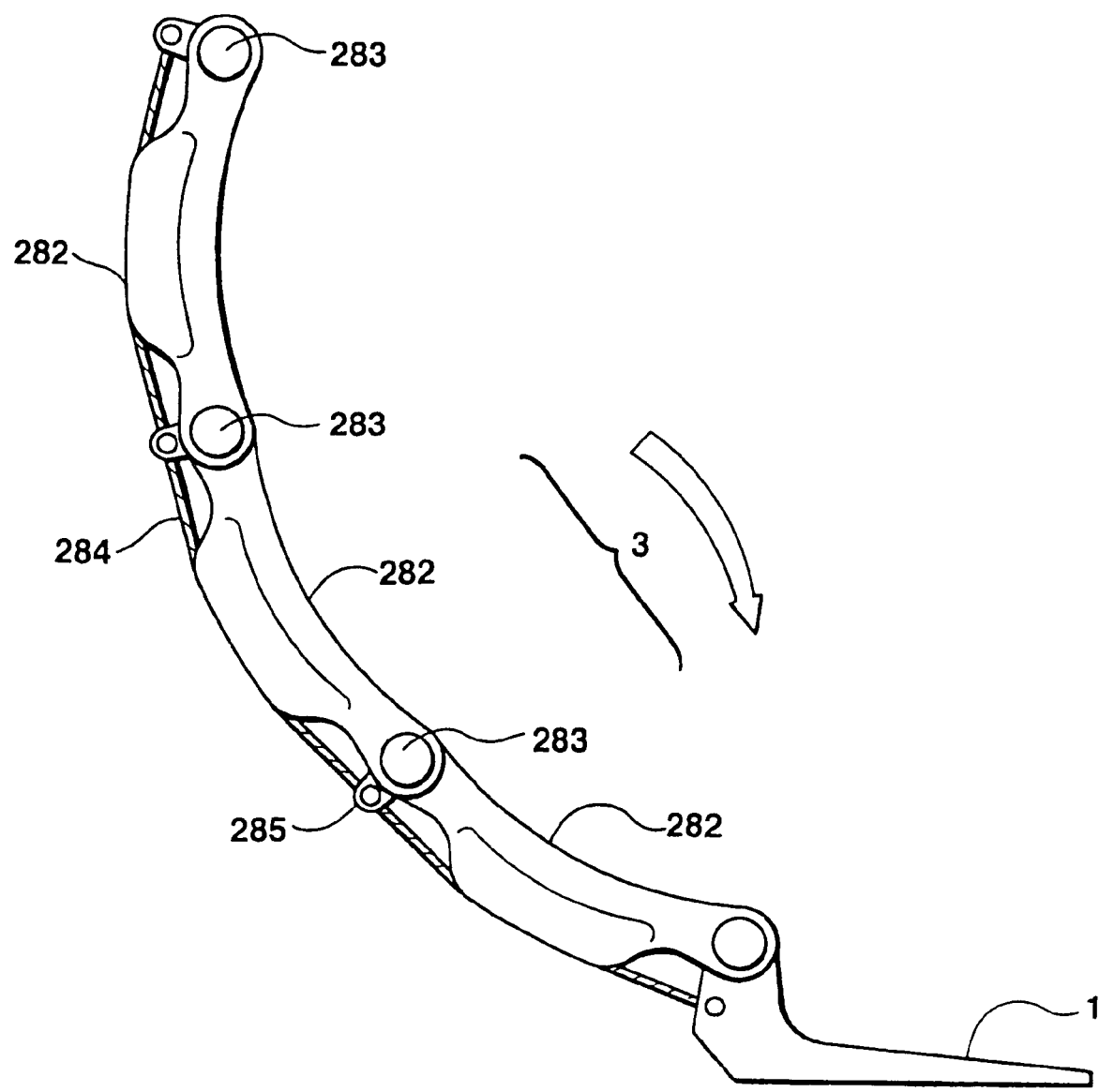
FIG. 53 is a shaft means comprised of an adjustable arm formed from several interlocking segments attached to a cable.

Referring to FIG. 53, an embodiment for the shaft means 3 of the invention is shown having a plurality of linked members 282, each of which connected to the adjacent linked member 282 by a hinge 283, and a torsion spring connected to each hinge (not shown) and which are interconnected by a cable 284 connected to each linked member 282, preferably at an attachment point 285 adjacent to the hinges 283. By providing a plurality of discrete interconnected linked members 282 with an arcuate shape, and by providing an interconnecting cable 284, a curved shaft means 3 is provided with the ability to coil and uncoil as the tension is exerted, released, or reversed, on the cable 284. Preferably, the most distal linked member 282 and the end of the cable 284 is affixed to contact member(s) in any of the several embodiments described previously.

Figures 54A, 54B, 54C:
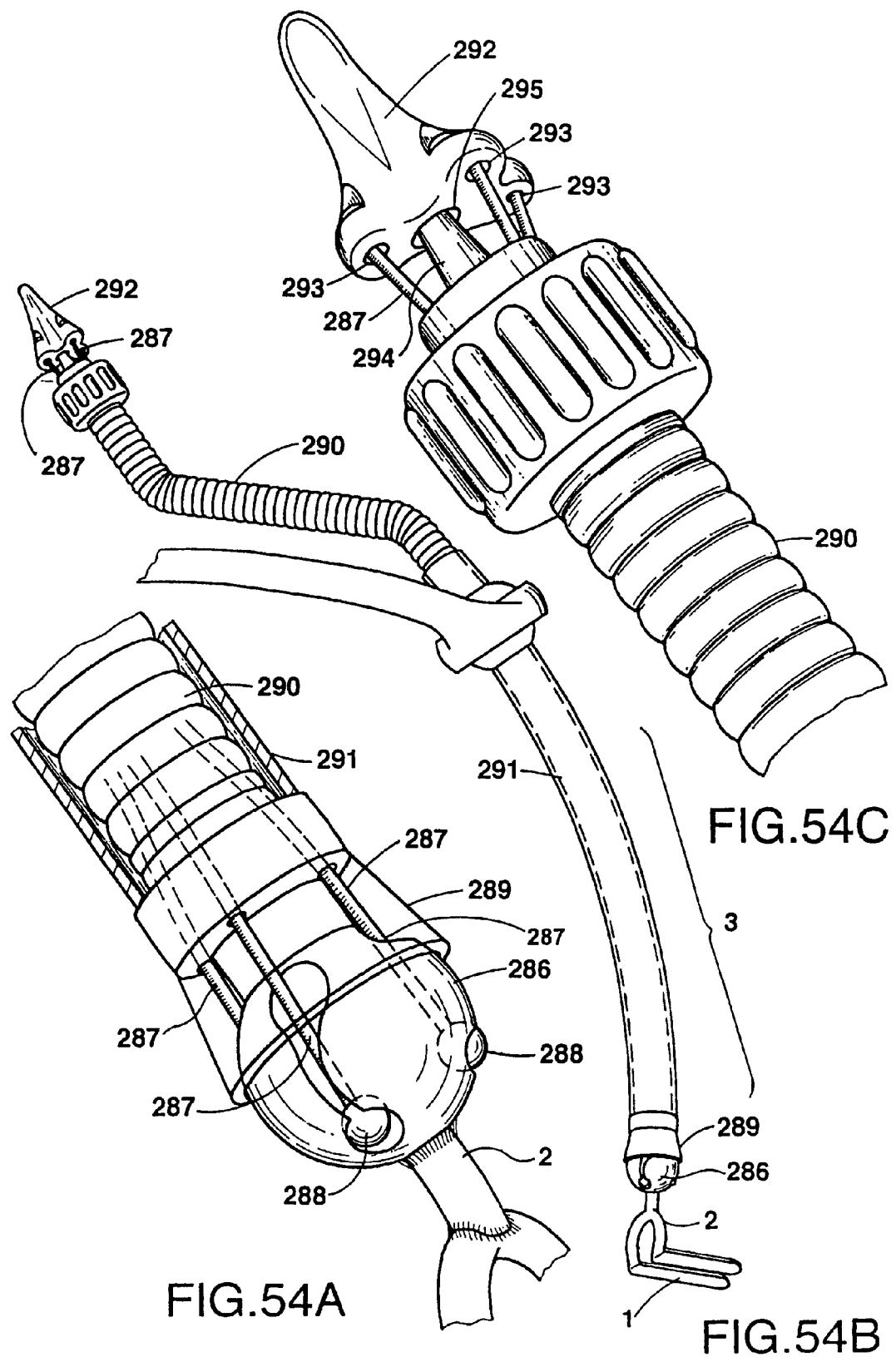
FIGS. 54A through 54C are an adjustable shaft means of the invention wherein the position of the contact members are adjusted by a positioning handle located at the proximal portion of the shaft means and connected to a ball joint at the distal portion by a plurality of positioning wires.

To take advantage of the minimally invasive procedures enabled by the invention, the positioning of the contact members 1 by manipulation of the configuration of the shaft means 3 may be achieved remotely, i.e., from outside the incision, by any of a variety of mechanisms attached to and operably associated with the shaft means 3. Referring to FIGS. 54A through 54C, remote manipulation of the positioning of the contact members 1 may be provided by a shaft means 3 having a ball joint 286 at the distal end thereof which is connected to the contact members 1 or the connecting shaft 2. Continuous positioning of the ball joint 286 may be provided by a plurality of cables 287 which are affixed to the ball joint at opposing points 288 at the exterior surface of the ball joint 286. The ball joint 286 is maintained in a socket 289 at the distal end of the shaft means 3. The shaft means 3 itself may be rigid or flexible, or may be fixed into a pre-determined position by the surgeon depending on the clinical environment. Additionally, the shaft means 3 may be comprised of a plurality of shafts, including an inner flexible shaft 290 contained within a rigid shaft 291 wherein the flexible shaft 290 extends above the rigid portion, terminating at the positioning handle 292. The contact members 1 are positioned by means of the plurality of cables 287 attached to the ball joint 286. The plurality cables 287 runs from the ball joint 286 through the length of the shaft means and terminate in a positioning handle 292 at the proximal end of the shaft means 3. The shaft 3 may be of any convenient length but is preferably long enough to extend the positioning handle 292 to a point sufficiently beyond the incision that manipulation of the position of the contact members 1 does not interfere with the surgeon's ability to visualize the surgical site. Thus, each cable 287 has a distal portion affixed to the ball joint 280, and a proximal portion affixed to a positioning handle 292 having the cables attached thereto. In one configuration, the plurality of positioning cables 287 are affixed about a plurality of attachment points 293, respectively, on the positioning handle 292.

In the embodiment of FIGS. 54B and 54C, the positioning handle-292 has a recessed area 295 in the bottom surface and a post 294 disposed in the recessed area 295 about which the cables 287 are affixed at several points. The most proximal portion of the positioning handle 292 is adapted to be grasped by the hand and may be rotated about the post 294 to provide selective tension on the cables 287, thereby repositioning the contact members 1 at the distal end of the shaft means 3.

As is apparent from the foregoing description, an important function of a shaft means is to selectively place the contact members at the appropriate site on the beating heart, while providing sufficient flexibility and positioning adjustability for different clinical situations and for different surgical access techniques. Also, the shaft is typically mounted or attached to a stable support at a proximal end and typically at a point outside the patient's chest. Thus, it is advantageous to provide a shaft means having the ability to be positioned in several configurations, particularly relative to a stable support such as a surgical retractor or access platform which is used to provide access to the beating heart.

Figure 55A:
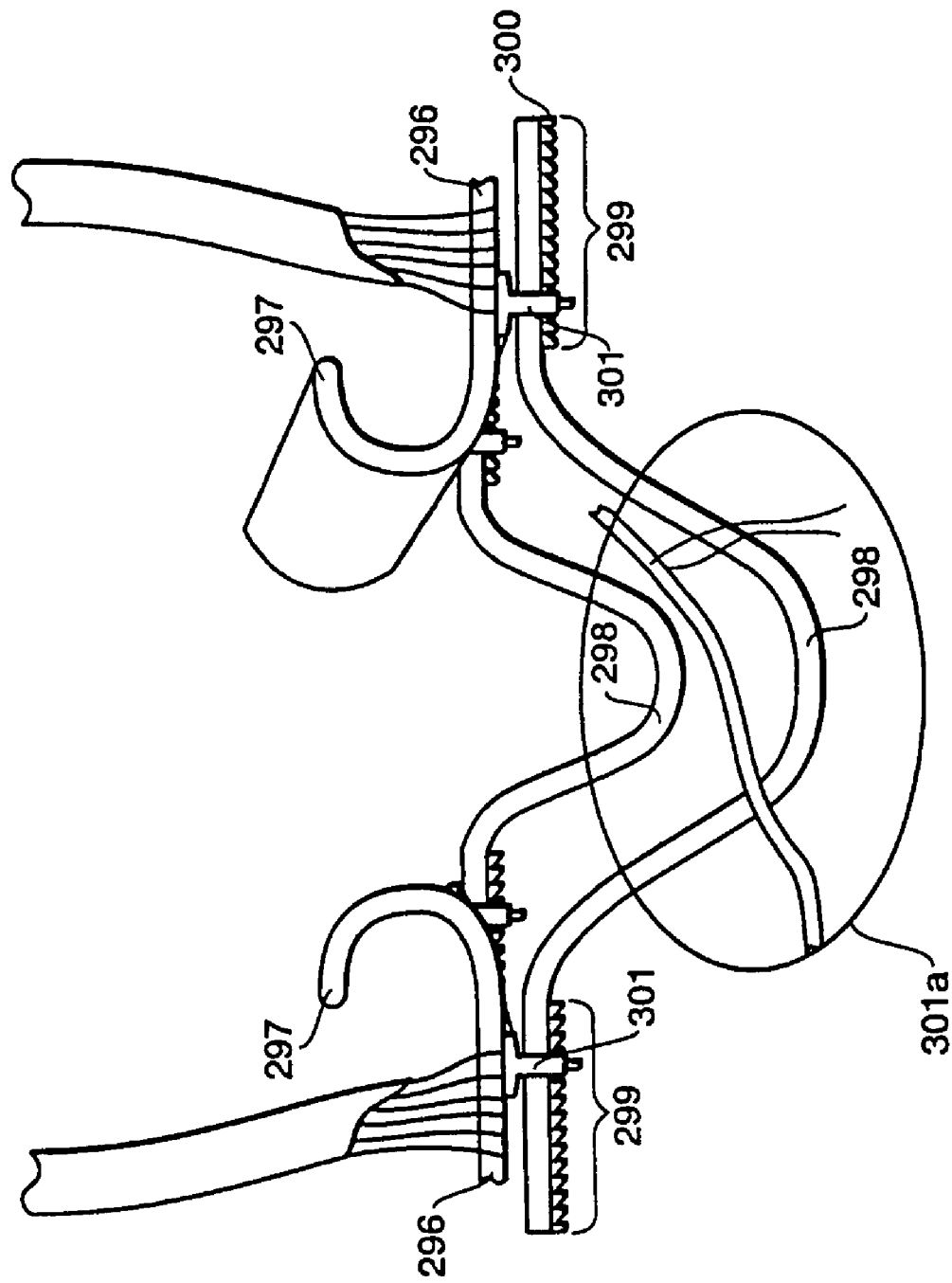
FIG. 55A is an embodiment of the stabilizing means of the invention having stabilizer bars suspended from the bottom side of a rib retractor wherein the stabilizer bars engage a ratchet means.
Figure 55B:
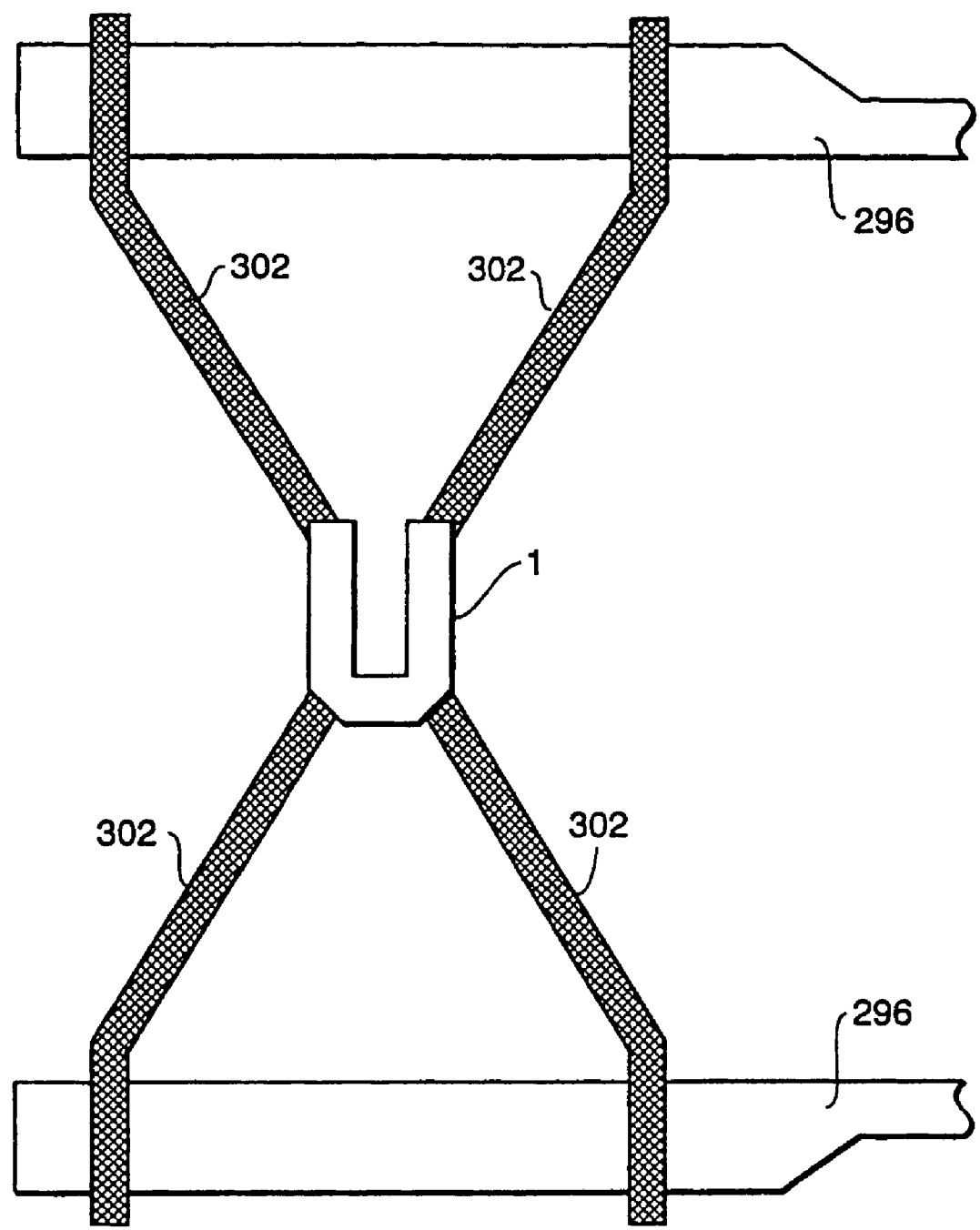
FIG. 55B has malleable shafts attached to a retractor and to the contact members.

Referring to FIGS. 55A and 55B, because the available access and working space for the surgeon may be limited, certain embodiments of the invention may be contained substantially within the chest cavity. Preferably, such a stabilizing means is connected to the rib retractor and may be affixed to one or both sides of the opening created by spreading the ribs using the rib: retractor.

Referring to FIG. 55A, rib retractor 296 is shown in an open position whereby blades 297 engage and spread the ribs. A pair of stabilizing bars 298 having a conventional ratchet means 299 attached at the end thereof are positioned beneath the retractor. The ratchet means 299 is comprised of a plurality of teeth 300 on the stabilizing bars 298 and a ratcheting aperture 301 permitting one-way passage of the stabilizing bars 298 unless released by a release mechanism. The stabilizing bars 298 are curved downward such that as the bars are advanced through the ratchet means 299, the lowermost portion of the stabilizing bars 298 engages the beating heart 301a proximate to the anastomosis site.

Referring to FIG. 55B, the orientation of the portion of the stabilizing means which engages the heart relative to the rib retractor 296 is similar to the embodiment shown in FIG. 55A. In this embodiment, a contact member 1 is attached on opposite ends to at least two malleable supports 302 which are in turn attached to the rib retractor 296. The malleable supports 302 are preferably made of stainless steel bands which are woven in a mesh or have a repeating serpentine configuration to allow for substantial extension into the chest cavity. This configuration yields a malleable support 302 with sufficient tensile strength to maintain a stabilizing force at the anastomosis site while allowing the surgeon to manipulate the malleable supports 302 within the chest cavity to achieve the desired orientation relative to the beating heart.

As noted above, at the upper end of the shaft means 3, the shaft means 3 may be attached to a fixed support which may be any surface or structure which does not move with the beating heart. For example, the shaft means 3 may be attached to a fixture on the retractor system used to spread the ribs for access to the heart or may be attached to a fixed structure such as the surgical table or associated aperture which is not connected to the patient. In a preferred embodiment, the shaft means 3 is directly attached to a component of the retractor system which is designed to receive the shaft means 3 and to maintain the position and orientation of the shaft means 3 during the procedure.

Referring to FIGS. 56A and 56B, an adjustable slide mechanism is provided to the shaft means 3 such that the shaft means can be continuously positioned relative to a retractor. For example, in FIG. 56A, a curved shaft 303 traverses a ball joint 304 disposed at the end of an adjustable arm 305 which connects the shaft means to the retractor 306 and is lockable relative to the retractor 306. The curved shaft 303 traverses the ball joint 304, as described previously, and is positioned by sliding the shaft 303 relative to the ball joint 304, providing the ability for the contact members 1 to be positioned at any point within a given arc as defined by the flexible shaft 303. Also, the entirety of the curved shaft 303 may be positioned in a perpendicular direction away from the length of the retractor blade 307 using the adjustable arm 305. FIG. 56B shows a top view from LVI-LVI of the adjustable arm 305 which may have a slot or groove formed in the body thereof allowing continuous positioning until the arm is fixed in position by a locking mechanism 308. Thumbscrew 312c locks the position of ball 304 in member in place.

In FIG. 56C, the shaft means 3 is comprised of pair of parallel shafts 309 and 310 which slide around an axle 311 disposed in a tightening mechanism 312 affixed to the retractor 313. The position of the shaft means 3 relative to the retractor 313 is adjustable by sliding the shaft means 3 along the axle 311. Moving handle 311a causes a corresponding motion in the contact members 1. Tightening thumbscrew 312c locks clamp members 312a, 312b onto port 312d and shafts 309, 310 simultaneously.

Figure 57:
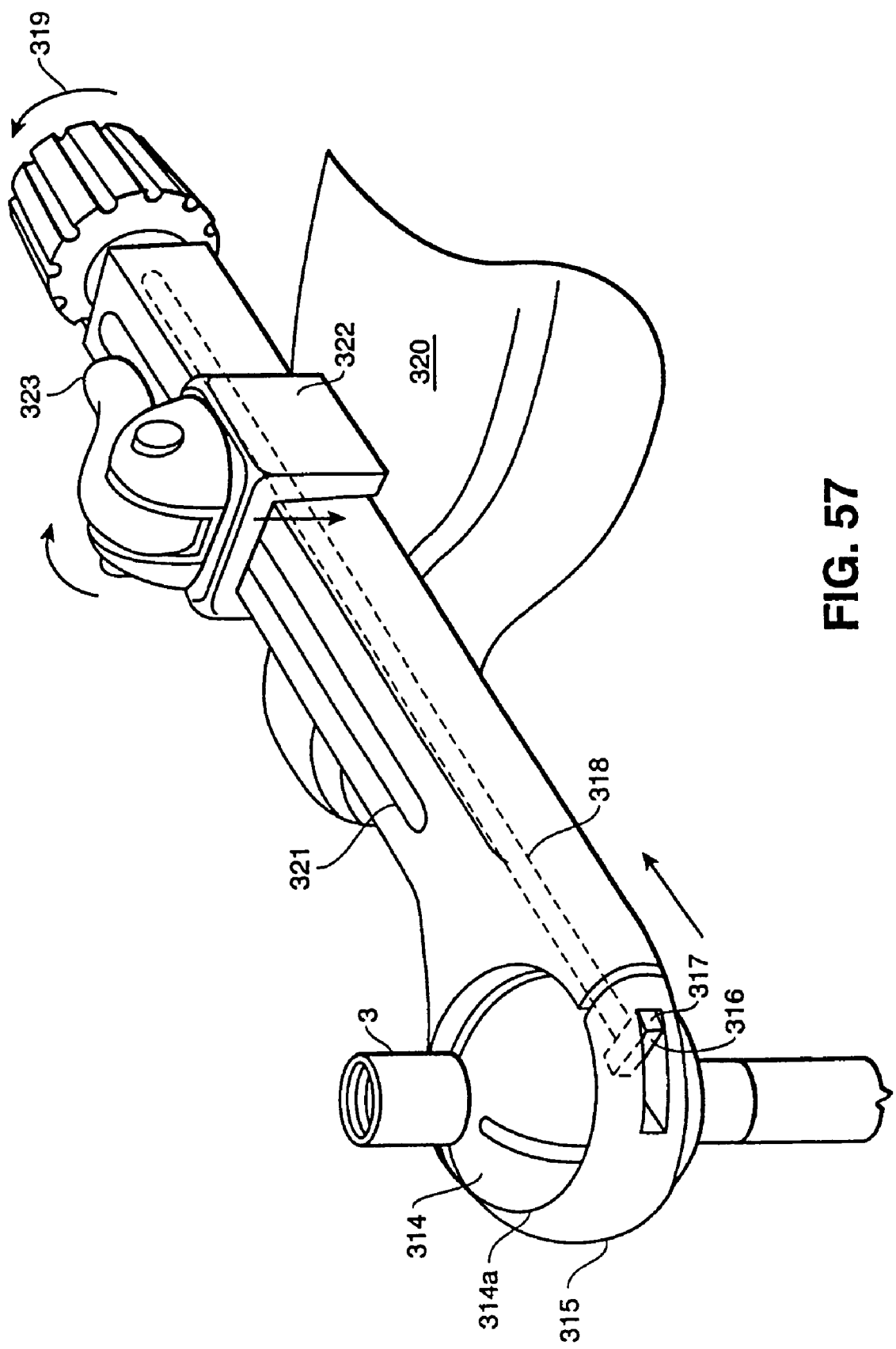
FIG. 57 is an adjustable arm for attaching a shaft means of the invention to a stable support wherein the shaft means passes through a ball joint that is adjustable by a fixture on the arm and wherein the arm is locked in place on the stable support by a latch mechanism.

Referring to FIG. 57, an adjustable arm may be provided for continuously adjusting the distance between the retractor or other stable support and the shaft means of the means for stabilizing the beating heart of the invention. At one end of the adjustable arm, the shaft means 3 traverse a ball joint 314 which is contained in a socket 315 formed in the body of the adjustable arm. The tightness of the ball joint 314 may be adjusted by tightening a shaft 316 affixed to the socket 315 and which passes through the body 318 of the adjustable arm. The tightening shaft 316 which is in turn connected to a rotating knob 319 that may tighten or loosen the ball joint 314 by tightening the socket 315 via the tightening shaft 316. The distance between the shaft means 3 and the ball joint 314 is also adjustable relative to the stable support 320 by virtue of a slit or groove 321 formed in the body of the adjustable arm. A locking mechanism 322 is disposed within the groove 321 such that actuating a locking handle 323 fixes the position of the adjustable arm by tightening the locking mechanism 322 about the groove 321.

Figure 58A:
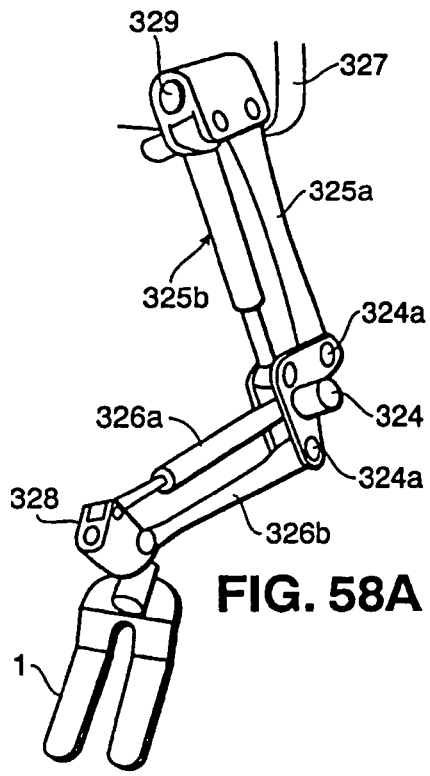
FIGS. 58A through 58C are embodiments of the shaft means of the invention for adjustable positioning of the shaft means relative to a retractor blade.
Figure 58B:
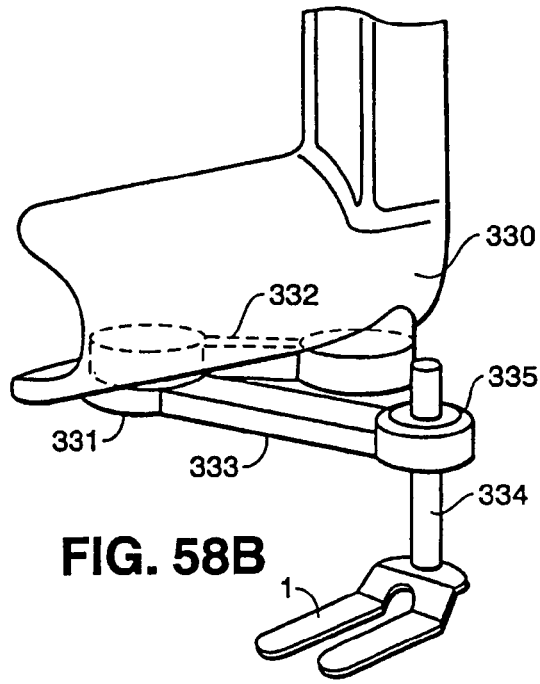
Figure 58C:
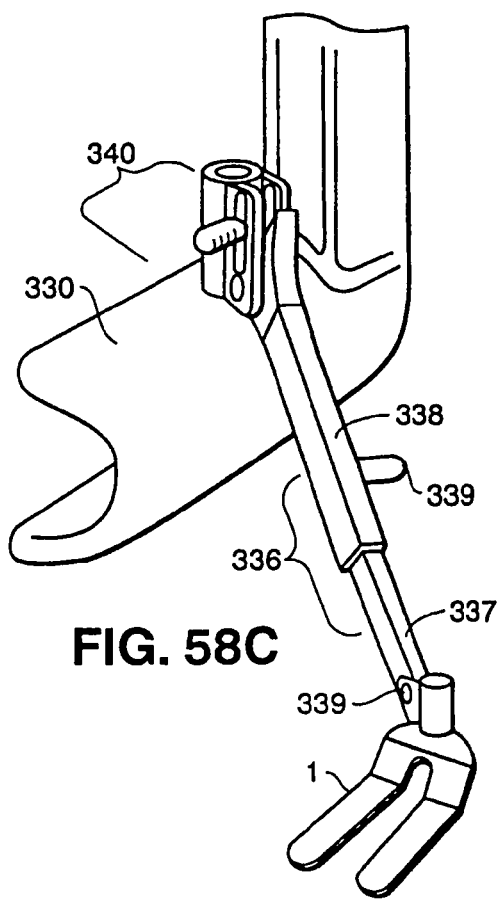

FIGS. 58A, 58B, and 58C are multiple segment shaft means 3 having alternate configurations to permit adjustable positioning. FIG. 58A has an elbow joint 324 with a hinge attaching upper and lower dual shaft members 325a, 325b, and 326a, 326b, such that the upper and lower shafts members are continuously positioned relative to a retractor or other stable support 327. The assembly may be attached to the retractor and the lower dual blade shaft members 325a, 325b are attached to the contact members by rotating joints 328 while the upper dual shaft members 326a, 326b are attached to the support by a second rotating joint 329. FIG. 58B has two shafts which are positioned to extend in a horizontal plane by extending from beneath a retractor blade 330 and by rotating around at least one circular joint 331 disposed between a first and second shaft 332 and 333. At the end of the second shaft 333, the contact members 1 may be provided with a third vertical shaft 334 having a ball joint 335 disposed at a proximal end thereof and which is affixed to the second shaft member 333.

One particularly useful feature of the shaft means of the invention is the ability to extend the distal end of the shaft in a continuous or telescopic fashion such that the contact members can be continuously positioned downwards relative to the proximal end of the shaft that is in turn attached to a retractor or other stable support. The degree of downward extension may be provided by several mechanical embodiments. FIG. 58C is a telescoping shaft member 336 having a lower shaft 337 concentrically oriented within an upper shaft 338 and a locking means 339 for fixing the position of the lower shaft 337 relative to the upper shaft 338. Additionally, the contact members 1 may be positioned by pivot 339 located at the proximal distal ends of the lower shaft 337. The upper shaft 338 may also be positioned relative to the retractor blade 330 by a tilting mechanism 340 that adjusts the angle of the upper shaft 338 relative to the retractor blade 330.

Figure 59A:
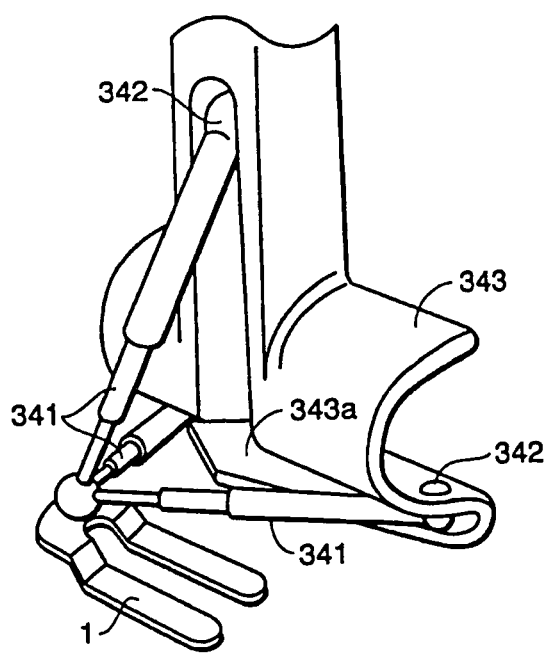
FIGS. 59A through 59C are adjustable shaft means of the invention that extend from a retractor blade or a retractor arm and are continuously positioned relative to the retractor blade or retractor arm.
Figure 59B:
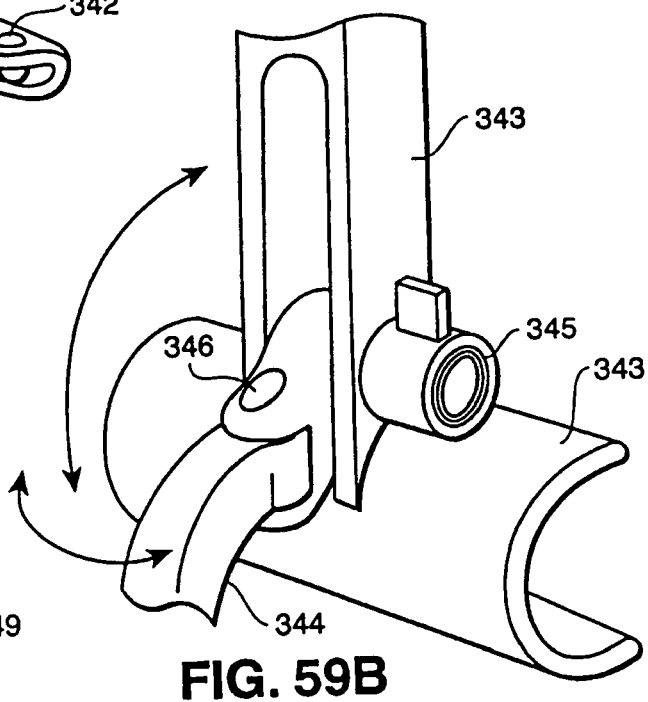
Figure 59C:
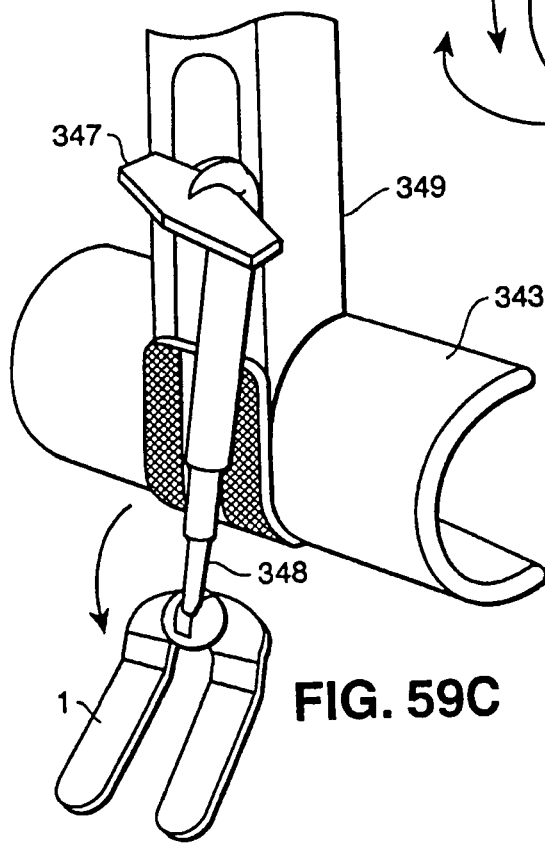

Referring to FIGS. 59A, 59B, and 59C, the stabilizing means of the invention may be provided by a plurality of adjustable attachments that affix the proximal end of a shaft or shafts to a retractor. For example, in FIG. 59A, a plurality of telescoping shaft means 341 are affixed to several pivoted joints 342 or hinges on a retractor blade 343 such that the contact members 1 can be continually positioned in three dimensions relative to the retractor blade 343 which grips one edge of an incision. When retracted, the contract members 1 are contained entirely within a recessed housing 343a formed in the retractor blade 343.

In the embodiment of FIG. 59B, a lockable rotatable arm 344 is provided that may be locked or unlocked to be positioned vertically by a first hinge 345 and to swing or rotate around a second hinge 346 wherein both hinges are mounted in a retractor arm or a retractor blade 343.

In FIG. 59C, the shaft means has an adjusting knob 347 affixed to the proximal end of a telescoping shaft means 348 at a point along the retractor arm 349 or the retractor blade 343. By loosening the adjusting knob 347, the telescoping shaft means 348 may be extended or retracted relative to the retractor arm 349 and the retractor blade 343 thereby allowing the contact members 1 to swing into position to be brought into contact with the beating heart.

Figure 60:
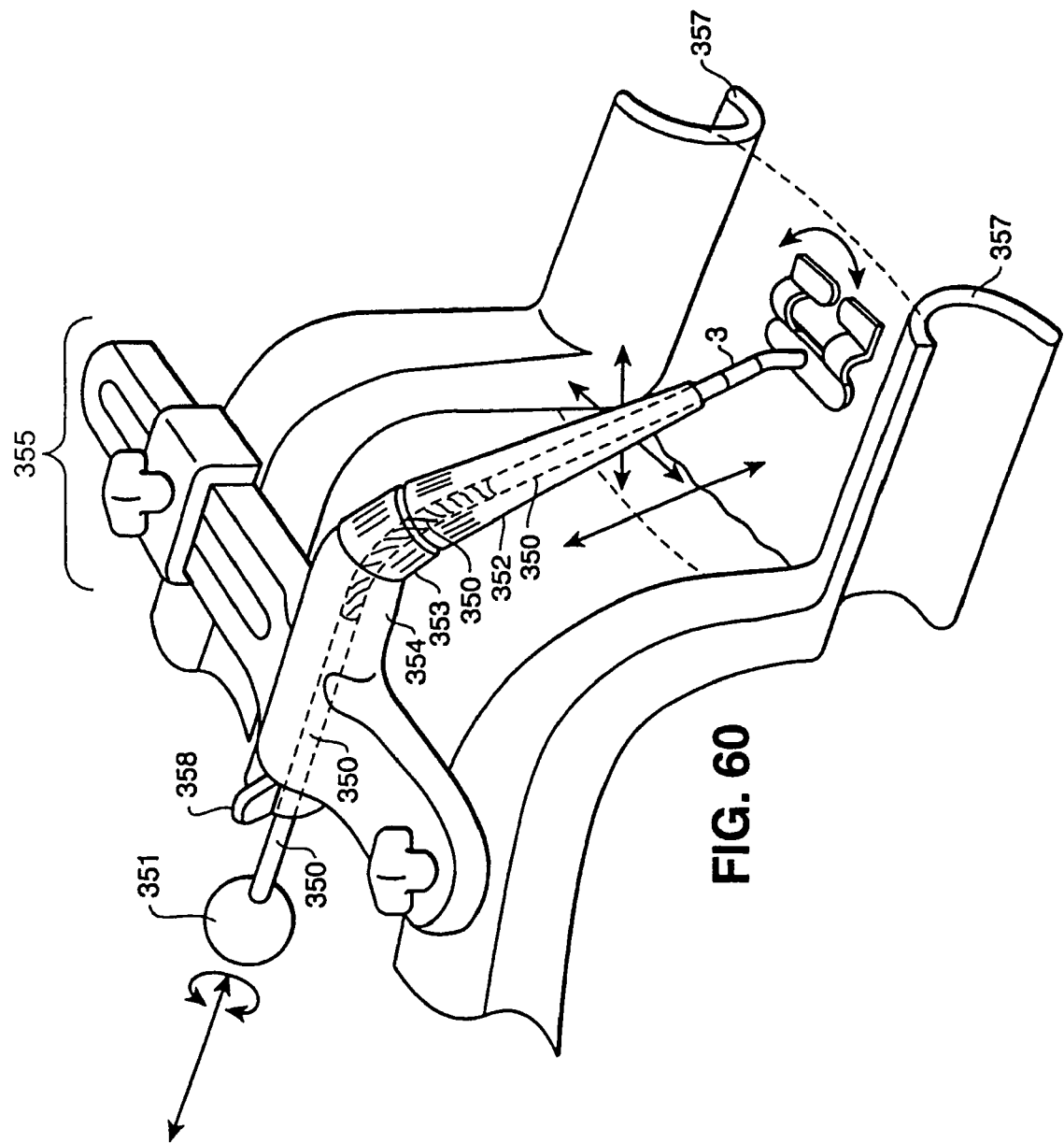
FIG. 60 is an embodiment having a central shaft with a handle at the proximal end that is positioned by a plurality of shaft guides which are preferably attached to a interconnecting arm affixed to a retractor.

In the embodiment of FIG. 60, a flexible central shaft 350 having a handle 351 at the most proximal end is disposed within at least one shaft guide 352, and preferably a series of shaft guides 352, 353, and 354. The handle 351 is adapted to be held by the hand and allows both rotation of the flexible central shaft 350 and positioning of the contact members 1 by extension or retraction of the handle 351. Any of the series of shaft guides 352, 353, and 354 may be straight or formed to have a predetermined curve to alter the direction of the central shaft 350. A proximal shaft guide 354 may be integral with a retractor 355 used to open a surgical incision. A particularly preferred low profile embodiment of FIG. 60 has a shaft guide 354 integrally associated with a cross-member 356 that connects the arms of retractor blades 357. The shaft means 3 at the distal end of the central shaft 350 may be straight of curved and rigid or flexible as desired. To fix the position of the central shaft 350, a lock mechanism 358 is provided, preferably at a proximal portion of the central shaft 350, to fix the position of the central shaft relative to the shaft guides 352, 353, and 354.

Figure 61:
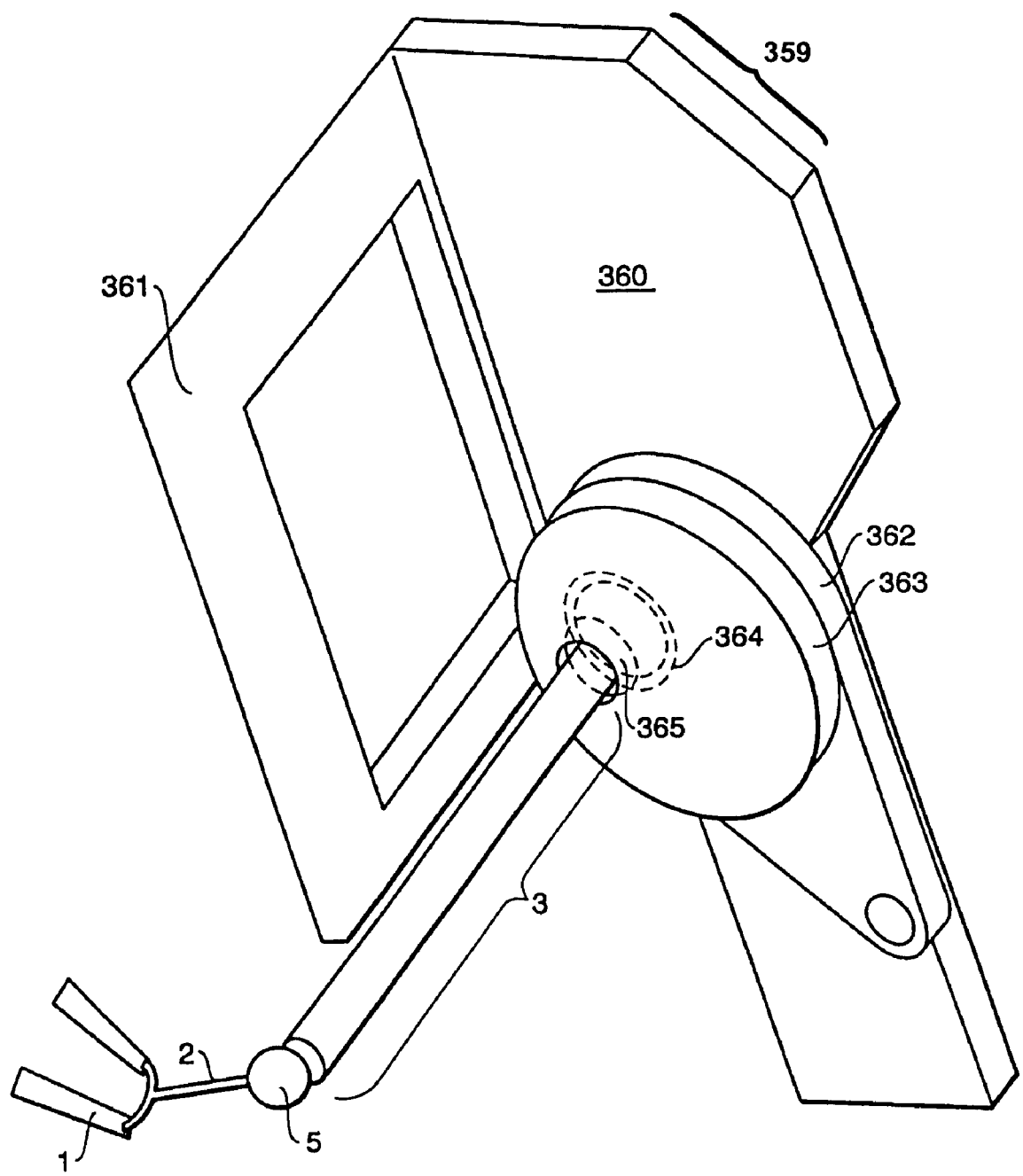
FIG. 61 is an embodiment of the stabilizing means of the invention having a pair of plates operably associated with a rib retractor and a sphere disposed between the plates to facilitate orientation of the shaft means.

Referring to FIG. 61, as noted above, attachment to a rib retractor is a preferred technique for fixing the position and orientation of the stabilizing means. The stabilizing means of the invention may therefore advantageously attached to a fixture attached to a rib retractor 359 or may be configured to be directly incorporated into the body of a portion of the rib retractor 359. A surgical rib retractor 359 is generally comprised of a body 360 having blades 361 attached thereto, which engage the ribs and spread the ribs when the retractor 359 is operated to move the blades 361 apart from one another. The space created by the retracted blades 361 provides access to the heart. Thus, once the retractor 359 is locked into the open position, the stabilizing means may be applied to the heart and a stabilizing force maintained at the site of the anastomosis by fixing the position and orientation of the shaft means 3 relative to the rib retractor 359. Referring again to FIG. 61, the shaft means 3 may traverse the width of the body 360 of the retractor 359 and is held in place by an upper plate 362 and a lower plate 363 having circular openings 364 therein through which the shaft means 3 passes and which maintain the position of a sphere 365 positioned between the upper plate 362 and lower plate 363. The size of the openings 364 is larger than the diameter of the shaft means 3 but smaller than the largest diameter of the sphere 365. Thus, the shaft means 3 passes through the sphere 365 and may pivot about a point approximately at the center of the sphere 365.

Figure 62:
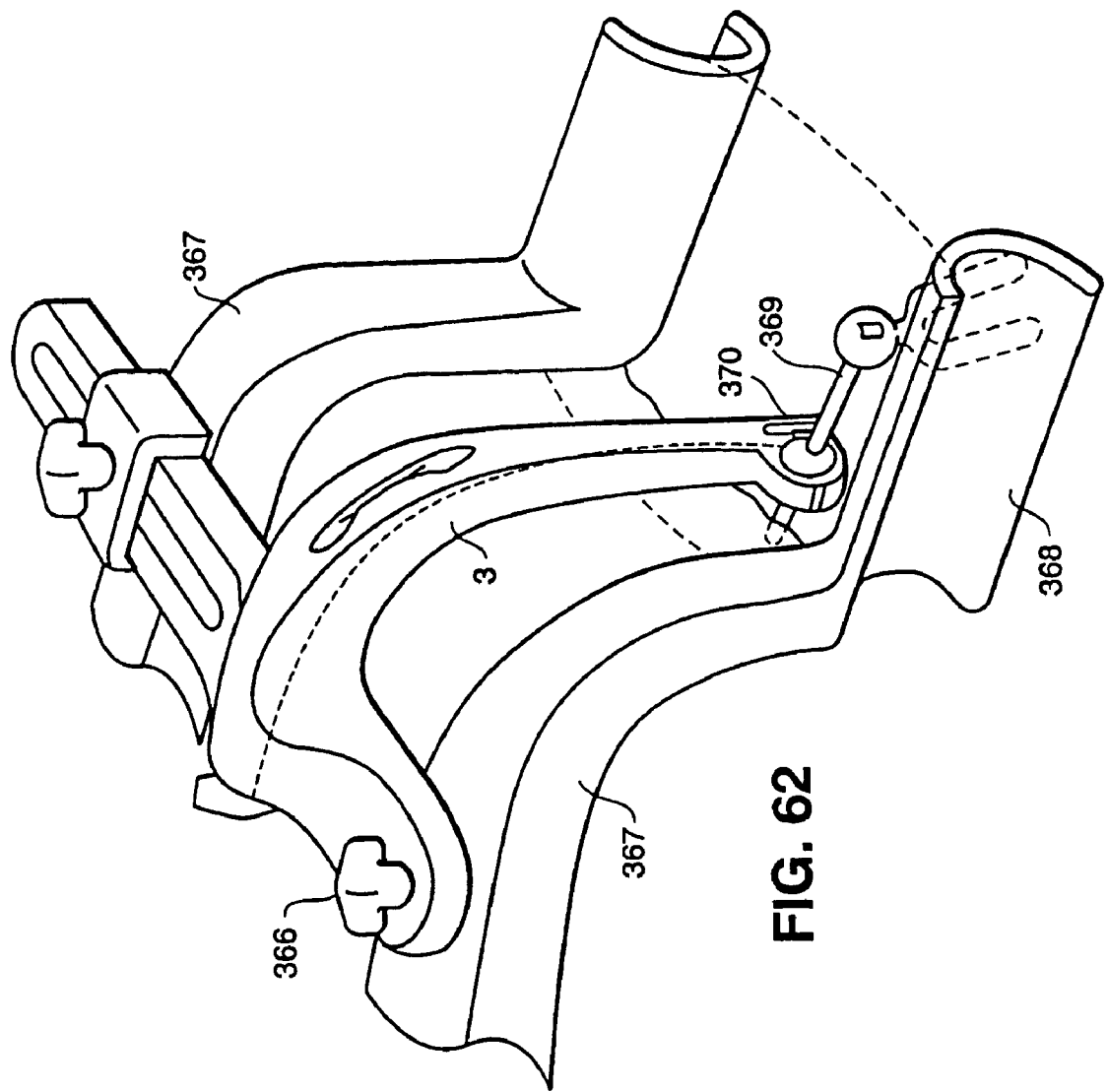
FIG. 62 is an embodiment of the invention having a shaft means comprised of an arm which extends from the interconnecting bar of a retractor to a position below the retractor blades and has a substantially horizontal shaft.

Referring to FIG. 62, the stabilizing means of the invention may be provided by a shaft means 3 that extends from a cross-arm 366 connecting the individual arms 367 of a surgical retractor such that the shaft means 3 extends between the arms 367 attached to the retractor blades 368 and below the level of the retractor blades 368 such that the contact members 1 and separate shaft 369 is positioned beneath the level of the retractor blades 368 and is generally contained within the chest cavity. This embodiment is a low profile design wherein a portion of the shaft means 3 extends into the chest cavity and has a second substantially horizontal shaft 369 extending from the distal end 370 thereof.

Figure 63:
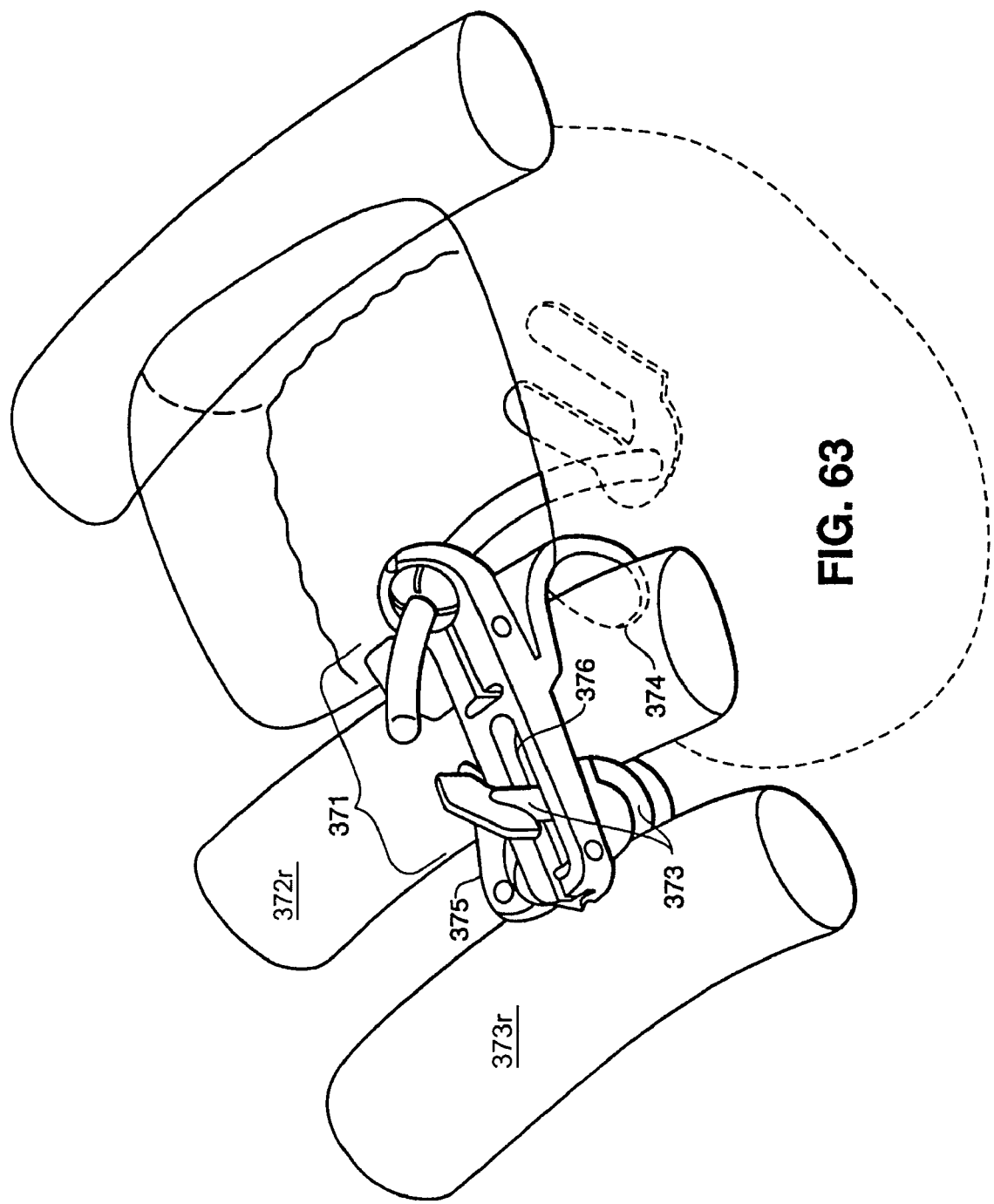
FIG. 63 is the means for stabilizing the beating heart of the invention operably associated with a rib locking mechanism.

Referring to FIG. 63, the stabilizing means of the invention may advantageously be provided with a rib locking mechanism 371 affixed to either side of a rib 372r to form a stable support for shaft means 3 that extends from the rib locking mechanism 371 into the chest cavity. The rib locking mechanism 371 is comprised of an adjustable post 373 preferably disposed with a slot 376 formed in the body of the rib locking mechanism 371 and its positioned between two adjacent ribs 372r, 373r and a blade 374 affixed to the opposite side of the rib 372r most adjacent to the incision. The position of the blade 374 is adjustable relative to the post 373 by sliding the mechanism 371 along the slot 376 and fixing it in place with a locking latch 373.

Figure 64:
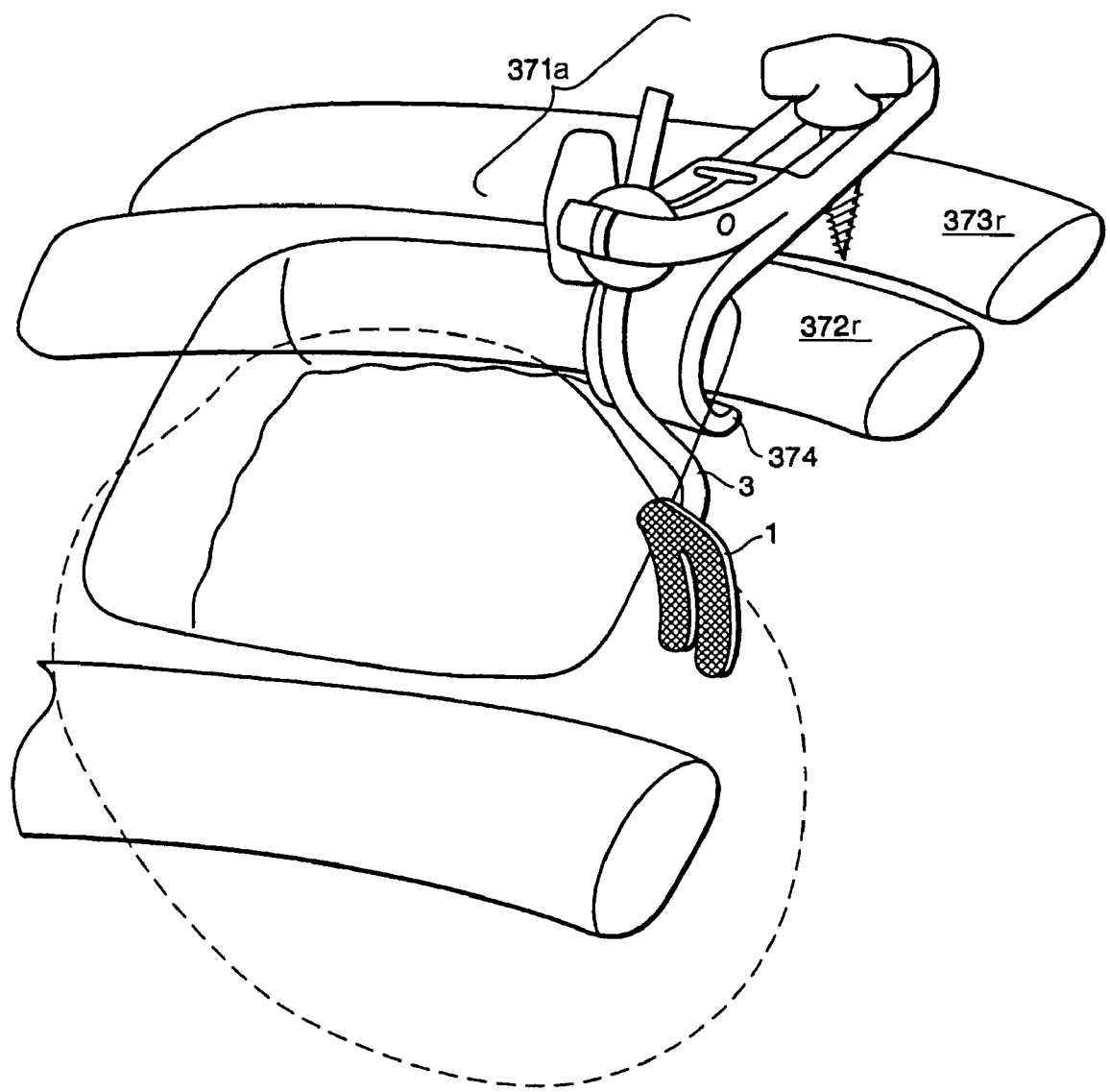
FIG. 64 is the stabilizing means of the invention adapted to be used as a means for positioning the beating heart, wherein the means are operably associated with a rib locking mechanism.

As noted herein, the embodiments of the stabilizing means of the invention may also be used to position the heart to facilitate performing the bypass surgery or any other cardiac procedure where the position of the beating heart may be adjusted. Referring to FIG. 64, the embodiment of FIG. 63 may be utilized as a heart positioning device requiring only the modification that the shaft means 3 affixed to an identical or equivalent rib locking mechanism 371a and the contact members 1 have a length and tensile strength such that the contact member 1 can maintained in a position about the periphery of the beating heart as desired.

Figure 65A:
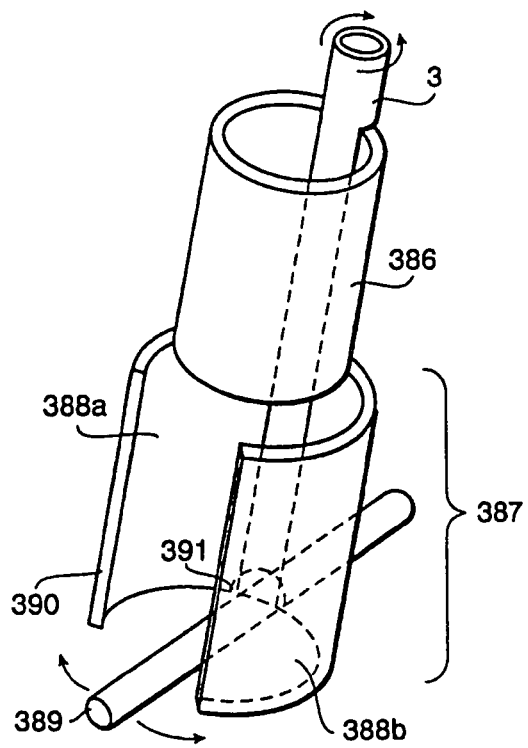
FIGS. 65A through 65D are embodiments of the invention where the shaft means is comprised of a unitary hollow shaft.

In combination with the several designs for contact members and related features described previously herein, the configuration and construction of the element which is attached to the contact members principally the shaft means, may partially comprise the contact members and may be provided in several alternative designs without departing from the spirit of the invention. As indicated previously, certain variations may depend on the surgical demands of a particular procedure, and will depend on the nature of the surgical incision(s) used to access the beating heart. For example, some embodiments of the invention are particularly useful where a minimally invasive incision is created, and the procedure is performed by introducing instruments through a cannula or a hollow shaft that provides access to the heart. FIGS. 65A through 65D show an embodiment of the invention whereby a means for stabilizing the beating heart is provided that is integral or closely associated with a hollow shaft 386 that defines a surgical field around the site of the anastomosis. In FIG. 65A a hollow shaft 386 is provided having a lower cylindrical portion 387 that splits into two semi-cylindrical portions 388 and 388b that define the surgical field for an anastomosis of a target vessel 389.

Preferably, the bottom surface 390 has an opening 391 through which the vessel 389 passes such that the vessel lies within the opening 391 and within the larger space created by splitting of the hollow shaft 386 to create the surgical field. In this embodiment, instruments may be introduced either through the hollow shaft portion 386 of the device or through the split portion of the lower portion 387 of the shaft to provide stabilization and access to the vessel 389. The opening action of the lower portion 387 of the shaft may be provided by a rotating shaft means 3 which, when rotated, forces the lower portion 387 to split into the semi-cylindrical portions 388a and 388b.

Figure 65B:
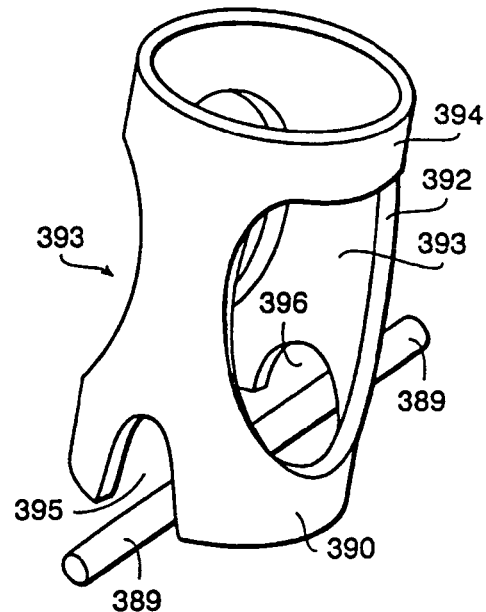

Referring to FIG. 65B, a unitary hollow shaft 392 may be provided that contacts the beating heart about the bottom surface 390, to provide the stabilization function, and has a plurality of openings 393 disposed in the body 394 thereof. Preferably at least one passage 395 is provided in the bottom surface 390 such that the target vessel 389 may be disposed within the passage 395. A second passage 396 may be provided in the bottom surface 390 of the unitary hollow shaft 392, preferably at an opposite end, such that the vessel may pass through the openings 395, 396, or where a single opening is provided (not shown) the edge of the bottom surface opposite the opening 395 acts as an occluder. Larger openings 397 in the body of the unitary shaft 392 may be provided to enable the surgeon to have access to the target 389 vessel through the body of the unitary shaft 392.

Figure 65C:
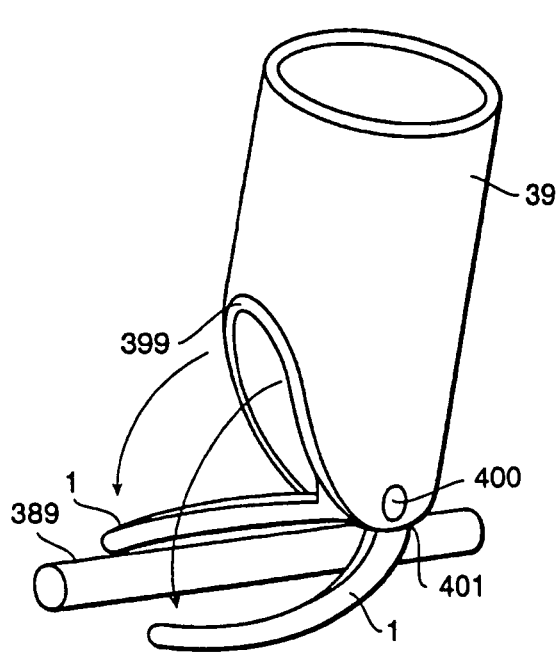

FIG. 65C is a hollow shaft element 398 having formed therein a pair of contact members 1 of the type described previously, but which fold out from the body 399 of the shaft by virtue of a hinge or pivot 400 at the lower portion 40 of the shaft element 399. By folding out the contact members 1, which are maintained substantially integral to the shaft element during insertion of the shaft element 398 through a surgical incision, the contact members 1 engage the surface of the beating heart and provide the stabilization function. The surgeon may introduce instruments through the hollow portion of the shaft element 398, or from another direction to achieve the anastomosis.

Figure 65D:
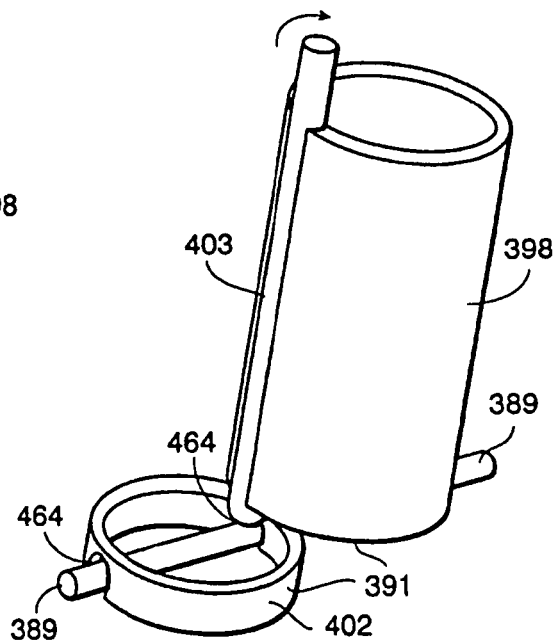

Referring to FIG. 65D, the application of the stabilizing force need not be applied directly below the surgical field created by the shaft element 398. The embodiment of FIG. 65D has an annular ring 402 formed in the bottom portion 391 of the shaft element 398 and that may rotate about the axis provided by a rod 403 or the shaft means 3 passing through the wall of the shaft element 398, and which is affixed to the annular ring 402. By rotating the rod 403, the annular ring 402 rotates out from under the bottom 391 of the shaft element 398, and may be positioned to contact the surface of the beating heart in an annular fashion adjacent and tangent to the shaft element 398. As with other embodiments described herein, the annular ring structure 402 that applies the stabilizing function may have at least one passage 464 formed in the bottom surface such that the vessel 389 may be positioned therein. The passage 464 may pass through the entirety of the ring 402 making it a "C" or "V" shaped contact member (not shown), which will allow easy removal from the field after construction of the anastomosis fastening the graft to the heart. Alternatively, the ring structure 402 may be cut or broken for removal if necessary.

Figure 66:
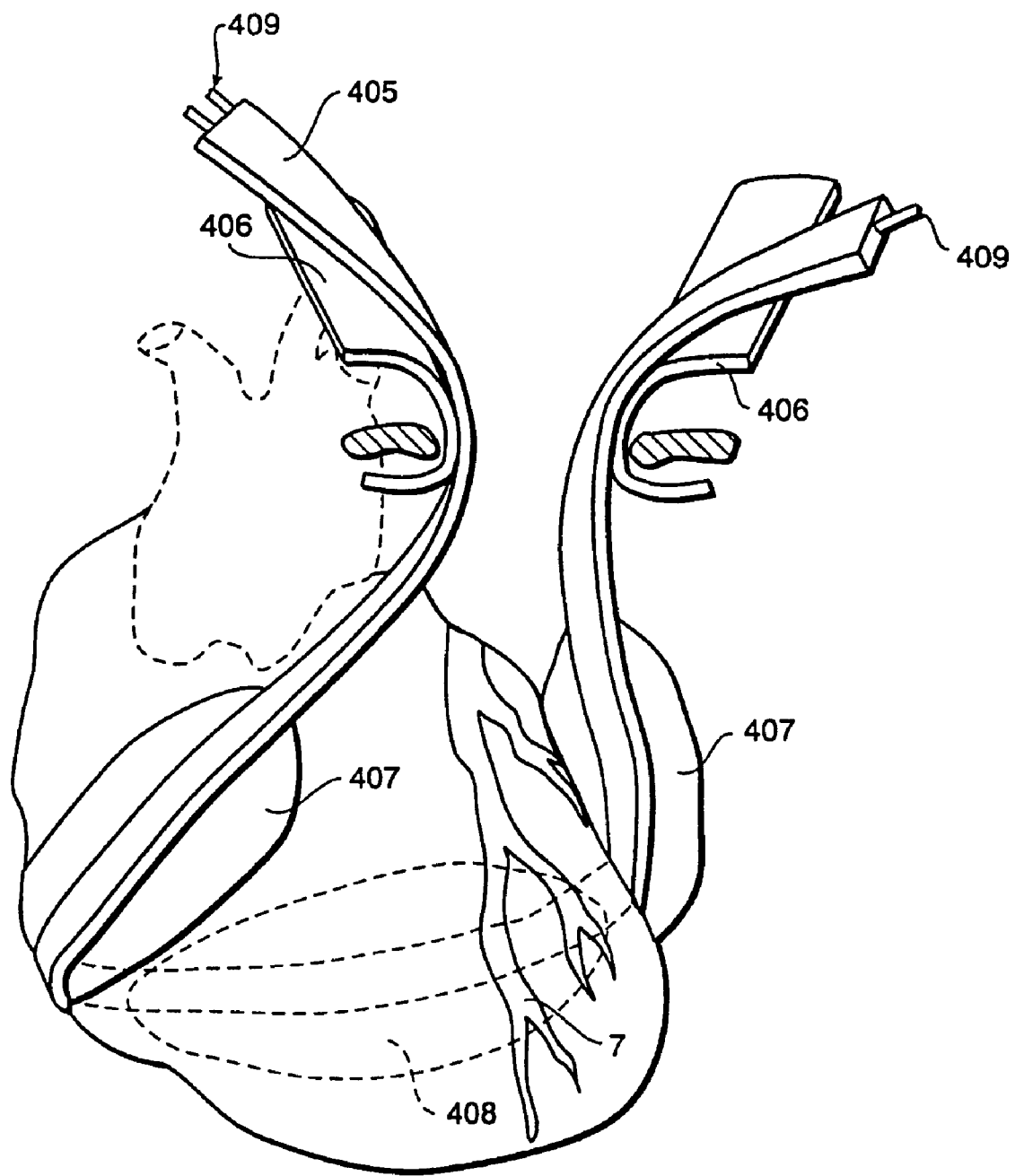
FIG. 66 is a means for stabilizing the beating heart having a sheath member with several pliable support attachments associated therewith which may include or be comprised of inflatable members which are positioned at one or several locations surrounding the heart and may have a lumen disposed within the sheath member for the introduction of air or a biocompatible fluid.

Referring to FIG. 66, this embodiment of the stabilizing means is comprised of an elongated sheath member 405 which wraps around the heart in a strap-like fashion to restrict the motion of the heart. This embodiment may be used with a thoracotomy providing surgical access, but is particularly useful when access to the beating heart is provided by a sternotomy. The sheath member 405 is positioned to surround the heart and manipulated so that each end of the sheath member 405 extends out of the chest cavity through the sternotomy. If desired, at least one end of each sheath member 405 is attached to a retractor 406 to secure the position of the sheath member 405. The sheath member 405 may have a plurality of support attachment 407 which engage the exterior of the heart to hold it in place. At the point where the support attachments 407 contact the surface of the heart, the support attachments 407 may have friction means 4 (not shown) attached to the surface which is in direct contact with the heart. The support attachments 407 may have or be comprised of fluid-filled members 408 which cushion the heart against the sheath member 405, and absorb the motion of the heart while it is stabilized. Where the sheath member 405 has one or more fluid-filled members 408, the sheath member 405 may also include at least one lumen 409 for introduction of air or a biocompatible fluid to the inflatable members 408, which may be inflated separately or simultaneously. In the former instance, a separate lumen 409 is provided for each inflatable member 408. The insertion of the sheath member 405 into the chest cavity may be performed while the inflatable members 408 are deflated and is achieved manually or by a conventional guide and/or guide wire. Each of the support attachments 407 may be permanently attached to the sheath member 405 or may slide along the length of the sheath member 405. Alternatively, alone or in combination with other inflatable members, the inflatable member 408 is positioned immediately proximate to the target coronary artery to achieve a more localized stabilization. Thus, the inflatable members of the invention may lie next to, or may surround, the heart of the target coronary artery and may have openings or apertures placed in the body thereof through which surgical procedures are performed. An additional stabilizing force may be applied when the inflatable member 408 fills the space between the heart and the enclosing structure, such as the pericardial ling or the back of the ribs. When the inflatable table member 408 is appropriately inflated, the target artery site may be pressed against a proximate stabilizing structure, such as contact member 1, the back of edge of the surgical incision. The fluid-filled or inflatable cushioning, stabilizing, or positioning means could also be applied via a rigid, malleable, deformable, or removable shaft, handle, mounting, or inflation means.

Similarly, referring to FIG. 67, a strap 410 may be provided which is arranged to pass over opposite retractor blades 411, to pass underneath the heart, and which may be mounted at both ends to a crank 412 for selective movement of the strap 411. By turning the crank 412, or by otherwise manipulating the position of the strap 411, the heart may be rotated for selective positioning or to provide access to various regions of the heart. The cranks 412 are advantageously attached to the retractor used to maintain spreading of the ribs in a minimally invasive thoracotomy.

Figure 68C:
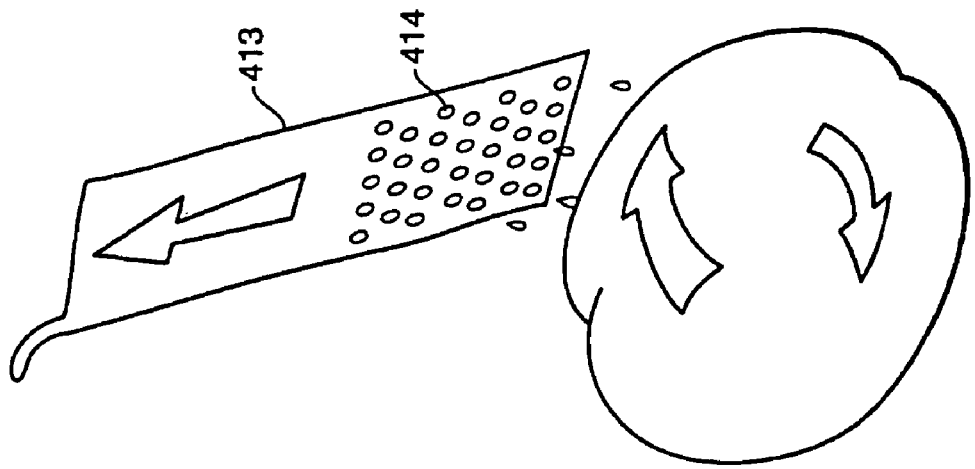
FIGS. 68A through 68C are a device for advantageous positioning of the heart comprised of a flexible sheet, preferably having a hydrogel coating on one side.
Figure 68B:
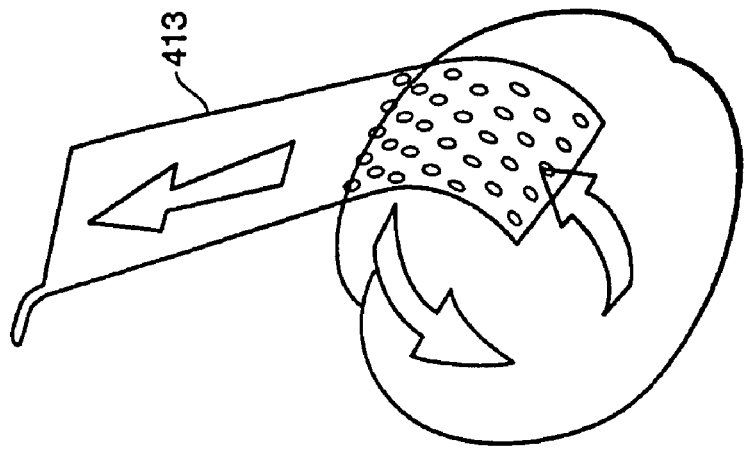
Figure 68A:
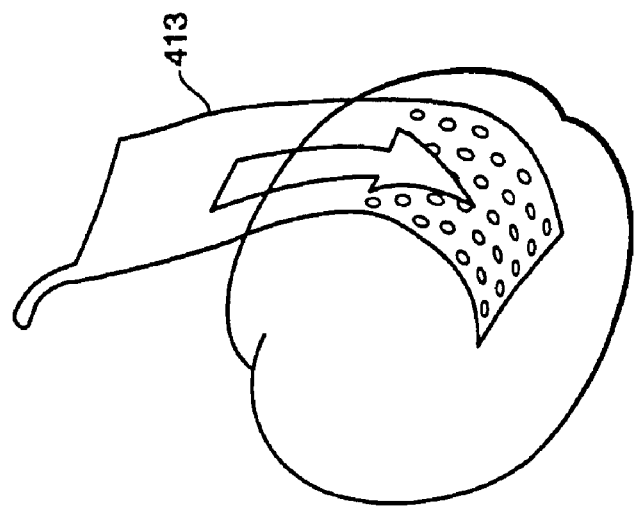

As noted above, in addition to stabilization of the beating heart, the devices and methods of the invention may be used as shown in FIGS. 66 and 67 to selectively position the heart. Additionally, as shown in FIG. 68, an alternate to a continuous strap 411 is shown in FIGS. 68A, 68B, and 68C and is comprised of a substantially flat, flexible sheet 413 positioned under the heart. One side of the sheet 413 may have a hydrogel 414 coating, or a coating of a similar material that adheres to the epicardial surface. Preferably, the other side of the sheet 413 is smooth. In a preferred embodiment, two sheets 413 are joined at their respective edges to form an interstitial space (not shown) therebetween. Perfusion of the interstitial space with fluid softens the hydrogel 414, allowing ready repositioning or removal of the sheets 413.

Figure 69:
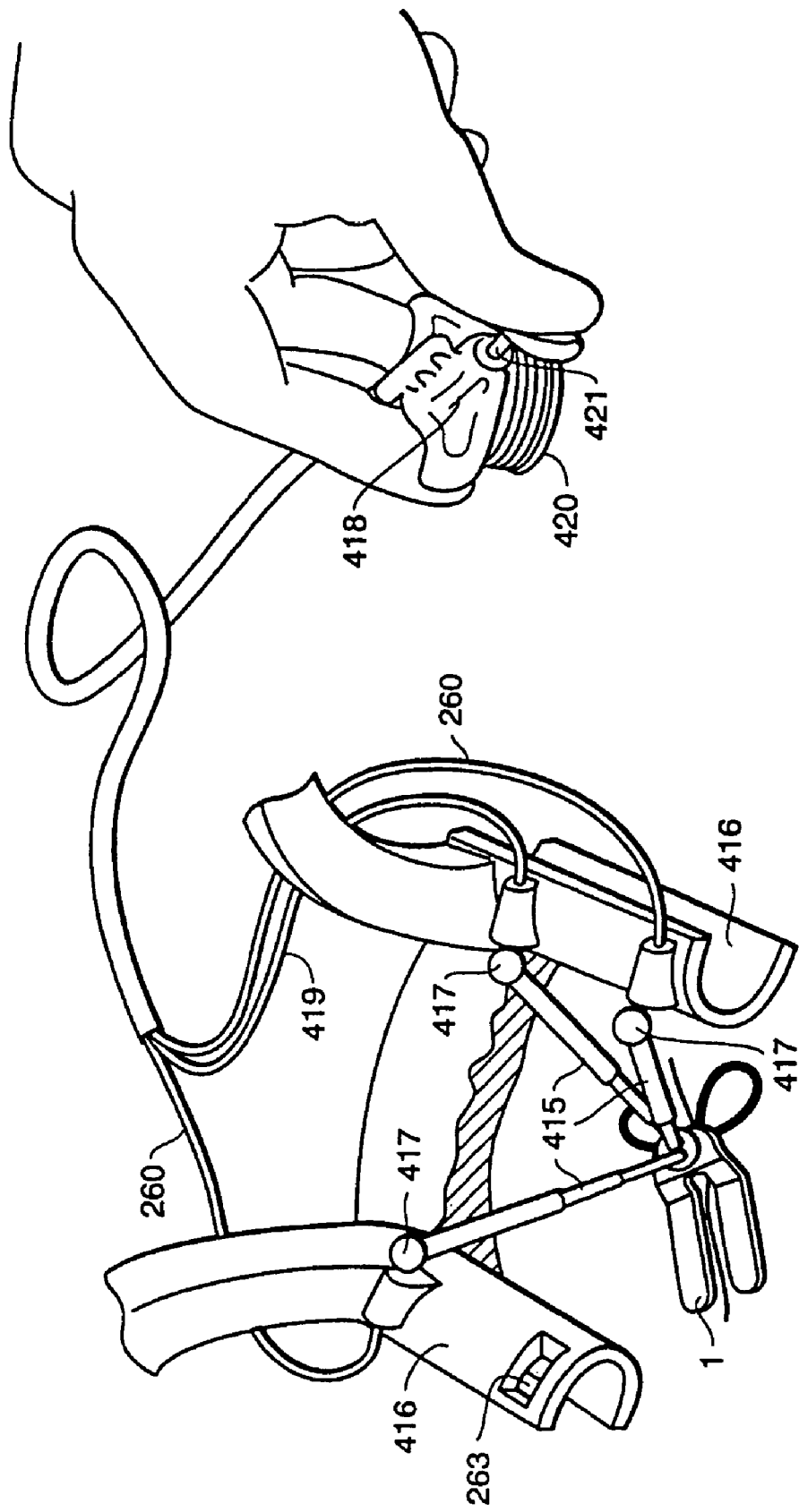
FIG. 69 is an embodiment of the invention comprised of a plurality of telescoping shafts having the contact member affixed at their distal end and wherein the position of the telescoping shaft is manipulated and fixed by a hydraulic actuators.

Depending on the nature of the surgical procedure, it may be desirable to lock the contact members 1 in place by manipulating their position from a location remote from the surgical field. In the embodiment of FIG. 69, a plurality of telescoping shafts 415 are provided which engage a contact member 1 at their most distal end. Preferably, each telescopic shaft 415 is affixed to a point on the retractor blade 416, thereby allowing the telescopic shafts 258 to be collectively adjustable to position the contact members 1 at any point within the range of movement of the telescoping shafts 415 within the surgical field. At the most proximal point of each telescopic shaft 258, the shaft is affixed to the retractor blade 416 by virtue of a hydraulic actuator 417 that fixes the orientation of each telescopic shaft 415 relative to the retractor blade 416. Each hydraulic actuator 417 is attached to a lock valve 418 via non-expanding hydraulic hoses 419. Typically, the lock valve comprises a reservoir 420 and a hand-activated switch 421 for closing the lock valve 418 to lock the hydraulic actuators 417 into position. Any number of telescopic shafts 415 may be provided, however, it is preferable that a plurality of mounting points are available at various locations on the retractor blade 418 such that the surgeon can individually attach several, preferably at least three, telescopic shafts 415 to the retractor blades 416 at the locations best suited for each surgical procedure.

Referring to the embodiment of FIGS. 70A through 70D, a stabilizing means is provided with a shaft means 3 comprised of a plurality of arms connected by joints having selectively placed friction surfaces associated therewith that freeze the joints and adjustable arms into a set configuration when the contact members are displaced upwards by the motion of the beating heart. Referring to FIG. 70B, the retractor blade 416 has a locking mechanism 422 with an internal cam shaft 422a actuated by a handle 422b that expands a first curved leaf spring 422c to fix the position of a first shaft 424 relative to the retractor blade 416. As shown in FIG. 70A, the first shaft 424 is attached to a first friction joint 425 permitting rotation of the joint about an axis perpendicular to first shaft 424. Referring to FIG. 70C, the friction joint 425 is comprised of a lower housing 426 affixed to the first shaft 424 and an upper housing 427 affixed to a second shaft 428 which may be a discrete cylindrical shaft as the first or may be an extension of the housing of the friction joint 425. A ball pivot 429 is positioned between the upper 427 and lower housing 426 to allow the individual housings to rotate about each other. Either the upper 427 or lower 426 housing has disposed therein a friction surface 430, and the opposite housing has a friction engaging means such as teeth 431. When either housing is displaced by tilting about the ball pivot 429, the friction surface 430 contacts the friction engaging means 431 and freezes the position of the friction joint 425. The second shaft may be connected to a second friction joint 432 having an equivalent construction to the first.

Referring to FIGS. 70A and 70D, a rotatable shaft means 433 is comprised of a central rod 434 disposed within a housing 438 having a ratcheting mechanism formed from tongues 435 engaging teeth around said central rod 434 to fix the rotatable position of the rotatable shaft means 433. The rotatable shaft means 433 is connected to the contact members 1, for example, by a hinge 436 having a shaft 439 resistant to rotation by teeth (not shown) engaged by molded tongues 437.

In the embodiment of FIGS. 71A through 71D, a retractor blade 440 is adapted to receive a clip into which is inserted a flexible slide having a contractible shaft means at the distal end thereof and means for extending the contractible shaft. Referring first to FIG. 71C, the assembly includes a C-shaped clip 441 for attaching the stabilizing means to the retractor blade 440. The clip has at least one groove 442 adapted to fit within a guide 443 formed in the retractor blade 440. The body of the clip 441 also has a slot 444 around the outside of the curved portion as shown in FIGS. 71A and 71B and in phantom in FIG. 71C for insertion of a flexible slide 445. FIG. 71D shows the flexible slide 445 that fits inside the slot 444 formed in the clip 441 such that the flexible slide enters the clip 441 through the slot 444 and curves around to conform to the shape of the clip 441. A block 440 is mounted at the distal end of the flexible slide 445.

An extendable shaft means 447 is attached to the block 446 and has an unexpandable hydraulic tube 448 affixed thereto which is in fluid connection with a syringe 449 or other such fluid containing apparatus to apply hydraulic pressure through the tube 448 to extend the shaft means 447. Preferably, the syringe has a one-way valve 450 with a release valve 451 such that hydraulic fluid pressure is applied to progressively advance the extendable shaft means 447, while the one-way valve 450 prevents the extendable shaft means 447 from contracting. Upon completion of the procedure, the hydraulic pressure is released by activating release valve 451.

Referring to FIG. 71A, the surgeon would first insert the clip 441 onto the retractor blade 440 by inserting the flexible slide 445 into the slot 444. The flexible slide 445 is thereby advanced from the top of the clip 441 through to the bottom until the extendable shaft means 447 is in position to be extended to bring the contact members 1 into conforming engagement with the heart. With one hand, i.e., via the syringe 449, fluid is injected into the extendable shaft 447 to cause the contact members 1 to engage the heart. Note also that the guide 443 in the retractor blade 440 may extend the length of the blade 455, allowing selective positioning of t clip 441 along the blade 440.

Figure 72:
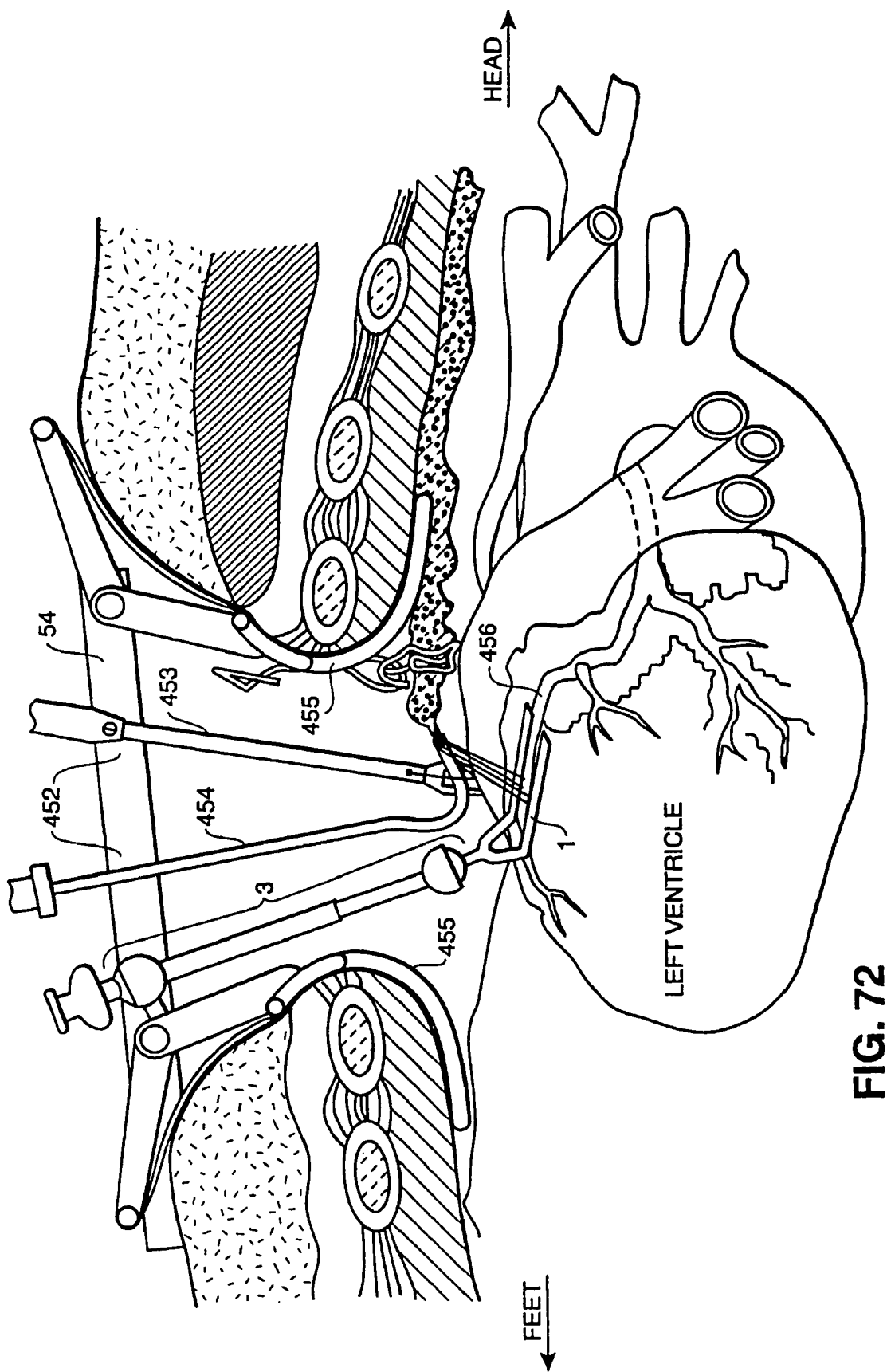
FIG. 72 is a view of the interior of the chest cavity during a CABG procedure on the beating heart with the stabilizing means operably associated with a retractor and being used in conjunction with other surgical apparatus to facilitate completing the anastomosis.

Referring to FIG. 72, the means for stabilizing the beating heart of the invention is shown in use together with a rib retractor 452 and additional apparatus 453, 454 which may be used during the beating heart CABG procedure. In use, the blades 455 of the retractor separate the ribs, thereby providing an access space for the introduction of surgical instruments, including the stabilizing means of the invention. The stabilizing means is thus brought into contact with the heart such that the contact members 1 are proximate to the target artery 456. A stabilizing force is exerted in an amount sufficient to minimize the motion of the beating heart, including fixing the stabilizing means in place, preferably by attachment to the rib retractor 452.

Figure 73:
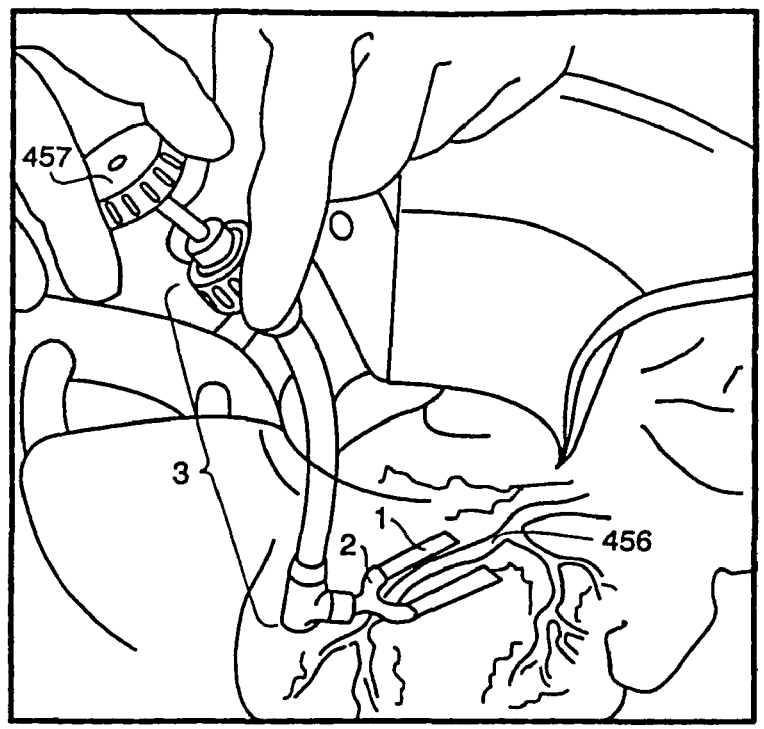
FIGS. 73 and 74 show the stabilizing means of the invention having been introduced through a thoracotomy to contact the beating heart to engage the heart tissue on either side of a target coronary artery to which an anastomosis is sewn.
Figure 74:
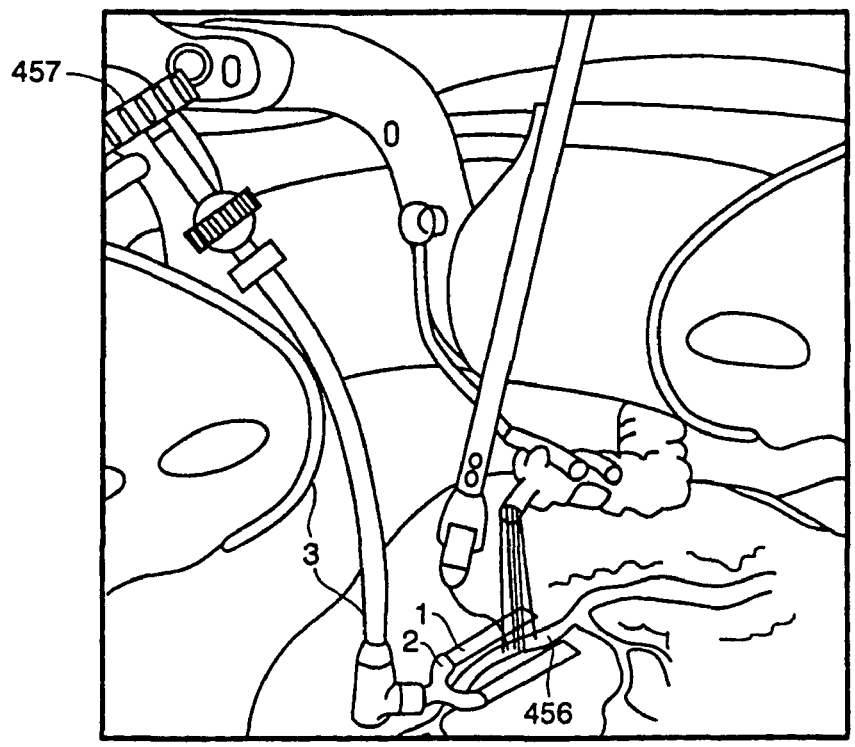

Referring to FIG. 73, the stabilizing means is comprised of a pair of rectangular, substantially planar contact members 1, which are placed proximate to a target artery 456. The shaft means 3 is conformable such that it may be conveniently attached to the rib retractor 452. As shown in FIG. 73, the surgeon may readily adjust the orientation and positioning of the connecting shaft 2 and the contact members 1 relative to the shaft means 3 while the stabilizing means is in continuous contact with the heart by manipulating the thumbscrew 457 at the proximal end of the instrument. FIG. 74 shows a later stage of the procedure at a point where the anastomosis is being completed by suturing at target artrery 456. The stabilizing means thus maintains a stabilizing force at the anastomosis site for the duration of the procedure.

Figure 75:
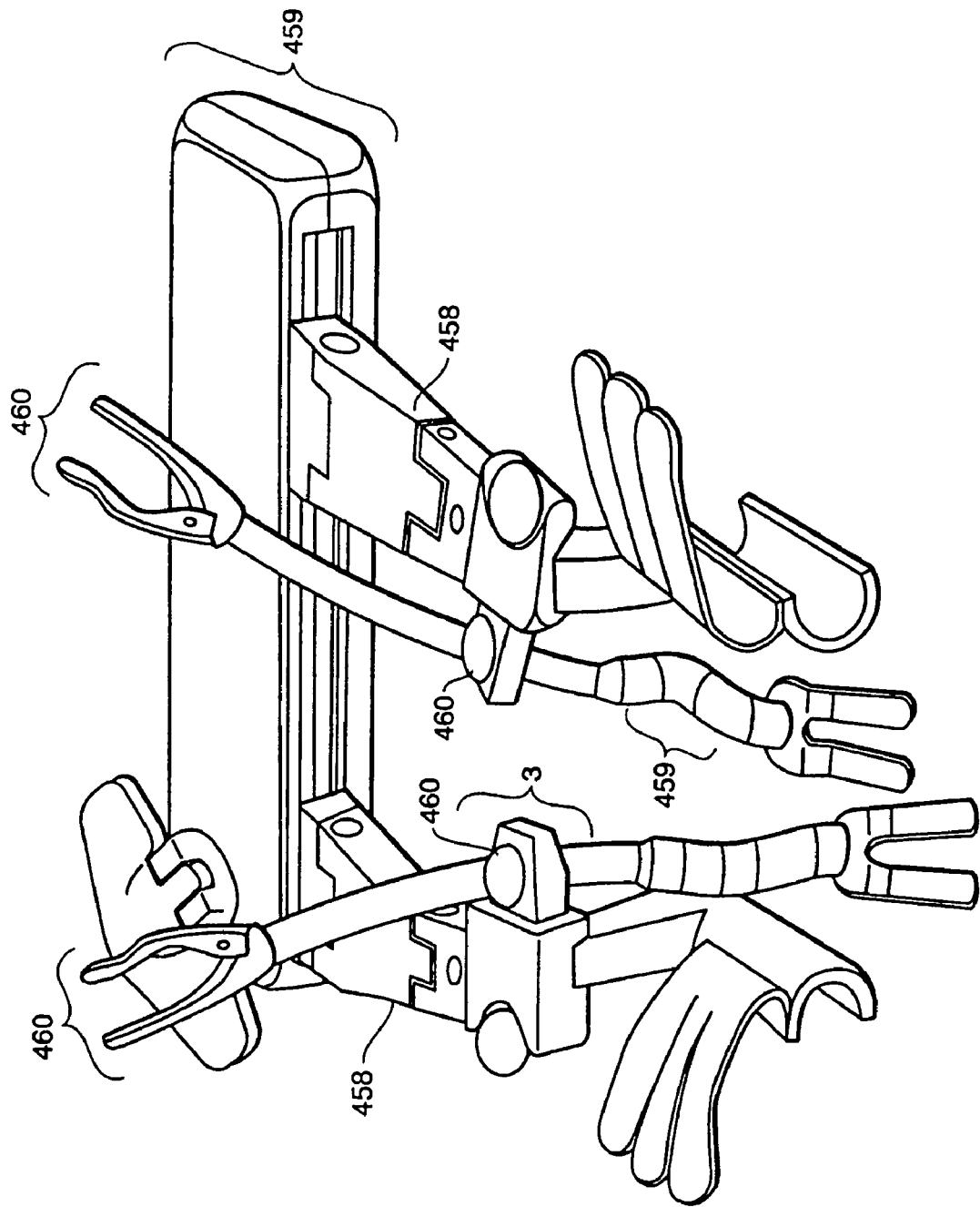
FIG. 75 is an embodiment of the invention having a pair of shaft means operably associated with ball joints that are affixed to opposing arms of a retractor.

As described above in several embodiments of invention, the stabilizing means may advantageously be integrated with a related surgical device such as a retractor that is used to spread the ribs in preparation for the cardiac surgery. FIG. 75 is an embodiment of the invention having a pair of shaft means 3 integrated with the arms of a retractor 459 suitable for spreading the ribs in a minimally invasive cardiac surgery. The stabilizing means are comprised of shafts having adjustable links 459 as previously described bed that provide for positioning of the contact members 1. The shaft means 3 also traverse ball joints 460 that are directly affixed to the arm 458 of the retractor blade, and terminate with adjustable handles 460 for locking the position of the shaft means 3 and contact members 1 in place.

As mentioned previously, it is the goal of the present invention to provide an apparatus, or collection of apparatus, to facilitate completing a minimally invasive CABG procedure on the beating heart. Thus, each of the devices disclosed herein is preferably provided in an integrated kit, having several individual instruments packaged therein to provide the surgeon with each of the instruments necessary to complete the anastomosis on the beating heart. Since it is intended that the means for stabilizing the beating heart as described herein, will be introduced directly into the thoracic cavity, and brought into direct physical contact with the beating heart, it is necessary that each of the devices disclosed herein be subjected to the sterilization techniques suitable for other surgical instruments. It is particularly preferred that a substantial portion of the devices described herein be formed of a biocompatible and sterilizable plastic and maintained in a sterile container completely enclosing the instrument whereby the container provides a barrier against microorganisms and wherein the stabilizer means of the invention and the container in which the instruments are packaged are sterilized. Sterilization of the container and the instruments contained therein may be provided by conventional sterilization methods such as ETO gas, high temperature and pressure, or gamma radiation. Preferably, the container in a sealable flexible bag that may be sterilized either before or after having the instruments of the invention sealed therein.

The particular examples set forth herein are instructional and should not be interpreted as limitations on the applications to which those of ordinary skill are able to apply this invention. Modifications and other uses are available to those skilled in the art which are encompassed within the spirit and scope of the following claims.

The invention claimed is:

1. A device for use in a cardiovascular surgery for insertion into the chest cavity to stabilize the beating heart through communication with a fixed support or retractor located at least partially outside of the chest cavity, the device comprising:
   a shaft having a proximal end portion and a distal end portion;
   a plurality of contact members attachable to said distal end portion of said shaft, said contact members each comprising a flexible main body having a contact surface and an elongated malleable member extending along a length of said flexible main body member;
   wherein said malleable members are shapeable to engage the surface of the beating heart and are configured to be placed on opposite sides of a site of anastomosis, wherein each of said malleable members is continuously adjustably shapeable by manipulation thereof to any one of a plurality of desired shapes, and wherein upon release of manipulation forces, said malleable member maintains said desired shape into which it was adjustably shaped and maintains said contact surface in said desired shape; and
   wherein said shaft has sufficient strength to withstand a stabilizing force exerted on the heart via manipulation or fixation of said shaft to cause said contact member to exert a stabilizing force on the beating heart.

2. The device of claim 1, wherein introduction of positive or negative pressure to said contact members fixes a present shape of said contact surface.

3. The device of claim 1, wherein said contact members further comprise a vacuum lumen connectable to a source of positive or negative fluid pressure.

4. The device of claim 1, wherein said elongated malleable members are substantially cylindrical.

5. The device of claim 1, wherein said elongated malleable members comprise a wire.

6. The device of claim 1, wherein said shaft is adapted for insertion into a fixture attached to the fixed support or retractor.

7. The device of claim 1, wherein said malleable members are shapeable into said any one of a plurality of desired shapes prior to insertion of said malleable members, and retain said desired shapes that said malleable members have been shaped into after insertion of said malleable members into the chest cavity.

8. The device of claim 1, wherein said plurality of contact members are attached to said distal end portion of said shaft.

9. A device for use in cardiovascular surgery on the beating heart, comprising:
   a shaft member having a distal end portion and a proximal end portion; and
   a plurality of continuously adjustable contact members connectable to said distal end portion of said shaft member and each said contact member comprising a flexible main body member having a contact surface and an elongated malleable member extending along a length of said flexible main body member;
   wherein said malleable members are shapeable to engage the surface of the beating heart and are configured to be placed on opposite sides of a site of anastomosis, wherein each of said malleable members is continuously adjustably shapeable by manipulation thereof to any of a plurality of desired shapes, and wherein upon release of manipulation forces, each said malleable member maintains said desired shape it has been shaped into and maintains said contact surface in said desired shape.

10. The device of claim 9, wherein said contact members further comprise a vacuum lumen connectable to a source of positive or negative fluid pressure.

11. The device of claim 9, wherein said shaft member is configured to assume a rigid configuration in which said shaft member has sufficient strength to withstand a stabilizing force exerted on the heart via manipulation or fixation of said shaft to cause said contact members to exert a stabilizing force on the beating heart.

12. The device of claim 9, wherein said shaft is adapted for insertion into a fixture attached to a fixed support or retractor.

13. The device of claim 9, wherein said malleable members are shapeable into said any one of a plurality of desired shapes prior to insertion of said malleable members, and retain said desired shapes that said malleable members have been shaped into after insertion of said malleable members into the chest cavity.

14. The device of claim 9, wherein said plurality of contact members are connected to said distal end portion of said shaft.

15. A device for use in a cardiovascular surgery for insertion into the chest cavity to stabilize the beating heart through communication with a fixed support or retractor located at least partially outside of the chest cavity, the device comprising:
   a shaft having a proximal end portion and a distal end portion;
   a plurality of contact members attachable to the distal end portion of the shaft, said contact members each comprising:
      a flexible main body having a contact surface and an elongated malleable member extending along a length of the flexible main body member; and
      a vacuum lumen connectable to a source of positive or negative fluid pressure;
   wherein said each of said contact members when attached to the distal end portion of the shaft (i) is shapeable to engage the surface of the beating heart, (ii) is continuously adjustably shapeable by manipulation thereof to any of a plurality of desired shapes, and (iii) maintains the desired shape it has been shaped into and maintains the contact surface in the desired shape upon release of manipulation forces; and
   wherein the shaft has sufficient strength to withstand a stabilizing force exerted on the heart via manipulation or fixation of the shaft to cause the contact members to exert a stabilizing force on the beating heart.

16. The device of claim 15, wherein introduction of negative pressure to said contact members to fix a present shape of said contact surface is continuously adjustable.

17. The device of claim 15, wherein each said elongated malleable member is substantially cylindrical.

18. The device of claim 15, wherein each said elongated malleable member comprises a wire.

19. The device of claim 15, wherein said shaft is adapted for insertion into a fixture attached to the fixed support or retractor.

20. The device of claim 15, wherein said malleable members are shapeable into said any one of a plurality of desired shapes prior to insertion of said malleable members, and retain said desired shapes that said malleable members have been shaped into after insertion of said malleable members into the chest cavity.

21. The device of claim 15, wherein said plurality of contact members are attached to said distal end portion of said shaft.

* * * * *